(12) United States Patent
Payne et al.

(10) Patent No.: US 10,988,789 B2
(45) Date of Patent: Apr. 27, 2021

(54) GLUCOSYLTRANSFERASE ENZYMES FOR PRODUCTION OF GLUCAN POLYMERS

(71) Applicant: NUTRITION & BIOSCIENCES USA 4, INC., Rochester, NY (US)

(72) Inventors: Mark S. Payne, Wilmington, DE (US); Yefim Brun, Wilmington, DE (US); Hongxian He, Wilmington, DE (US); Thomas Scholz, Bear, DE (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 0 days.

(21) Appl. No.: 16/791,030

(22) Filed: Feb. 14, 2020

(65) Prior Publication Data

US 2020/0325513 A1 Oct. 15, 2020

Related U.S. Application Data

(60) Continuation of application No. 16/401,166, filed on May 2, 2019, now Pat. No. 10,590,450, which is a continuation of application No. 16/163,701, filed on Oct. 18, 2018, now Pat. No. 10,308,968, which is a continuation of application No. 15/080,691, filed on Mar. 25, 2016, now abandoned, which is a division of application No. 14/490,869, filed on Sep. 19, 2014, now Pat. No. 9,296,997, which is a division of application No. 14/036,049, filed on Sep. 25, 2013, now Pat. No. 8,871,474.

(60) Provisional application No. 61/705,177, filed on Sep. 25, 2013, provisional application No. 61/705,178, filed on Sep. 25, 2012, provisional application No. 61/705,179, filed on Sep. 25, 2012, provisional application No. 61/705,180, filed on Sep. 25, 2012, provisional application No. 61/705,181, filed on Sep. 25, 2012.

(51) Int. Cl.
| | | |
|---|---|---|
| *C12P 19/18* | (2006.01) | |
| *C12N 9/10* | (2006.01) | |
| *C08B 37/00* | (2006.01) | |
| *C12P 19/04* | (2006.01) | |

(52) U.S. Cl.
CPC .......... *C12P 19/18* (2013.01); *C08B 37/0009* (2013.01); *C12N 9/1048* (2013.01); *C12N 9/1051* (2013.01); *C12P 19/04* (2013.01); *C12Y 204/01005* (2013.01); *C12Y 204/01267* (2013.01); *Y02P 20/52* (2015.11)

(58) Field of Classification Search
CPC ..... C12N 9/1048; C12N 9/1051; C12P 19/18; C12P 19/04; C08B 37/0009
See application file for complete search history.

*Primary Examiner* — Maryam Monshipouri

(57) ABSTRACT

Reaction solutions are disclosed herein comprising water, sucrose and a glucosyltransferase enzyme that synthesizes poly alpha-1,3-glucan. The glucosyltransferase enzyme can synthesize insoluble glucan polymer having at least 50% alpha-1,3 glycosidic linkages and a number average degree of polymerization of at least 100. Further disclosed are methods of using such glucosyltransferase enzymes to produce insoluble poly alpha-1,3-glucan.

22 Claims, No Drawings

Specification includes a Sequence Listing.

GLUCOSYLTRANSFERASE ENZYMES FOR PRODUCTION OF GLUCAN POLYMERS

This application is a continuation of U.S. application Ser. No. 16/401,166 (filed May 2, 2019) (now U.S. Pat. No. 10,590,450), which is a continuation of U.S. application Ser. No. 16/163,701 (filed Oct. 18, 2018) (now U.S. Pat. No. 10,308,968), which is a continuation of U.S. application Ser. No. 15/080,691 (filed Mar. 25, 2016), which is a divisional of U.S. application Ser. No. 14/490,869 (filed Sep. 19, 2014) (now U.S. Pat. No. 9,296,997), which is a divisional of U.S. application Ser. No. 14/036,049 (filed Sep. 25, 2013) (now U.S. Pat. No. 8,871,474), which claims the benefit of U.S. Provisional Application Nos. 61/705,177; 61/705,178; 61/705,179; 61/705,180 and 61/705,181, each filed Sep. 25, 2012. All of these prior applications are incorporated herein by reference in their entirety.

FIELD OF INVENTION

The invention is in the field of enzyme catalysis. Specifically, this invention pertains to producing high molecular weight, insoluble poly alpha-1,3-glucan using a glucosyltransferase enzyme.

REFERENCE TO SEQUENCE LISTING SUBMITTED ELECTRONICALLY

The official copy of the sequence listing is transferred into the instant application from parent application Ser. No. 16/401,166. This sequence listing was submitted electronically in the parent application on May 2, 2019 via EFS-Web as an ASCII-formatted sequence listing with a file having a size of about 566 kilobytes. The sequence listing contained in this transferred ASCII-formatted document is part of the specification and is herein incorporated by reference in its entirety.

BACKGROUND

Driven by a desire to find new structural polysaccharides using enzymatic syntheses or genetic engineering of microorganisms or plant hosts, researchers have discovered polysaccharides that are biodegradable and can be made economically from renewably sourced feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase (gtf) enzyme isolated from *Streptococcus salivarius* (Simpson et al., *Microbiology* 141:1451-1460, 1995). Films prepared from poly alpha-1, 3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber using an *S. salivarius* gtfJ enzyme. At least 50% of the hexose units within the polymer of this fiber were linked via alpha-1,3-glycosidic linkages. *S. salivarius* gtfJ enzyme utilizes sucrose as a substrate in a polymerization reaction producing poly alpha-1,3-glucan and fructose as end-products (Simpson et al., 1995). The disclosed polymer formed a liquid crystalline solution when it was dissolved above a critical concentration in a solvent or in a mixture comprising a solvent. Continous, strong, cotton-like fibers were obtained from this solution that could be spun and used in textile applications.

Not all glucosyltransferase enzymes can produce glucan with a molecular weight and percentage of alpha-1,3 glycosidic linkages suitable for use in spinning fibers. For example, most glucosyltransferase enzymes do not produce glucan having at least 50% alpha-1,3 glycosidic linkages and a number average degree of polymerization of at least 100. Therefore, it is desirable to identify glucosyltransferase enzymes that can convert sucrose to glucan polymers having a high percentage of alpha-1,3 glycosidic linkages and high molecular weight.

SUMMARY OF INVENTION

In one embodiment, the invention concerns a reaction solution comprising water, sucrose and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34.

In a second embodiment, the glucosyltransferase enzyme in the reaction solution synthesizes poly alpha-1,3-glucan having at least 50% alpha-1,3 glycosidic linkages and a number average degree of polymerization of at least 100. In a third embodiment, the glucosyltransferase synthesizes poly alpha-1,3-glucan having 100% alpha-1,3 glycosidic linkages and a number average degree of polymerization of at least 100. In a fourth embodiment, the glucosyltransferase enzyme synthesizes poly alpha-1,3-glucan having 100% alpha-1,3 glycosidic linkages and a number average degree of polymerization of at least 250.

In a fifth embodiment, the reaction solution comprises a primer. In a sixth embodiment, this primer can be dextran or hydrolyzed glucan.

In a seventh embodiment, the invention concerns a method for producing poly alpha-1,3-glucan comprising the step of contacting at least water, sucrose, and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. The poly alpha-1,3-glucan produced in this method can optionally be isolated.

In an eighth embodiment, the glucosyltransferase enzyme used in the method synthesizes poly alpha-1,3-glucan having at least 50% alpha-1,3 glycosidic linkages and a number average degree of polymerization of at least 100. In a ninth embodiment, the glucosyltransferase enzyme synthesizes poly alpha-1,3-glucan having 100% alpha-1,3 glycosidic linkages and a number average degree of polymerization of at least 100. In a tenth embodiment, the glucosyltransferase enzyme synthesizes poly alpha-1,3-glucan having 100% alpha-1,3 glycosidic linkages and a number average degree of polymerization of at least 250.

In an eleventh embodiment, the contacting step of the method further comprises contacting a primer with the water, sucrose, and glucosyltransferase enzyme. In a twelfth embodiment, this primer can be dextran or hydrolyzed glucan.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
|---|---|---|
| "0874 gtf", *Streptococcus sobrinus*. DNA codon-optimized for expression in *E. coli*. The first 156 amino acids of the protein are deleted compared to GENBANK Identification No. 450874, which discloses "glucosyltransferase-I". | 1 | 2 (1435 aa) |
| "6855 gtf", *Streptococcus salivarius* SK126. DNA codon-optimized for expression in *E. coli*. The first 178 amino acids of the protein are deleted compared to GENBANK Identification No. 228476855, which discloses "glucosyltransferase-SI". | 3 | 4 (1341 aa) |
| "2379 gtf", *Streptococcus salivarius*. DNA codon-optimized for expression in *E. coli*. The first 203 amino acids of the protein are deleted compared to GENBANK Identification No. 662379, which discloses "glucosyltransferase". | 5 | 6 (1247 aa) |
| "7527" or "gtfJ", *Streptococcus salivarius*. DNA codon-optimized for expression in *E. coli*. The first 42 amino acids of the protein are deleted compared to GENBANK Identification No. 47527, which discloses "glucosyltransferase-I". | 7 | 8 (1477 aa) |
| "1724 gtf", *Streptococcus downei*. DNA codon-optimized for expression in *E. coli*. The first 162 amino acids of the protein are deleted compared to GENBANK Identification No. 121724, which discloses "glucosyltransferase-I". | 9 | 10 (1436 aa) |
| "0544 gtf", *Streptococcus mutans*. DNA codon-optimized for expression in *E. coli*. The first 164 amino acids of the protein are deleted compared to GENBANK Identification No. 290580544, which discloses "glucosyltransferase-I". | 11 | 12 (1313 aa) |
| "5926 gtf", *Streptococcus dentirousetti*. DNA codon-optimized for expression in *E. coli*. The first 144 amino acids of the protein are deleted compared to GENBANK Identification No. 167735926, which discloses "glucosyltransferase-I". | 13 | 14 (1323 aa) |
| "4297 gtf", *Streptococcus oralis*. DNA codon-optimized for expression in *E. coli*. The first 228 amino acids of the protein are deleted compared to GENBANK Identification No. 7684297, which discloses "glucosyltransferase". | 15 | 16 (1348 aa) |
| "5618 gtf", *Streptococcus sanguinis*. DNA codon-optimized for expression in *E. coli*. The first 223 amino acids of the protein are deleted compared to GENBANK Identification No. 328945618, which discloses "glucosyltransferase-S". | 17 | 18 (1348 aa) |
| "2765 gtf", unknown *Streptococcus* sp. C150. DNA codon-optimized for expression in *E. coli*. The first 193 amino acids of the protein are deleted compared to GENBANK Identification No. 322372765, which discloses "glucosyltransferase-S". | 19 | 20 (1340 aa) |
| "4700 gtf", *Leuconostoc mesenteroides*. DNA codon-optimized for expression in *E. coli*. The first 36 amino acids of the protein are deleted compared to GENBANK Identification No. 21654700, which discloses "dextransucrase DsrD". | 21 | 22 (1492 aa) |

TABLE 1-continued

Summary of Nucleic Acid and Protein SEQ ID Numbers

| Description | Nucleic acid SEQ ID NO. | Protein SEQ ID NO. |
|---|---|---|
| "1366 gtf", *Streptococcus criceti*. DNA codon-optimized for expression in *E. coli*. The first 139 amino acids of the protein are deleted compared to GENBANK Identification No. 146741366, which discloses "glucosyltransferase". | 23 | 24 (1323 aa) |
| "0427 gtf", *Streptococcus sobrinus*. DNA codon-optimized for expression in *E. coli*. The first 156 amino acids of the protein are deleted compared to GENBANK Identification No. 940427, which discloses "GTF-I". | 25 | 26 (1435 aa) |
| "2919 gtf", *Streptococcus salivarius* PS4. DNA codon-optimized for expression in *E. coli*. The first 92 amino acids of the protein are deleted compared to GENBANK Identification No. 383282919, which discloses "putative glucosyltransferase". | 27 | 28 (1340 aa) |
| "2678 gtf", *Streptococcus salivarius* K12. DNA codon-optimized for expression in *E. coli*. The first 188 amino acids of the protein are deleted compared to GENBANK Identification No. 400182678, which discloses "dextransucrase-S". | 29 | 30 (1341 aa) |
| "2381 gtf", *Streptococcus salivarius*. DNA codon-optimized for expression in *E. coli*. The first 273 amino acids of the protein are deleted compared to GENBANK Identification No. 662381, which discloses "glucosyltransferase". | 31 | 32 (1305 aa) |
| "3929 gtf", *Streptococcus salivarius* JIM8777. DNA codon-optimized for expression in *E. coli*. The first 178 amino acids of the protein are deleted compared to GENBANK Identification No. 387783929, which discloses "glucosyltransferase-S precursor (GTF-S) (Dextransucrase) (Sucrose 6-glucosyltransferase)". | 33 | 34 (1341 aa) |
| "6907 gtf", *Streptococcus salivarius* SK126. DNA codon-optimized for expression in *E. coli*. The first 161 amino acids of the protein are deleted compared to GENBANK Identification No. 228476907, which discloses "glucosyltransferase-SI". | 35 | 36 (1331 aa) |
| "6661 gtf", *Streptococcus salivarius* SK126. DNA codon-optimized for expression in *E. coli*. The first 265 amino acids of the protein are deleted compared to GENBANK Identification No. 228476661, which discloses "glucosyltransferase-SI". | 37 | 38 (1305 aa) |
| "0339 gtf", *Streptococcus gallolyticus* ATCC 43143. DNA codon-optimized for expression in *E. coli*. The first 213 amino acids of the protein are deleted compared to GENBANK Identification No. 334280339, which discloses "glucosyltransferase". | 39 | 40 (1310 aa) |
| "0088 gtf", *Streptococcus mutans*. DNA codon-optimized for expression in *E. coli*. The first 189 amino acids of the protein are deleted compared to GENBANK Identification No. 3130088, which discloses "glucosyltransferase-SI". | 41 | 42 (1267 aa) |
| "9358 gtf", *Streptococcus mutans* UA159. DNA codon-optimized for expression in *E. coli*. The first 176 amino acids of the protein are deleted compared to GENBANK Identification No. 24379358, which discloses "glucosyltransferase-S". | 43 | 44 (1287 aa) |

TABLE 1-continued

Summary of Nucleic Acid and Protein SEQ ID Numbers

| Description | Nucleic acid SEQ ID NO. | Protein SEQ ID NO. |
|---|---|---|
| "8242 gtf", *Streptococcus gallolyticus* ATCC BAA-2069. DNA codon-optimized for expression in *E. coli*. The first 191 amino acids of the protein are deleted compared to GENBANK Identification No. 325978242, which discloses "glucosyltransferase-I". | 45 | 46 (1355 aa) |
| "3442 gtf", *Streptococcus sanguinis* SK405. DNA codon-optimized for expression in *E. coli*. The first 228 amino acids of the protein are deleted compared to GENBANK Identification No. 324993442, which discloses a " . . . signal domain protein". | 47 | 48 (1348 aa) |
| "7528 gtf", *Streptococcus salivarius*. DNA codon-optimized for expression in *E. coli*. The first 173 amino acids of the protein are deleted compared to GENBANK Identification No. 47528, which discloses "glucosyltransferase S". | 49 | 50 (1427 aa) |
| "3279 gtf", *Streptococcus* sp. C150. DNA codon-optimized for expression in *E. coli*. The first 178 amino acids of the protein are deleted compared to GENBANK Identification No. 322373279, which discloses "glucosyltransferase S". | 51 | 52 (1393 aa) |
| "6491 gtf", *Leuconostoc citreum* KM20. DNA codon-optimized for expression in *E. coli*. The first 244 amino acids of the protein are deleted compared to GENBANK Identification No. 170016491, which discloses "glucosyltransferase". | 53 | 54 (1262 aa) |
| "6889 gtf", *Streptococcus salivarius* SK126. DNA codon-optimized for expression in *E. coli*. The first 173 amino acids of the protein are deleted compared to GENBANK Identification No. 228476889, which discloses "glucosyltransferase-I". | 55 | 56 (1427 aa) |
| "4154 gtf", *Lactobacillus reuteri*. DNA codon-optimized for expression in *E. coli*. The first 38 amino acids of the protein are deleted compared to GENBANK Identification No. 51574154, which discloses "glucansucrase". | 57 | 58 (1735 aa) |
| "3298 gtf", *Streptococcus* sp. C150. The first 209 amino acids of the protein are deleted compared to GENBANK Identification No. 322373298, which discloses "glucosyltransferase-S". | | 59 (1242 aa) |
| "Wild type gtfJ", *Streptococcus salivarius*. GENBANK Identification No. 47527. | | 60 (1518 aa) |
| Wild type gtf corresponding to 2678 gtf, *Streptococcus salivarius* K12. GENBANK Identification No. 400182678, which discloses "dextransucrase-S". | | 61 (1528 aa) |
| Wild type gtf corresponding to 6855 gtf, *Streptococcus salivarius* SK126. GENBANK Identification No. 228476855, which discloses "glucosyltransferase-SI". | | 62 (1518 aa) |
| Wild type gtf corresponding to 2919 gtf, *Streptococcus salivarius* PS4. GENBANK Identification No. 383282919, which discloses "putative glucosyltransferase". | | 63 (1431 aa) |
| Wild type gtf corresponding to 2765 gtf, *Streptococcus* sp. C150. GENBANK Identification No. 322372765, which discloses "glucosyltransferase-S". | | 64 (1532 aa) |

DETAILED DESCRIPTION OF THE INVENTION

The disclosures of all cited patent and non-patent literature are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. Poly alpha-1,3-glucan is a type of polysaccharide.

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of the poly alpha-1,3-glucan herein can be represented as number-average molecular weight ($M_n$) or as weight-average molecular weight ($M_w$). Alternatively, molecular weight can be represented as Daltons, grams/mole, DPw (weight average degree of polymerization), or DPn (number average degree of polymerization). Various means are known in the art for calculating these molecular weight measurements such as with high-pressure liquid chromatography (HPLC), size exclusion chromatography (SEC), or gel permeation chromatography (GPC).

The terms "glucosyltransferase enzyme", "gtf enzyme", "gtf enzyme catalyst", "gtf", and "glucansucrase" are used interchangeably herein. The activity of a gtf enzyme herein catalyzes the reaction of the substrate sucrose to make the products poly alpha-1,3-glucan and fructose. Other products (byproducts) of a gtf reaction can include glucose (where glucose is hydrolyzed from the glucosyl-gtf enzyme intermediate complex), various soluble oligosaccharides (DP2-DP7), and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The terms "reaction" and "enzymatic reaction" are used interchangeably herein and refer to a reaction that is performed by a glucosyltransferase enzyme. A "reaction solution" as used herein generally refers to a solution comprising at least one active glucosyltransferase enzyme in a solution comprising sucrose and water, and optionally other components. It is in the reaction solution where the step of contacting water, sucrose and a glucosyltransferase enzyme is performed. The term "under suitable reaction conditions" as used herein, refers to reaction conditions that support conversion of sucrose to poly alpha-1,3-glucan via glucosyltransferase enzyme activity. The reaction herein is not naturally occurring.

The terms "percent by volume", "volume percent", "vol %" and "v/v %" are used interchangeably herein. The percent by volume of a solute in a solution can be determined using the formula:

[(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture, or solution.

The terms "increased", "enhanced" and "improved" are used interchangeably herein. These terms refer to a greater quantity or activity such as a quantity or activity slightly greater than the original quantity or activity, or a quantity or activity in large excess compared to the original quantity or activity, and including all quantities or activities in between. Alternatively, these terms may refer to, for example, a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. "Chimeric gene" refers to any gene that is not a native gene, comprising regulatory and coding sequences that are not found together in nature. A "foreign" or "heterologous" gene refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of the host cell.

A native amino acid sequence or polynucleotide sequence is naturally occurring, whereas a non-native amino acid sequence or polynucleotide sequence does not occur in nature.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used in certain embodiments refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic" or "recombinant" or "transformed" organisms or "transformants".

The term "recombinant" or "heterologous" refers to an artificial combination of two otherwise separate segments of sequence, e.g., by chemical synthesis or by the manipulation of isolated segments of nucleic acids by genetic engineering techniques.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% A identity with a sequence disclosed herein. The variant amino acid sequence or polynucleotide sequence has the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence.

The term "isolated" as used in certain embodiments refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, the isolated polynucleotide or polypeptide molecule can be comprised within a cell or organism in a heterologous manner. Another example is an isolated glucosyltransferase enzyme.

Embodiments of the disclosed invention concern a reaction solution comprising water, sucrose and a glucosyltransferase enzyme that synthesizes poly alpha-1,3-glucan. The glucosyltransferase enzyme comprises an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. Significantly, these glucosyltransferase enzymes can synthesize poly alpha-1,3-glucan having at least 50% alpha-1,3 glycosidic linkages and a number average degree of polymerization of at least 100. Such glucan is suitable for use in spinning fibers and in other industrial applications.

The molecular weight of the poly alpha-1,3-glucan produced by the glucosyltransferase enzymes herein can be measured as $DP_n$ (number average degree of polymerization). Alternatively, the molecular weight of the poly alpha-1,3-glucan can be measured in terms of Daltons, grams/mole, or as $DP_w$ (weight average degree of polymerization). The poly alpha-1,3-glucan in certain embodiments of the invention can have a molecular weight in $DP_n$ or $DP_w$ of at least about 100. The molecular weight of the poly alpha-1,3-glucan can alternatively be at least about 250 $DP_n$ or $DP_w$. Alternatively still, the $DP_n$ or $DP_w$ of the poly alpha-1,3-glucan can be at least about 100, 150, 200, 250, 300, 350, 400, 450, 500, 550, 600, 650, 700, 750, 800, 850, 900, 950, or 1000 (or any integer between 100 and 1000).

The molecular weight of the poly alpha-1,3-glucan herein can be measured using any of several means known in the art. For example, glucan polymer molecular weight can be measured using high-pressure liquid chromatography (HPLC), size exclusion chromatography (SEC), or gel permeation chromatography (GPC).

The poly alpha-1,3-glucan herein is preferably linear/unbranched. The percentage of glycosidic linkages between the glucose monomer units of the poly alpha-1,3-glucan that are alpha-1,3 is at least about 50%, 60%, 70%, 80%, 90%, 95%, 96%, 97%, 98%, 99%, or 100%. In such embodiments, accordingly, the poly alpha-1,3-glucan has less than about 50%, 40%, 30%, 20%, 10%, 5%, 4%, 3%, 2%, 1%, or 0% of glycosidic linkages that are not alpha-1,3.

It is understood that the higher the percentage of alpha-1,3-glycosidic linkages present in the poly alpha-1,3-glucan, the greater the probability that the poly alpha-1,3-glucan is linear, since there are lower occurrences of certain glycosidic linkages forming branch points in the polymer. In certain embodiments, the poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glycosidic linkage profile of the poly alpha-1,3-glucan can be determined using any method known in the art. For example, the linkage profile can be determined using methods that use nuclear magnetic resonance (NMR) spectroscopy (e.g., $^{13}C$ NMR or $^1H$ NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The poly alpha-1,3-glucan herein may be characterized by any combination of the aforementioned percentages of alpha-1,3 linkages and molecular weights. For example, the poly alpha-1,3-glucan produced in a reaction solution herein can have at least 50% alpha-1,3 glycosidic linkages and a $DP_n$ or $DP_w$ of at least 100. As another example, the poly alpha-1,3-glucan can have 100% alpha-1,3 glycosidic linkages and a $DP_n$ or $DP_w$ of at least 100. The poly alpha-1,3-glucan in still another example can have 100% alpha-1,3 glycosidic linkages and a $DP_n$ or $DP_w$ of at least 250.

The glucosyltransferase enzyme in certain embodiments of the invention may be derived from a *Streptococcus* species, *Leuconostoc* species or *Lactobacillus* species, for example. Examples of *Streptococcus* species from which the glucosyltransferase may be derived include *S. salivarius, S. sobrinus, S. dentirousetti, S. downei, S. mutans, S. oralis, S. gallolyticus* and *S. sanguinis*. Examples of *Leuconostoc* species from which the glucosyltransferase may be derived include *L. mesenteroides, L. amelibiosum, L. argentinum, L. carnosum, L. citreum, L. cremoris, L. dextranicum* and *L. fructosum*. Examples of *Lactobacillus* species from which the glucosyltransferase may be derived include *L. acidophilus, L. delbrueckii, L. helveticus, L. salivarius, L. casei, L. curvatus, L. plantarum, L. sakei, L. brevis, L. buchneri, L. fermentum* and *L. reuteri*.

The glucosyltransferase enzyme herein can comprise, or consist of, an amino acid sequence that is at least 90% identical to the amino acid sequence provided in SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34, wherein the glucosyltransferase enzyme has activity. Alternatively, the glucosyltransferase enzyme can comprise, or consist of, an amino acid sequence that is at least 90%, 91%, 92%, 93%, 94%, 95%, 96%, 97%, 98%, or 99% identical to SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34, wherein the glucosyltransferase enzyme has activity.

All the amino acid residues disclosed herein at each amino acid position of motifs (i), (ii) and (iii) and the gtf enzyme sequences are examples. Given that certain amino acids share similar structural and/or charge features with each other (i.e., conserved), one or more amino acids of the disclosed motifs and gtf enzyme sequences may be substituted with a conserved amino acid residue ("conservative amino acid substitution") as follows:
1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

Examples of glucosyltransferase enzymes may be any of the amino acid sequences disclosed herein and that further include 1-300 (or any integer there between) residues on the N-terminus and/or C-terminus. Such additional residues may be from a corresponding wild type sequence from which the glucosyltransferase enzyme is derived, or may be another sequence such as an epitope tag (at either N- or C-terminus) or a heterologous signal peptide (at N-terminus), for example. Thus, examples of glucosyltransferase enzymes include SEQ ID NOs:61, 62, 63 and 64, which represent the wild type sequences from which SEQ ID NOs:30, 4, 28 and 20 are derived, respectively.

The glucosyltransferase enzyme can be encoded by the polynucleotide sequence provided in SEQ ID NO:3, SEQ ID NO:9, SEQ ID NO:11, SEQ ID NO:13, SEQ ID NO:19, SEQ ID NO:25, SEQ ID NO:27, SEQ ID NO:29, or SEQ ID NO:33, for example. Alternatively, the glucosyltransferase enzyme can be encoded by a polynucleotide sequence that is at least 90%, 91%, 92%, 93%, 94%, 95%, 96%, 97%, 98%, or 99% identical to SEQ ID NO:3, SEQ ID NO:9, SEQ ID NO:11, SEQ ID NO:13, SEQ ID NO:19, SEQ ID NO:25, SEQ ID NO:27, SEQ ID NO:29, or SEQ ID NO:33.

The glucosyltransferase enzyme in certain embodiments synthesizes poly alpha-1,3-glucan in which at least about 50%, 60%, 70%, 80%, 90%, 95%, 96%, 97%, 98%, 99%, or 100% (or any integer between 50% and 100%) of the constituent glycosidic linkages are alpha-1,3 linkages. In such embodiments, accordingly, the glucosyltransferase enzyme synthesizes poly alpha-1,3-glucan in which there is less than about 50%, 40%, 30%, 20%, 10%, 5%, 4%, 3%, 2%, or 1% of glycosidic linkages that are not alpha-1,3.

In other aspects, the glucosyltransferase enzyme synthesizes poly alpha-1,3-glucan with no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glucosyltransferase enzyme can synthesize poly alpha-1,3-glucan having a molecular weight in $DP_n$ or $DP_w$ of at least about 100. Alternatively, the glucosyltransferase enzyme can synthesize poly alpha-1,3-glucan having a molecular weight in $DP_n$ or $DP_w$ of at least about 400. Alternatively still, the glucosyltransferase enzyme can synthesize poly alpha-1,3-glucan having a molecular weight in $DP_n$ or $DP_w$ of at least about 100, 150, 200, 250, 300, 350, 400, 450, 500, 550, 600, 650, 700, 750, 800, 850, 900, 950, or 1000 (or any integer between 100 and 1000).

One or more different glucosyltransferase enzymes may be used in the disclosed invention. The glucosyltransferase enzyme preferably does not have, or has very little (less than 1%), dextransucrase, reuteransucrase, or alternansucrase activity. The glucosyltransferase in certain embodiments does not comprise amino acid residues 2-1477 of SEQ ID NO:8 or amino acid residues 138-1477 of SEQ ID NO:8, which are derived from the glucosyltransferase identified in GENBANK under GI number 47527 (SEQ ID NO:60).

The glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Oligosaccharides and polysaccharides can serve a primers herein, for example. Primers that can be used in certain embodiments include dextran and other carbohydrate-based primers, such as hydrolyzed glucan, for example. Hydrolyzed glucan can be prepared by acid hydrolysis of a glucan such as poly alpha-glucan. International Appl. Publ. No. WO2013/036918, which is incorporated herein by reference, discloses such preparation of hydrolyzed glucan using poly alpha-1,3-glucan as the starting material. Dextran for use as a primer herein can be dextran T10 (i.e., dextran having a molecular weight of 10 kD). Alternatively, the dextran can have a molecular weight of about 2, 4, 6, 8, 10, 12, 14, 16, 18, 20, or 25 kD, for example.

The glucosyltransferase enzyme used herein may be produced by any means known in the art (e.g., U.S. Pat. No. 7,000,000, which is incorporated herein by reference). For example, the glucosyltransferase enzyme may be produced recombinantly in any bacterial (e.g., *E. coli* such as TOP10, *Bacillus* sp.) or eukaryotic (e.g., yeasts such as *Pichia* sp. and *Saccharomyces* sp.) heterologous gene expression system. Any of the above-listed nucleic acid sequences can be used for this purpose, for example.

The glucosyltransferase enzyme used herein may be purified and/or isolated prior to its use, or may be used in the form of a cell lysate, for example. A cell lysate or extract may be prepared from a bacteria (e.g., *E. coli*) used to heterologously express the enzyme. For example, the bacteria may be subjected to disruption using a French pressure cell (French press). The glucosyltransferase enzyme is soluble in these type of preparations. The lysate or extract may be used at about 0.15-0.3% (v/v) in a reaction solution for producing poly alpha-1,3-glucan from sucrose. In certain embodiments, a bacterial cell lysate is first cleared of insoluble material by means such as centrifugation or filtration.

In certain embodiments, the heterologous gene expression system may be one that is designed for protein secretion. The glucosyltransferase enzyme comprises a signal peptide (signal sequence) in such embodiments. The signal peptide may be either its native signal peptide or a heterologous signal peptide.

The activity of the glucosyltransferase enzyme can be determined using any method known in the art. For example, glucosyltransferase enzyme activity can be determined by measuring the production of reducing sugars (fructose and glucose) in a reaction solution containing sucrose (50 g/L), dextran T10 (1 mg/mL) and potassium phosphate buffer (pH 6.5, 50 mM), where the solution is held at 22-25° C. for 24-30 hours. The reducing sugars can be measured by adding 0.01 mL of the reaction solution to a mixture containing 1 N NaOH and 0.1% triphenyltetrazolium chloride and then monitoring the increase in absorbance at $OD_{480\ nm}$ for five minutes.

The temperature of the reaction solution herein can be controlled, if desired. In certain embodiments, the solution has a temperature between about 5° C. to about 50° C. The temperature of the solution in certain other embodiments is between about 20° C. to about 40° C. Alternatively, the temperature of the solution may be about 20, 21, 22, 23, 24, 25, 26, 27, 28, 29, 30, 31, 32, 33, 34, 35, 36, 37, 38, 39, or 40° C.

The temperature of the reaction solution may be maintained using various means known in the art. For example, the temperature of reaction solution can be maintained by placing the vessel containing the reaction solution in an air or water bath incubator set at the desired temperature.

The initial concentration of the sucrose in the solution can be about 20 g/L to about 400 g/L, for example. Alternatively, the initial concentration of the sucrose can be about 75 g/L to about 175 g/L, or from about 50 g/L to about 150 g/L. Alternatively still, the initial concentration of the sucrose can be about 40, 50, 60, 70, 80, 90, 100, 110, 120, 130, 140, 150, or 160 g/L (or any integer between 40 and 160 g/L), for example. The "initial concentration of sucrose" refers to the sucrose concentration in the solution just after all the reaction solution components have been added (water, sucrose, gtf enzyme).

Sucrose used in the reaction solution can be highly pure 99.5%) or be of any other purity or grade. For example, the sucrose can have a purity of at least 99.0%, or be reagent grade sucrose. The sucrose may be derived from any renewable sugar source such as sugar cane, sugar beets, cassava, sweet sorghum, or corn. The sucrose can be provided in any form such as crystalline form or non-crystalline form (e.g., syrup or cane juice).

The pH of the reaction solution herein can be between about 4.0 to about 8.0. Alternatively, the pH can be about 4.0, 4.5, 5.0, 5.5, 6.0, 6.5, 7.0, 7.5, or 8.0. In certain embodiments, the pH of a solution containing water and sucrose may be set before adding the glucosyltransferase enzyme. The pH of the reaction solution can be adjusted or controlled by the addition or incorporation of a suitable buffer, including but not limited to: phosphate, tris, citrate, or a combination thereof. The concentration of the buffer can be from 0 mM to about 100 mM, or about 10, 20, or 50 mM, for example. A suitable amount of DTT (dithiothreitol, e.g., about 1.0 mM) can optionally be added to the reaction solution.

The disclosed invention also concerns a method for producing poly alpha-1,3-glucan comprising the step of contacting at least water, sucrose, and a glucosyltransferase enzyme that synthesizes poly alpha-1,3-glucan. The glucosyltransferase enzyme can comprise an amino acid sequence that is at least 90% identical to the amino acid sequence of SEQ ID NO:4, SEQ ID NO:10, SEQ ID NO:12, SEQ ID NO:14, SEQ ID NO:20, SEQ ID NO:26, SEQ ID NO:28, SEQ ID NO:30, or SEQ ID NO:34. The poly alpha-1,3-glucan produced in this method can optionally be isolated.

Water, sucrose, and a glucosyltransferase enzyme as described herein are contacted in a reaction solution. Thus, the method can comprise providing a reaction solution comprising water, sucrose and a glucosyltransferase enzyme as described herein. It will be understood that, as the glucosyltransferase enzyme synthesizes poly alpha-1,3-glucan, the reaction solution becomes a reaction mixture given that insoluble poly alpha-1,3-glucan falls out of solution as indicated by clouding of the reaction. The contacting step of the disclosed method can be performed in any number of ways. For example, the desired amount of sucrose can first be dissolved in water (optionally, other components may also be added at this stage of preparation, such as buffer components), followed by the addition of the glucosyltransferase enzyme. The solution may be kept still, or agitated via stirring or orbital shaking, for example. The reaction can be, and typically is, cell-free.

The glucosyltransferase enzyme can optionally be added to water or an aqueous solution (e.g., sucrose in water) that does not contain salt or buffer when initially preparing the reaction solution. The pH of such a preparation can then be modified as desired, such as to pH 5-6 for example. The reaction can be carried out to completion without any added buffer, if desired.

Completion of the reaction in certain embodiments can be determined visually (no more accumulation of precipitated poly alpha-1,3-glucan) and/or by measuring the amount of sucrose left in the solution (residual sucrose), where a percent sucrose consumption of over about 90% can indicate reaction completion. Typically, a reaction of the disclosed process will take about 12, 24, 36, 48, 60, 72, 84, or 96 hours to complete, depending on certain parameters such as the amount of sucrose and glucosyltransferase enzyme used in the reaction.

The percent sucrose consumption of a reaction in certain embodiments of the disclosed process is at least 90%, 91%, 92%, 93%, 94%, 95%, 96%, 97%, 98%, 99%, or 100%. Alternatively, the percent sucrose consumption may be >90% or >95%.

The yield of the poly alpha-1,3-glucan produced in the disclosed invention can be at least about 5%, 6%, 7%, 8%, 9%, 10%, 11%, 12%, 13%, 14%, 15%, 16%, 17%, 18%, 19%, or 20%, based on the weight of the sucrose used in the reaction solution.

The poly alpha-1,3-glucan produced in the disclosed method may optionally be isolated. For example, insoluble poly alpha-1,3-glucan may be separated by centrifugation or filtration. In doing so, the poly alpha-1,3-glucan is separated from the rest of the reaction solution, which may comprise water, fructose and certain byproducts (e.g., leucrose, soluble oligosaccharides DP2-DP7). This solution may also comprise residual sucrose and glucose monomer.

Poly alpha-1, 3 glucan is a potentially low cost polymer which can be enzymatically produced from renewable resources containing sucrose using glucosyltransferase enzymes. It has been shown that this polymer can form ordered liquid crystalline solutions when the polymer is dissolved in a solvent under certain conditions (U.S. Pat. No. 7,000,000). Such solutions can be spun into continuous, high strength, cotton-like fibers. The poly alpha-1,3-glucan produced using the disclosed invention has comparable utilities.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meanings of some of the abbreviations used herein are as follows: "g" means gram(s), "h" means hour(s), "mL"

means milliliter(s), "psi" means pound(s) per square inch, "wt %" means weight percentage, "μm" means micrometer(s), "° C." means degrees Celsius, "mg" means milligram(s), "mm" means millimeter(s), "A" means microliter(s), "mmol" means millimole(s), "min" means minute(s), "mol %" means mole percent, "M" means molar, "rpm" means revolutions per minute, "MPa" means megaPascals.

General Methods

Preparation of Crude Extracts of Glucosyltransferase (Gtf) Enzymes

Gtf enzymes were prepared as follows. *E. coli* TOP10® cells (Invitrogen, Carlsbad Calif.) were transformed with a pJexpress404®-based construct containing a particular gtf-encoding DNA sequence. Each sequence was codon-optimized to express the gtf enzyme in *E. coli*. Individual *E. coli* strains expressing a particular gtf enzyme were grown in LB (Luria broth) medium (Becton, Dickinson and Company, Franklin Lakes, N.J.) with ampicillin (100 μg/mL) at 37° C. with shaking to $OD_{600}$=0.4-0.5, at which time IPTG (isopropyl beta-D-1-thiogalactopyranoside, Cat. No. 16758, Sigma-Aldrich, St. Louis, Mo.) was added to a final concentration of 0.5 mM. The cultures were incubated for 2-4 hours at 37° C. following IPTG induction. Cells were harvested by centrifugation at 5,000×g for 15 minutes and resuspended (20% w/v) in 50 mM phosphate buffer pH 7.0 supplemented with dithiothreitol (DTT, 1.0 mM). Resuspended cells were passed through a French Pressure Cell (SLM Instruments, Rochester, N.Y.) twice to ensure >95% cell lysis. Lysed cells were centrifuged for 30 minutes at 12,000×g at 4° C. The resulting supernatant was analyzed by the BCA (bicinchoninic acid) protein assay (Sigma-Aldrich) and SDS-PAGE to confirm expression of the gtf enzyme, and the supernatant was stored at −20° C.

Determination of Gtf Enzymatic Activity

Gtf enzyme activity was confirmed by measuring the production of reducing sugars (fructose and glucose) in a gtf reaction solution. A reaction solution was prepared by adding a gtf extract (prepared as above) to a mixture containing sucrose (50 or 150 g/L), potassium phosphate buffer (pH 6.5, 50 mM), and optionally dextran (1 mg/mL, dextran T10, Cat. No. D9260, Sigma-Aldrich); the gtf extract was added to 2.5%-5% by volume. The reaction solution was then incubated at 22-25° C. for 24-30 hours, after which it was centrifuged. Supernatant (0.01 mL) was added to a mixture containing 1 N NaOH and 0.1% triphenyltetrazolium chloride (Sigma-Aldrich). The mixture was incubated for five minutes after which its $OD_{480\ nm}$ was determined using an ULTROSPEC spectrophotometer (Pharmacia LKB, New York, N.Y.) to gauge the presence of the reducing sugars fructose and glucose.

Determination of Glycosidic Linkages

Glycosidic linkages in the glucan product synthesized by a gtf enzyme were determined by $^{13}C$ NMR (nuclear magnetic resonance). Dry glucan polymer (25-30 mg) was dissolved in 1 mL of deuterated dimethyl sulfoxide (DMSO) containing 3% by weight of LiCl with stirring at 50° C. Using a glass pipet, 0.8 mL of the solution was transferred into a 5-mm NMR tube. A quantitative $^{13}C$ NMR spectrum was acquired using a Bruker Avance 500-MHz NMR spectrometer (Billerica, Mass.) equipped with a CPDUL cryoprobe at a spectral frequency of 125.76 MHz, using a spectral window of 26041.7 Hz. An inverse gated decoupling pulse sequence using waltz decoupling was used with an acquisition time of 0.629 second, an inter-pulse delay of 5 seconds, and 6000 pulses. The time domain data was transformed using an exponential multiplication of 2.0 Hz.

Determination of Number Average Degree of Polymerization ($DP_n$)

The $DP_n$ of a glucan product synthesized by a gtf enzyme was determined by size-exclusion chromatography (SEC). Dry glucan polymer was dissolved at 5 mg/mL in N,N-dimethyl-acetamide (DMAc) and 5% LiCl with overnight shaking at 100° C. The SEC system used was an Alliance™ 2695 separation module from Waters Corporation (Milford, Mass.) coupled with three on-line detectors: a differential refractometer 2410 from Waters, a multiangle light scattering photometer Heleos™ 8+ from Wyatt Technologies (Santa Barbara, Calif.), and a differential capillary viscometer ViscoStar™ from Wyatt. The columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 μL. The software packages used for data reduction were Empower™ version 3 from Waters (calibration with broad glucan polymer standard) and Astra® version 6 from Wyatt (triple detection method with column calibration).

Example 1

Production of Gtf Enzyme 0874 (SEQ ID NO:2)

This Example describes preparing an N-terminally truncated version of a *Streptococcus sobrinus* gtf enzyme identified in GENBANK under GI number 450874 (SEQ ID NO:2, encoded by SEQ ID NO:1; herein referred to as "0874").

A nucleotide sequence encoding gtf 0874 was synthesized using codons optimized for protein expression in *E. coli* (DNA2.0, Inc., Menlo Park, Calif.). The nucleic acid product (SEQ ID NO:1), encoding gtf 0874 (SEQ ID NO:2), was subcloned into pJexpress404® (DNA2.0, Inc.) to generate the plasmid construct identified as pMP57. This plasmid construct was used to transform *E. coli* TOP10 cells (Invitrogen, Carlsbad, Calif.) to generate the strain identified as TOP10/pMP57.

Production of gtf 0874 by bacterial expression and determination of its enzymatic activity were performed following the procedures disclosed in the General Methods section. The enzymatic activity of gtf 0874 is shown in Table 2 (see Example 18 below).

Example 2

Production of Gtf Enzyme 6855 (SEQ ID NO:4)

This Example describes preparing an N-terminally truncated version of a *Streptococcus salivarius* gtf enzyme identified in GENBANK under GI number 228476855 (SEQ ID NO:4, encoded by SEQ ID NO:3; herein referred to as "6855").

A nucleotide sequence encoding gtf 6855 was synthesized using codons optimized for protein expression in *E. coli* (DNA2.0, Inc.). The nucleic acid product (SEQ ID NO:3), encoding gtf 6855 (SEQ ID NO:4), was subcloned into pJexpress404® to generate the plasmid construct identified as pMP53. This plasmid construct was used to transform *E. coli* TOP10 cells to generate the strain identified as TOP10/pMP53.

Production of gtf 6855 by bacterial expression and determination of its enzymatic activity were performed following the procedures disclosed in the General Methods section. The enzymatic activity of gtf 6855 is shown in Table 2 (see Example 18 below).

Example 3

Production of Gtf Enzyme 2379 (SEQ ID NO:6)

This Example describes preparing an N-terminally truncated version of a *Streptococcus salivarius* gtf enzyme identified in GENBANK under GI number 662379 (SEQ ID NO:6, encoded by SEQ ID NO:5; herein referred to as "2379").

A nucleotide sequence encoding gtf 2379 was synthesized using codons optimized for protein expression in *E. coli* (DNA2.0, Inc.). The nucleic acid product (SEQ ID NO:5), encoding gtf 2379 (SEQ ID NO:6), was subcloned into pJexpress404® to generate the plasmid construct identified as pMP66. This plasmid construct was used to transform *E. coli* TOP10 cells to generate the strain identified as TOP10/pMP66.

Production of gtf 2379 by bacterial expression and determination of its enzymatic activity were performed following the procedures disclosed in the General Methods section. The enzymatic activity of gtf 2379 is shown in Table 2 (see Example 18 below).

Example 4

Production of Gtf Enzyme 7527 (GtfJ, SEQ ID NO:8)

This Example describes preparing an N-terminally truncated version of a *Streptococcus salivarius* gtf enzyme identified in GENBANK under GI number 47527 (SEQ ID NO:8, encoded by SEQ ID NO:7; herein referred to as "7527" or "GtfJ").

A nucleotide sequence encoding gtf 7527 was synthesized using codons optimized for protein expression in *E. coli* (DNA2.0, Inc.). The nucleic acid product (SEQ ID NO:7), encoding gtf 7527 (SEQ ID NO:8), was subcloned into pJexpress404® to generate the plasmid construct identified as pMP65. This plasmid construct was used to transform *E. coli* TOP10 cells to generate the strain identified as TOP10/pMP65.

Production of gtf 7527 by bacterial expression and determination of its enzymatic activity were performed following the procedures disclosed in the General Methods section. The enzymatic activity of gtf 7527 is shown in Table 2 (see Example 18 below).

Example 5

Production of Gtf Enzyme 1724 (SEQ ID NO:10)

This Example describes preparing an N-terminally truncated version of a *Streptococcus downei* gtf enzyme identified in GENBANK under GI number 121724 (SEQ ID NO:10, encoded by SEQ ID NO:9; herein referred to as "1724").

A nucleotide sequence encoding gtf 1724 was synthesized using codons optimized for protein expression in *E. coli* (DNA2.0, Inc.). The nucleic acid product (SEQ ID NO:9), encoding gtf 1724 (SEQ ID NO:10), was subcloned into pJexpress404® to generate the plasmid construct identified as pMP52. This plasmid construct was used to transform *E. coli* TOP10 cells to generate the strain identified as TOP10/pMP52.

Production of gtf 1724 by bacterial expression and determination of its enzymatic activity were performed following the procedures disclosed in the General Methods section. The enzymatic activity of gtf 1724 is shown in Table 2 (see Example 18 below).

Example 6

Production of Gtf Enzyme 0544 (SEQ ID NO:12)

This Example describes preparing an N-terminally truncated version of a *Streptococcus mutans* gtf enzyme identified in GENBANK under GI number 290580544 (SEQ ID NO:12, encoded by SEQ ID NO:11; herein referred to as "0544").

A nucleotide sequence encoding gtf 0544 was synthesized using codons optimized for protein expression in *E. coli* (DNA2.0, Inc.). The nucleic acid product (SEQ ID NO:11), encoding gtf 0544 (SEQ ID NO:12), was subcloned into pJexpress404® to generate the plasmid construct identified as pMP55. This plasmid construct was used to transform *E. coli* TOP10 cells to generate the strain identified as TOP10/pMP55.

Production of gtf 0544 by bacterial expression and determination of its enzymatic activity were performed following the procedures disclosed in the General Methods section. The enzymatic activity of gtf 0544 is shown in Table 2 (see Example 18 below).

Example 7

Production of Gtf Enzyme 5926 (SEQ ID NO:14)

This Example describes preparing an N-terminally truncated version of a *Streptococcus dentirousetti* gtf enzyme identified in GENBANK under GI number 167735926 (SEQ ID NO:14, encoded by SEQ ID NO:13; herein referred to as "5926").

A nucleotide sequence encoding gtf 5926 was synthesized using codons optimized for protein expression in *E. coli* (DNA2.0, Inc.). The nucleic acid product (SEQ ID NO:13), encoding gtf 5926 (SEQ ID NO:14), was subcloned into pJexpress404® to generate the plasmid construct identified as pMP67. This plasmid construct was used to transform *E. coli* TOP10 cells to generate the strain identified as TOP10/pMP67.

Production of gtf 5926 by bacterial expression and determination of its enzymatic activity were performed following the procedures disclosed in the General Methods section. The enzymatic activity of gtf 5926 is shown in Table 2 (see Example 18 below).

Example 8

Production of Gtf Enzyme 4297 (SEQ ID NO:16)

This Example describes preparing an N-terminally truncated version of a *Streptococcus oralis* gtf enzyme identified in GENBANK under GI number 7684297 (SEQ ID NO:16, encoded by SEQ ID NO:15; herein referred to as "4297").

A nucleotide sequence encoding gtf 4297 was synthesized using codons optimized for protein expression in *E. coli* (DNA2.0, Inc.). The nucleic acid product (SEQ ID NO:15), encoding gtf 4297 (SEQ ID NO:16), was subcloned into pJexpress404® to generate the plasmid construct identified as pMP62. This plasmid construct was used to transform *E. coli* TOP10 cells to generate the strain identified as TOP10/pMP62.

Production of gtf 4297 by bacterial expression and determination of its enzymatic activity were performed following the procedures disclosed in the General Methods section. The enzymatic activity of gtf 4297 is shown in Table 2 (see Example 18 below).

Example 9

Production of Gtf Enzyme 5618 (SEQ ID NO:18)

This Example describes preparing an N-terminally truncated version of a *Streptococcus sanguinis* gtf enzyme identified in GENBANK under GI number 328945618 (SEQ ID NO:18, encoded by SEQ ID NO:17; herein referred to as "5618").

A nucleotide sequence encoding gtf 5618 was synthesized using codons optimized for protein expression in *E. coli* (DNA2.0, Inc.). The nucleic acid product (SEQ ID NO:17), encoding gtf 5618 (SEQ ID NO:18), was subcloned into pJexpress404® to generate the plasmid construct identified as pMP56. This plasmid construct was used to transform *E. coli* TOP10 cells to generate the strain identified as TOP10/pMP56.

Production of gtf 5618 by bacterial expression and determination of its enzymatic activity were performed following the procedures disclosed in the General Methods section. The enzymatic activity of gtf 5618 is shown in Table 2 (see Example 18 below).

Example 10

Production of Gtf Enzyme 2765 (SEQ ID NO:20)

This Example describes preparing an N-terminally truncated version of a *Streptococcus* sp. gtf enzyme identified in GENBANK under GI number 322372765 (SEQ ID NO:20, encoded by SEQ ID NO:19; herein referred to as "2765").

A nucleotide sequence encoding gtf 2765 was synthesized using codons optimized for protein expression in *E. coli* (DNA2.0, Inc.). The nucleic acid product (SEQ ID NO:19), encoding gtf 2765 (SEQ ID NO:20), was subcloned into pJexpress404® to generate the plasmid construct identified as pMP73. This plasmid construct was used to transform *E. coli* TOP10 cells to generate the strain identified as TOP10/pMP73.

Production of gtf 2765 by bacterial expression and determination of its enzymatic activity were performed following the procedures disclosed in the General Methods section. The enzymatic activity of gtf 2765 is shown in Table 2 (see Example 18 below).

Example 11

Production of Gtf Enzyme 4700 (SEQ ID NO:22)

This Example describes preparing an N-terminally truncated version of a *Leuconostoc mesenteroides* gtf enzyme identified in GENBANK under GI number 21654700 (SEQ ID NO:22, encoded by SEQ ID NO:21; herein referred to as "4700").

A nucleotide sequence encoding gtf 2765 was synthesized using codons optimized for protein expression in *E. coli* (DNA2.0, Inc.). The nucleic acid product (SEQ ID NO:21), encoding gtf 4700 (SEQ ID NO:22), was subcloned into pJexpress404® to generate the plasmid construct identified as pMP83. This plasmid construct was used to transform *E. coli* TOP10 cells to generate the strain identified as TOP10/pMP83.

Production of gtf 4700 by bacterial expression and determination of its enzymatic activity were performed following the procedures disclosed in the General Methods section. The enzymatic activity of gtf 4700 is shown in Table 2 (see Example 18 below).

Example 12

Production of Gtf Enzyme 1366 (SEQ ID NO:24)

This Example describes preparing an N-terminally truncated version of a *Streptococcus criceti* gtf enzyme identified in GENBANK under GI number 146741366 (SEQ ID NO:24, encoded by SEQ ID NO:23; herein referred to as "1366").

A nucleotide sequence encoding gtf 1366 was synthesized using codons optimized for protein expression in *E. coli* (DNA2.0, Inc.). The nucleic acid product (SEQ ID NO:23), encoding gtf 1366 (SEQ ID NO:24), was subcloned into pJexpress404® to generate the plasmid construct identified as pMP86. This plasmid construct was used to transform *E. coli* TOP10 cells to generate the strain identified as TOP10/pMP86.

Production of gtf 1366 by bacterial expression and determination of its enzymatic activity were performed following the procedures disclosed in the General Methods section. The enzymatic activity of gtf 1366 is shown in Table 2 (see Example 18 below).

Example 13

Production of Gtf Enzyme 0427 (SEQ ID NO:26)

This Example describes preparing an N-terminally truncated version of a *Streptococcus sobrinus* gtf enzyme identified in GENBANK under GI number 940427 (SEQ ID NO:26, encoded by SEQ ID NO:25; herein referred to as "0427").

A nucleotide sequence encoding gtf 0427 was synthesized using codons optimized for protein expression in *E. coli* (DNA2.0, Inc.). The nucleic acid product (SEQ ID NO:25), encoding gtf 0427 (SEQ ID NO:26), was subcloned into pJexpress404® to generate the plasmid construct identified as pMP87. This plasmid construct was used to transform *E. coli* TOP10 cells to generate the strain identified as TOP10/pMP87.

Production of gtf 0427 by bacterial expression and determination of its enzymatic activity were performed following the procedures disclosed in the General Methods section. The enzymatic activity of gtf 0427 is shown in Table 2 (see Example 18 below).

Example 14

Production of Gtf Enzyme 2919 (SEQ ID NO:28)

This Example describes preparing an N-terminally truncated version of a *Streptococcus salivarius* gtf enzyme identified in GENBANK under GI number 383282919 (SEQ ID NO:28, encoded by SEQ ID NO:27; herein referred to as "2919").

A nucleotide sequence encoding gtf 2919 was synthesized using codons optimized for protein expression in *E. coli* (DNA2.0, Inc.). The nucleic acid product (SEQ ID NO:27), encoding gtf 2919 (SEQ ID NO:28), was subcloned into pJexpress404® to generate the plasmid construct identified as pMP88. This plasmid construct was used to transform *E. coli* TOP10 cells to generate the strain identified as TOP10/pMP88.

Production of gtf 2919 by bacterial expression and determination of its enzymatic activity were performed following the procedures disclosed in the General Methods section. The enzymatic activity of gtf 2919 is shown in Table 2 (see Example 18 below).

Example 15

Production of Gtf Enzyme 2678 (SEQ ID NO:30)

This Example describes preparing an N-terminally truncated version of a *Streptococcus salivarius* gtf enzyme identified in GENBANK under GI number 400182678 (SEQ ID NO:30 encoded by SEQ ID NO:29; herein referred to as "2678").

A nucleotide sequence encoding gtf 2678 was synthesized using codons optimized for protein expression in *E. coli* (DNA2.0, Inc.). The nucleic acid product (SEQ ID NO:29), encoding gtf 2678 (SEQ ID NO:30), was subcloned into pJexpress404® to generate the plasmid construct identified as pMP89. This plasmid construct was used to transform *E. coli* TOP10 cells to generate the strain identified as TOP10/pMP89.

Production of gtf 2678 by bacterial expression and determination of its enzymatic activity were performed following the procedures disclosed in the General Methods section. The enzymatic activity of gtf 2678 is shown in Table 2 (see Example 18 below).

Example 16

Production of Gtf Enzyme 2381 (SEQ ID NO:32)

This Example describes preparing an N-terminally truncated version of a *Streptococcus salivarius* gtf enzyme identified in GENBANK under GI number 662381 (SEQ ID NO:32 encoded by SEQ ID NO:31; herein referred to as "2381").

A nucleotide sequence encoding gtf 2381 was synthesized using codons optimized for protein expression in *E. coli* (DNA2.0, Inc.). The nucleic acid product (SEQ ID NO:31), encoding gtf 2381 (SEQ ID NO:32), was subcloned into pJexpress404® to generate the plasmid construct identified as pMP96. This plasmid construct was used to transform *E. coli* TOP10 cells to generate the strain identified as TOP10/pMP96.

Production of gtf 2381 by bacterial expression and determination of its enzymatic activity were performed following the procedures disclosed in the General Methods section. The enzymatic activity of gtf 2381 is shown in Table 2 (see Example 18 below).

Example 17

Production of Gtf Enzyme 3929 (SEQ ID NO:34) and Additional Gtf Enzymes

This Example describes preparing an N-terminally truncated version of a *Streptococcus salivarius* gtf enzyme identified in GENBANK under GI number 387783929 (SEQ ID NO:34 encoded by SEQ ID NO:33; herein referred to as "3929").

A nucleotide sequence encoding gtf 3929 was synthesized using codons optimized for protein expression in *E. coli* (DNA2.0, Inc.). The nucleic acid product (SEQ ID NO:33), encoding gtf 3929 (SEQ ID NO:34), was subcloned into pJexpress404® to generate the plasmid construct identified as pMP97. This plasmid construct was used to transform *E. coli* TOP10 cells to generate the strain identified as TOP10/pMP97.

Production of gtf 3929 by bacterial expression and determination of its enzymatic activity were performed following the procedures disclosed in the General Methods section. The enzymatic activity of gtf 3929 is shown in Table 2 (see Example 18 below).

Additional gtf enzymes were produced in a similar manner. Briefly, N-terminally truncated versions of enzymes identified in GENBANK under GI numbers 228476907 (a *Streptococcus salivarius* gtf, SEQ ID NO:36, herein referred to as "6907"), 228476661 (a *Streptococcus salivarius* gtf, SEQ ID NO:38, herein referred to as "6661"), 334280339 (a *Streptococcus gallolyticus* gtf, SEQ ID NO:40, herein referred to as "0339"), 3130088 (a *Streptococcus mutans* gtf, SEQ ID NO:42, herein referred to as "0088"), 24379358 (a *Streptococcus mutans* gtf, SEQ ID NO:44, herein referred to as "9358"), 325978242 (a *Streptococcus gallolyticus* gtf, SEQ ID NO:46, herein referred to as "8242"), 324993442 (a *Streptococcus sanguinis* gtf, SEQ ID NO:48, herein referred to as "3442"), 47528 (a *Streptococcus salivarius* gtf, SEQ ID NO:50, herein referred to as "7528"), 322373279 (a *Streptococcus* sp. gtf, SEQ ID NO:52, herein referred to as "3279"), 170016491 (a *Leuconostoc citreum* gtf, SEQ ID NO:54, herein referred to as "6491"), 228476889 (a *Streptococcus salivarius* gtf, SEQ ID NO:56, herein referred to as "6889"), 51574154 (a *Lactobacillus reuteri* gtf, SEQ ID NO:58, herein referred to as "4154"), and 322373298 (a *Streptococcus* sp. gtf, SEQ ID NO:59, herein referred to as "3298") were prepared and tested for enzymatic activity (Table 2, see Example 18 below).

Example 18

Production of Insoluble Glucan Polymer with Gtf Enzymes

This Example describes using the gtf enzymes prepared in the above Examples to synthesize glucan polymer.

Reactions were performed with each of the above gtf enzymes following the procedures disclosed in the General Methods section. Briefly, gtf reaction solutions were prepared comprising sucrose (50 g/L), potassium phosphate buffer (pH 6.5, 50 mM) and a gtf enzyme (2.5% extract by volume). After 24-30 hours at 22-25° C., insoluble glucan polymer product was harvested by centrifugation, washed three times with water, washed once with ethanol, and dried at 50° C. for 24-30 hours.

Following the procedures disclosed in the General Methods section, the glycosidic linkages in the insoluble glucan polymer product from each reaction were determined by $^{13}$C NMR, and the $DP_n$ for each product was determined by SEC. The results of these analyses are shown in Table 2.

TABLE 2

Linkages and $DP_n$ of Glucan Produced by Various Gtf Enzymes

| Gtf | SEQ ID NO. | Reducing Sugars Produced? | Insoluble Glucan Produced? | Glucan Alpha Linkages %1.3 | Glucan Alpha Linkages %1.6 | $DP_n$ |
|---|---|---|---|---|---|---|
| 0874 | 2 | yes | yes | 100 | 0 | 60 |
| 6855 | 4 | yes | yes | 100 | 0 | 440 |
| 2379 | 6 | yes | yes | 37 | 63 | 310 |
| 7527 | 8 | yes | yes | 100 | 0 | 440 |
| 1724 | 10 | yes | yes | 100 | 0 | 250 |
| 0544 | 12 | yes | yes | 62 | 36 | 980 |
| 5926 | 14 | yes | yes | 100 | 0 | 260 |
| 4297 | 16 | yes | yes | 31 | 67 | 800 |
| 5618 | 18 | yes | yes | 34 | 66 | 1020 |
| 2765 | 20 | yes | yes | 100 | 0 | 280 |
| 4700 | 22 | yes | no | | | |
| 1366 | 24 | yes | no | | | |
| 0427 | 26 | yes | yes | 100 | 0 | 120 |
| 2919 | 28 | yes | yes | 100 | 0 | 250 |
| 2678 | 30 | yes | yes | 100 | 0 | 390 |
| 2381 | 32 | yes | no | | | |
| 3929 | 34 | yes | yes | 100 | 0 | 280 |
| 6907 | 36 | yes | no | | | |
| 6661 | 38 | yes | no | | | |
| 0339 | 40 | yes | no | | | |
| 0088 | 42 | yes | no | | | |
| 9358 | 44 | yes | no | | | |
| 8242 | 46 | yes | no | | | |
| 3442 | 48 | yes | no | | | |
| 7528 | 50 | yes | no | | | |
| 3279 | 52 | yes | no | | | |
| 6491 | 54 | yes | no | | | |
| 6889 | 56 | yes | no | | | |
| 4154 | 58 | yes | no | | | |
| 3298 | 59 | yes | no | | | |
| none | na | no | no | | | |

Several gtf enzymes produced insoluble glucan products (Table 2). However, only gtf enzymes 6855 (SEQ ID NO:4), 7527 (gtfJ, SEQ ID NO:8), 1724 (SEQ ID NO:10), 0544 (SEQ ID NO:12), 5926 (SEQ ID NO:14), 2765 (SEQ ID NO:20), 0427 (SEQ ID NO:26), 2919 (SEQ ID NO:28), 2678 (SEQ ID NO:30), and 3929 (SEQ ID NO:34) produced glucan comprising at least 50% alpha-1,3 linkages and having a $DP_n$ of at least 100. These enzymes are therefore suitable for producing glucan polymers for fiber applications.

Only gtfs 6855 (SEQ ID NO:4), 7527 (gtfJ, SEQ ID NO:8), 1724 (SEQ ID NO:10), 5926 (SEQ ID NO:14), 2765 (SEQ ID NO:20), 0427 (SEQ ID NO:26), 2919 (SEQ ID NO:28), 2678 (SEQ ID NO:30), and 3929 (SEQ ID NO:34) produced glucan polymer comprising 100% alpha-1,3 linkages and having a $DP_n$ of at least 100. These results, in which only nine out of thirty gtfs were able to produce glucan with 100% alpha-1,3 linkages and a $DP_n$ of at least 100, indicate that not all gtf enzymes are capable of producing high molecular weight, insoluble glucan with a high level of alpha-1,3 linkages. Fewer gtf enzymes were able to produce glucan polymer comprising 100% alpha-1,3 linkages and having a $DP_n$ of at least 250.

Thus, gtf enzymes capable of producing glucan polymer comprising 100% alpha-1,3 linkages and a $DP_n$ of at least 100 were identified. These enzymes can be used to produce glucan suitable for producing fibers.

What is claimed is:

1. A composition comprising (i) an insoluble poly alpha-1,3-glucan having at least 90% alpha-1,3 glycosidic linkages, and (ii) a genetically engineered cell that expresses an isolated glucosyltransferase enzyme comprising an amino acid sequence that is at least 90% identical to SEQ ID NO:4.

2. The composition of claim 1, wherein said insoluble poly alpha-1,3-glucan has a number average degree of polymerization of at least 100.

3. The composition of claim 1, wherein said insoluble poly alpha-1,3-glucan has at least 95% alpha-1,3 glycosidic linkages.

4. The composition of claim 1, wherein said insoluble poly alpha-1,3-glucan has at least 97% alpha-1,3 glycosidic linkages.

5. The composition of claim 1, wherein said insoluble poly alpha-1,3-glucan has at least 99% alpha-1,3 glycosidic linkages.

6. The composition of claim 1, wherein said insoluble poly alpha-1,3-glucan has about 100% alpha-1,3 glycosidic linkages.

7. The composition of claim 1, wherein said glucosyltransferase enzyme comprises an amino acid sequence that is at least 93% identical to SEQ ID NO:4.

8. The composition of claim 1, wherein said glucosyltransferase enzyme comprises an amino acid sequence that is at least 95% identical to SEQ ID NO:4.

9. The composition of claim 1, wherein said glucosyltransferase enzyme comprises an amino acid sequence that is at least 97% identical to SEQ ID NO:4.

10. The composition of claim 1, wherein said glucosyltransferase enzyme comprises an amino acid sequence that is at least 98% identical to SEQ ID NO:4.

11. The composition of claim 1, wherein said glucosyltransferase enzyme comprises an amino acid sequence that is at least 99% identical to SEQ ID NO:4.

12. The composition of claim 1, wherein a heterologous amino acid sequence of 1-300 residues is at the N-terminus and/or C-terminus of said glucosyltransferase enzyme.

13. The composition of claim 1, wherein the composition further comprises fructose.

14. The composition of claim 13, wherein the composition further comprises glucose, sucrose, or leucrose.

15. The composition of claim 13, wherein the composition further comprises glucose, sucrose and leucrose.

16. The composition of claim 1, wherein the genetically engineered cell is a bacteria cell.

17. The composition of claim 16, wherein the bacteria cell is an *E. coli* cell.

18. The composition of claim 16, wherein the bacteria cell is a *Bacillus* species cell.

19. The composition of claim 1, wherein the genetically engineered cell is a yeast cell.

20. The composition of claim 19, wherein the yeast cell is a *Saccharomyces* species cell.

21. The composition of claim 19, wherein the yeast cell is a *Pichia* species cell.

22. The composition of claim 1, wherein composition further comprises water.

* * * * *

SEQUENCE LISTING

<160> NUMBER OF SEQ ID NOS: 64

<210> SEQ ID NO 1
<211> LENGTH: 4308
<212> TYPE: DNA
<213> ORGANISM: Streptococcus sobrinus

<400> SEQUENCE: 1

```
atggttgacg gcaaatacta ctattatgat caggacggta acgtaaagaa gaatttcgcg      60
gtgagcgttg gtgacaaaat ctactacttc gatgaaactg gtgcatataa ggataccagc     120
aaagtggacg ccgacaagag cagcagcgcg gttagccaaa acgcgaccat ctttgcggcg     180
aataaccgtg cgtacagcac ctctgcaaag aatttttgaag cggtggataa ctacctgacc     240
gcagacagct ggtatcgtcc gaaatccatc ctgaaggacg gcaaaacctg gaccgagagc     300
ggtaaggatg atttccgtcc actgctgatg gcatggtggc ctgacaccga aactaagcgc     360
aactacgtga actatatgaa taaagtggtc ggtattgaca agacgtacac tgcggaaacg     420
tcgcaagcgg atttgaccgc agcggcggag ctggttcaag cgcgtatcga gcagaagatt     480
accagcgaaa acaaccaccaa atggctgcgc gaagcaatct ccgcgttcgt taagacgcag     540
cctcagtgga acggcgagtc cgaaaagccg tatgacgatc acttgcagaa cggtgcgctg     600
ctgtttgata ccaaaccga cctgacgcca gacacccaaa gcaattaccg tttgctgaac     660 cgtacccga ccaatcagac tggtagcctg gatagccgtt ttacgtataa tccgaatgac     720
```

```
ccgttgggcg gctacgattt cttgctggcg aacgacgttg acaatagcaa tccggtcgtc    780
caggctgaac agttgaactg gctgcattat ctgctgaact ttggctctat ttacgctaac    840
gatgccgacg ccaattttga cagcattcgc gttgatgccg tcgataatgt cgatgctgat    900
ctgctgcaaa tcagcagcga ttacctgaaa gcagcgtatg gcatcgacaa gaataacaag    960
aatgcgaaca accatgttag catcgtcgaa gcgtggagcg acaatgatac cccgtatttg   1020
cacgacgatg gcgataatct gatgaacatg gacaacaaat ttcgcctgtc catgctgtgg   1080
agcctggcaa agccgctgga caaacgtagc ggtttgaacc cgctgattca aatagcctg    1140
gtggaccgcg aggtggacga tcgtgaagtg gaaaccgtgc cgtcctacag ctttgctcgt   1200
gcacatgata gcgaggtgca ggacatcatc cgtgacatta tcaaggctga gattaaccca   1260
aatagctttg gttatagctt cactcaagaa gagatcgagc aagcctttaa gatttacaac   1320
gaggatttga agaaaacgga caagaaatac acccactaca atgtgccgct gagctacacc   1380
ctgctgctga ccaacaaggg cagcatcccg cgtgtgtact atggtgatat gttcaccgat   1440
gatggccaat acatggcaaa caagaccgtc aactacgacg caatcgagag cctgctgaaa   1500
gcccgtatga aatatgtcag cggtggccaa gcaatgcaga actatcaaat tggtaatggc   1560
gagattttga ccagcgtgcg ctatggtaaa ggtgccctga gcagagcga taagggtgac   1620
gcgacgacgc gcactagcgg tgttggcgtg gttatgggta atcagccgaa cttctccctg   1680
gacggtaaag ttgtggccct gaatatgggt gcggcccatg cgaatcaaga ataccgtgca   1740
ctgatggtca gcactaaaga cggtgtggca acttacgcaa ccgatgctga cgcatccaaa   1800
gcgggcctgg tcaagcgtac cgacgagaac ggctacctgt acttcctgaa tgatgatctg   1860
aagggcgtcg cgaaccctca ggtttccggc ttcttgcaag tgtgggttcc agttggtgcc   1920
gccgatgacc aggacattcg cgtcgccgcc agcgacacgg cgagcacgga tggtaaaagc   1980
ctgcatcaag atgcggcgat ggacagccgc gtcatgtttg agggtttcag caattttcaa   2040
tccttcgcga ccaaagaaga agaatacacg aatgttgtta tcgcgaacaa tgtcgataag   2100
ttcgttagct ggggtatcac cgatttttgaa atggctccgc agtatgttag cagcaccgac   2160
ggtcagttct tggacagcgt catccagaat ggctatgcgt ttactgatcg ctatgatctg   2220
ggtatgtcca aggcgaacaa gtatggcacg gcagaccaac tggttaaggc aatcaaagcc   2280
ctgcacgcta aaggcctgaa agttatgcgc gactgggtcc cggatcaaat gtacacctt    2340
ccaaaacagg aagttgtgac cgttacccgc accgacaaat tcggtaaacc gatcgccggc   2400
tctcaaatca atcacagctt gtatgtgacc gacaccaaat ccagcggcga cgactaccaa   2460
gcgaagtacg gcggtgcctt cctggatgaa ctgaaagaaa agtacccgga actgttcacg   2520
aaaaagcaaa ttagcacggg ccaagcgatt gatccgagcg tgaaaatcaa gcagtggagc   2580
gcaaaatact tcaatggttc gaatatcctg ggtcgcggtg cggactatgt gctgagcgac   2640
caggtcagca ataagtattt caacgtgcg agcgacacct tgttcctgcc gtccagcctg    2700
ctgggcaagg tcgtggagag cggcattcgt tacgacggca agggttacat ctacaacagc   2760
tccgcgaccg gcgatcaggt caaagcgtct tcattacgg aagccggtaa cctgtattac    2820
ttcggcaaag acggttacat ggttactggt gcccagacga ttaatggcgc caactacttc   2880
ttcctggaaa acggtacggc actgcgtaat acgatttaca ccgatgctca aggtaatagc   2940
cactattacg cgaatgatgg caaacgctat gaaaatggct atcaacagtt cggtaacgat   3000
tggcgctact ttaaagatgg taacatggca gtcggcctga ccacggttga tggcaacgtg   3060
```

```
caatactttg acaaagacgg cgtccaggca aaggataaga ttatcgtcac ccgtgatggc    3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaactgta cttcgaggcc aacggtcaac aagttaaagg tgactttgtt    3300
acgtccgatg agggcaaact gtatttctat gacgttgatt ctggtgacat gtggacggac    3360
accttcatcg aggataaggc gggcaactgg ttctatttgg caaggatgg tgcggcagtt     3420 acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
gatggtgtcg cggtggaccc tagcgtggtt aaaggtcaaa cctttaagga cgcttcgggc    3660
gctctgcgtt tctacaactt gaagggtcaa ctggtcactg gcagcggctg gtatgaaacc    3720
gcgaaccatg actgggttta cattcagtcc ggcaaggcac tgaccggcga acagaccatt    3780
aacggtcaac acctgtattt caaagaagat ggtcaccaag tcaagggtca gttggtcacg    3840
ggcaccgatg gtaaagtgcg ttactatgac gccaacagcg gtgaccaagc attcaacaag    3900
agcgtcactg tgaatggtaa aacctattac tttggcaacg atggtacggc gcagactgct    3960
ggcaacccga gggtcagac gttcaaggat ggctccgaca tccgttttta ctctatggaa     4020
ggccaactgg tgaccggctc gggttggtac gagaacgcgc aaggccagtg gctgtatgtg    4080
aaaaacggta aggtgctgac tggtctgcaa accgttggca gccagcgtgt tacttcgac    4140 gagaatggta ttcaggccaa gggcaaagca gtgcgtacca gcgatggcaa aattcgttat    4200
ttcgacgaaa acagcggcag catgatcacg aatcaatgga agttcgtcta tggtcagtat    4260
tactactttg gtaacgacgg tgcacgtatt taccgtggtt ggaactaa                 4308
```

<210> SEQ ID NO 2
<211> LENGTH: 1435
<212> TYPE: PRT
<213> ORGANISM: Streptococcus sobrinus

<400> SEQUENCE: 2

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160
```

```
Thr Ser Glu Asn Asn Thr Lys Trp Leu Arg Glu Ala Ile Ser Ala Phe
            165                 170                 175

Val Lys Thr Gln Pro Gln Trp Asn Gly Glu Ser Glu Lys Pro Tyr Asp
        180                 185                 190

Asp His Leu Gln Asn Gly Ala Leu Leu Phe Asp Asn Gln Thr Asp Leu
            195                 200                 205

Thr Pro Asp Thr Gln Ser Asn Tyr Arg Leu Leu Asn Arg Thr Pro Thr
        210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
            245                 250                 255

Asn Pro Val Val Gln Ala Glu Gln Leu Asn Trp Leu His Tyr Leu Leu
        260                 265                 270

Asn Phe Gly Ser Ile Tyr Ala Asn Asp Ala Asp Ala Asn Phe Asp Ser
            275                 280                 285

Ile Arg Val Asp Ala Val Asp Asn Val Asp Ala Asp Leu Leu Gln Ile
        290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
            325                 330                 335

Thr Pro Tyr Leu His Asp Asp Gly Asp Asn Leu Met Asn Met Asp Asn
        340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
        370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
            405                 410                 415

Glu Ile Asn Pro Asn Ser Phe Gly Tyr Ser Phe Thr Gln Glu Glu Ile
        420                 425                 430

Glu Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
        450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
            485                 490                 495

Ser Leu Leu Lys Ala Arg Met Lys Tyr Val Ser Gly Gly Gln Ala Met
        500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
        530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
            565                 570                 575
```

```
Glu Tyr Arg Ala Leu Met Val Ser Thr Lys Asp Gly Val Ala Thr Tyr
                580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
        915                 920                 925

Ala Ser Phe Ile Thr Glu Ala Gly Asn Leu Tyr Phe Gly Lys Asp
    930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp  Trp Arg Tyr Phe Lys  Asp Gly Asn
```

995              1000             1005
Met Ala Val Gly Leu Thr Thr Val Asp Gly Asn Val Gln Tyr Phe
            1010             1015             1020

Asp Lys Asp Gly Val Gln Ala Lys Asp Lys Ile Ile Val Thr Arg
            1025             1030             1035

Asp Gly Lys Val Arg Tyr Phe Asp Gln His Asn Gly Asn Ala Ala
            1040             1045             1050

Thr Asn Thr Phe Ile Ala Asp Lys Thr Gly His Trp Tyr Tyr Leu
            1055             1060             1065

Gly Lys Asp Gly Val Ala Val Thr Gly Ala Gln Thr Val Gly Lys
            1070             1075             1080

Gln Lys Leu Tyr Phe Glu Ala Asn Gly Gln Gln Val Lys Gly Asp
            1085             1090             1095

Phe Val Thr Ser Asp Glu Gly Lys Leu Tyr Phe Tyr Asp Val Asp
            1100             1105             1110

Ser Gly Asp Met Trp Thr Asp Thr Phe Ile Glu Asp Lys Ala Gly
            1115             1120             1125

Asn Trp Phe Tyr Leu Gly Lys Asp Gly Ala Ala Val Thr Gly Ala
            1130             1135             1140

Gln Thr Ile Arg Gly Gln Lys Leu Tyr Phe Lys Ala Asn Gly Gln
            1145             1150             1155

Gln Val Lys Gly Asp Ile Val Lys Gly Thr Asp Gly Lys Ile Arg
            1160             1165             1170

Tyr Tyr Asp Ala Lys Ser Gly Glu Gln Val Phe Asn Lys Thr Val
            1175             1180             1185

Lys Ala Ala Asp Gly Lys Thr Tyr Val Ile Gly Asn Asp Gly Val
            1190             1195             1200

Ala Val Asp Pro Ser Val Val Lys Gly Gln Thr Phe Lys Asp Ala
            1205             1210             1215

Ser Gly Ala Leu Arg Phe Tyr Asn Leu Lys Gly Gln Leu Val Thr
            1220             1225             1230

Gly Ser Gly Trp Tyr Glu Thr Ala Asn His Asp Trp Val Tyr Ile
            1235             1240             1245

Gln Ser Gly Lys Ala Leu Thr Gly Glu Gln Thr Ile Asn Gly Gln
            1250             1255             1260

His Leu Tyr Phe Lys Glu Asp Gly His Gln Val Lys Gly Gln Leu
            1265             1270             1275

Val Thr Gly Thr Asp Gly Lys Val Arg Tyr Tyr Asp Ala Asn Ser
            1280             1285             1290

Gly Asp Gln Ala Phe Asn Lys Ser Val Thr Val Asn Gly Lys Thr
            1295             1300             1305

Tyr Tyr Phe Gly Asn Asp Gly Thr Ala Gln Thr Ala Gly Asn Pro
            1310             1315             1320

Lys Gly Gln Thr Phe Lys Asp Gly Ser Asp Ile Arg Phe Tyr Ser
            1325             1330             1335

Met Glu Gly Gln Leu Val Thr Gly Ser Gly Trp Tyr Glu Asn Ala
            1340             1345             1350

Gln Gly Gln Trp Leu Tyr Val Lys Asn Gly Lys Val Leu Thr Gly
            1355             1360             1365

Leu Gln Thr Val Gly Ser Gln Arg Val Tyr Phe Asp Glu Asn Gly
            1370             1375             1380

Ile Gln Ala Lys Gly Lys Ala Val Arg Thr Ser Asp Gly Lys Ile
            1385             1390             1395

Arg Tyr Phe Asp Glu Asn Ser Gly Ser Met Ile Thr Asn Gln Trp
      1400            1405                1410

Lys Phe Val Tyr Gly Gln Tyr Tyr Tyr Phe Gly Asn Asp Gly Ala
      1415            1420                1425

Arg Ile Tyr Arg Gly Trp Asn
      1430            1435

<210> SEQ ID NO 3
<211> LENGTH: 4026
<212> TYPE: DNA
<213> ORGANISM: Streptococcus salivarius

<400> SEQUENCE: 3

```
atgatcgacg gcaaatacta ttatgttaat gaggacggta gccacaaaga aaactttgcg      60
attacggtta atggtcaact gctgtatttc ggtaaggacg gcgcactgac ctctagcagc     120
acttacagct ttaccccagg tacgacgaac atcgtggatg cttttctat  caacaaccgc     180
gcgtatgact ccagcgaagc gtcctttgaa ctgattgatg ctacttgac  tgccgactcc     240
tggtatcgtc cggcttccat catcaaggac ggtgtcacgt ggcaggccag caccgcagag     300
gactttcgcc cgctgctgat ggcgtggtgg ccaaacgtgg atacccaggt gaactatctg     360
aactacatgt ctaaagtgtt taacctggac gcaaagtata gcagcaccga taaacaagag     420
actctgaagg ttgcagctaa ggatattcag attaagatcg agcagaaaat tcaggcggag     480
aaaagcaccc aatggctgcg cgaaacgatc agcgcttttg tgaaacccca accacagtgg     540
aacaaagaga ctgagaatta ctcgaaaggt ggtggtgagg atcatctgca aggcggtgca     600
ctgctgtacg tgaatgatag ccgtaccccg tgggcaaata gcgattatcg ccgcctgaac     660
cgcaccgcta ccaatcaaac gggtacgatt gacaagtcca ttctggacga gcagagcgac     720
ccaaatcaca tgggcggttt cgacttcctg ctggcgaatg atgttgacct gtccaacccg     780
gttgtgcagg cagagcagct gaaccagatt cactacttga tgaattgggg ctctatcgtg     840
atgggtgaca agacgcaaa  ctttgatggt atccgtgtcg atgcagttga caacgtcgat     900
gccgacatgc tgcaactgta taccaactac ttccgtgaat actacggtgt taacaaaagc     960
gaagcgaacg cactggcgca cattagcgtt ttggaagcgt ggagcttgaa tgataatcac    1020
tacaacgaca aaaccgatgg tgcagcattg gcgatggaga ataagcagcg tctggcgctg    1080
ctgtttagcc tggctaaacc gattaaagag cgcacccccg gcagtgagcc cgctgtataac   1140
aacaccttca atacgaccca acgcgatgag aaaaccgact ggatcaataa agacggttct    1200
aaggcctata acgaggatgg tactgtgaag cagagcacca ttggtaagta caatgaaaaa    1260
tatggtgatg catcgggcaa ttatgtgttc atccgtgccc atgataacaa tgtccaagac    1320
atcattgcgg agatcattaa gaaagaaatc aacccgaaaa gcgatggttt caccatcact    1380
gacgccgaaa tgaaacaagc gttcgagatt acaataagg  acatgctgag cagcgacaag    1440
aagtacaccc tgaataacat cccggcagct tatgccgtga tgttgcagaa catggaaacg    1500
attcccgtg  tctattatgg tgacctgtac accgacgacg ccactacat  ggaaaccaag    1560
tccccgtatt acgacaccat cgttaacctg atgaaaagcc gtatcaagta cgtcagcggt    1620
ggccaggccc aacgtagcta ctggctgccg accgacggca agatggacaa tagcgacgtt    1680
gagctgtatc gcaccaacga agtgtatacc agcgtccgtt acggtaaaga cattatgacc    1740
gcgaacgata ccgagggtag caagtacagc cgcaccagcg gccaggtcac cctggttgca    1800
aacaacccga agctgacccgt ggaccagagc gcgaagctga atgtggaaat gggtaagatt   1860
```

```
cacgcgaatc agaaataccg tgccctgatt gtgggcacgg ctgacggtat caagaatttc    1920
accagcgacg cagatgctat cgcggcaggc tacgtgaaag aaaccgactc caatggcgtt    1980
ctgacttttg cgctaatgca catcaaaggt tatgaaacct cgacatgtc cggctttgtt     2040 gctgtttggg tgccggtcgg cgcgagcgat gatcaggaca ttcgtgtcgc tcctagcact    2100
gaggccaaga agagggtga attgaccctg aaagcgaccg aagcatacga ttcccagctg     2160
atctatgaag gttttagcaa ttttcaaacc atcccggatg gtagcgaccc gagcgtgtac    2220
accaatcgca agatcgcaga gaacgtggac ctgttcaagt cctggggtgt acctcgttt    2280 gaaatggcac cgcagttcgt ttccgcagat gatggcactt ttctggactc tgtgatccaa    2340
aacggctatg cgtttgccga tcgttacgat ttggcgatga gcaagaacaa caaatacggc    2400
agcaaagagg acttgcgtga cgcgctgaaa gccctgcata agcaggcat ccaggcgatt    2460 gcagactggg tcccggacca gatttatcag ttgccgggca agaagtggt cacggcgact   2520 cgcaccgacg gcgcaggccg taaaatcgcg gacgcgatca ttgatcatag cctgtacgtt   2580
gcgaacacta agagcagcgg caaagattac caggcgaagt acggtggtga gttcttggcg   2640
gagctgaagg ccaagtaccc ggagatgttc aaagtgaaca tgatttctac cggcaaaccg   2700
attgatgaca gcgtcaaact gaaacagtgg aaagcagaat actttaacgg caccaacgtc   2760
ttggagcgcg gtgtgggtta tgtcctgagc gatgaagcca cgggtaaata ctttaccgtc   2820
acgaaggatg gcaacttcat tccgttgcag ctgacgggta atgagaaagt cgtgaccggc   2880
tttagcaatg atggcaaagg tatcacctac ttcggtacga gcggcactca agcgaaatct   2940
gcgttcgtta cgttcaatgg taatacttac tattttgacg ctcgtggtca catggttacg   3000
aacggcgagt attcgccgaa cggtaaggat gtttaccgtt tcctgccgaa tggtattatg   3060
ctgtctaacg ctttttacgt tgatgcaaat ggtaacacgt acctgtacaa cagcaagggc   3120
caaatgtaca aaggcggtta caccaaattt gacgttaccg aaacggacaa agatggtaag   3180
gaaagcaagg tggtgaagtt tcgttacttt acgaacgaag gtgtcatggc aaaaggcgtt   3240
accgtgattg acggcttcac gcaatacttt ggtgaagatg gtttccaagc gaaagacaag   3300
ctggtcacgt tcaagggcaa gacgtactac ttcgatgcac acaccggcaa tgcgatcaag   3360
gacacctggc gtaatatcaa tggcaagtgg tatcatttcg acgcgaacgg cgttgcagcg   3420
accggcgctc aggtcatcaa tggccaaaaa ctgtatttca acgaggacgg cagccaagtg   3480
aaaggcggtg ttgtcaaaaa cgcggacggt acgtattcta aatacaaaga gggttctggt   3540
gaactggtta ccaacgagtt cttcacgacg gatggcaatg tttggtacta cgcaggcgcg   3600
aatggcaaga ccgttacggg tgcccaggtg attaacggcc aacacctgta cttcaatgcg   3660
gacggttcgc aagtgaaggg cggtgtggtc aagaacgcgg atggcaccta tagcaaatat   3720
gatgcgtcta ccggcgaacg cctgaccaat gagttttca ccacgggtga taacaactgg    3780
tactacattg gcgcaaacgg caagagcgtg acgggcgagg tcaagatcgg tgacgatacc   3840
tatttctttg ccaaagatgg caagcaagtt aagggtcaaa ctgtcagcgc gggtaacggt   3900
cgtattagct actactatgg tgatagcggt aagcgtgcgg tgagcacttg gatcgaaatc   3960
caaccgggtg tttatgtcta cttcgacaag aacggcattg cctatccgcc tcgtgtgctg   4020
aattaa                                                              4026
```

<210> SEQ ID NO 4
<211> LENGTH: 1341
<212> TYPE: PRT

<213> ORGANISM: Streptococcus salivarius

<400> SEQUENCE: 4

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
            115                 120                 125

Leu Asp Ala Lys Tyr Ser Ser Thr Asp Lys Gln Glu Thr Leu Lys Val
        130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400
```

```
Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
```

-continued

```
                820                 825                 830
Gly Lys Glu Val Val Thr Ala Thr Arg Thr Asp Gly Ala Gly Arg Lys
            835                 840                 845
Ile Ala Asp Ala Ile Ile Asp His Ser Leu Tyr Val Ala Asn Thr Lys
850                 855                 860
Ser Ser Gly Lys Asp Tyr Gln Ala Lys Tyr Gly Gly Glu Phe Leu Ala
865                 870                 875                 880
Glu Leu Lys Ala Lys Tyr Pro Glu Met Phe Lys Val Asn Met Ile Ser
                885                 890                 895
Thr Gly Lys Pro Ile Asp Asp Ser Val Lys Leu Lys Gln Trp Lys Ala
            900                 905                 910
Glu Tyr Phe Asn Gly Thr Asn Val Leu Glu Arg Gly Val Gly Tyr Val
            915                 920                 925
Leu Ser Asp Glu Ala Thr Gly Lys Tyr Phe Thr Val Thr Lys Asp Gly
            930                 935                 940
Asn Phe Ile Pro Leu Gln Leu Thr Gly Asn Glu Lys Val Val Thr Gly
945                 950                 955                 960
Phe Ser Asn Asp Gly Lys Gly Ile Thr Tyr Phe Gly Thr Ser Gly Thr
                965                 970                 975
Gln Ala Lys Ser Ala Phe Val Thr Phe Asn Gly Asn Thr Tyr Tyr Phe
            980                 985                 990
Asp Ala Arg Gly His Met Val Thr Asn Gly Glu Tyr Ser Pro Asn Gly
            995                 1000                1005
Lys Asp Val Tyr Arg Phe Leu Pro Asn Gly Ile Met Leu Ser Asn
    1010                1015                1020
Ala Phe Tyr Val Asp Ala Asn Gly Asn Thr Tyr Leu Tyr Asn Ser
    1025                1030                1035
Lys Gly Gln Met Tyr Lys Gly Gly Tyr Thr Lys Phe Asp Val Thr
    1040                1045                1050
Glu Thr Asp Lys Asp Gly Lys Glu Ser Lys Val Val Lys Phe Arg
    1055                1060                1065
Tyr Phe Thr Asn Glu Gly Val Met Ala Lys Gly Val Thr Val Ile
    1070                1075                1080
Asp Gly Phe Thr Gln Tyr Phe Gly Glu Asp Gly Phe Gln Ala Lys
    1085                1090                1095
Asp Lys Leu Val Thr Phe Lys Gly Lys Thr Tyr Tyr Phe Asp Ala
    1100                1105                1110
His Thr Gly Asn Ala Ile Lys Asp Thr Trp Arg Asn Ile Asn Gly
    1115                1120                1125
Lys Trp Tyr His Phe Asp Ala Asn Gly Val Ala Ala Thr Gly Ala
    1130                1135                1140
Gln Val Ile Asn Gly Gln Lys Leu Tyr Phe Asn Glu Asp Gly Ser
    1145                1150                1155
Gln Val Lys Gly Gly Val Val Lys Asn Ala Asp Gly Thr Tyr Ser
    1160                1165                1170
Lys Tyr Lys Glu Gly Ser Gly Glu Leu Val Thr Asn Glu Phe Phe
    1175                1180                1185
Thr Thr Asp Gly Asn Val Trp Tyr Tyr Ala Gly Ala Asn Gly Lys
    1190                1195                1200
Thr Val Thr Gly Ala Gln Val Ile Asn Gly Gln His Leu Tyr Phe
    1205                1210                1215
Asn Ala Asp Gly Ser Gln Val Lys Gly Gly Val Val Lys Asn Ala
    1220                1225                1230
```

```
Asp Gly Thr Tyr Ser Lys Tyr Asp Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Ile Ala Tyr Pro Pro Arg
    1325                1330                1335

Val Leu Asn
    1340

<210> SEQ ID NO 5
<211> LENGTH: 3744
<212> TYPE: DNA
<213> ORGANISM: Streptococcus salivarius

<400> SEQUENCE: 5
atgccaagcc acattaagac catcaacggc aaacaatact acgtggagga tgacggtacg      60
attcgcaaga attacgtcct ggagcgtatc ggtggcagcc aatactttaa tgcagaaacc     120
ggtgaactgt ctaatcagaa agagtatcgt ttcgacaaaa atggtggtac tggtagcagc     180
gcggacagca cgaacaccaa cgtgactgtg aacggtgaca aaaacgcatt ttacggtacc     240
acggacaaag acattgagct ggtcgacggc tatttcaccg cgaacacctg gtatcgcccg     300
aaagaaatcc tgaaagacgg caaagaatgg accgccagca cggagaacga taaacgcccg     360
ctgctgaccg tctggtggcc tagcaaagca atccaggcgt cttatctgaa ctacatgaaa     420
gagcaaggcc tgggtaccaa ccaaacgtac acgagcttct ccagccaaac ccaaatggat     480
caagcagccc tggaagtgca aaagcgtatt gaagagcgca tcgcacgcga gggcaatacc     540
gactggctgc gcacgaccat caagaacttc gtgaaaaccc aaccgggttg aacagcacc     600 tctgaaaatc tggacaataa tgatcatctg caaggtggcg ccctgctgta caataacgac     660
tcccgcacga gccacgcgaa cagcgactat cgcctgctga tcgtacgcc gaccagccag     720 accggcaaac acaatccgaa atacaccaaa gataccagca tggtggttt cgaatttctg     780 ctggcgaacg acatcgataa ctctaatccg gcggttcaag cagagcaact gaactggctg     840
cattacatta tgaacatcgg taccatcacg ggcggttctg aggatgaaaa cttcgacggc     900
gttcgtgttg acgctgtgga atgtgaat gcggatctgc tgcaaatcgc gagcgactat     960
ttcaaagcaa atacggtgc tgatcaaagc caagatcagg cgatcaaaca cttgagcatc    1020
ctggaagcgt ggtcccataa cgacgcctac tataacgaag ataccaaagg cgcgcagttg    1080
ccgatggatg atccgatgca cctggctctg gtctactcgc tgctgcgtcc gatcggcaat    1140
cgcagcggtg tggaaccgct gatttccaac agcctgaatg accgtagcga gtccggtaag    1200
aacagcaaac gtatggcgaa ctacgcgttc gtacgcgcgc atgatagcga ggtgcaatcg    1260
attattggcc agatcatcaa aaacgagatc aatccgcaaa gcaccggtaa tacgttcacc    1320
ctggatgaga tgaagaaagc gtttgagatt tacaacaagg atatgcgtag cgcgaataag    1380
```

```
cagtatacgc agtacaacat cccgagcgcg tatgcgttga tgctgaccca caaggatacc    1440
gttccgcgtg tgtattacgg tgatatgtat acggacgacg gtcagtacat ggcgcaaaag    1500
agcccatact atgatgcgat cgaaacgctg ctgaaaggtc gcatccgcta tgccgcaggt    1560
ggtcaggaca tgaaggtcaa ctatattggt tacggtaaca ctaacggctg ggatgctgcg    1620
ggcgtgctga ccagcgtacg ttatggcacg ggcgcaaata gcgccagcga tacgggtacc    1680
gccgaaacgc gtaatcaagg tatggcagtg attgttagca accaaccggc gctgcgtctg    1740
actagcaatt tgaccattaa catgggtgcc gcacaccgta atcaggctta ccgtccgctg    1800
ctgctgacga ccaacgatgg cgtcgcgacc tatttgaacg atagcgatgc gaatggtatc    1860
gttaagtaca ccgacggtaa tggtaatctg accttctccg caaacgagat tcgtggcatc    1920
cgtaacccgc aagttgatgg ctatctggcc gtctgggttc cggtaggtgc gtcggagaat    1980
caggatgttc gtgtggcgcc gagcaaagag aagaacagct ccggtctggt ttacgagagc    2040
aatgctgccc tggatagcca agttatctac gaaggcttca gcaacttcca ggacttcgtt    2100
cagaatccga gccagtatac caacaaaaag attgcagaga atgcaaattt gttcaaatcc    2160
tggggtatta ccagctttga atttgcgccg cagtacgtga gctcggatga tggtagcttc    2220
ctggacagcg ttattcagaa cggttatgcg tttacggacc gctacgacat tggtatgagc    2280
aaagacaaca aatatggttc gctggcggat ttgaaggcag cactgaagag cttgcatgcc    2340
gttggtatta gcgcaatcgc ggattgggtt cctgatcaga tctacaatct gccaggcgac    2400
gaggtcgtca ccgcaacccg cgttaacaac tacggcgaaa ccaaagatgg tgcaatcatt    2460
gatcactctt tgtacgcggc caaaacccgt acttttggta acgactacca gggtaagtat    2520
ggtggtgcgt tcctggacga gctgaaacgt ctgtatccgc agatctttga ccgcgttcag    2580
atttctaccg gtaagcgcat gaccacggac gagaagatca cccaatggtc tgcaaagtat    2640
atgaacggta cgaacatctt ggaccgtggc tctgaatacg ttttgaagaa tggtctgaat    2700
ggttactatg gcaccaatgg tggcaaagtt tcgctgccga agttgtgggg tagcaatcaa    2760
agcacgaatg gcgacaatca aaacggcgac ggtagcggca gtttgaaaaa gcgtctgttc    2820
agcgtgcgtt accgttataa caatggccag tacgcgaaaa atgcctttat caaagataac    2880
gacggcaatg tttactattt cgacaatagc ggtcgtatgg ctgtcggtga aaaacgatt     2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga gcctgacaa caataacaat gcgagcggcc gtaatcaatt cgtccagatc     3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                           3744
```

<210> SEQ ID NO 6
<211> LENGTH: 1247
<212> TYPE: PRT
<213> ORGANISM: Streptococcus salivarius

<400> SEQUENCE: 6

```
Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
            20                  25                  30

Ser Gln Tyr Phe Asn Ala Glu Thr Gly Glu Leu Ser Asn Gln Lys Glu
        35                  40                  45

Tyr Arg Phe Asp Lys Asn Gly Thr Gly Ser Ser Ala Asp Ser Thr
    50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
    130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
                165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
        195                 200                 205

His Leu Gln Gly Gly Ala Leu Leu Tyr Asn Asn Asp Ser Arg Thr Ser
    210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
        275                 280                 285

Ile Thr Gly Gly Ser Glu Asp Glu Asn Phe Asp Gly Val Arg Val Asp
    290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
        355                 360                 365

Ala Leu Val Tyr Ser Leu Leu Arg Pro Ile Gly Asn Arg Ser Gly Val
```

-continued

```
                370                 375                 380
Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
                420                 425                 430

Gln Ser Thr Gly Asn Thr Phe Thr Leu Asp Glu Met Lys Lys Ala Phe
                435                 440                 445

Glu Ile Tyr Asn Lys Asp Met Arg Ser Ala Asn Lys Gln Tyr Thr Gln
                450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
                500                 505                 510

Gly Arg Ile Arg Tyr Ala Ala Gly Gly Gln Asp Met Lys Val Asn Tyr
                515                 520                 525

Ile Gly Tyr Gly Asn Thr Asn Gly Trp Asp Ala Ala Gly Val Leu Thr
                530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
                580                 585                 590

Arg Asn Gln Ala Tyr Arg Pro Leu Leu Leu Thr Thr Asn Asp Gly Val
                595                 600                 605

Ala Thr Tyr Leu Asn Asp Ser Asp Ala Asn Gly Ile Val Lys Tyr Thr
                610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
                660                 665                 670

Ser Ser Gly Leu Val Tyr Glu Ser Asn Ala Ala Leu Asp Ser Gln Val
                675                 680                 685

Ile Tyr Glu Gly Phe Ser Asn Phe Gln Asp Phe Val Gln Asn Pro Ser
                690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
                740                 745                 750

Asp Arg Tyr Asp Ile Gly Met Ser Lys Asp Asn Lys Tyr Gly Ser Leu
                755                 760                 765

Ala Asp Leu Lys Ala Ala Leu Lys Ser Leu His Ala Val Gly Ile Ser
                770                 775                 780

Ala Ile Ala Asp Trp Val Pro Asp Gln Ile Tyr Asn Leu Pro Gly Asp
785                 790                 795                 800
```

```
Glu Val Val Thr Ala Thr Arg Val Asn Asn Tyr Gly Glu Thr Lys Asp
            805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu
            835                 840                 845

Lys Arg Leu Tyr Pro Gln Ile Phe Asp Arg Val Gln Ile Ser Thr Gly
            850                 855                 860

Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
            885                 890                 895

Asn Gly Leu Asn Gly Tyr Tyr Gly Thr Asn Gly Gly Lys Val Ser Leu
            900                 905                 910

Pro Lys Val Val Gly Ser Asn Gln Ser Thr Asn Gly Asp Asn Gln Asn
            915                 920                 925

Gly Asp Gly Ser Gly Lys Phe Glu Lys Arg Leu Phe Ser Val Arg Tyr
            930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
            965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln Asn Arg Arg Gly Gln Val Phe Tyr
            995                 1000                1005

Tyr Asp Gln Asn Gly Val Leu Asn Ala Asn Gly Lys Gln Asp Pro
            1010                1015                1020

Lys Pro Asp Asn Asn Asn Ala Ser Gly Arg Asn Gln Phe Val
            1025                1030                1035

Gln Ile Gly Asn Asn Val Trp Ala Tyr Tyr Asp Gly Asn Gly Lys
            1040                1045                1050

Arg Val Thr Gly His Gln Asn Ile Asn Gly Gln Glu Leu Phe Phe
            1055                1060                1065

Asp Asn Asn Gly Val Gln Val Lys Gly Arg Thr Val Asn Glu Asn
            1070                1075                1080

Gly Ala Ile Arg Tyr Tyr Asp Ala Asn Ser Gly Glu Met Ala Arg
            1085                1090                1095

Asn Arg Phe Ala Glu Ile Glu Pro Gly Val Trp Ala Tyr Phe Asn
            1100                1105                1110

Asn Asp Gly Thr Ala Val Lys Gly Ser Gln Asn Ile Asn Gly Gln
            1115                1120                1125

Asp Leu Tyr Phe Asp Gln Asn Gly Arg Gln Val Lys Gly Ala Leu
            1130                1135                1140

Ala Asn Val Asp Gly Asn Leu Arg Tyr Tyr Asp Val Asn Ser Gly
            1145                1150                1155

Glu Leu Tyr Arg Asn Arg Phe His Glu Ile Asp Gly Ser Trp Tyr
            1160                1165                1170

Tyr Phe Asp Gly Asn Gly Asn Ala Val Lys Gly Met Val Asn Ile
            1175                1180                1185

Asn Gly Gln Asn Leu Leu Phe Asp Asn Asn Gly Lys Gln Ile Lys
            1190                1195                1200
```

| | | | |
|---|---|---|---|
| Gly | His Leu Val Arg Val | Asn Gly Val Val Arg | Tyr Phe Asp Pro |
| 1205 | 1210 | | 1215 |

| | | | |
|---|---|---|---|
| Asn Ser | Gly Glu Met Ala Val | Asn Arg Trp Val Glu | Val Ser Pro |
| 1220 | 1225 | | 1230 |

| | | | |
|---|---|---|---|
| Gly Trp | Trp Val Tyr Phe Asp | Gly Glu Gly Arg Gly | Gln Ile |
| 1235 | 1240 | | 1245 |

<210> SEQ ID NO 7
<211> LENGTH: 4434
<212> TYPE: DNA
<213> ORGANISM: Streptococcus salivarius

<400> SEQUENCE: 7

```
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga acgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacggatgct ccggcggtca cgaccgagaa gcggaagaa     300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatggc     420
aagtattact atgttaatga ggatggcagc cacaaagaga atttcgctat accgtgaat      480
ggccagctgc tgtactttgg taaagacggt gcgctgacgt cctctagcac gtattctttt     540
accccaggca ctaccaatat cgtggacggt tttagcatta caaccgcgc ttacgacagc     600
agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagttttca acctggacgc gaaatactct agcaccgaca acaggaaac cctgaaagtg     840
gcagcaaaag acattcaaat caagattgaa caaaagattc aagcggagaa gagcacgcag     900
tggctgcgtg aaactatcag cgcctttgtg aaaacccagc cgcagtggaa caaagaaacc     960
gagaattaca gcaagggtgg tggtgaggac cacctgcaag gtggcgcact gctgtatgtt    1020
aacgacagcc gtaccccttg ggcgaatagc gattaccgtc gtctgaatcg caccgcaacc    1080
aatcagacgg gcacgatcga taagtctatt ctggacgagc agtctgaccc aaaccacatg    1140
ggcggtttcg actttctgct ggcgaacgac gtcgacctga gcaatccggt cgtgcaggct    1200
gagcagctga atcaaatcca ctatctgatg aattggggtt ccattgtgat gggtgacaag    1260
gatgcgaact tgacggcat tcgtgtcgat gcagttgaca acgtggacgc ggacatgttg    1320
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagagcg taccccggca gtgagcccgc tgtataacaa caccttcaat    1560
accacccagc gtgatgaaaa gaccgattgg attaacaaag acggtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtatacctg    1860
```

```
aataacattc cggcagcgta tgccgtgatg ttgcagaata tggaaacgat tacccgcgtc    1920
tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct tggtcgcgaa caatccgaag    2220
ctgaatctgg accaaagcgc caagttgaat gtggagatgg gcaaaatcca tgcgaatcag    2280
aagtatcgcg cactgattgt cggcactgcg gacggcatta agaactttac ttccgacgcg    2340
gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata gccagctgat ttacgaaggc    2580
tttagcaatt ccagacgat cccagatggc agcgatccgt ccgtgtatac gaaccgcaag     2640
attgcggaga acgtggatct gttcaaaagc tggggtgtca ccagctttga tggcaccg      2700
caatttgtct cggcggatga tggcaccttt ctggatagcg ttattcagaa tggctacgcc    2760
ttcgccgacc gttatgacct ggccatgtcc aagaacaaca agtatggtag caaagaggac    2820
ctgcgtgatg cactgaaagc actgcataag gcgggtattc aagctatcgc agactgggtt    2880
ccagaccaga tctaccagct gccgggcaaa gaagttgtca ccgccacccg tacggatggt    2940
gctggccgta agatcgcaga gcgattatc gaccattctc tgtatgttgc aaacagcaaa     3000
agcagcggca agattatca gcaaagtac ggtggcgagt tcctggccga gctgaaagcc      3060
aaatacccgg aaatgttcaa agttaacatg attagcacgg taagccgat tgatgactcc     3120
gtgaaattga agcaatggaa agccgagtac ttcaatggca ccaacgtttt ggaacgtggt    3180
gtcggctatg ttctgagcga cgaggcgacc ggtaagtatt tcacggtgac caaagaaggc    3240
aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg caaggacgt ctaccgtttt ctgccgaacg gtatcatgct gagcaatgcg     3480
ttttacattg atgcgaacgg taatacctac ctgtacaact ctaagggtca aatgtacaaa    3540
ggcggttaca cgaaattcga tgtttctgaa acggataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
aatatcaatg gtaaatggta ctatttcgac gcgaatggcg ttgctgcgac cggtgcgcag    3840
gtgattaacg gccagaaact gtacttcaac gaggatggct cccaagtcaa aggcggcgtg    3900
gttaagaacg cagacggcac ctatagcaaa tacaagaag gttttggtga gctggttact    3960
aacgagtttt tcacgactga tggcaatgtt tggtactacg ccggtgcaaa tggtaaaacc    4020
gttaccggtg cacaagtgat caacggccaa catttgtact tcaatgcgga cggttcccag    4080
gtgaaggggtg gcgttgtcaa gaacgcggat ggcacctaca gcaagtacaa tgctagcact    4140
ggtgaacgtc tgacgaacga gttctttacg accggtgata caattggta ttacattggc     4200
gcaaacggta agagcgtgac gggtgaggtc aagattggtg atgatactta cttttttcgcg   4260
```
aaggatggca acaagttaa aggtcaaacc gtcagcgccg gtaatggtcg cattagctac   4320
tactacggtg acagcggcaa gcgtgcggtt agcacctgga ttgagattca gccgggtgtt   4380
tatgtgtatt tcgacaaaaa cggtttggcg taccctccgc gtgttctgaa ttaa         4434

<210> SEQ ID NO 8
<211> LENGTH: 1477
<212> TYPE: PRT
<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Thr Asn Thr Gln Ala Thr Ala Glu
    50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
            260                 265                 270

Asp Lys Gln Glu Thr Leu Lys Val Ala Ala Lys Asp Ile Gln Ile Lys
        275                 280                 285

Ile Glu Gln Lys Ile Gln Ala Glu Lys Ser Thr Gln Trp Leu Arg Glu
    290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Gly Glu Asp His Leu Gln Gly Gly Ala
                325                 330                 335

Leu Leu Tyr Val Asn Asp Ser Arg Thr Pro Trp Ala Asn Ser Asp Tyr
```

```
                340                 345                 350
Arg Arg Leu Asn Arg Thr Ala Thr Asn Gln Thr Gly Thr Ile Asp Lys
            355                 360                 365

Ser Ile Leu Asp Glu Gln Ser Asp Pro Asn His Met Gly Gly Phe Asp
    370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
            420                 425                 430

Asp Asn Val Asp Ala Asp Met Leu Gln Leu Tyr Thr Asn Tyr Phe Arg
        435                 440                 445

Glu Tyr Tyr Gly Val Asn Lys Ser Glu Ala Asn Ala Leu Ala His Ile
    450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
            500                 505                 510

Pro Leu Tyr Asn Asn Thr Phe Asn Thr Thr Gln Arg Asp Glu Lys Thr
        515                 520                 525

Asp Trp Ile Asn Lys Asp Gly Ser Lys Ala Tyr Asn Glu Asp Gly Thr
    530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
                565                 570                 575

Ile Ile Ala Glu Ile Ile Lys Lys Glu Ile Asn Pro Lys Ser Asp Gly
            580                 585                 590

Phe Thr Ile Thr Asp Ala Glu Met Lys Gln Ala Phe Glu Ile Tyr Asn
        595                 600                 605

Lys Asp Met Leu Ser Ser Asp Lys Lys Tyr Thr Leu Asn Asn Ile Pro
    610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
                645                 650                 655

Ser Pro Tyr Tyr Asp Thr Ile Val Asn Leu Met Lys Ser Arg Ile Lys
            660                 665                 670

Tyr Val Ser Gly Gly Gln Ala Gln Arg Ser Tyr Trp Leu Pro Thr Asp
        675                 680                 685

Gly Lys Met Asp Asn Ser Asp Val Glu Leu Tyr Arg Thr Asn Glu Val
    690                 695                 700

Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
                725                 730                 735

Asn Asn Pro Lys Leu Asn Leu Asp Gln Ser Ala Lys Leu Asn Val Glu
            740                 745                 750

Met Gly Lys Ile His Ala Asn Gln Lys Tyr Arg Ala Leu Ile Val Gly
        755                 760                 765
```

-continued

Thr Ala Asp Gly Ile Lys Asn Phe Thr Ser Asp Ala Asp Ala Ile Ala
            770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
                805                 810                 815

Ala Val Trp Val Pro Val Gly Ala Ser Asp Asn Gln Asp Ile Arg Val
            820                 825                 830

Ala Pro Ser Thr Glu Ala Lys Lys Glu Gly Glu Leu Thr Leu Lys Ala
        835                 840                 845

Thr Glu Ala Tyr Asp Ser Gln Leu Ile Tyr Gly Phe Ser Asn Phe
    850                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
                885                 890                 895

Glu Met Ala Pro Gln Phe Val Ser Ala Asp Asp Gly Thr Phe Leu Asp
            900                 905                 910

Ser Val Ile Gln Asn Gly Tyr Ala Phe Ala Asp Arg Tyr Asp Leu Ala
        915                 920                 925

Met Ser Lys Asn Asn Lys Tyr Gly Ser Lys Glu Asp Leu Arg Asp Ala
    930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Val Val Thr Ala Thr
                965                 970                 975

Arg Thr Asp Gly Ala Gly Arg Lys Ile Ala Asp Ala Ile Ile Asp His
            980                 985                 990

Ser Leu Tyr Val Ala Asn Ser Lys  Ser Ser Gly Lys Asp  Tyr Gln Ala
        995                 1000                1005

Lys Tyr Gly Gly Glu Phe Leu  Ala Glu Leu Lys Ala  Lys Tyr Pro
    1010                1015                1020

Glu Met  Phe Lys Val Asn Met  Ile Ser Thr Gly Lys  Pro Ile Asp
    1025                1030                1035

Asp Ser  Val Lys Leu Lys Gln  Trp Lys Ala Glu Tyr  Phe Asn Gly
    1040                1045                1050

Thr Asn Val Leu Glu Arg Gly  Val Gly Tyr Val Leu  Ser Asp Glu
    1055                1060                1065

Ala Thr  Gly Lys Tyr Phe Thr  Val Thr Lys Glu Gly  Asn Phe Ile
    1070                1075                1080

Pro Leu  Gln Leu Thr Gly Lys  Glu Lys Val Ile Thr  Gly Phe Ser
    1085                1090                1095

Ser Asp  Gly Lys Gly Ile Thr  Tyr Phe Gly Thr Ser  Gly Thr Gln
    1100                1105                1110

Ala Lys  Ser Ala Phe Val Thr  Phe Asn Gly Asn Thr  Tyr Tyr Phe
    1115                1120                1125

Asp Ala  Arg Gly His Met Val  Thr Asn Ser Glu Tyr  Ser Pro Asn
    1130                1135                1140

Gly Lys  Asp Val Tyr Arg Phe  Leu Pro Asn Gly Ile  Met Leu Ser
    1145                1150                1155

Asn Ala  Phe Tyr Ile Asp Ala  Asn Gly Asn Thr Tyr  Leu Tyr Asn
    1160                1165                1170

```
Ser Lys Gly Gln Met Tyr Lys Gly Gly Tyr Thr Lys Phe Asp Val
1175                1180                1185

Ser Glu Thr Asp Lys Asp Gly Lys Glu Ser Lys Val Val Lys Phe
    1190                1195                1200

Arg Tyr Phe Thr Asn Glu Gly Val Met Ala Lys Gly Val Thr Val
1205                1210                1215

Ile Asp Gly Phe Thr Gln Tyr Phe Gly Glu Asp Gly Phe Gln Ala
1220                1225                1230

Lys Asp Lys Leu Val Thr Phe Lys Gly Lys Thr Tyr Tyr Phe Asp
1235                1240                1245

Ala His Thr Gly Asn Gly Ile Lys Asp Thr Trp Arg Asn Ile Asn
1250                1255                1260

Gly Lys Trp Tyr Tyr Phe Asp Ala Asn Gly Val Ala Ala Thr Gly
1265                1270                1275

Ala Gln Val Ile Asn Gly Gln Lys Leu Tyr Phe Asn Glu Asp Gly
1280                1285                1290

Ser Gln Val Lys Gly Gly Val Val Lys Asn Ala Asp Gly Thr Tyr
1295                1300                1305

Ser Lys Tyr Lys Glu Gly Phe Gly Glu Leu Val Thr Asn Glu Phe
1310                1315                1320

Phe Thr Thr Asp Gly Asn Val Trp Tyr Tyr Ala Gly Ala Asn Gly
1325                1330                1335

Lys Thr Val Thr Gly Ala Gln Val Ile Asn Gly Gln His Leu Tyr
1340                1345                1350

Phe Asn Ala Asp Gly Ser Gln Val Lys Gly Gly Val Val Lys Asn
1355                1360                1365

Ala Asp Gly Thr Tyr Ser Lys Tyr Asn Ala Ser Thr Gly Glu Arg
1370                1375                1380

Leu Thr Asn Glu Phe Phe Thr Thr Gly Asp Asn Asn Trp Tyr Tyr
1385                1390                1395

Ile Gly Ala Asn Gly Lys Ser Val Thr Gly Glu Val Lys Ile Gly
1400                1405                1410

Asp Asp Thr Tyr Phe Phe Ala Lys Asp Gly Lys Gln Val Lys Gly
1415                1420                1425

Gln Thr Val Ser Ala Gly Asn Gly Arg Ile Ser Tyr Tyr Tyr Gly
1430                1435                1440

Asp Ser Gly Lys Arg Ala Val Ser Thr Trp Ile Glu Ile Gln Pro
1445                1450                1455

Gly Val Tyr Val Tyr Phe Asp Lys Asn Gly Leu Ala Tyr Pro Pro
1460                1465                1470

Arg Val Leu Asn
1475

<210> SEQ ID NO 9
<211> LENGTH: 4311
<212> TYPE: DNA
<213> ORGANISM: Streptococcus downei

<400> SEQUENCE: 9
atggttgacg gcaaatacta ctactacgat caggacggca acgtaaagaa aaacttcgcg      60
gttagcgtgg gcgagaaaat ctattacttt gacgaaactg gcgcctacaa agacaccagc     120
aaagttgagg cggacaaaag cggcagcgac attagcaagg aagagactac cttcgcggca     180
aacaaccgcg cctacagcac cagcgcggag aattttgagg cgatcgacaa ttatctgacc     240
```

```
gcggactcct ggtatcgtcc taaatccatc ctgaaggatg caaaacgtg  gacggaaagc    300
agcaaagatg actttcgtcc gctgctgatg gcgtggtggc cggataccga acgaagcgc    360
aattacgtga actacatgaa caaagttgtt ggcatcgaca agacctatac cgcggaaacc    420
agccaggccg acttgaccgc tgcggcggaa ctggtgcaag cacgcattga gcagaagatc    480
acgaccgaac agaacacgaa atggctgcgt gaggcaatct cggcatttgt taaaacgcaa    540
ccgcagtgga acggtgaaag cgagaagccg tacgacgatc acctgcaaaa cggtgctctg    600
aaatttgata atcagagcga cctgaccccg gatacgcaaa gcaactaccg tctgttgaac    660
cgtaccccga ctaatcagac gggtagcctg gacagccgct tcacttataa cgcgaacgac    720
cctttgggcg gttatgagct gctgctggca aatgacgtcg ataacagcaa tccgatcgtg    780
caggcggagc agctgaactg gctgcattac ctgctgaatt ttggtacgat ctacgccaaa    840
gatgccgacg ctaacttcga tagcattcgt gtggacgcgg ttgataacgt cgatgcggat    900
ctgctgcaaa ttagcagcga ttacctgaaa gcagcctacg gcattgataa gaataacaaa    960
aacgcgaaca accacgtgag cattgtcgaa gcctggagcg ataatgatac cccgtacctg   1020
catgacgatg gtgacaacct gatgaatatg gataacaaat ttcgcctgtc catgctgtgg   1080
tcgctggcca accgctggaa caagcgtagc ggtctgaacc cgctgattca taacagcttg   1140
gtggatcgtg aagttgatga ccgcgaggtt gaaacggttc cgagctattc ttttgcacgt   1200
gcgcatgata gcgaggtcca ggacttgatc cgtgacatca tcaaggcaga gatcaatccg   1260
aacgcattcg gttatagctt tacccaagac gagattgacc aggcctttaa gatttacaat   1320
gaggatctga agaaaacgga taagaaatac acccactata atgtgccgtt gagctacacc   1380
ctgctgctga cgaataaggg tagcatccca cgtgtctact atggtgatat gtttaccgac   1440
gatggtcagt atatggcgaa caaaaccgtc aactatgacg ccattgaatc tctgctgaaa   1500
gcgcgtatga agtatgtcgc tggcggtcaa gcaatgcaga actaccaaat cggtaatggt   1560
gagatcctga ccagcgttcg ttatggtaag ggtgccctga acagagcga caaaggtgat    1620
gcgaccacgc gcaccagcgg tgtcggtgtc gttatgggca atcagccaaa ctttagcttg   1680
gacggcaaag tggtggctct gaacatgggc gcagctcatg cgaatcagga gtatcgtgcg   1740
ctgatggtta gcacgaaaga cggtgttgcc acgtatgcga ccgatgcaga tgcgagcaaa   1800
gccggtctgg tcaaacgtac cgacgaaaac ggctacctgt atttcctgaa tgacgacctg   1860
aagggtgtgg ccaatcctca ggtgagcggt tcttgcagg  tgtgggttcc ggtgggtgcc   1920
gcggatgatc aagatatccg tgttgcagct agcgataccg catccaccga tggcaagagc   1980
ctgcaccaag acgccgcgat ggatagccgt gttatgtttg aaggcttctc taactttcag   2040
tcctttgcca cgaaagaaga ggaatatacc aacgtcgtta tcgccaacaa tgtggataag   2100
ttcgttagct ggggtatcac ggatttcgag atggccccac aatatgtttc cagcaccgac   2160
ggtcaattcc tggactctgt cattcagaac ggttatgctt ttacgaccg  ttatgacttg   2220
ggcatgtcta aggcaaacaa atacggcacg gccgatcaac tggttaaggc cattaaggcc   2280
ctgcacgcga agggcctgaa ggttatggca gattgggtgc cggatcagat gtataccttc   2340
ccgaaacagg aagtcgtgac cgttacccgt accgacaaat ttggcaaacc gatcgcaggt   2400
tcccaaatca atcatagcct gtatgttacc gataccaagt ccagcggcga tgactatcag   2460
gccaaatatg gtggtgcgtt tctggacgag ctgaaggaga aatatccgga gctgttcacg   2520
aagaaacaaa tcagcacggg tcaagctatt gacccgagcg tgaaaatcaa acagtggtct   2580
gctaagtatt tcaatggctc caacatcctg gtcgcggtg  cggactacgt actgtcggat   2640
```

```
caggcgagca acaaatacct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaaagt taccgattcc ttcattacgg aggcaggtaa tctgtactac    2820
ttcggtcaag acggctatat ggtgaccggc gcacagaaca ttaagggcag caactattac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt cgataaaga tggtgtccag gccaaggata gatcattgt cacccgcgat    3120 ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta acagcatttt gtactttgaa gcgaacggtc aacaagtcaa gggtgacttc    3300
gtgacggcta agacggtaa actgtacttc tatgatgtgg acagcggcga catgtggacc    3360 aatacctta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagg tctttaacaa gtccgttagc gtcaacggta agacctacta tttcggtagc    3600
gacggcaccg cgcaaaccca ggcgaatccg aaaggccaaa cctttaagga tggtagcggc    3660
gttctgcgtt tctacaattt ggagggccag tatgtctcgg gcagcggctg gtacgaaacg    3720
gccgagcacg agtgggtata tgtgaaatcc ggtaaagttc tgaccggtgc ccagacgatt    3780
ggtaatcaac gtgtttactt caaggacaat ggtcaccagg tgaaaggcca gctggtcacg    3840
ggtaatgacg gtaaattgcg ttactacgac gcgaacagcg gtgatcaagc attcaacaaa    3900
tccgtcacgg ttaacggtaa aacctactac tttggcagcg atggtacggc gcagacgcag    3960
gctaatccta agggtcagac cttcaaagat ggtagcggcg tgctgcgttt ttacaacttg    4020
gaaggccaat acgtgtctgg cagcggttgg tacaagaatg cgcagggcca gtggctgtac    4080
gtgaaagatg caaggtcct gaccggtctg caaacggtcg caatcagaa ggtctacttc    4140 gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a              4311
```

<210> SEQ ID NO 10  
<211> LENGTH: 1436  
<212> TYPE: PRT  
<213> ORGANISM: Streptococcus downei

<400> SEQUENCE: 10

```
Met Val Asp Gly Lys Tyr Tyr Tyr Asp Gln Asp Gly Asn Val Lys
 1               5                  10                  15

Lys Asn Phe Ala Val Ser Val Gly Glu Lys Ile Tyr Tyr Phe Asp Glu
            20                  25                  30

Thr Gly Ala Tyr Lys Asp Thr Ser Lys Val Glu Ala Asp Lys Ser Gly
        35                  40                  45

Ser Asp Ile Ser Lys Glu Glu Thr Thr Phe Ala Ala Asn Asn Arg Ala
    50                  55                  60

Tyr Ser Thr Ser Ala Glu Asn Phe Glu Ala Ile Asp Asn Tyr Leu Thr
65                  70                  75                  80
```

```
Ala Asp Ser Trp Tyr Arg Pro Lys Ser Ile Leu Lys Asp Gly Lys Thr
             85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
                180                 185                 190

Asp His Leu Gln Asn Gly Ala Leu Lys Phe Asp Asn Gln Ser Asp Leu
                195                 200                 205

Thr Pro Asp Thr Gln Ser Asn Tyr Arg Leu Leu Asn Arg Thr Pro Thr
            210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Ala Asn Asp Val Asp Asn Ser
                245                 250                 255

Asn Pro Ile Val Gln Ala Glu Gln Leu Asn Trp Leu His Tyr Leu Leu
                260                 265                 270

Asn Phe Gly Thr Ile Tyr Ala Lys Asp Ala Asp Ala Asn Phe Asp Ser
                275                 280                 285

Ile Arg Val Asp Ala Val Asp Asn Val Asp Ala Asp Leu Leu Gln Ile
            290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ala Phe Gly Tyr Ser Phe Thr Gln Asp Glu Ile
            420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
            450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495
```

-continued

Ser Leu Leu Lys Ala Arg Met Lys Tyr Val Ala Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
    770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
    850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Lys Leu Phe Leu
                885                 890                 895

Pro Lys Thr Leu Leu Gly Gln Val Val Glu Ser Gly Ile Arg Phe Asp
            900                 905                 910

Gly Thr Gly Tyr Val Tyr Asn Ser Ser Thr Thr Gly Glu Lys Val Thr

```
            915                 920                 925
Asp Ser Phe Ile Thr Glu Ala Gly Asn Leu Tyr Tyr Phe Gly Gln Asp
    930                 935                 940
Gly Tyr Met Val Thr Gly Ala Gln Asn Ile Lys Gly Ser Asn Tyr Tyr
945                 950                 955                 960
Phe Leu Ala Asn Gly Ala Ala Leu Arg Asn Thr Val Tyr Thr Asp Ala
                965                 970                 975
Gln Gly Gln Asn His Tyr Tyr Gly Asn Asp Gly Lys Arg Tyr Glu Asn
                980                 985                 990
Gly Tyr Gln Gln Phe Gly Asn Asp Ser Trp Arg Tyr Phe Lys Asn Gly
            995                 1000                1005
Val Met Ala Leu Gly Leu Thr Thr Val Asp Gly His Val Gln Tyr
    1010                1015                1020
Phe Asp Lys Asp Gly Val Gln Ala Lys Asp Lys Ile Ile Val Thr
    1025                1030                1035
Arg Asp Gly Lys Val Arg Tyr Phe Asp Gln His Asn Gly Asn Ala
    1040                1045                1050
Val Thr Asn Thr Phe Val Ala Asp Lys Thr Gly His Trp Tyr Tyr
    1055                1060                1065
Leu Gly Lys Asp Gly Val Ala Val Thr Gly Ala Gln Thr Val Gly
    1070                1075                1080
Lys Gln His Leu Tyr Phe Glu Ala Asn Gly Gln Gln Val Lys Gly
    1085                1090                1095
Asp Phe Val Thr Ala Lys Asp Gly Lys Leu Tyr Phe Tyr Asp Val
    1100                1105                1110
Asp Ser Gly Asp Met Trp Thr Asn Thr Phe Ile Glu Asp Lys Ala
    1115                1120                1125
Gly Asn Trp Phe Tyr Leu Gly Lys Asp Gly Ala Ala Val Thr Gly
    1130                1135                1140
Ala Gln Thr Ile Lys Gly Gln Lys Leu Tyr Phe Lys Ala Asn Gly
    1145                1150                1155
Gln Gln Val Lys Gly Asp Ile Val Lys Asp Ala Asp Gly Lys Ile
    1160                1165                1170
Arg Tyr Tyr Asp Ala Gln Thr Gly Glu Gln Val Phe Asn Lys Ser
    1175                1180                1185
Val Ser Val Asn Gly Lys Thr Tyr Tyr Phe Gly Ser Asp Gly Thr
    1190                1195                1200
Ala Gln Thr Gln Ala Asn Pro Lys Gly Gln Thr Phe Lys Asp Gly
    1205                1210                1215
Ser Gly Val Leu Arg Phe Tyr Asn Leu Glu Gly Gln Tyr Val Ser
    1220                1225                1230
Gly Ser Gly Trp Tyr Glu Thr Ala Glu His Glu Trp Val Tyr Val
    1235                1240                1245
Lys Ser Gly Lys Val Leu Thr Gly Ala Gln Thr Ile Gly Asn Gln
    1250                1255                1260
Arg Val Tyr Phe Lys Asp Asn Gly His Gln Val Lys Gly Gln Leu
    1265                1270                1275
Val Thr Gly Asn Asp Gly Lys Leu Arg Tyr Tyr Asp Ala Asn Ser
    1280                1285                1290
Gly Asp Gln Ala Phe Asn Lys Ser Val Thr Val Asn Gly Lys Thr
    1295                1300                1305
Tyr Tyr Phe Gly Ser Asp Gly Thr Ala Gln Thr Gln Ala Asn Pro
    1310                1315                1320
```

```
Lys Gly Gln Thr Phe Lys Asp Gly Ser Gly Val Leu Arg Phe Tyr
    1325            1330                1335

Asn Leu Glu Gly Gln Tyr Val Ser Gly Ser Gly Trp Tyr Lys Asn
    1340            1345                1350

Ala Gln Gly Gln Trp Leu Tyr Val Lys Asp Gly Lys Val Leu Thr
    1355            1360                1365

Gly Leu Gln Thr Val Gly Asn Gln Lys Val Tyr Phe Asp Lys Asn
    1370            1375                1380

Gly Ile Gln Ala Lys Gly Lys Ala Val Arg Thr Ser Asp Gly Lys
    1385            1390                1395

Val Arg Tyr Phe Asp Glu Asn Ser Gly Ser Met Ile Thr Asn Gln
    1400            1405                1410

Trp Lys Phe Val Tyr Gly Gln Tyr Tyr Tyr Phe Gly Ser Asp Gly
    1415            1420                1425

Ala Ala Val Tyr Arg Gly Trp Asn
    1430            1435

<210> SEQ ID NO 11
<211> LENGTH: 3942
<212> TYPE: DNA
<213> ORGANISM: Streptococcus mutans

<400> SEQUENCE: 11
```

| | | | | | |
|---|---|---|---|---|---|
| atgattgacg | gcaaatacta | ctactatgac | aacaacggca | aagtacgcac | caatttcacg | 60 |
| ttgatcgcgg | acggtaaaat | cctgcatttt | gatgaaactg | gcgcgtacac | cgacactagc | 120 |
| attgataccg | tgaacaagga | tattgtcacg | acgcgtagca | acctgtataa | gaaatacaat | 180 |
| caagtgtatg | atcgcagcgc | gcagagcttc | gagcatgttg | atcactacct | gacggcggaa | 240 |
| tcttggtacc | gtccgaaata | cattctgaaa | gatggcaaga | cctggaccca | gagcaccgag | 300 |
| aaggacttcc | gtcctctgct | gatgacctgg | tggccgagcc | aggaaacgca | gcgccagtat | 360 |
| gtcaacttca | tgaacgccca | gttgggtatc | aacaaaacgt | acgacgacac | cagcaatcag | 420 |
| ctgcaattga | acatcgctgc | tgcaacgatc | aagcaaaga | tcgaagccaa | atcacgacg | 480 |
| ctgaagaaca | ccgattggct | gcgtcaaacg | atcagcgcgt | tcgtcaaaac | ccaaagcgct | 540 |
| tggaatagcg | cagcgaaaa | gccgtttgat | gaccatctgc | aaaacggtgc | ggttctgtat | 600 |
| gataacgaag | gtaaattgac | gccgtatgcc | aatagcaact | atcgtattct | gaaccgcacg | 660 |
| ccgaccaacc | agaccggtaa | gaaggacccg | cgttataccg | ccgacaacac | gatcggcggc | 720 |
| tacgagtttc | tgctggccaa | cgacgtggat | aatagcaacc | cggtggttca | ggccgagcag | 780 |
| ctgaactggc | tgcacttcct | gatgaacttt | ggtaatatct | acgcaaacga | ccctgacgct | 840 |
| aacttcgact | ccatccgcgt | tgacgctgtc | gataatgtgg | acgccgatct | gttacagatc | 900 |
| gcgggtgact | atctgaaagc | ggcaaagggc | atccataaga | atgacaaagc | ggcgaacgac | 960 |
| cacctgtcca | ttctggaagc | gtggagcgac | aatgacactc | cgtatctgca | tgatgatggc | 1020 |
| gacaacatga | ttaacatgga | taacaaactg | cgcctgagcc | tgctgttctc | cctggcgaaa | 1080 |
| ccgctgaatc | agcgtagcgg | tatgaacccg | ttgattacga | cagcctggt | caaccgtact | 1140 |
| gatgataatg | ccgaaacggc | ggcagtgcca | agctactctt | ttatccgtgc | ccacgatagc | 1200 |
| gaggtccagg | atttgattcg | tgatatcatt | aaggctgaga | ttaacccgaa | cgtcgtcggt | 1260 |
| tacagcttca | cgatggaaga | gattaagaag | gcatttgaga | tctacaataa | ggacctgttg | 1320 |
| gccacggaga | agaagtatac | ccactataac | accgcattga | gctacgcgtt | gctgctgacg | 1380 |

```
aacaagagca gcgtgccgcg tgtctactat ggtgatatgt ttacggacga tggtcaatac    1440
atggcccaca agaccattaa ctacgaggca atcgaaaccc tgctgaaagc acgtatcaag    1500
tacgtgtccg gtggtcaggc tatgcgcaac cagcaagtgg gtaattcgga gatcatcacc   1560
agcgtgcgtt acggtaaagg tgcgctgaag gcgatggata cgggtgaccg cactacccgt   1620
acctctggtg tggcggtcat tgagggcaac aacccgagct tgcgcctgaa ggcttctgat   1680
cgtgtggttg tgaatatggg tgcggcccac aaaaatcaag cctatcgccc gctgctgttg   1740
acgaccgata acggcattaa ggcctatcac agcgaccaag aagcggcagg cctggtgcgt   1800
tacaccaacg accgtggcga actgatcttt accgcagccg acattaaggg ctacgcaaat   1860
ccgcaagtta gcggctacct gggcgtctgg gtccctgttg gcgcagcagc tgatcaggac   1920
gttcgtgttg cggcgagcac cgcgccaagc acggacggca agagcgttca ccagaacgcg   1980
gctctggaca gccgtgtgat gttcgagggt ttctcgaact tccaggcatt tgctaccaag   2040
aaagaagagt ataccaatgt ggtcatcgct aagaatgtgg ataagttcgc ggagtggggt   2100
gtcaccgatt tcgagatggc tccgcaatac gtttctagcc ccgacggtag cttttttggat  2160 agcgtgattc aaaacggtta tgcttttacc gaccgttacg acctgggcat cagcaagccg   2220
aacaaatatg gcaccgcgga cgatctggtt aaagcgatta aggcattgca cagcaaaggc   2280
atcaaagtta tggcggattg ggttccggac cagatgtatg ccctgccgga aaagaggtt    2340 gtgacggcaa cccgtgttga caaatacggt acgccgtag ctggcagcca gatcaaaaac    2400
acgctgtacg tggtcgatgg taaatctagc ggtaaggacc agcaggcgaa gtacggtggt   2460
gccttcctgg aagagctgca agcgaagtat ccggaactgt tcgcgcgcaa acagattagc   2520
accggtgttc cgatggaccc gagcgtcaag attaagcaat ggagcgcaaa atacttcaac   2580
ggcacgaata tcctgggtcg tggtgctggt tacgtgctga aagatcaggc aaccaacacc   2640
tactttaaca tcagcgacaa taaagagatc aatttcctgc aaagacgttt gctgaaccag   2700
gattctcaag ttggctttag ctacgacggt aagggctatg tgtactacag cacctcgggc   2760
taccaggcta aaaacacgtt catcagcgag ggtgacaagt ggtattactt cgacaataac   2820
ggttatatgg ttaccggcgc acagagcatt aatggtgtga actattactt cctgccgaat   2880
ggtttacagc tgcgtgatgc gattctgaaa aatgaggacg gtacgtacgc gtattatggc   2940
aatgatggtc gccgctacga gaatggctat tatcagtttta tgagcggtgt ttggcgccat  3000
ttcaataatg gcgagatgtc cgttggtctg accgtcattg acggtcaagt tcaatacttt   3060
gacgagatgg gttaccaggc gaaaggcaaa ttcgttacca ccgcggatgg taagatccgt   3120
tacttcgata gcagagcgg caatatgtat cgtaatcgtt tcattgagaa cgaagagggc    3180
aaatggctgt acctgggtga ggacggcgcg gcagtcaccg gtagccagac gatcaatggt   3240
cagcacctgt attttcgtgc taacggcgtt caggttaagg gtgagttcgt gaccgatcgt   3300
catggccgca tctcttatta cgacggcaac agcggtgatc agatccgcaa ccgtttcgtc   3360
cgcaatgcgc aaggccagtg gttttacttt gacaacaatg gctatgcagt aactggtgct   3420
cgtacgatca acggccagca cctgtatttc cgcgcgaacg tgttcaggt aaaaggtgag    3480 tttgttacgg accgccacgg ccgcattagc tattatgatg gtaatagcgg tgaccaaatt   3540
cgcaatcgtt tcgtgcgtaa tgcacagggt cagtggttct acttcgacaa taatggttat   3600
gcagtcacgg gtgcacgtac cattaacggc caacacctgt actttcgcgc caatggtgtg   3660
caagtgaaag gcgaatttgt tactgatcgt tatggtcgta tcagctacta tgatggcaat   3720
tctggcgacc aaattcgcaa tcgctttgtt cgtaacgccc aaggtcaatg gttctatttc   3780
```

```
gacaacaacg gttacgcggt gaccggtgcc cgcacgatta atggtcaaca cttgtacttc  3840
cgtgccaacg tgtccaggt gaagggtgaa tttgtgaccg accgctatgg tcgcatttct  3900
tactacgacg caaattccgg tgaacgcgtc cgtatcaatt aa                     3942
```

<210> SEQ ID NO 12
<211> LENGTH: 1313
<212> TYPE: PRT
<213> ORGANISM: Streptococcus mutans

<400> SEQUENCE: 12

```
Met Ile Asp Gly Lys Tyr Tyr Tyr Asp Asn Asn Gly Lys Val Arg
1               5                  10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
        115                 120                 125

Gly Ile Asn Lys Thr Tyr Asp Asp Thr Ser Asn Gln Leu Gln Leu Asn
130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
        195                 200                 205

Tyr Ala Asn Ser Asn Tyr Arg Ile Leu Asn Arg Thr Pro Thr Asn Gln
210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
        275                 280                 285

Ala Val Asp Asn Val Asp Ala Asp Leu Leu Gln Ile Ala Gly Asp Tyr
290                 295                 300

Leu Lys Ala Ala Lys Gly Ile His Lys Asn Lys Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
```

```
                340             345             350
Ser Leu Leu Phe Ser Leu Ala Lys Pro Leu Asn Gln Arg Ser Gly Met
            355             360             365

Asn Pro Leu Ile Thr Asn Ser Leu Val Asn Arg Thr Asp Asp Asn Ala
        370             375             380

Glu Thr Ala Ala Val Pro Ser Tyr Ser Phe Ile Arg Ala His Asp Ser
385             390             395             400

Glu Val Gln Asp Leu Ile Arg Asp Ile Ile Lys Ala Glu Ile Asn Pro
                405             410             415

Asn Val Val Gly Tyr Ser Phe Thr Met Glu Glu Ile Lys Lys Ala Phe
            420             425             430

Glu Ile Tyr Asn Lys Asp Leu Leu Ala Thr Glu Lys Lys Tyr Thr His
            435             440             445

Tyr Asn Thr Ala Leu Ser Tyr Ala Leu Leu Thr Asn Lys Ser Ser
        450             455             460

Val Pro Arg Val Tyr Tyr Gly Asp Met Phe Thr Asp Asp Gly Gln Tyr
465             470             475             480

Met Ala His Lys Thr Ile Asn Tyr Glu Ala Ile Glu Thr Leu Leu Lys
                485             490             495

Ala Arg Ile Lys Tyr Val Ser Gly Gly Gln Ala Met Arg Asn Gln Gln
                500             505             510

Val Gly Asn Ser Glu Ile Ile Thr Ser Val Arg Tyr Gly Lys Gly Ala
            515             520             525

Leu Lys Ala Met Asp Thr Gly Asp Arg Thr Thr Arg Thr Ser Gly Val
        530             535             540

Ala Val Ile Glu Gly Asn Asn Pro Ser Leu Arg Leu Lys Ala Ser Asp
545             550             555             560

Arg Val Val Val Asn Met Gly Ala Ala His Lys Asn Gln Ala Tyr Arg
                565             570             575

Pro Leu Leu Leu Thr Thr Asp Asn Gly Ile Lys Ala Tyr His Ser Asp
            580             585             590

Gln Glu Ala Ala Gly Leu Val Arg Tyr Thr Asn Asp Arg Gly Glu Leu
        595             600             605

Ile Phe Thr Ala Ala Asp Ile Lys Gly Tyr Ala Asn Pro Gln Val Ser
    610             615             620

Gly Tyr Leu Gly Val Trp Val Pro Val Gly Ala Ala Asp Gln Asp
625             630             635             640

Val Arg Val Ala Ala Ser Thr Ala Pro Ser Thr Asp Gly Lys Ser Val
                645             650             655

His Gln Asn Ala Ala Leu Asp Ser Arg Val Met Phe Glu Gly Phe Ser
                660             665             670

Asn Phe Gln Ala Phe Ala Thr Lys Lys Glu Glu Tyr Thr Asn Val Val
            675             680             685

Ile Ala Lys Asn Val Asp Lys Phe Ala Glu Trp Gly Val Thr Asp Phe
        690             695             700

Glu Met Ala Pro Gln Tyr Val Ser Ser Thr Asp Gly Ser Phe Leu Asp
705             710             715             720

Ser Val Ile Gln Asn Gly Tyr Ala Phe Thr Asp Arg Tyr Asp Leu Gly
                725             730             735

Ile Ser Lys Pro Asn Lys Tyr Gly Thr Ala Asp Asp Leu Val Lys Ala
            740             745             750

Ile Lys Ala Leu His Ser Lys Gly Ile Lys Val Met Ala Asp Trp Val
        755             760             765
```

```
Pro Asp Gln Met Tyr Ala Leu Pro Glu Lys Glu Val Thr Ala Thr
    770             775             780

Arg Val Asp Lys Tyr Gly Thr Pro Val Ala Gly Ser Gln Ile Lys Asn
785             790             795             800

Thr Leu Tyr Val Val Asp Gly Lys Ser Ser Gly Lys Asp Gln Gln Ala
                805             810             815

Lys Tyr Gly Gly Ala Phe Leu Glu Glu Leu Gln Ala Lys Tyr Pro Glu
            820             825             830

Leu Phe Ala Arg Lys Gln Ile Ser Thr Gly Val Pro Met Asp Pro Ser
        835             840             845

Val Lys Ile Lys Gln Trp Ser Ala Lys Tyr Phe Asn Gly Thr Asn Ile
    850             855             860

Leu Gly Arg Gly Ala Gly Tyr Val Leu Lys Asp Gln Ala Thr Asn Thr
865             870             875             880

Tyr Phe Asn Ile Ser Asp Asn Lys Glu Ile Asn Phe Leu Pro Lys Thr
                885             890             895

Leu Leu Asn Gln Asp Ser Gln Val Gly Phe Ser Tyr Asp Gly Lys Gly
            900             905             910

Tyr Val Tyr Tyr Ser Thr Ser Gly Tyr Gln Ala Lys Asn Thr Phe Ile
        915             920             925

Ser Glu Gly Asp Lys Trp Tyr Tyr Phe Asp Asn Asn Gly Tyr Met Val
    930             935             940

Thr Gly Ala Gln Ser Ile Asn Gly Val Asn Tyr Tyr Phe Leu Pro Asn
945             950             955             960

Gly Leu Gln Leu Arg Asp Ala Ile Leu Lys Asn Glu Asp Gly Thr Tyr
                965             970             975

Ala Tyr Tyr Gly Asn Asp Gly Arg Arg Tyr Glu Asn Gly Tyr Tyr Gln
            980             985             990

Phe Met Ser Gly Val Trp Arg His Phe Asn Asn Gly Glu Met Ser Val
        995            1000            1005

Gly Leu Thr Val Ile Asp Gly Gln Val Gln Tyr Phe Asp Glu Met
       1010            1015            1020

Gly Tyr Gln Ala Lys Gly Lys Phe Val Thr Thr Ala Asp Gly Lys
       1025            1030            1035

Ile Arg Tyr Phe Asp Lys Gln Ser Gly Asn Met Tyr Arg Asn Arg
       1040            1045            1050

Phe Ile Glu Asn Glu Glu Gly Lys Trp Leu Tyr Leu Gly Glu Asp
       1055            1060            1065

Gly Ala Ala Val Thr Gly Ser Gln Thr Ile Asn Gly Gln His Leu
       1070            1075            1080

Tyr Phe Arg Ala Asn Gly Val Gln Val Lys Gly Glu Phe Val Thr
       1085            1090            1095

Asp Arg His Gly Arg Ile Ser Tyr Tyr Asp Gly Asn Ser Gly Asp
       1100            1105            1110

Gln Ile Arg Asn Arg Phe Val Arg Asn Ala Gln Gly Gln Trp Phe
       1115            1120            1125

Tyr Phe Asp Asn Asn Gly Tyr Ala Val Thr Gly Ala Arg Thr Ile
       1130            1135            1140

Asn Gly Gln His Leu Tyr Phe Arg Ala Asn Gly Val Gln Val Lys
       1145            1150            1155

Gly Glu Phe Val Thr Asp Arg His Gly Arg Ile Ser Tyr Tyr Asp
       1160            1165            1170
```

| | | | | | | | | | | |
|---|---|---|---|---|---|---|---|---|---|---|
|Gly|Asn|Ser|Gly|Asp|Gln|Ile|Arg|Asn|Arg|Phe|Val|Arg|Asn|Ala|
| |1175| | | |1180| | | |1185| |

Gln Gly Gln Trp Phe Tyr Phe Asp Asn Asn Gly Tyr Ala Val Thr
    1190            1195            1200

Gly Ala Arg Thr Ile Asn Gly Gln His Leu Tyr Phe Arg Ala Asn
    1205            1210            1215

Gly Val Gln Val Lys Gly Glu Phe Val Thr Asp Arg Tyr Gly Arg
    1220            1225            1230

Ile Ser Tyr Tyr Asp Gly Asn Ser Gly Asp Gln Ile Arg Asn Arg
    1235            1240            1245

Phe Val Arg Asn Ala Gln Gly Gln Trp Phe Tyr Phe Asp Asn Asn
    1250            1255            1260

Gly Tyr Ala Val Thr Gly Ala Arg Thr Ile Asn Gly Gln His Leu
    1265            1270            1275

Tyr Phe Arg Ala Asn Gly Val Gln Val Lys Gly Glu Phe Val Thr
    1280            1285            1290

Asp Arg Tyr Gly Arg Ile Ser Tyr Tyr Asp Ala Asn Ser Gly Glu
    1295            1300            1305

Arg Val Arg Ile Asn
    1310

<210> SEQ ID NO 13
<211> LENGTH: 3972
<212> TYPE: DNA
<213> ORGANISM: Streptococcus dentirousetti

<400> SEQUENCE: 13

```
atggttgacg gcaaatacta ctactacgat gcagacggca acgtaaagaa aaacttcgcg      60
gttagcgttg gcgatgccat tttctatttt gatgaaacgg gtgcctacaa agataccagc     120
aaagttgatg cggataagac cagctctagc gtcaatcaga ccacggaaac gttcgcagcg     180
aataaccgtg cgtatagcac cgcagccgag aactttgaag cgattgataa ctacctgact     240
gcggatagct ggtatcgtcc gaagtctatc ttgaaagatg gtacgacgtg gaccgaaagc     300
accaaggatg attttcgccc gctgctgatg cgtggtggc cggataccga aaccaaacgt     360
aactacgtga actatatgaa caaggtggtc ggtatcgaca aaacgtacac cgcggaaacg     420
tcccaagctg acctgacggc ggcagccgaa ctggtgcagg cgcgtatcga gcagaaaatc     480
actagcgaaa agaatacgaa gtggctgcgt gaggcgattt ccgcgttcgt taagactcaa     540
ccgcagtgga atggcgagag cgagaaacct tatgatgacc acctgcaaaa tggtgcgctg     600
aagttcgaca atgaaaccag cctgaccccg gatacgcaga gcggctatcg catcctgaac     660
cgtaccccga cgaatcaaac cggtagcctg acccgcgct tcacctttaa tcagaatgac     720
ccgctgggtg gttatgagta tttgctggct aatgatgtcg ataacagcaa cccggtcgtt     780
caggccgaga gcctgaactg gctgcattac ctgctgaatt ttggtagcat ttacgcgaat     840
gatccggagg ccaatttcga cagcatccgt gtggacgcgg tggacaatgt tgacgcagac     900
ctgctgcaaa ttagctcgga ttacctgaaa tcggcgtaca aaattgacaa gaacaacaaa     960
aatgcgaacg accacgttag catcgtcgag gcgtggagcg acaatgatac cccgtacctg    1020
aatgatgatg cgacaatctc gatgaacatg gataacaagt ttcgtctgag catgctgtgg    1080
agcctggcga agccaaccaa tgtccgtagc ggcttgaatc cgctgatcca aacagcgtg    1140
gttgaccgtg aggtggacga ccgtgaagtt gaggctaccc cgaattacag ctttgcacgc    1200
gcacacgaca gcgaagttca agatttgatt cgcgacatca tcaaagctga gatcaaccca    1260
```

```
aacagcttcg gttatagctt tacccaagag gaaatcgacc aggccttcaa gatctacaat    1320
gaggatttga agaaaaccaa taagaagtat acccactaca acgtcccgct gagctacacc    1380
ctgctgctga cgaacaaggg cagcattcca cgcatttact acggtgacat gtttacggat    1440
gacggtcagt atatggccaa caaaaccgtt aactatgacg ccattgagag cctgctgaaa    1500
gcacgtatga agtatgttag cggtggccaa gcgatgcaga attacaacat cggcaacggc    1560
gagattctga ccagcgtccg ttacggtaag ggtgccctga acagagcga caaaggcgat    1620 aagactactc gtaccagcgg tattggcgtt gtgatgggta accagagcaa tttcagcctg    1680
gagggcaagg tggtggccct gaatatgggt gcaacgcata ccaaacagaa gtatcgtgca    1740
ttgatggtgt ctacggaaac cggcgtggcg atttacaata gcgatgaaga agcagaggca    1800
gcaggcctga tcaaaacgac cgatgagaat ggttatttgt actttctgaa tgacgatctg    1860
aagggcgtgg ctaacccgca ggtcagcggc ttcctgcaag tgtgggttcc ggttggtgca    1920
ccggctgacc aggacattcg tgtggcgcg accgatgcgg cttctaccga cggtaagagc    1980
ctgcatcagg acgcagctct ggattctcgc gtcatgtttg aaggtttcag caacttccag    2040
agcttcgcaa ccaaggaaga ggaatacacc aacgttgtta ttgcaaagaa cgtggataag    2100
ttcgtgagct ggggtatcac cgacttcgag atggcaccgc agtacgttag ctctaccgat    2160
ggcacctttc tggatagcgt gattcaaaat ggctatgcct ttacgaccg ttacgacctg    2220 ggtatgagca aagcaaacaa gtatggtact gctgaccaac tggtggccgc gattaaagcg    2280
ctgcatgcga agggtctgcg tgtgatggcg gattgggtcc cagatcaaat gtacactttc    2340
cctaagaagg aagtggttac cgttacccgt acggacaaat ttggcaatcc agtggcaggc    2400
agccaaatca ccacaccttt gtacgtcact gatactaagg gtagcggtga cgactaccag    2460
gcgaagtacg gtggcgcatt cctggatgaa ctgaaagaaa agtacccgga gctgtttacc    2520
aagaagcaaa tcagcaccgg tcaggcaatc gacccgagcg tgaaaatcaa gcagtggagc    2580
gcgaagtact tcaacggtag caatatcttg ggtcgcggtg cgaactacgt gctgtccgac    2640
caggcgtcta acaagtactt taacgtggcc gaaggtaaag tctttctgcc agcgggcatg    2700
ctgggtaagg tcgtcgagag cggtatccgt ttcgacggta aggttatat ctataacagc    2760 agcaccactg gcgaacaagt gaaggacagc ttcattaccg aagcgggtaa cttgtactat    2820
tttggcaaag atggttatat ggtcatgggt gcacagaata tccagggtgc taactactac    2880
ttcttggcga atggtgcggc cctgcgcaat agcatcctga cggatcagga tggcaaaagc    2940 cactatatg caaatgacgg caagcgttat gagaacggct actatcaatt cggtaacgac    3000
tcctggcgct attttgaaaa cggcgttatg gccgttggtt tgacgcgcgt tgcgggccac    3060
gaccaatact ttgataagga tggtatccaa gcgaagaata agatcattgt tacgcgtgac    3120
ggtaaggtcc gctacttcga cgaacacaac ggcaatgctg ccacgaatac gtttatcagc    3180
gatcaagccg gccattggta ctacctgggt aaagatggtt cgccgtgac gggtgcgcag    3240 accgttggca agcaacacct gtacttcgag gctaacggcc aacaagtaaa aggcgatttt    3300
gttaccgcca aggacggtaa gttgtatttt ctggacggtg actctggcga catgtggacc    3360
gataccttcg tccaggataa ggctggtcat tggttctatc tgggcaaaga cggtgcggcg    3420
gtaaccggtg cccagaccgt ccgtggtcag aagctgtact tcaaagcgaa tggccagcag    3480
gttaagggtg acattgtgaa aggcgcggat ggtaaaatcc gttactatga tgcaaattcc    3540
ggtgaccagg tttacaatcg cacgtgaaa ggctccgacg gcaagaccta tatcattggt    3600
```

-continued

```
aatgacggcg tcgcaatcac gcaaaccatc gccaaaggcc agaccatcaa ggatggcagc    3660
gttctgcgct tctatagcat ggagggtcag ctggtgaccg gcagcggctg gtattccaac    3720
gcgaaaggtc aatggttgta tgtcaagaac ggtcaagtcc tgacgggttt gcagacggtg    3780
ggcagccagc gtgtgtactt tgacgcaaat ggtattcaag cgaaaggtaa agcagtgcgt    3840
acctccgatg gcaaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                        3972
```

```
<210> SEQ ID NO 14
<211> LENGTH: 1323
<212> TYPE: PRT
<213> ORGANISM: Streptococcus dentirousetti

<400> SEQUENCE: 14
```

```
Met Val Asp Gly Lys Tyr Tyr Tyr Asp Ala Asp Gly Asn Val Lys
1               5                  10                  15

Lys Asn Phe Ala Val Ser Val Gly Asp Ala Ile Phe Tyr Phe Asp Glu
            20                  25                  30

Thr Gly Ala Tyr Lys Asp Thr Ser Lys Val Asp Ala Asp Lys Thr Ser
        35                  40                  45

Ser Ser Val Asn Gln Thr Thr Glu Thr Phe Ala Ala Asn Asn Arg Ala
    50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300
```

-continued

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
            325                 330                 335

Thr Pro Tyr Leu Asn Asp Asp Gly Asp Asn Leu Met Asn Met Asp Asn
            340                 345                 350

Lys Phe Arg Leu Ser Met Leu Trp Ser Leu Ala Lys Pro Thr Asn Val
            355                 360                 365

Arg Ser Gly Leu Asn Pro Leu Ile His Asn Ser Val Val Asp Arg Glu
    370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
            435                 440                 445

Lys Tyr Thr His Tyr Asn Val Pro Leu Ser Tyr Thr Leu Leu Leu Thr
        450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Asn Ile Gly Asn Gly Glu Ile Leu Thr Ser Val Arg Tyr
        515                 520                 525

Gly Lys Gly Ala Leu Lys Gln Ser Asp Lys Gly Asp Lys Thr Thr Arg
    530                 535                 540

Thr Ser Gly Ile Gly Val Val Met Gly Asn Gln Ser Asn Phe Ser Leu
545                 550                 555                 560

Glu Gly Lys Val Val Ala Leu Asn Met Gly Ala Thr His Thr Lys Gln
                565                 570                 575

Lys Tyr Arg Ala Leu Met Val Ser Thr Glu Thr Gly Val Ala Ile Tyr
            580                 585                 590

Asn Ser Asp Glu Glu Ala Glu Ala Ala Gly Leu Ile Lys Thr Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Pro Ala Asp Gln Asp Ile Arg Val Ala Ala Thr Asp Ala Ala Ser Thr
                645                 650                 655

Asp Gly Lys Ser Leu His Gln Ala Ala Leu Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Lys Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Thr Phe Leu Asp Ser Val Ile Gln Asn Gly Tyr Ala Phe Thr Asp

```
                    725                 730                 735
Arg Tyr Asp Leu Gly Met Ser Lys Ala Asn Lys Tyr Gly Thr Ala Asp
                740                 745                 750

Gln Leu Val Ala Ala Ile Lys Ala Leu His Ala Lys Gly Leu Arg Val
            755                 760                 765

Met Ala Asp Trp Val Pro Asp Gln Met Tyr Thr Phe Pro Lys Lys Glu
770                 775                 780

Val Val Thr Val Thr Arg Thr Asp Lys Phe Gly Asn Pro Val Ala Gly
785                 790                 795                 800

Ser Gln Ile Asn His Thr Leu Tyr Val Thr Asp Thr Lys Gly Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
            850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
                885                 890                 895

Pro Ala Ala Met Leu Gly Lys Val Val Glu Ser Gly Ile Arg Phe Asp
                900                 905                 910

Gly Lys Gly Tyr Ile Tyr Asn Ser Ser Thr Thr Gly Glu Gln Val Lys
            915                 920                 925

Asp Ser Phe Ile Thr Glu Ala Gly Asn Leu Tyr Tyr Phe Gly Lys Asp
930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp Ser Trp Arg Tyr Phe Glu Asn Gly
            995                 1000                1005

Val Met Ala Val Gly Leu Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Ala Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Leu Asp Gly
    1100                1105                1110

Asp Ser Gly Asp Met Trp Thr Asp Thr Phe Val Gln Asp Lys Ala
    1115                1120                1125

Gly His Trp Phe Tyr Leu Gly Lys Asp Gly Ala Ala Val Thr Gly
    1130                1135                1140
```

| | | | | | | | | | | | |
|---|---|---|---|---|---|---|---|---|---|---|---|
|Ala|Gln|Thr|Val|Arg|Gly|Gln|Lys|Leu|Tyr|Phe|Lys|Ala|Asn|Gly|
| |1145| | | |1150| | | |1155| | | | | |

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185

Val Lys Gly Ser Asp Gly Lys Thr Tyr Ile Ile Gly Asn Asp Gly
    1190                1195                1200

Val Ala Ile Thr Gln Thr Ile Ala Lys Gly Gln Thr Ile Lys Asp
    1205                1210                1215

Gly Ser Val Leu Arg Phe Tyr Ser Met Glu Gly Gln Leu Val Thr
    1220                1225                1230

Gly Ser Gly Trp Tyr Ser Asn Ala Lys Gly Gln Trp Leu Tyr Val
    1235                1240                1245

Lys Asn Gly Gln Val Leu Thr Gly Leu Gln Thr Val Gly Ser Gln
    1250                1255                1260

Arg Val Tyr Phe Asp Ala Asn Gly Ile Gln Ala Lys Gly Lys Ala
    1265                1270                1275

Val Arg Thr Ser Asp Gly Lys Leu Arg Tyr Phe Asp Ala Asn Ser
    1280                1285                1290

Gly Ser Met Ile Thr Asn Gln Trp Lys Glu Val Asn Gly Gln Tyr
    1295                1300                1305

Tyr Tyr Phe Asp Asn Asn Gly Val Ala Ile Tyr Arg Gly Trp Asn
    1310                1315                1320

<210> SEQ ID NO 15
<211> LENGTH: 4047
<212> TYPE: DNA
<213> ORGANISM: Streptococcus oralis

<400> SEQUENCE: 15

```
atgatcgacg gcaaaaacta ctacgtacag gatgatggca cggtaaagaa gaatttcgcg    60
gtagaactga atggtcgtat cctgtatttt gatgcagaaa ccggcgctct ggttgatagc   120
aacgagtatc agttccaaca gggtacgagc agcctgaaca tgaatttttc tcagaagaac   180
gcattctatg gtacgaccga taaggatatt gagactgtgg atggctacct gaccgcagat   240
agctggtatc gcccgaaatt catcctgaag gatggcaaga cgtggaccgc gagcacggaa   300
acggatctgc gtccgctgtt gatggcatgg tggccggaca gcgtaccca atcaactat    360
ctgaactaca tgaaccagca gggtctgggt gcgggtgcgt ttgagaacaa agtggagcag   420
gccctgctga cgggtgcaag ccaacaggta caacgcaaga tcgaagagaa gattggtaaa   480
gagggtgata ccaagtggct gcgcaccctg atgggtgcgt cgtgaaaac gcaaccaaac   540
tggaatatca aaccgagtc tgaaacgacc ggcacgaaaa aggaccatct gcaaggcggt   600
gcactgctgt atacgaacaa cgagaaatcc ccgcacgcgg acagcaaatt tcgtctgctg   660
aatcgtaccc cgaccagcca aaccggcacg ccgaagtatt tcatcgacaa gtctaacggt   720
ggctacgaat ttctgctggc gaacgatttt gacaatagca atcctgcggt acaagctgag   780
cagctgaatt ggctgcacta catgatgaac tttggcagca ttgttgcgaa tgatccgacc   840
gcgaatttcg acggcgttcg tgtggatgct gttgataacg tcaatgcgga cttgttgcaa   900
attgcaagcg attactttaa gagccgttac aaagtcggtg agagcgaaga agaagcgatc   960
aagcacctgt ccatcctgga agcatggagc gataacgacc cggactacaa caaagatacc  1020
```

-continued

```
aagggtgcac agttggcgat tgataacaaa ctgcgcctga gcctgctgta ctctttcatg   1080
cgtaatctga gcatccgtag cggtgttgaa ccgacgatta ccaatagcct gaatgaccgt   1140
tccagcgaaa agaagaacgg cgagcgtatg gcaaattaca tcttcgtgcg tgcccacgat   1200
agcgaggtcc aaacggtgat cgccgacatc attcgcgaaa acatcaatcc gaacaccgac   1260
ggcctgacgt ttacgatgga cgagctgaag caggcattca agatttacaa cgaggacatg   1320
cgcaaggcgg acaaaaagta tacccagttt aacattccta ccgcacacgc gctgatgctg   1380
tctaataagg attctattac ccgcgtgtac tatggtgatc tgtatactga cgatggtcag   1440
tacatggaga agaaaagccc gtatcacgat gcgattgacg ctctgctgcg tgcacgtatt   1500
aaatacgtcg cgggtggcca ggatatgaaa gtgacctata tgggcgtgcc gcgtgaagcg   1560
gataagtgga gctataacgg cattctgacc agcgtgcgct atggcacggg cgctaacgaa   1620
gccacggatg agggcactgc ggaaacgcgc acgcaaggta tggcagtgat tgcgagcaat   1680
aatccaaatc tgaaactgaa tgaatgggac aagttgcaag tcaacatggg tgcggcgcat   1740
aagaatcaat attaccgtcc ggttctgctg accactaagg acggtatcag ccgttatctg   1800
accgatgaag aagtgcctca gagcctgtgg aaaaagacgg acgcaaacgg tattctgacc   1860
ttcgacatga atgatattgc tggctacagc aacgtgcaag ttagcggtta cctggccgtc   1920
tgggtcccgg tcggtgcgaa ggcggatcaa gatgcgcgca cgaccgcatc caagaagaaa   1980
aatgcgtcgg tcaggtgta cgaaagcagc gcggctctgg atagccagct gatttacgaa   2040
ggtttcagca actttcaaga ctttgccact cgcgatgatc agtacacgaa caaggtcatt   2100
gcgaaaaacg tgaatctgtt caagaatggg gtgtgacca gcttcgagct gccgccgcag   2160
tacgtgagca gccaagatgg caccttcctg acagcatta tccaaaacgg ctatgcattt   2220
gaagaccgtt acgatatggc gatgagcaag aataacaagt atggtagcct gaaagacctg   2280
ttgaacgcgc tgcgcgcact gcacagcgtc aacattcaag caatcgccga ttgggtgccg   2340
gaccaaattt acaacttgcc gggcaaagag gtggtgaccg caactcgtgt caacaactac   2400
ggcacctacc gtgagggtgc tgaaatcaaa gaaaagctgt atgtcgccaa tagcaagacc   2460
aacgaaaccg atttccaagg taaatacggt ggtgcgttcc tggatgagct gaaggcgaag   2520
tacccggaga ttttcgagcg tgtccaaatc agcaacggcc aaaagatgac taccgatgaa   2580
aagatcacca aatggagcgc gaaatacttt aatggcacca atattctggg tcgtggcgcg   2640
tactatgtcc tgaaagattg ggccagcaat gattacctga cgaaccgtaa cggcgagatt   2700
gttttgccga gcaactggt taacaagaat agctataccg gctttgtcag cgacgcgaac   2760
ggcacgaagt tctattctac ctctggctac caggcgaaga acagcttcat tcaagacgaa   2820
aacggtaatt ggtattactt tgacaaacgt ggttatctgg ttacgggcgc acacgagatt   2880
gatggcaagc atgtctactt cctgaaaaac ggtatccaac tgcgtgacag catccgtgag   2940
gatgagaacg gtaatcaata ctattacgac cagaccggcg cacaagtgct gaaccgttac   3000
tacacgacgg acggtcagaa ttggcgctat ttcgatgcga aaggtgttat ggcacgcggc   3060
ctggtaaaga ttggtgacgg ccaacagttt ttcgatgaaa acggttacca ggtcaagggc   3120
aagattgtta gcgcaaaaga cggcaagctg cgctactttg ataaagactc tggcaatgct   3180
gtcattaatc gtttcgcgca gggtgacaat ccgagcgact ggtactattt cggtgtggaa   3240
tttgctaaac tgacgggttt gcaaaagatc ggccagcaga cgctgtattt tgaccaagac   3300
ggtaagcaag tcaaggtaa gatcgtaact ctgtcggaca aaagcattcg ttacttcgat   3360
gccaacagcg gtgaaatggc ggttggcaag ttcgcggaag gtgcaaagaa tgagtggtat   3420
```

```
tatttcgata aaaccggcaa agcggttact ggtttgcaga aaattggtaa gcagaccctg      3480
tactttgacc aggacggtaa acaggttaaa ggcaaggttg tcacgctggc tgataaaagc      3540
atccgctact tcgacgcaga ctccggcgag atggcggtcg gtaagtttgc agagggtgcg      3600
aagaacgagt ggtactattt tgatcagact ggcaaggccg tgactggttt gcaaaagatt      3660
gacaagcaaa ccttgtactt cgaccaggac ggtaaacaag tcaagggtaa gattgtgacg      3720
ttgagcgaca agtcgatccg ttactttgat gctaatagcg gtgagatggc tactaacaaa      3780
ttcgtcgagg gctcgcagaa tgaatggtac tacttcgatc aagcgggtaa ggctgttacg      3840
ggcttgcaac aggtcggtca gcaaactctg tacttcaccc aggatggtaa gcaagtgaag      3900
ggtaaggtcg tggacgtgaa cggtgtttct cgttatttcg acgcaaactc cggtgacatg      3960
gctcgttcta atggattca actggaagat ggcagctgga tgtatttcga ccgtgacggt      4020
cgtggccaga attttggccg taactaa                                          4047
```

<210> SEQ ID NO 16
<211> LENGTH: 1348
<212> TYPE: PRT
<213> ORGANISM: Streptococcus oralis

<400> SEQUENCE: 16

```
Met Ile Asp Gly Lys Asn Tyr Tyr Val Gln Asp Gly Thr Val Lys
1               5                   10                  15

Lys Asn Phe Ala Val Glu Leu Asn Gly Arg Ile Leu Tyr Phe Asp Ala
                20                  25                  30

Glu Thr Gly Ala Leu Val Asp Ser Asn Glu Tyr Gln Phe Gln Gln Gly
            35                  40                  45

Thr Ser Leu Asn Asn Glu Phe Ser Gln Lys Asn Ala Phe Tyr Gly
        50                  55                  60

Thr Thr Asp Lys Asp Ile Glu Thr Val Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
        115                 120                 125

Leu Gly Ala Gly Ala Phe Glu Asn Lys Val Glu Gln Ala Leu Leu Thr
    130                 135                 140

Gly Ala Ser Gln Gln Val Gln Arg Lys Ile Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255
```

```
Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Glu Glu Ala Ile
305                 310                 315                 320

Lys His Leu Ser Ile Leu Glu Ala Trp Ser Asp Asn Pro Asp Tyr
                325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
        355                 360                 365

Val Glu Pro Thr Ile Thr Asn Ser Leu Asn Asp Arg Ser Ser Glu Lys
    370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Tyr Thr
        435                 440                 445

Gln Phe Asn Ile Pro Thr Ala His Ala Leu Met Leu Ser Asn Lys Asp
    450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
    530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Val Pro Gln Ser
        595                 600                 605

Leu Trp Lys Lys Thr Asp Ala Asn Gly Ile Leu Thr Phe Asp Met Asn
    610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Ala Arg Thr Thr Ala
                645                 650                 655

Ser Lys Lys Lys Asn Ala Ser Gly Gln Val Tyr Glu Ser Ser Ala Ala
            660                 665                 670

Leu Asp Ser Gln Leu Ile Tyr Glu Gly Phe Ser Asn Phe Gln Asp Phe
```

```
              675                 680                 685
Ala Thr Arg Asp Asp Gln Tyr Thr Asn Lys Val Ile Ala Lys Asn Val
690                 695                 700
Asn Leu Phe Lys Glu Trp Gly Val Thr Ser Phe Glu Leu Pro Pro Gln
705                 710                 715                 720
Tyr Val Ser Ser Gln Asp Gly Thr Phe Leu Asp Ser Ile Ile Gln Asn
                    725                 730                 735
Gly Tyr Ala Phe Glu Asp Arg Tyr Asp Met Ala Met Ser Lys Asn Asn
                    740                 745                 750
Lys Tyr Gly Ser Leu Lys Asp Leu Leu Asn Ala Leu Arg Ala Leu His
                    755                 760                 765
Ser Val Asn Ile Gln Ala Ile Ala Asp Trp Val Pro Asp Gln Ile Tyr
770                 775                 780
Asn Leu Pro Gly Lys Glu Val Val Thr Ala Thr Arg Val Asn Asn Tyr
785                 790                 795                 800
Gly Thr Tyr Arg Glu Gly Ala Glu Ile Lys Glu Lys Leu Tyr Val Ala
                    805                 810                 815
Asn Ser Lys Thr Asn Glu Thr Asp Phe Gln Gly Lys Tyr Gly Gly Ala
                    820                 825                 830
Phe Leu Asp Glu Leu Lys Ala Lys Tyr Pro Glu Ile Phe Glu Arg Val
                    835                 840                 845
Gln Ile Ser Asn Gly Gln Lys Met Thr Thr Asp Glu Lys Ile Thr Lys
850                 855                 860
Trp Ser Ala Lys Tyr Phe Asn Gly Thr Asn Ile Leu Gly Arg Gly Ala
865                 870                 875                 880
Tyr Tyr Val Leu Lys Asp Trp Ala Ser Asn Asp Tyr Leu Thr Asn Arg
                    885                 890                 895
Asn Gly Glu Ile Val Leu Pro Lys Gln Leu Val Asn Lys Asn Ser Tyr
                    900                 905                 910
Thr Gly Phe Val Ser Asp Ala Asn Gly Thr Lys Phe Tyr Ser Thr Ser
                    915                 920                 925
Gly Tyr Gln Ala Lys Asn Ser Phe Ile Gln Asp Glu Asn Gly Asn Trp
                    930                 935                 940
Tyr Tyr Phe Asp Lys Arg Gly Tyr Leu Val Thr Gly Ala His Glu Ile
945                 950                 955                 960
Asp Gly Lys His Val Tyr Phe Leu Lys Asn Gly Ile Gln Leu Arg Asp
                    965                 970                 975
Ser Ile Arg Glu Asp Glu Asn Gly Asn Gln Tyr Tyr Tyr Asp Gln Thr
                    980                 985                 990
Gly Ala Gln Val Leu Asn Arg Tyr Tyr Thr Thr Asp Gly Gln Asn Trp
                    995                 1000                1005
Arg Tyr Phe Asp Ala Lys Gly Val Met Ala Arg Gly Leu Val Lys
      1010                1015                1020
Ile Gly Asp Gly Gln Gln Phe Phe Asp Glu Asn Gly Tyr Gln Val
      1025                1030                1035
Lys Gly Lys Ile Val Ser Ala Lys Asp Gly Lys Leu Arg Tyr Phe
      1040                1045                1050
Asp Lys Asp Ser Gly Asn Ala Val Ile Asn Arg Phe Ala Gln Gly
      1055                1060                1065
Asp Asn Pro Ser Asp Trp Tyr Tyr Phe Gly Val Glu Phe Ala Lys
      1070                1075                1080
Leu Thr Gly Leu Gln Lys Ile Gly Gln Gln Thr Leu Tyr Phe Asp
      1085                1090                1095
```

```
Gln Asp Gly Lys Gln Val Lys Gly Lys Ile Val Thr Leu Ser Asp
    1100                1105                1110
Lys Ser Ile Arg Tyr Phe Asp Ala Asn Ser Gly Glu Met Ala Val
    1115                1120                1125
Gly Lys Phe Ala Glu Gly Ala Lys Asn Glu Trp Tyr Tyr Phe Asp
    1130                1135                1140
Lys Thr Gly Lys Ala Val Thr Gly Leu Gln Lys Ile Gly Lys Gln
    1145                1150                1155
Thr Leu Tyr Phe Asp Gln Asp Gly Lys Gln Val Lys Gly Lys Val
    1160                1165                1170
Val Thr Leu Ala Asp Lys Ser Ile Arg Tyr Phe Asp Ala Asp Ser
    1175                1180                1185
Gly Glu Met Ala Val Gly Lys Phe Ala Glu Gly Ala Lys Asn Glu
    1190                1195                1200
Trp Tyr Tyr Phe Asp Gln Thr Gly Lys Ala Val Thr Gly Leu Gln
    1205                1210                1215
Lys Ile Asp Lys Gln Thr Leu Tyr Phe Asp Gln Asp Gly Lys Gln
    1220                1225                1230
Val Lys Gly Lys Ile Val Thr Leu Ser Asp Lys Ser Ile Arg Tyr
    1235                1240                1245
Phe Asp Ala Asn Ser Gly Glu Met Ala Thr Asn Lys Phe Val Glu
    1250                1255                1260
Gly Ser Gln Asn Glu Trp Tyr Tyr Phe Asp Gln Ala Gly Lys Ala
    1265                1270                1275
Val Thr Gly Leu Gln Gln Val Gly Gln Gln Thr Leu Tyr Phe Thr
    1280                1285                1290
Gln Asp Gly Lys Gln Val Lys Gly Lys Val Val Asp Val Asn Gly
    1295                1300                1305
Val Ser Arg Tyr Phe Asp Ala Asn Ser Gly Asp Met Ala Arg Ser
    1310                1315                1320
Lys Trp Ile Gln Leu Glu Asp Gly Ser Trp Met Tyr Phe Asp Arg
    1325                1330                1335
Asp Gly Arg Gly Gln Asn Phe Gly Arg Asn
    1340                1345

<210> SEQ ID NO 17
<211> LENGTH: 4047
<212> TYPE: DNA
<213> ORGANISM: Streptococcus sanguinis

<400> SEQUENCE: 17
atgattgatg gtaaaaagta ttacgtacag gacgacggca cggttaagaa gaatttcgcg      60
gttgagctga atggcaagat cctgtacttc gatgcagaga ctggtgcgtt gattgacagc     120
gcggagtatc aattccaaca aggcaccagc agcctgaata atgagttcac tcaaaagaac     180 gcctttacg gtacgaccga taaggatgtg gaaaccattg atggttactt gaccgccgat      240
tcctggtatc gtccgaagtt cattctgaaa gatggcaaaa cctggacggc gagcacggaa     300
attgacttgc gtccgttgtt gatggcgtgg tggccggaca acagacccca ggttagctac     360
ctgaattaca tgaaccagca aggcttgggt gcaggcgcct tcgaaaacaa agtagagcag     420
gcaattctga ccggtgcgtc ccaacaggta caacgtaaaa tcgaagaacg catcggtaaa     480
gagggtgata ccaagtggct gcgtaccctg atgggtgcat tgtaaagac ccagccgaac     540 tggaacatta agaccgagtc cgaaaccact ggcacgaata agatcatcct gcaaggtggc     600
```

```
gcactgctgt atagcaattc cgacaagacg agccatgcca actctaagta ccgtatcctg    660
aaccgcaccc cgaccaacca aacgggcacg ccgaaatact ttattgacaa gagcaatggt    720
ggttatgaat ttctgctggc gaatgacttt gacaatagca atccggcagt gcaagcggaa    780
cagctgaact ggttgcactt tatgatgaat tttggctcca tcgttgcaaa tgatccgacg    840
gccaacttcg acggcgtccg cgttgacgct gtggataacg tgaatgcgga tctgttgcaa    900
attgcgagcg actatttcaa gagccgctat aaagtcggcg aaagcgaaga agaggccatt    960
aagcacctgt ccatcctgga agcgtggagc gacaacgacc cggactacaa caaggatact   1020
aaaggtgccc aactgccgat cgacaacaaa ctgcgtctga gcctgctgta ctccttcatg   1080
cgtaagctga gcatccgtag cggcgtcgag ccgaccatca ccaactctct gaatgatcgc   1140
agcacggaga agaagaatgg tgagcgtatg gcaaactata tcttcgttcg tgcacatgat   1200
agcgaggtgc aaacggtcat cgccgacatt atccgtgaga acatcaatcc gaataccgac   1260
ggcctgacgt tcacgatgga tgaactgaag caggccttta aaatttacaa tgaggatatg   1320
cgtaaagccg acaaaaagta cacgcagttc aatatcccga ccgcgcacgc gctgatgctg   1380
agcaacaaag attctatcac ccgcgtttac tacggtgacc tgtatacgga tgacggtcag   1440
tatatggaaa agaaaagccc gtatcacgac gccattgacg ctctgctgcg tgcgcgtatc   1500
aaatatgttg cgggtggtca ggacatgaag gtgacctata tgggcgtgcc gcgtgaggca   1560
gataaatgga gctataacgg catcctgacc agcgttcgtt atggtacggg tgccaacgag   1620
gcaaccgacg agggtacggc agaaacccgt acccagggca tggccgtcat tgccagcaac   1680
aatccgaacc tgaaactgaa cgagtgggac aagttgcagg tcaacatggg tgcagctcac   1740
aaaaaccaat actatcgtcc ggtgctgctg accaccaagg acggcatctc gcgctacctg   1800
accgacgaag aagtcccgca gagcctgtgg aaaaagaccg atgcgaacgg catcttgacg   1860
tttgacatga atgatattgc gggttacagc aacgtccaag tgagcggtta tctggccgtc   1920
tgggttcctg tgggtgcgaa ggcggaccag gacgctcgtg ttacggcatc taagaagaaa   1980
aatgcctctg gccaagttta cgaaagcagc gcagccctgg actcccagct gatctatgag   2040
ggcttcagca attttcagga ctttgccacc cgtgacgacc agtacactaa caaggttatc   2100
gcgaaaaacg tcaatctgtt taaagagtgg ggcgtcacca gcttcgaatt gccgccacag   2160
tatgtgagca gccaagacgg tacgttcctg gatagcatca tccagaatgg ttatgcattc   2220
gaagatcgct atgatatggc gatgagcaaa aacaataagt acggtagctt gaacgacctg   2280
ttgaacgcct tgcgtgcact gcatagcgtg aatatccaag cgattgcgga ttgggtgccg   2340
gaccagattt acaatctgcc gggtaaagaa gttgtcactg caacccgtgt taacaattat   2400
ggcacgtatc gtgagggtag cgagattaaa gagaacctgt acgttgctaa caccaaaaacc   2460 aatggtacgg actaccaagg taagtatggt ggtgcgttct tggacgagct gaaagccaaa   2520
taccctgaga tttttgagcg cgtccaaatc agcaacggcc agaagatgac caccgacgag   2580
aagattacga aatggtccgc caaacacttt aacggcacga acattctggg tcgtggtgcg   2640
tattatgtgc tgaaagactg ggcgagcaac gagtacctga ataacaaaaa tggcgagatg   2700
gttctgccga agcagctggt taataaaaat gcatataccg gcttcgtcag cgacgcgagc   2760
ggcaccaaat actattctac cagcggctat caggctcgta atagctttat tcaagatgaa   2820
aatggtaatt ggtactactt caataaccgt ggttatttgg tgacgggtgc acaggaaatc   2880
gacggtaagc aactgtattt cctgaaaaac ggcattcagc tgcgtgattc tctgcgtgag   2940
```

```
gacgaaaacg gcaaccagta ttactatgat aagacgggtg cgcaagttct gaatcgttat    3000
tacactacgg acggccaaaa ttggcgctac ttcgacgtta aaggcgtcat ggcccgtggt    3060
ctggtcacga tgggtggtaa ccaacaattc tttgaccaaa acggttacca ggttaaaggc    3120
aaaattgcgc gtgcaaaaga cggtaaactg cgttacttcg ataaagacag cggtaatgcg    3180
gcagctaacc gtttcgccca aggcgataac cctagcgact ggtactattt cggtgcagat    3240
ggtgttgcgg ttacgggcct gcaaaaggtt ggtcagcaaa ctctgtactt tgatcaggac    3300
ggcaagcagg tgaaaggtaa agttgttacc ttggcggaca aaagcattcg ttatttcgat    3360
gcaaacagcg gcgagatggc ggtgaacaag tttgtggaag gtgctaagaa cgtgtggtac    3420
tacttcgatc aagcaggcaa agcggtgacc ggcctgcaaa ccatcaataa acaagtgctg    3480
tatttcgacc aggatggtaa acaagtcaaa ggtaaggtgg tcacgctggc tgataagtct    3540
atccgctact tcgacgcgaa cagcggtgag atggcagtgg gcaaattcgc cgaaggcgca    3600
aagaatgagt ggtattactt tgaccaggcg ggcaaggctg ttaccggtct gcaaaagatc    3660
ggccaacaga cgctgtattt cgaccagaac ggtaaacagg ttaagggtaa agtggtcacc    3720
ctggcggata gagcatccg ctatttcgac gctaactctg gcgaaatggc aagcaataag    3780
ttcgttgagg gtgccaaaaa tgaatggtac tatttcgatc aggctggcaa ggcagtgacg    3840
ggtctgcaac aaattggcca gcagaccctg tattttgacc agaatggcaa acaggtgaag    3900
ggtaagattg tgtatgttaa tggtgcgaat cgctactttg atgccaatag cggtgaaatg    3960
gcgcgtaaca gtggattca gctggaagat ggcagctgga tgtattttga ccgcaatggt    4020
cgtggtcgtc gtttcggttg gaactaa                                       4047
```

<210> SEQ ID NO 18
<211> LENGTH: 1348
<212> TYPE: PRT
<213> ORGANISM: Streptococcus sanguinis
<400> SEQUENCE: 18

```
Met Ile Asp Gly Lys Lys Tyr Tyr Val Gln Asp Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175
```

```
Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
            195                 200                 205

Lys Thr Ser His Ala Asn Ser Lys Tyr Arg Ile Leu Asn Arg Thr Pro
210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Ser Asn Pro Ala
            245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
            275                 280                 285

Asp Ala Val Asp Asn Val Asn Ala Asp Leu Leu Gln Ile Ala Ser Asp
            290                 295                 300

Tyr Phe Lys Ser Arg Tyr Lys Val Gly Glu Ser Glu Glu Glu Ala Ile
305                 310                 315                 320

Lys His Leu Ser Ile Leu Glu Ala Trp Ser Asp Asn Asp Pro Asp Tyr
            325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
            355                 360                 365

Val Glu Pro Thr Ile Thr Asn Ser Leu Asn Asp Arg Ser Thr Glu Lys
            370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
            405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
            450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
            485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
            515                 520                 525

Leu Thr Ser Val Arg Tyr Gly Thr Gly Ala Asn Glu Ala Thr Asp Glu
            530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
            565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
```

-continued

```
            595                 600                 605
Leu Trp Lys Lys Thr Asp Ala Asn Gly Ile Leu Thr Phe Asp Met Asn
610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                    645                 650                 655

Ser Lys Lys Asn Ala Ser Gly Gln Val Tyr Glu Ser Ser Ala Ala
                    660                 665                 670

Leu Asp Ser Gln Leu Ile Tyr Glu Gly Phe Ser Asn Phe Gln Asp Phe
                    675                 680                 685

Ala Thr Arg Asp Asp Gln Tyr Thr Asn Lys Val Ile Ala Lys Asn Val
690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                    725                 730                 735

Gly Tyr Ala Phe Glu Asp Arg Tyr Asp Met Ala Met Ser Lys Asn Asn
                    740                 745                 750

Lys Tyr Gly Ser Leu Asn Asp Leu Leu Asn Ala Leu Arg Ala Leu His
                    755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800

Gly Thr Tyr Arg Glu Gly Ser Glu Ile Lys Glu Asn Leu Tyr Val Ala
                    805                 810                 815

Asn Thr Lys Thr Asn Gly Thr Asp Tyr Gln Gly Lys Tyr Gly Gly Ala
                    820                 825                 830

Phe Leu Asp Glu Leu Lys Ala Lys Tyr Pro Glu Ile Phe Glu Arg Val
                    835                 840                 845

Gln Ile Ser Asn Gly Gln Lys Met Thr Thr Asp Glu Lys Ile Thr Lys
850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                    885                 890                 895

Asn Gly Glu Met Val Leu Pro Lys Gln Leu Val Asn Lys Asn Ala Tyr
                    900                 905                 910

Thr Gly Phe Val Ser Asp Ala Ser Gly Thr Lys Tyr Tyr Ser Thr Ser
                    915                 920                 925

Gly Tyr Gln Ala Arg Asn Ser Phe Ile Gln Asp Glu Asn Gly Asn Trp
                    930                 935                 940

Tyr Tyr Phe Asn Asn Arg Gly Tyr Leu Val Thr Gly Ala Gln Glu Ile
945                 950                 955                 960

Asp Gly Lys Gln Leu Tyr Phe Leu Lys Asn Gly Ile Gln Leu Arg Asp
                    965                 970                 975

Ser Leu Arg Glu Asp Glu Asn Gly Asn Gln Tyr Tyr Asp Lys Thr
                    980                 985                 990

Gly Ala Gln Val Leu Asn Arg Tyr Tyr Thr Thr Asp Gly Gln Asn Trp
                    995                1000                1005

Arg Tyr Phe Asp Val Lys Gly Val Met Ala Arg Gly Leu Val Thr
                   1010                1015                1020
```

Met Gly Gly Asn Gln Gln Phe Phe Asp Gln Asn Gly Tyr Gln Val
    1025                1030                1035

Lys Gly Lys Ile Ala Arg Ala Lys Asp Gly Lys Leu Arg Tyr Phe
    1040                1045                1050

Asp Lys Asp Ser Gly Asn Ala Ala Ala Asn Arg Phe Ala Gln Gly
    1055                1060                1065

Asp Asn Pro Ser Asp Trp Tyr Tyr Phe Gly Ala Asp Gly Val Ala
    1070                1075                1080

Val Thr Gly Leu Gln Lys Val Gly Gln Gln Thr Leu Tyr Phe Asp
    1085                1090                1095

Gln Asp Gly Lys Gln Val Lys Gly Lys Val Val Thr Leu Ala Asp
    1100                1105                1110

Lys Ser Ile Arg Tyr Phe Asp Ala Asn Ser Gly Glu Met Ala Val
    1115                1120                1125

Asn Lys Phe Val Glu Gly Ala Lys Asn Val Trp Tyr Tyr Phe Asp
    1130                1135                1140

Gln Ala Gly Lys Ala Val Thr Gly Leu Gln Thr Ile Asn Lys Gln
    1145                1150                1155

Val Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asn Ser
    1175                1180                1185

Gly Glu Met Ala Val Gly Lys Phe Ala Glu Gly Ala Lys Asn Glu
    1190                1195                1200

Trp Tyr Tyr Phe Asp Gln Ala Gly Lys Ala Val Thr Gly Leu Gln
    1205                1210                1215

Lys Ile Gly Gln Gln Thr Leu Tyr Phe Asp Gln Asn Gly Lys Gln
    1220                1225                1230

Val Lys Gly Lys Val Val Thr Leu Ala Asp Lys Ser Ile Arg Tyr
    1235                1240                1245

Phe Asp Ala Asn Ser Gly Glu Met Ala Ser Asn Lys Phe Val Glu
    1250                1255                1260

Gly Ala Lys Asn Glu Trp Tyr Tyr Phe Asp Gln Ala Gly Lys Ala
    1265                1270                1275

Val Thr Gly Leu Gln Gln Ile Gly Gln Gln Thr Leu Tyr Phe Asp
    1280                1285                1290

Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

<210> SEQ ID NO 19
<211> LENGTH: 4023
<212> TYPE: DNA
<213> ORGANISM: Unknown
<220> FEATURE:
<223> OTHER INFORMATION: unknown Streptococcus species

<400> SEQUENCE: 19
atgatcgacg gcaaatacta ctacgtaaac gaggacggca gccacaaaga gaatttcgcg      60

-continued

| | |
|---|---|
| atcacggtta atggtcaact gctgtatttt ggtaaggatg gcgcgctgac cagcagcagc | 120 |
| acgtacagct tcacccaagg cactaccaat attgtggacg gttttagcat taacaaccgt | 180 |
| gcgtatgact ccagcgaggc ctctttcgag ctgattgacg gttatctgac tgcggactct | 240 |
| tggtaccgtc cggcgagcat tatcaaagac ggtgtgacgt ggcaagcatc caccgccgag | 300 |
| gacttccgcc cgttgctgat ggcgtggtgg ccgaacgttg atactcaggt gaactacctg | 360 |
| aactacatgt ccaaagtctt taatctggat gctaaataca gctcgactga taaacaggaa | 420 |
| accctgaagg tggcggcgaa agatatccag atcaaaattg aacaaaagat tcaggcggaa | 480 |
| aagtccacgc aatggctgcg tgaaacgatc agcgcctttg taaaaaccca gccgcaatgg | 540 |
| aacaaagaga ctgagaacta cagcaagggc ggtggtgagg accatctgca aggtggtgcc | 600 |
| ctgctgtatg ttaatgactc tcgtacccg tgggcgaaca gcaactatcg tttgctgaac | 660 |
| cgcacggcga ccaaccagac cggtacgatc gacaagagca tcctggacga gcagagcgat | 720 |
| ccgaatcaca tgggtggttt tgatttcttg ctggctaatg acgttgactt gagcaatccg | 780 |
| gtcgtccagg cggaacaact gaatcagatc cactacctga tgaattgggg ttctattgtc | 840 |
| atgggtgata agacgcgaa ttttgacggt attcgtgtag acgcggtgga taatgttgat | 900 |
| gcggacatgc tgcaattgta caccaactat ttccgcgaat actatggtgt caacaaaagc | 960 |
| gaggcaaacg cgctggcgca cattagcgtc ctggaagcct ggagcctgaa tgacaaccat | 1020 |
| tacaatgata gactgatgt tgcgcgctg gcaatggaga taagcagcg cttggcactg | 1080 |
| ttgtttagcc tggcgaaacc gattaaagaa cgcacgcctg ccgtgtctcc gctgtacaac | 1140 |
| aatacgttta acaccactca gcgtgatgaa aagacggact ggatcaataa agatggttcg | 1200 |
| aaagcctaca atgaggatgg cactgtcaag aaaagcacca tcggcaagta taacgagaag | 1260 |
| tatggtgatg ctagcggcaa ctacgttttc atccgcgctc acgacaataa cgtgcaagac | 1320 |
| atcatcgcgg agatcattaa gaaagagatt aacgagaaat ctgacggttt taccattacg | 1380 |
| gattcggaga tgaagcgtgc atttgagatc tataacaaag acatgctgtc taatgacaaa | 1440 |
| aagtacacgc tgaataacat cccggcggcg tacgcggtta tgctgcaaaa catggaaacg | 1500 |
| attaccccgcg tgtattacgg cgatctgtac acggacgacg gtaattacat ggaagcgaaa | 1560 |
| agcccgtact acgatacgat tgttaacttg atgaagtctc gcatcaaata cgtgagcggt | 1620 |
| ggccaggcgc agcgcagcta ctggctgccg accgatggta agatggataa gtcggatgtt | 1680 |
| gagctgtacc gtacgaacga agtgtacacg agcgtccgtt acggcaaaga cattatgacc | 1740 |
| gccgatgaca cgcaaggtag caaatacagc cgtaccagcg gtcaggtgac cctggtcgtc | 1800 |
| aacaacccaa aactgacctt ggaccaaagc gcaaagctga acgtggttat gggcaagatt | 1860 |
| catgctaatc agaagtaccg cgcactgatt gtcggtaccc cgaacggtat taagaatttc | 1920 |
| accagcgacg cagaggctat tgccgcaggc tatgtcaaag aaaccgatgg caatggcgtg | 1980 |
| ctgaccttcg gtgcaaacga catcaagggt tatgaaactt tcgatatgag cggcttcgtc | 2040 |
| gctgtttggg ttccggtcgg tgcgagcgac gaccaagata ttcgtgtggc ggcgtctacg | 2100 |
| gcagcaaaga aagagggtga gctgacgctg aaagcgaccg aagcctatga ctcccaactg | 2160 |
| atctatgaag ctttagcaa tttccagacc atcccagatg gcagcgatcc ttctgtttat | 2220 |
| accaatcgta agatcgcgga aaatgttgat tgttcaaga gctgggtgt cacgagcttc | 2280 |
| gaaatggctc cgcagttcgt ttctgcggac gatggcacgt ttctggacag cgtcattcaa | 2340 |
| aacggctatg cgttcgcaga ccgttatgat ctggccatga gcaaaacaa taagtacggt | 2400 |
| agcaaagaag atctgcgtaa cgcgctgaag gcactgcaca aagcaggcat tcaggcgatt | 2460 |

-continued

```
gcagattggg tgccagacca aatctaccag ctgcctggca agaagttgt tactgccacc    2520 cgcacggacg gtgctggtcg caaaatcagc gatgcaatca tcgatcattc cctgtacgtt    2580
gcgaactcca agagctccgg taaggactac caagcgaagt acggtggcga gttcttggcg    2640
gaactgaagg cgaaataccc ggaaatgttc aaagtgaaca tgattagcac cggcaaaccg    2700
attgatgata gcgtgaaact gaagcagtgg aaagcagaat acttcaacgg caccaatgtg    2760
ctggatcgcg gtgtcggtta tgttctgagc gatgaggcaa ccgtaagta tttcaccgtt    2820 accaaagagg gtaactttat cccgttgcag ctgaagggta caagaaggt gattaccggc    2880 ttttccagcg acggtaaggg cattacctat ttcggtacta gcgtaaccaa gctaaatcc    2940 gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgtacaa ctccaaaggc    3120
caaatgtata aggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac catttttgatg ctaacggtgt cgcggctact    3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga cttttgtgaag aatagcgacg gcacctactc caagtatgac    3720
gctgcgagcg cgaacgtct gaccaacgag ttcttcacta cgggcgacaa tcattggtac    3780
tatattggcg ccaacggtaa gaccgttacc ggtgaagtta agattggtga cgacacgtat    3840
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt tgtttttctt cgacaaaaac ggcctggctt acccaccgga gaatatgaac    4020
tga                                                                 4023
```

<210> SEQ ID NO 20
<211> LENGTH: 1340
<212> TYPE: PRT
<213> ORGANISM: Unknown
<220> FEATURE:
<223> OTHER INFORMATION: unknown Streptococcus species

<400> SEQUENCE: 20

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Ser Thr Tyr Ser Phe Thr Gln Gly Thr
            35                  40                  45

Thr Asn Ile Val Asp Gly Phe Ser Ile Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80
```

-continued

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Glu Lys Ser Asp Gly Phe Thr Ile Thr Asp Ser Glu Met
    450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
                485                 490                 495

```
Asn Met Glu Thr Ile Thr Arg Val Tyr Tyr Gly Asp Leu Tyr Thr Asp
            500                 505                 510
Asp Gly Asn Tyr Met Glu Ala Lys Ser Pro Tyr Tyr Asp Thr Ile Val
        515                 520                 525
Asn Leu Met Lys Ser Arg Ile Lys Tyr Val Ser Gly Gly Gln Ala Gln
    530                 535                 540
Arg Ser Tyr Trp Leu Pro Thr Asp Gly Lys Met Asp Lys Ser Asp Val
545                 550                 555                 560
Glu Leu Tyr Arg Thr Asn Glu Val Tyr Thr Ser Val Arg Tyr Gly Lys
                565                 570                 575
Asp Ile Met Thr Ala Asp Asp Thr Gln Gly Ser Lys Tyr Ser Arg Thr
            580                 585                 590
Ser Gly Gln Val Thr Leu Val Val Asn Asn Pro Lys Leu Thr Leu Asp
        595                 600                 605
Gln Ser Ala Lys Leu Asn Val Val Met Gly Lys Ile His Ala Asn Gln
    610                 615                 620
Lys Tyr Arg Ala Leu Ile Val Gly Thr Pro Asn Gly Ile Lys Asn Phe
625                 630                 635                 640
Thr Ser Asp Ala Glu Ala Ile Ala Ala Gly Tyr Val Lys Glu Thr Asp
                645                 650                 655
Gly Asn Gly Val Leu Thr Phe Gly Ala Asn Asp Ile Lys Gly Tyr Glu
            660                 665                 670
Thr Phe Asp Met Ser Gly Phe Val Ala Val Trp Val Pro Val Gly Ala
        675                 680                 685
Ser Asp Asp Gln Asp Ile Arg Val Ala Ala Ser Thr Ala Ala Lys Lys
    690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
            740                 745                 750
Lys Ser Trp Gly Val Thr Ser Phe Glu Met Ala Pro Gln Phe Val Ser
        755                 760                 765
Ala Asp Asp Gly Thr Phe Leu Asp Ser Val Ile Gln Asn Gly Tyr Ala
    770                 775                 780
Phe Ala Asp Arg Tyr Asp Leu Ala Met Ser Lys Asn Asn Lys Tyr Gly
785                 790                 795                 800
Ser Lys Glu Asp Leu Arg Asn Ala Leu Lys Ala Leu His Lys Ala Gly
                805                 810                 815
Ile Gln Ala Ile Ala Asp Trp Val Pro Asp Gln Ile Tyr Gln Leu Pro
            820                 825                 830
Gly Lys Glu Val Val Thr Ala Thr Arg Thr Asp Gly Ala Gly Arg Lys
        835                 840                 845
Ile Ser Asp Ala Ile Asp His Ser Leu Tyr Val Ala Asn Ser Lys
    850                 855                 860
Ser Ser Gly Lys Asp Tyr Gln Ala Lys Tyr Gly Gly Glu Phe Leu Ala
865                 870                 875                 880
Glu Leu Lys Ala Lys Tyr Pro Glu Met Phe Lys Val Asn Met Ile Ser
                885                 890                 895
Thr Gly Lys Pro Ile Asp Asp Ser Val Lys Leu Lys Gln Trp Lys Ala
            900                 905                 910
Glu Tyr Phe Asn Gly Thr Asn Val Leu Asp Arg Gly Val Gly Tyr Val
```

-continued

```
            915                 920                 925
Leu Ser Asp Glu Ala Thr Gly Lys Tyr Phe Thr Val Thr Lys Glu Gly
        930                 935                 940
Asn Phe Ile Pro Leu Gln Leu Lys Gly Asn Lys Lys Val Ile Thr Gly
945                 950                 955                 960
Phe Ser Ser Asp Gly Lys Gly Ile Thr Tyr Phe Gly Thr Ser Gly Asn
                965                 970                 975
Gln Ala Lys Ser Ala Phe Val Thr Phe Asn Gly Asn Thr Tyr Tyr Phe
                    980                 985                 990
Asp Ala Arg Gly His Met Val Thr Asn Gly Glu Tyr Ser Pro Asn Gly
                995                 1000                1005
Lys Asp Val Tyr Arg Phe Leu Pro Asn Gly Ile Met Leu Ser Asn
    1010                1015                1020
Ala Phe Tyr Val Asp Gly Asn Gly Asn Thr Tyr Leu Tyr Asn Ser
    1025                1030                1035
Lys Gly Gln Met Tyr Lys Gly Tyr Ser Lys Phe Asp Val Thr
    1040                1045                1050
Glu Thr Lys Asp Gly Lys Glu Ser Lys Val Val Lys Phe Arg Tyr
    1055                1060                1065
Phe Thr Asn Glu Gly Val Met Ala Lys Gly Val Thr Val Val Asp
    1070                1075                1080
Gly Phe Thr Gln Tyr Phe Asn Glu Asp Gly Ile Gln Ser Lys Asp
    1085                1090                1095
Glu Leu Val Thr Tyr Asn Gly Lys Thr Tyr Tyr Phe Glu Ala His
    1100                1105                1110
Thr Gly Asn Ala Ile Lys Asn Thr Trp Arg Asn Ile Lys Gly Lys
    1115                1120                1125
Trp Tyr His Phe Asp Ala Asn Gly Val Ala Ala Thr Gly Ala Gln
    1130                1135                1140
Val Ile Asn Gly Gln His Leu Tyr Phe Asn Glu Asp Gly Ser Gln
    1145                1150                1155
Val Lys Gly Ser Ile Val Lys Asn Ala Asp Gly Thr Phe Ser Lys
    1160                1165                1170
Tyr Lys Asp Ser Ser Gly Asp Leu Val Val Asn Glu Phe Phe Thr
    1175                1180                1185
Thr Gly Asp Asn Val Trp Tyr Tyr Ala Gly Ala Asn Gly Lys Thr
    1190                1195                1200
Val Thr Gly Ala Gln Val Ile Asn Gly Gln His Leu Phe Phe Lys
    1205                1210                1215
Glu Asp Gly Ser Gln Val Lys Gly Asp Phe Val Lys Asn Ser Asp
    1220                1225                1230
Gly Thr Tyr Ser Lys Tyr Asp Ala Ala Ser Gly Glu Arg Leu Thr
    1235                1240                1245
Asn Glu Phe Phe Thr Thr Gly Asp Asn His Trp Tyr Tyr Ile Gly
    1250                1255                1260
Ala Asn Gly Lys Thr Val Thr Gly Glu Val Lys Ile Gly Asp Asp
    1265                1270                1275
Thr Tyr Phe Phe Ala Lys Asp Gly Lys Gln Leu Lys Gly Gln Ile
    1280                1285                1290
Val Thr Thr Arg Ser Gly Arg Ile Ser Tyr Tyr Phe Gly Asp Ser
    1295                1300                1305
Gly Lys Lys Ala Ile Ser Thr Trp Val Glu Ile Gln Pro Gly Val
    1310                1315                1320
```

Phe Val Phe Phe Asp Lys Asn Gly Leu Ala Tyr Pro Pro Glu Asn
    1325                1330                1335

Met Asn
    1340

<210> SEQ ID NO 21
<211> LENGTH: 4479
<212> TYPE: DNA
<213> ORGANISM: Leuconostoc mesenteroides

<400> SEQUENCE: 21

| | | | | | |
|---|---|---|---|---|---|
| atgaccccat | ccgtattagg | tgattcttcc | gtcccagatg | tatcggctaa | caatgtgcaa | 60 |
| tccgcgagcg | ataatacgac | ggacacccag | caaaatacca | ccatcaccga | ggaaaatgat | 120 |
| aaggtccaga | gcgctgcgac | caacgataac | gtgaccacgg | cagcgtccga | cacgacgcag | 180 |
| agcgccgata | caacgttac | cgagaaacaa | tctgatgatc | acgcgctgga | taatgaaaag | 240 |
| gttgacaata | agcaggacga | ggtcgcccag | accaacgtga | ctagcaaaaa | cgaggagagc | 300 |
| gcggtggcct | ctaccgacac | cgatccggca | gagactacca | cggacgaaac | gcaacaggtt | 360 |
| agcggcaagt | atgtggaaaa | ggatggttct | tggtattact | actttgacga | cggtaagaac | 420 |
| gcgaagggtc | tgagcacgat | tgacaacaat | atccaatact | tgatgaaag | cggtaagcag | 480 |
| gtcaaaggtc | agtatgtgac | gattgataac | cagacctatt | actttgataa | agatagcggt | 540 |
| gatgaactga | ccggcctgca | atctattgac | ggtaacattg | ttgccttcaa | tgacgagggc | 600 |
| cagcagatct | ttaatcaata | ctaccagagc | gagaacggta | cgacctacta | ttttgatgat | 660 |
| aagggccacg | ctgccaccgg | tattaagaat | attgagggca | agaactacta | ttttgacaat | 720 |
| ctgggtcaac | tgaaaaaggg | cttctccggc | gtgatcgacg | tcagattat | gacgtttgac | 780 |
| caggaaactg | gtcaagaggt | tccaatacc | acgtccgaga | tcaaagaggg | cctgacgact | 840 |
| cagaacactg | attactctga | acataatgcg | gcgcacggta | ccgacgccga | agattttgag | 900 |
| aacatcgatg | gctatctgac | cgccagctcc | tggtaccgtc | cgacggacat | tctgcgcaat | 960 |
| ggcactgact | gggaaccgag | caccgacacg | gactttcgtc | caatcttgag | cgtttggtgg | 1020 |
| ccggataaga | atacgcaggt | caactatctg | aactacatgg | cggacctggg | cttcattagc | 1080 |
| aacgcagaca | gcttcgaaac | gggtgactct | cagagcctgc | tgaacgaggc | gtccaattac | 1140 |
| gtccagaaaa | gcatcgagat | gaaaatctcc | gcgcaacaga | gcaccgagtg | gctgaaagac | 1200 |
| gccatggccg | cgtttattgt | tacgcagccg | caatggaatg | aaacttccga | agatatgagc | 1260 |
| aacgaccact | gcaaaacgg | tgcgctgacc | tacgttaaca | gcccgctgac | cccggacgca | 1320 |
| aacagcaact | ttcgcctgct | gaatcgtacc | cctaccaacc | agaccggcga | acaggcgtac | 1380 |
| aacctggata | attctaaagg | tggctttgag | ctgctgctgg | caaatgatgt | ggataacagc | 1440 |
| aaccccggtgg | ttcaagcgga | acaactgaat | tggctgtact | acctgatgaa | tttcggtacg | 1500 |
| attaccgcca | atgacgcgga | tgccaacttt | gacggcattc | gcgtcgatgc | agtggataac | 1560 |
| gtggatgctg | atctgttgca | gattgcggca | gactacttta | aactggccta | cggtgtggac | 1620 |
| cagaatgata | gcaccgcaaa | ccaacaccctg | tctatcctgg | aagattggag | ccacaacgac | 1680 |
| ccgctgtatg | tcacgatca | aggcagcgac | cagctgacta | tggacgacta | cgtgcatacg | 1740 |
| caattgatt | ggagcctgac | caaaagcagc | gatatccgtg | gtaccatgca | acgttttgtg | 1800 |
| gattactata | tggtggaccg | ttccaatgac | tccacggaga | atgaagcgat | cccgaattac | 1860 |
| agctttgtcc | gcgcacacga | tagcgaagtt | caaaccgtta | tcgcgcaaat | cgtgagcgat | 1920 |

```
ctgtatccag atgttgagaa tagcctggct ccgaccaccg agcagctggc agcagcattc    1980
aaggtgtata atgaagatga gaaattggcc gacaaaaagt atacccaata caacatggcg    2040
agcgcctatg cgatgctgct gaccaataaa gacacggtgc cgcgtgtcta ctatggcgac    2100
ctgtataccg atgacggtca atacatggca acgaagagcc cgtattacga cgcgattaac    2160
accctgctga aagctcgtgt tcaatatgtc gcgggtggcc aaagcatgag cgtggatagc    2220
aacgatgtgc tgaccagcgt tcgctatggc aaagacgcga tgacggcgag cgacacgggc    2280
accagcgaga ctcgtaccga gggcgtcggt gtcattgtgt ccaacaatgc ggagctgcaa    2340
ctggaagatg tcatacggt taccctgcac atgggtgccg cgcacaaaaa tcaggcatac    2400
cgtgcgttgt tgtccaccac ggccgacggt ctggcgtatt atgatacgga cgagaatgcc    2460
ccggtggcat atacggatgc gaacggtgac ttgattttca ccaatgagtc catctacggc    2520
gttcagaatc cgcaagtcag cggttacctg gcggtgtggg tcccggttgg tgcacaacag    2580
gaccaggacg cgcgcacggc aagcgatacc accactaaca ccagcgataa agttttccac    2640
agcaacgcgg ctctggacag ccaagtgatc tacgagggct tcagcaactt ccaagcgttt    2700
gcgactgatt ccagcgaata caccaatgtt gttattgctc agaacgctga tcaattcaaa    2760
caatggggcg tgacctcgtt tcagctggct ccgcagtacc gcagcagcac ggacacttcc    2820
ttcctggata gcatcatcca aaatggttac gcgtttacgg accgctatga tctgggttat    2880
ggcacgccga cgaagtacgg taccgcggac caactgcgtg atgcaatcaa agcactgcat    2940
gcgagcggca tccaagcgat tgcagattgg gttccggacc agatttacaa tctgccggag    3000
caagaactgg cgactgtcac gcgcacgaat agcttcggtg atgatgatac tgacagcgac    3060
attgataatg ctctgtatgt ggttcaaagc cgcggtggtg gtcagtacca agagatgtat    3120
ggcggtgcgt ttctggagga gttgcaagcg ctgtacccta gcctgtttaa ggtgaaccag    3180
atttctactg gtgtcccgat cgatggtagc gtgaagatta ccgagtgggc tgcgaaatac    3240
ttcaacggca gcaatatcca gggtaagggt gcgggttacg tgttgaaaga catgggtagc    3300
aataagtact tcaaggtcgt gagcaatacc gaggacggcg actatctgcc gaaacagctg    3360
accaacgacc tgagcgaaac cggtttcacc cacgacgaca agggtatcat ctactacacc    3420
ctgagcggct atcgtgcaca gaacgccttc attcaagacg atgataacaa ttactattac    3480
tttgacaaga ccggtcacct ggtcacgggt ttgcagaaaa tcaacaacca tacgtacttc    3540
ttcctgccga atggcattga gctggtgaaa tccttcttgc agaacgagga tggcacgatc    3600
gtttacttcg ataagaaagg tcatcaagtc tttgatcaat acattacgga tcaaaatggc    3660
aacgcgtact atttcgacga tgccggtgtt atgctgaagt ctggtctggc aacgattgat    3720
ggtcatcagc agtacttcga tcagaatggc gttcaagtta aggacaagtt cgttatcggt    3780
acggatggct acaagtacta cttcgagccg ggttgcggca atttggcaat tttgcgttac    3840
gtgcaaaata gcaagaacca atggttctat ttcgatggca atggccacgc agtcacgggt    3900
ttccaaacca tcaacggcaa gaagcagtat ttctacaacg atggtcacca aagcaagggc    3960
gaatttatca atgcggacgg tgacaccttc tacaccagcg ccaccgacgg tcgtttggtg    4020
acgggtgttc agaagatcaa cggtatcacc tacgcgtttg acaataccgg caacctgatc    4080
acgaaccagt attatcagct ggcggacggt aagtacatgc tgctggacga ctctggtcgc    4140
gcaaaaacgg gctttgtcct gcaagacggt gtcctgcgtt atttcgacca gaacggtgaa    4200
caagtgaagg acgccattat cgtcgacccg gacaccaacc tgtcttatta ctttaacgcg    4260
acccagggtg tcgcggtgaa aaacgattac ttcgagtacc aaggcaactg gtacctgacc    4320
```

```
gatgcaaact accagctgat taaaggcttc aaagcagttg acgactcgct gcaacacttc    4380
gacgaagtta cgggtgtgca gaccaaggaa agcgctctga ttagcgcaca gggcaaagtt    4440
taccagttcg acaacaatgg taacgcggtg agcgcataa                          4479
```

<210> SEQ ID NO 22
<211> LENGTH: 1492
<212> TYPE: PRT
<213> ORGANISM: Leuconostoc mesenteroides

<400> SEQUENCE: 22

```
Met Thr Pro Ser Val Leu Gly Asp Ser Val Pro Asp Val Ser Ala
1               5                   10                  15

Asn Asn Val Gln Ser Ala Ser Asp Asn Thr Thr Asp Thr Gln Gln Asn
            20                  25                  30

Thr Thr Ile Thr Glu Glu Asn Asp Lys Val Gln Ser Ala Ala Thr Asn
        35                  40                  45

Asp Asn Val Thr Thr Ala Ala Ser Asp Thr Thr Gln Ser Ala Asp Asn
    50                  55                  60

Asn Val Thr Glu Lys Gln Ser Asp Asp His Ala Leu Asp Asn Glu Lys
65                  70                  75                  80

Val Asp Asn Lys Gln Asp Glu Val Ala Gln Thr Asn Val Thr Ser Lys
                85                  90                  95

Asn Glu Glu Ser Ala Val Ala Ser Thr Asp Thr Asp Pro Ala Glu Thr
            100                 105                 110

Thr Thr Asp Glu Thr Gln Gln Val Ser Gly Lys Tyr Val Glu Lys Asp
        115                 120                 125

Gly Ser Trp Tyr Tyr Tyr Phe Asp Asp Gly Lys Asn Ala Lys Gly Leu
    130                 135                 140

Ser Thr Ile Asp Asn Asn Ile Gln Tyr Phe Asp Glu Ser Gly Lys Gln
145                 150                 155                 160

Val Lys Gly Gln Tyr Val Thr Ile Asp Asn Gln Thr Tyr Tyr Phe Asp
                165                 170                 175

Lys Asp Ser Gly Asp Glu Leu Thr Gly Leu Gln Ser Ile Asp Gly Asn
            180                 185                 190

Ile Val Ala Phe Asn Asp Glu Gly Gln Gln Ile Phe Asn Gln Tyr Tyr
        195                 200                 205

Gln Ser Glu Asn Gly Thr Thr Tyr Tyr Phe Asp Asp Lys Gly His Ala
    210                 215                 220

Ala Thr Gly Ile Lys Asn Ile Glu Gly Lys Asn Tyr Tyr Phe Asp Asn
225                 230                 235                 240

Leu Gly Gln Leu Lys Lys Gly Phe Ser Gly Val Ile Asp Gly Gln Ile
                245                 250                 255

Met Thr Phe Asp Gln Glu Thr Gly Gln Glu Val Ser Asn Thr Thr Ser
            260                 265                 270

Glu Ile Lys Glu Gly Leu Thr Thr Gln Asn Thr Asp Tyr Ser Glu His
        275                 280                 285

Asn Ala Ala His Gly Thr Asp Ala Glu Asp Phe Glu Asn Ile Asp Gly
    290                 295                 300

Tyr Leu Thr Ala Ser Ser Trp Tyr Arg Pro Thr Asp Ile Leu Arg Asn
305                 310                 315                 320

Gly Thr Asp Trp Glu Pro Ser Thr Asp Thr Asp Phe Arg Pro Ile Leu
                325                 330                 335

Ser Val Trp Trp Pro Asp Lys Asn Thr Gln Val Asn Tyr Leu Asn Tyr
```

```
                340                 345                 350
Met Ala Asp Leu Gly Phe Ile Ser Asn Ala Asp Ser Phe Glu Thr Gly
                355                 360                 365

Asp Ser Gln Ser Leu Leu Asn Glu Ala Ser Asn Tyr Val Gln Lys Ser
            370                 375                 380

Ile Glu Met Lys Ile Ser Ala Gln Gln Ser Thr Glu Trp Leu Lys Asp
385                 390                 395                 400

Ala Met Ala Ala Phe Ile Val Thr Gln Pro Gln Trp Asn Glu Thr Ser
                405                 410                 415

Glu Asp Met Ser Asn Asp His Leu Gln Asn Gly Ala Leu Thr Tyr Val
            420                 425                 430

Asn Ser Pro Leu Thr Pro Asp Ala Asn Ser Asn Phe Arg Leu Leu Asn
            435                 440                 445

Arg Thr Pro Thr Asn Gln Thr Gly Glu Gln Ala Tyr Asn Leu Asp Asn
            450                 455                 460

Ser Lys Gly Gly Phe Glu Leu Leu Leu Ala Asn Asp Val Asp Asn Ser
465                 470                 475                 480

Asn Pro Val Val Gln Ala Glu Gln Leu Asn Trp Leu Tyr Tyr Leu Met
                485                 490                 495

Asn Phe Gly Thr Ile Thr Ala Asn Asp Ala Asp Ala Asn Phe Asp Gly
                500                 505                 510

Ile Arg Val Asp Ala Val Asp Asn Val Asp Ala Asp Leu Leu Gln Ile
            515                 520                 525

Ala Ala Asp Tyr Phe Lys Leu Ala Tyr Gly Val Asp Gln Asn Asp Ser
            530                 535                 540

Thr Ala Asn Gln His Leu Ser Ile Leu Glu Asp Trp Ser His Asn Asp
545                 550                 555                 560

Pro Leu Tyr Val Thr Asp Gln Gly Ser Asp Gln Leu Thr Met Asp Asp
                565                 570                 575

Tyr Val His Thr Gln Leu Ile Trp Ser Leu Thr Lys Ser Ser Asp Ile
            580                 585                 590

Arg Gly Thr Met Gln Arg Phe Val Asp Tyr Tyr Met Val Asp Arg Ser
            595                 600                 605

Asn Asp Ser Thr Glu Asn Glu Ala Ile Pro Asn Tyr Ser Phe Val Arg
            610                 615                 620

Ala His Asp Ser Glu Val Gln Thr Val Ile Ala Gln Ile Val Ser Asp
625                 630                 635                 640

Leu Tyr Pro Asp Val Glu Asn Ser Leu Ala Pro Thr Thr Glu Gln Leu
                645                 650                 655

Ala Ala Ala Phe Lys Val Tyr Asn Glu Asp Glu Lys Leu Ala Asp Lys
                660                 665                 670

Lys Tyr Thr Gln Tyr Asn Met Ala Ser Ala Tyr Ala Met Leu Leu Thr
            675                 680                 685

Asn Lys Asp Thr Val Pro Arg Val Tyr Tyr Gly Asp Leu Tyr Thr Asp
            690                 695                 700

Asp Gly Gln Tyr Met Ala Thr Lys Ser Pro Tyr Tyr Asp Ala Ile Asn
705                 710                 715                 720

Thr Leu Leu Lys Ala Arg Val Gln Tyr Val Ala Gly Gly Gln Ser Met
                725                 730                 735

Ser Val Asp Ser Asn Asp Val Leu Thr Ser Val Arg Tyr Gly Lys Asp
            740                 745                 750

Ala Met Thr Ala Ser Asp Thr Gly Thr Ser Glu Thr Arg Thr Glu Gly
            755                 760                 765
```

-continued

Val Gly Val Ile Val Ser Asn Asn Ala Glu Leu Gln Leu Glu Asp Gly
        770                 775                 780

His Thr Val Thr Leu His Met Gly Ala Ala His Lys Asn Gln Ala Tyr
785                 790                 795                 800

Arg Ala Leu Leu Ser Thr Thr Ala Asp Gly Leu Ala Tyr Tyr Asp Thr
                805                 810                 815

Asp Glu Asn Ala Pro Val Ala Tyr Thr Asp Ala Asn Gly Asp Leu Ile
            820                 825                 830

Phe Thr Asn Glu Ser Ile Tyr Gly Val Gln Asn Pro Gln Val Ser Gly
        835                 840                 845

Tyr Leu Ala Val Trp Val Pro Val Gly Ala Gln Gln Asp Gln Asp Ala
    850                 855                 860

Arg Thr Ala Ser Asp Thr Thr Asn Thr Ser Asp Lys Val Phe His
865                 870                 875                 880

Ser Asn Ala Ala Leu Asp Ser Gln Val Ile Tyr Glu Gly Phe Ser Asn
                885                 890                 895

Phe Gln Ala Phe Ala Thr Asp Ser Ser Glu Tyr Thr Asn Val Val Ile
            900                 905                 910

Ala Gln Asn Ala Asp Gln Phe Lys Gln Trp Gly Val Thr Ser Phe Gln
        915                 920                 925

Leu Ala Pro Gln Tyr Arg Ser Ser Thr Asp Thr Ser Phe Leu Asp Ser
    930                 935                 940

Ile Ile Gln Asn Gly Tyr Ala Phe Thr Asp Arg Tyr Asp Leu Gly Tyr
945                 950                 955                 960

Gly Thr Pro Thr Lys Tyr Gly Thr Ala Asp Gln Leu Arg Asp Ala Ile
                965                 970                 975

Lys Ala Leu His Ala Ser Gly Ile Gln Ala Ile Ala Asp Trp Val Pro
            980                 985                 990

Asp Gln Ile Tyr Asn Leu Pro Glu Gln Glu Leu Ala Thr Val Thr Arg
        995                 1000                1005

Thr Asn Ser Phe Gly Asp Asp Thr Asp Ser Asp Ile Asp Asn
    1010                1015                1020

Ala Leu Tyr Val Val Gln Ser Arg Gly Gly Gln Tyr Gln Glu
    1025                1030                1035

Met Tyr Gly Gly Ala Phe Leu Glu Glu Leu Gln Ala Leu Tyr Pro
    1040                1045                1050

Ser Leu Phe Lys Val Asn Gln Ile Ser Thr Gly Val Pro Ile Asp
    1055                1060                1065

Gly Ser Val Lys Ile Thr Glu Trp Ala Ala Lys Tyr Phe Asn Gly
    1070                1075                1080

Ser Asn Ile Gln Gly Lys Gly Ala Gly Tyr Val Leu Lys Asp Met
    1085                1090                1095

Gly Ser Asn Lys Tyr Phe Lys Val Val Ser Asn Thr Glu Asp Gly
    1100                1105                1110

Asp Tyr Leu Pro Lys Gln Leu Thr Asn Asp Leu Ser Glu Thr Gly
    1115                1120                1125

Phe Thr His Asp Asp Lys Gly Ile Ile Tyr Tyr Thr Leu Ser Gly
    1130                1135                1140

Tyr Arg Ala Gln Asn Ala Phe Ile Gln Asp Asp Asp Asn Asn Tyr
    1145                1150                1155

Tyr Tyr Phe Asp Lys Thr Gly His Leu Val Thr Gly Leu Gln Lys
    1160                1165                1170

| | | | | | | | | | | |
|---|---|---|---|---|---|---|---|---|---|---|
| Ile | Asn | Asn | His | Thr | Tyr | Phe | Phe | Leu | Pro | Asn | Gly | Ile | Glu | Leu |
| 1175 | | | | | 1180 | | | | | 1185 | | | | |

Ile Asn Asn His Thr Tyr Phe Phe Leu Pro Asn Gly Ile Glu Leu
1175                1180              1185

Val Lys Ser Phe Leu Gln Asn Glu Asp Gly Thr Ile Val Tyr Phe
1190                1195              1200

Asp Lys Lys Gly His Gln Val Phe Asp Gln Tyr Ile Thr Asp Gln
1205                1210              1215

Asn Gly Asn Ala Tyr Tyr Phe Asp Asp Ala Gly Val Met Leu Lys
1220                1225              1230

Ser Gly Leu Ala Thr Ile Asp Gly His Gln Gln Tyr Phe Asp Gln
1235                1240              1245

Asn Gly Val Gln Val Lys Asp Lys Phe Val Ile Gly Thr Asp Gly
1250                1255              1260

Tyr Lys Tyr Tyr Phe Glu Pro Gly Cys Gly Asn Leu Ala Ile Leu
1265                1270              1275

Arg Tyr Val Gln Asn Ser Lys Asn Gln Trp Phe Tyr Phe Asp Gly
1280                1285              1290

Asn Gly His Ala Val Thr Gly Phe Gln Thr Ile Asn Gly Lys Lys
1295                1300              1305

Gln Tyr Phe Tyr Asn Asp Gly His Gln Ser Lys Gly Glu Phe Ile
1310                1315              1320

Asn Ala Asp Gly Asp Thr Phe Tyr Thr Ser Ala Thr Asp Gly Arg
1325                1330              1335

Leu Val Thr Gly Val Gln Lys Ile Asn Gly Ile Thr Tyr Ala Phe
1340                1345              1350

Asp Asn Thr Gly Asn Leu Ile Thr Asn Gln Tyr Tyr Gln Leu Ala
1355                1360              1365

Asp Gly Lys Tyr Met Leu Leu Asp Asp Ser Gly Arg Ala Lys Thr
1370                1375              1380

Gly Phe Val Leu Gln Asp Gly Val Leu Arg Tyr Phe Asp Gln Asn
1385                1390              1395

Gly Glu Gln Val Lys Asp Ala Ile Ile Val Asp Pro Asp Thr Asn
1400                1405              1410

Leu Ser Tyr Tyr Phe Asn Ala Thr Gln Gly Val Ala Val Lys Asn
1415                1420              1425

Asp Tyr Phe Glu Tyr Gln Gly Asn Trp Tyr Leu Thr Asp Ala Asn
1430                1435              1440

Tyr Gln Leu Ile Lys Gly Phe Lys Ala Val Asp Asp Ser Leu Gln
1445                1450              1455

His Phe Asp Glu Val Thr Gly Val Gln Thr Lys Glu Ser Ala Leu
1460                1465              1470

Ile Ser Ala Gln Gly Lys Val Tyr Gln Phe Asp Asn Asn Gly Asn
1475                1480              1485

Ala Val Ser Ala
1490

<210> SEQ ID NO 23
<211> LENGTH: 3972
<212> TYPE: DNA
<213> ORGANISM: Streptococcus criceti

<400> SEQUENCE: 23
atggttgatg gcaaatacta ctactacgac gcagatggca acgttaagaa gaatttcgcg    60
attagcgtcg gtgacgcaat cttctacttt gacgaaaccg gtgcttacaa ggacaccagc   120
aaagttggtg cggataaaac cagcagcagc gcgaatcaaa ccacggccac cttcgcggca   180

```
aacaaccgtg cctatagcac tgcggcggag aactttgagg caattgacaa ctatttgacc    240
gcagacagct ggtatcgtcc gaagagcatt ctgaaagatg gtaagacgtg gaccgaatcc    300
accaaagacg acttccgtcc gctgctgatg gcttggtggc cggataccga aactaaacgc    360
aactatgtca actatatgaa taaggtcgtc ggcattgata aaacctatac cgcggagact    420
agccaagccg acctgacggc agctgcggag ctggttcaag cgcgcattga gcaacgcatc    480
acgtctgaga agaacacgaa atggctgcgc gaggctatta gcgcgtttgt caagacccag    540
ccgcaatgga atggcgagtc cgaaaagccg tatgatgatc atttgcagaa cggtgcactg    600
aagttcgaca acgaaacctc tctgaccccg gacacccagt ctggttatcg tatcttgaat    660
cgcacgccga ccaatcaaac gggcagcctg gacccgcgtt tcacctttaa tcaaaatgat    720
ccgctgggtg gctatgaata tctgctggca acgacgtgg ataatagcaa cccggtggtg    780
caagcggaga gcttgaattg gctgcactac ctgctgaact tcggcagcat ctacgcgaat    840
gatccggaag cgaatttcga ttccattcgt gtagacgccg tggataacgt ggatgcggat    900
ctgttgcaga ttagcagcga ctacctgaaa tctgcgtaca aaatcgataa gaacaacaaa    960
aatgcgaatg accacgtgag catcgttgag gcgtggagcg ataacgacac cccgtacctg   1020
cacgatgaag gcgataactt gatgaatatg gacaataagt ttcgcctgag catgttgcgc   1080
tccctggcga agcctctgga caaacgtagc ggcctgaacc ctctgatcca taatagcgtc   1140
gttgatcgcg aggtggatga ccgtgaggtt gagaaaattc cgagctactc ttttgcacgc   1200
gctcacgaca cgcgaggttca ggatctgatt cgtgacatca ttaaggcaga atcaatccg    1260 aacagcttcg gctacagctt tacccaagaa gaaatcgatc aagcgttcaa gatctacaac   1320
gaggacctga gaaaaaccaa caagaagtac acccattaca atgtcccgct gtcttacacc   1380
ttgctgctga cgaataaggg tagcattccg cgtatttact acggcgacat gtttaccgac   1440
gatggccagt atatggcgaa caaaacggtg aattacaatg ctattgagag cctgctgaag   1500
gctcgtatga agtatgtgag cggtggtcag gcgatgcaaa actatcaaat tggtaatggt   1560
gaaattctga cgtcggtgcg ctacggtaaa ggtgcgctga agcaatcgga caagggcgac   1620
gcaacgacgc gtacctctgg tattggtatt gtcatgggca accagccgaa tttctcgctg   1680
gaaggtaaag tcgttgccct gaacatgggt gcagcgcatg ccaatcagga gtatcgtgcc   1740
ctgatggtga gcactaaaga cggcgtggcg acctatgcga cggatgcaga cgcgagcaaa   1800
gcgggtatga cgaaacgtac cgacgagaac ggctacttgt atttcctgaa tgacgacttg   1860
aagggtgttg caaatccaca gatctccggt tttctgcaag tatgggtgcc ggtcggtgct   1920
cctgccgacc aggatattcg cgttgccgcg acgaacgctg caagcacgga tggtaagtcc   1980
ctgcaccaag atgcggcgat ggatagccgt gttatgttcg agggttttc caactttcag   2040 gcgttcgcaa cgaaagaaga tgagtatgct aatgttgtta ttgcgaaaaa tgtggataag   2100
tttgttagct ggggcatcac tgactttgag atggcaccgc agtataccte tagcgatgac   2160 ggtcagttcc tggatagcgt tattcagaat ggttatgcat tcacggaccg ttatgatctg   2220
ggtatgagca aggcaaacaa atatggtacg gcggaacacc tggtcaaagc tatcaaagcg   2280
ttgcacaaag caggtctgaa agttatgcg gattgggtcc cggaccagat gtatacccttt   2340 ccgaagaaag aggttgtcac cgttacgcgt acggacaagt tcggtaaacc ggttgcgggc   2400
agccaaatca atcatacccct gtatgtgact gacaccaaag gtagcggtga tgactatcag   2460
gccaaatacg gtggtgcgtt tctggacgag ctgaaagaga ataccccgga attgtttacg   2520
```

```
aaaaagcaga tttctacggg ccaagcaatc gacccaagcg tcaagattaa gcagtggagc    2580
gcgaaatact ttaacggcag caatatcttg ggtcgtggtg caaattacgt cctgagcgac    2640
caggccagca acaagtattt caatgtggcg gaaggtaagg tttttctgcc aggcgccatg    2700
ctgggcaagg tggtggaaag cggcatccgt tttgacggca agggctacat ctataacagc    2760
tcgaccaccg gcgaacaagt caaagatagc ttcatcacgg aagcaggtaa tttgtattac    2820
ttcggtaaag acggttacat ggtcatgggt gcgcagaaca ttcaaggcgc caattactac    2880
ttcctggcca acggtgcggc actgcgtaat agcatcctga ccgatcaaga cggcaagtcc    2940
cactactacg cgaacgacgg caaacgttat gaaaacggct attatcagtt tggtaacgat    3000
tcctggcgct acttcgagaa tggtgtaatg gccgtcggcg tgacccgtgt ggctggccat    3060
gaccagtact tcgataagga tggtattcaa gcgaagaaca agatcatcgt tacccgcgat    3120
ggtaaggttc gttacttcga tgagcacaat ggcaatgcag tcaccaacac gttcattagc    3180
gatcaggcag gtcactggta ctatctgggt aaggacggtg tggcggtgac gggtgcccaa    3240
acggtgggca acagcacct  gtatttcgag gccaacggcc agcaggtcaa aggcgatttt    3300
gtgaccgcga agacggtaa  actgtatttc ttcgatggcg atagcggtga catgtggacc    3360
gacacgttcg tccaagacaa aactggccat tggttttacc tgggtaaaga tggtgcggcg    3420
gtcaccggtg cacagaccgt gcgcggtcag aaattgtact ttaaagccaa cggtcagcaa    3480
gttaagggcg acattgtcaa aggtgctgat ggtaaaatcc gttactatga tgcaaattcg    3540
ggcgatcagg tctacaaccg tactgtgaag ggttccgacg gtaaaaccta catcatcggc    3600
aaagacggtt tgccattac  gcagaccatc gcgaagggtc aaaccattaa ggacggcagc    3660
gttctgcgtt tctacagcat ggaaggccag ctggttaccg gtagcggctg gtattctaac    3720
gcgaaaggtc agtggctgta cgtgaagaat ggtcaggttc tgaccggtct gcaaaccgtt    3780
ggttcccaac gtgtgtactt cgacgctaac ggtatccaag cgaagggcaa ggccgtgcgc    3840
accagcgacg gtaagctgcg ttactttgat gcgaacagcg gtagcatgat cactaaccag    3900
tggaaagagg tgaacggtca atactattac tttgacaaca atggcgtcgc catctaccgc    3960
ggctggaact aa                                                       3972
```

<210> SEQ ID NO 24
<211> LENGTH: 1323
<212> TYPE: PRT
<213> ORGANISM: Streptococcus criceti

<400> SEQUENCE: 24

```
Met Val Asp Gly Lys Tyr Tyr Tyr Asp Ala Asp Gly Asn Val Lys
1               5                   10                  15

Lys Asn Phe Ala Ile Ser Val Gly Asp Ala Ile Phe Tyr Phe Asp Glu
            20                  25                  30

Thr Gly Ala Tyr Lys Asp Thr Ser Lys Val Gly Ala Asp Lys Thr Ser
        35                  40                  45

Ser Ser Ala Asn Gln Thr Thr Ala Thr Phe Ala Ala Asn Asn Arg Ala
    50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Thr Lys Asp Asp Phe Arg Pro Leu Leu Met Ala Trp
            100                 105                 110
```

```
Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
        130                 135                 140

Leu Thr Ala Ala Ala Glu Leu Val Gln Ala Arg Ile Glu Gln Arg Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
    210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu His Asp Glu Gly Asp Asn Leu Met Asn Met Asp Asn
            340                 345                 350

Lys Phe Arg Leu Ser Met Leu Arg Ser Leu Ala Lys Pro Leu Asp Lys
        355                 360                 365

Arg Ser Gly Leu Asn Pro Leu Ile His Asn Ser Val Val Asp Arg Glu
    370                 375                 380

Val Asp Asp Arg Glu Val Glu Lys Ile Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asn Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
```

```
              530            535            540
Thr Ser Gly Ile Gly Ile Val Met Gly Asn Gln Pro Asn Phe Ser Leu
545                550                555                560

Glu Gly Lys Val Val Ala Leu Asn Met Gly Ala His Ala Asn Gln
            565                570                575

Glu Tyr Arg Ala Leu Met Val Ser Thr Lys Asp Gly Val Ala Thr Tyr
            580                585                590

Ala Thr Asp Ala Asp Ala Ser Lys Ala Gly Met Thr Lys Arg Thr Asp
            595                600                605

Glu Asn Gly Tyr Leu Tyr Phe Leu Asn Asp Asp Leu Lys Gly Val Ala
            610                615                620

Asn Pro Gln Ile Ser Gly Phe Leu Gln Val Trp Val Pro Val Gly Ala
625                630                635                640

Pro Ala Asp Gln Asp Ile Arg Val Ala Ala Thr Asn Ala Ala Ser Thr
                645                650                655

Asp Gly Lys Ser Leu His Gln Asp Ala Ala Met Asp Ser Arg Val Met
                660                665                670

Phe Glu Gly Phe Ser Asn Phe Gln Ala Phe Ala Thr Lys Glu Asp Glu
                675                680                685

Tyr Ala Asn Val Val Ile Ala Lys Asn Val Asp Lys Phe Val Ser Trp
690                695                700

Gly Ile Thr Asp Phe Glu Met Ala Pro Gln Tyr Thr Ser Ser Asp Asp
705                710                715                720

Gly Gln Phe Leu Asp Ser Val Ile Gln Asn Gly Tyr Ala Phe Thr Asp
                725                730                735

Arg Tyr Asp Leu Gly Met Ser Lys Ala Asn Lys Tyr Gly Thr Ala Glu
                740                745                750

His Leu Val Lys Ala Ile Lys Ala Leu His Lys Ala Gly Leu Lys Val
                755                760                765

Met Ala Asp Trp Val Pro Asp Gln Met Tyr Thr Phe Pro Lys Lys Glu
770                775                780

Val Val Thr Val Thr Arg Thr Asp Lys Phe Gly Lys Pro Val Ala Gly
785                790                795                800

Ser Gln Ile Asn His Thr Leu Tyr Val Thr Asp Thr Lys Gly Ser Gly
                805                810                815

Asp Asp Tyr Gln Ala Lys Tyr Gly Gly Ala Phe Leu Asp Glu Leu Lys
                820                825                830

Glu Lys Tyr Pro Glu Leu Phe Thr Lys Lys Gln Ile Ser Thr Gly Gln
                835                840                845

Ala Ile Asp Pro Ser Val Lys Ile Lys Gln Trp Ser Ala Lys Tyr Phe
850                855                860

Asn Gly Ser Asn Ile Leu Gly Arg Gly Ala Asn Tyr Val Leu Ser Asp
865                870                875                880

Gln Ala Ser Asn Lys Tyr Phe Asn Val Ala Glu Gly Lys Val Phe Leu
                885                890                895

Pro Gly Ala Met Leu Gly Lys Val Val Glu Ser Gly Ile Arg Phe Asp
                900                905                910

Gly Lys Gly Tyr Ile Tyr Asn Ser Ser Thr Thr Gly Glu Gln Val Lys
                915                920                925

Asp Ser Phe Ile Thr Glu Ala Gly Asn Leu Tyr Tyr Phe Gly Lys Asp
                930                935                940

Gly Tyr Met Val Met Gly Ala Gln Asn Ile Gln Gly Ala Asn Tyr Tyr
945                950                955                960
```

```
Phe Leu Ala Asn Gly Ala Ala Leu Arg Asn Ser Ile Leu Thr Asp Gln
            965                 970                 975

Asp Gly Lys Ser His Tyr Tyr Ala Asn Asp Gly Lys Arg Tyr Glu Asn
        980                 985                 990

Gly Tyr Tyr Gln Phe Gly Asn Asp Ser Trp Arg Tyr Phe Glu Asn Gly
        995                1000                1005

Val Met Ala Val Gly Val Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Val Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Phe Asp Gly
    1100                1105                1110

Asp Ser Gly Asp Met Trp Thr Asp Thr Phe Val Gln Asp Lys Thr
    1115                1120                1125

Gly His Trp Phe Tyr Leu Gly Lys Asp Gly Ala Ala Val Thr Gly
    1130                1135                1140

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr
    1175                1180                1185

Val Lys Gly Ser Asp Gly Lys Thr Tyr Ile Ile Gly Lys Asp Gly
    1190                1195                1200

Val Ala Ile Thr Gln Thr Ile Ala Lys Gly Gln Thr Ile Lys Asp
    1205                1210                1215

Gly Ser Val Leu Arg Phe Tyr Ser Met Glu Gly Gln Leu Val Thr
    1220                1225                1230

Gly Ser Gly Trp Tyr Ser Asn Ala Lys Gly Gln Trp Leu Tyr Val
    1235                1240                1245

Lys Asn Gly Gln Val Leu Thr Gly Leu Gln Thr Val Gly Ser Gln
    1250                1255                1260

Arg Val Tyr Phe Asp Ala Asn Gly Ile Gln Ala Lys Gly Lys Ala
    1265                1270                1275

Val Arg Thr Ser Asp Gly Lys Leu Arg Tyr Phe Asp Ala Asn Ser
    1280                1285                1290

Gly Ser Met Ile Thr Asn Gln Trp Lys Glu Val Asn Gly Gln Tyr
    1295                1300                1305

Tyr Tyr Phe Asp Asn Gly Val Ala Ile Tyr Arg Gly Trp Asn
    1310                1315                1320

<210> SEQ ID NO 25
<211> LENGTH: 4308
<212> TYPE: DNA
<213> ORGANISM: Streptococcus sobrinus
```

-continued

```
<400> SEQUENCE: 25
atggttgacg gcaaatacta ctattatgat caggatggca acgttaagaa gaatttcgcg      60
gttagcgttg gtgacaagat ctactacttt gacgagactg gtgcctacaa agacacctct     120
aaagtggacg cggacaagtc tagcagcgcc gttagccaaa atgcgacgat ctttgcggct     180
aacaatcgtg cgtatagcac ctctgctgag aactttgagg ccgttgataa ctatctgacg     240
gcagatagct ggtatcgtcc taaatctatt ctgaaagatg gcaagacgtg gaccgagtcg     300
ggtaaggacg acttccgtcc gctgctgatg gcgtggtggc cggacacgga gactaaacgc     360
aattacgtga attacatgaa cctggttgtc ggcatcgaca agacgtacac cgcggaaacc     420
tctcaagcag atttgaccgc agcggcggag ctggtccagg cgcgtattga acagaaaatc     480
accacggaac agaatacgaa atggctgcgc gaggcgatct ctgctttcgt caagacccag     540
ccgcagtgga atggtgaaag cgagaagccg tatgacgacc acctgcaaaa cggtgctctg     600
aaattcgata tcagagcga cctgacccccg acacccaga gcaactatcg cctgctgaat      660
cgcaccccga ctaaccagac tggcagcctg acagccgtt tcacctataa tgcgaacgat     720
ccgttgggtg gctacgaatt tctgctggct aacgacgtgg ataatagcaa ccctgtggtg     780
caggcagaac aactgaactg gttgcattac ctgttgaatt ttggtagcat ttacgcgaaa     840
gatgcggatg caaacttcga ttccatccgt gtggacgccg tggacaacgt cgatgcagat     900
ctgttgcaga ttagcagcga ttacctgaag gcagcctatg cattgacaa gaacaataag      960 aacgcgaaca accatgttag cattgttgag gcttggagcg ataacgatac gccgtacctg    1020
cacgatgacg gtgataacct gatgaacatg gacaataagt tccgcttgag catgctgtgg    1080
agcctggcca agccgctgga caagcgcagc ggtctgaatc ctctgattca taacagcctg    1140
gtggaccgtg aggttgatga ccgtgaagtg gaaacggttc cgagctactc ttttgcgcgt    1200
gcgcatgatt ccgaggtcca agacattatc cgcgacatta tcaaggccga aatcaacccg    1260
aatagctttg gttatagctt cacccaagaa gagattgacc aggcgtttaa gatctataat    1320
gaagatctga agaaaaccga caagaaatac acccactata atgtcccgtt gagctatact    1380
ttgctgctga cgaataaagg ttcgattccg cgtgtgtatt acggtgatat gttcaccgat    1440
gatggtcaat acatggcgaa caaaacggtt aactatgatg ccattgagtc gctgctgaaa    1500
gcgcgcatga gtacgttag cggcggtcaa gcgatgcaaa actatcaaat cggcaatggt    1560
gagattctga ccagcgttcg ttatggtaag ggtgcattga agcaatccga caagggtgac    1620
gcgaccacgc gtacgtccgg tgtgggcgtc gtgatgggca accagccgaa ctttagcctg    1680
gacggcaagg tggtggcatt gaacatgggt gccgctcatg caaatcagga gtatcgtgcg    1740
ctgatggtga gcaccaagga tggcgttgcc acgtatgcca ccgacgcgga cgcaagcaag    1800
gcaggtctgg tcaaacgcac cgatgaaaat ggttatttgt actttctgaa cgacgatctg    1860
aagggtgtgg caaacccaca agtcagcggt tccttgcagg tgtgggtccc agtgggtgcg    1920
gctgacgatc aggacattcg tgttgcagcg agcgacacgg ctagcacgga cggtaagtcc    1980
ctgcatcaag atgcggcaat ggatagccgt gttatgtttg agggttttag caacttccag    2040
agctttgcaa ccaaagaaga agagtacacc aacgtagtta ttgcgaacaa cgtggacaaa    2100
ttcgttagct ggggtattac cgactttgag atggcaccgc aatatgtcag ctccaccgat    2160
ggccagtttc tggatagcgt tatccagaat ggttacgcgt tcaccgaccg ttatgatctg    2220
ggtatgagca aagccaacaa atacggtacc gcggatcagc tggttaaagc aatcaaagcg    2280
ttgcacgcga agggtctgaa ggtgatggcg gactgggttc cagaccagat gtacacgttt    2340
```

-continued

```
ccgaagcagg aagttgtcac tgtcacgcgc accgacaaat ttggtaagcc gattgcgggc   2400
agccaaatca atcacagcct gtacgtgacg gacaccaaat ccagcggtga tgattaccag   2460
gccaaatatg gtggtgcgtt cctggatgag ctgaaagaga atacccgga gctgttcacc   2520 aaaaagcaga tctcgaccgg tcaggcgatc gacccgagcg tgaagattaa gcagtggagc   2580
gcgaaatact ttaatggtag caacattctg gtcgtggtg ccgactacgt cctgtccgat   2640
caagttagca acaagtattt caatgtggcc agcgacacgc tgtttctgcc gtctagcctg   2700
ttgggtaagg ttgtcgaaag cggtattcgt tacgatggca aaggttatat ctataacagc   2760
agcgcgactg gcgaccaagt caaggcgtct tttatcacgg aagcaggcaa tctgtactac   2820 tcggcaaag acggttacat ggttactggt gcgcagacca ttaacggtgc gaattacttc   2880
ttcttggaaa atggtacggc cctgcgtaat accatctaca ccgatgcaca gggcaactcc   2940
cactattatg ctaatgatgg caagcgttac gagaacggtt accagcagtt cggcaacgat   3000
tggcgttact tcaaagatgg taacatggcc gtcggtctga ccacggtgga tggtaacgtt   3060
cagtatttcg acaaggacgg tgtccaagct aaagacaaga ttattgtgac ccgcgatggt   3120
aaggtgcgct actttgatca acacaatggc aacgcggtca cgaatacctt tatcgccgac   3180
aagaccggtc actggtacta cctgggcaaa gatggcgtcg cggtcaccgg cgctcaaacc   3240
gtcggtaagc aaaaactgta ttttgaggcg aacggtgagc aggtgaaagg cgactttgtg   3300
actagccatg aaggcaaact gtactttat gatgttgaca gcggcgacat gtggaccgat   3360
accttcatcg aggataaggc cggcaactgg ttctacctgg gtaaagacgg cgcagcagtt   3420
agcggtgcac agaccattcg cggtcaaaag ctgtacttca aggcgtacgg tcaacaggtc   3480
aaaggtgaca tcgttaaagg caccgacggc aagatccgtt actacgatgc gaaatccggc   3540
gagcaggttt tcaataagac ggtcaaagcc gctgatggca aaacctatgt gatcggcaac   3600
aatggtgtgg cggtcgatcc gagcgttgtt aagggtcaga cgttcaaaga cgccagcggc   3660
gcactgcgtt tttacaatct gaaaggtcaa ctggttacgg gctccggttg gtatgaaacg   3720
gccaatcacg attgggtgta tattcagagc ggtaaagcac tgaccggtga gcaaaccatc   3780
aatggtcagc acctgtactt taaagaagat ggccaccaag ttaaaggtca gctggtcacc   3840
cgtacggacg gcaaagtgcg ttactatgac gcaaattctg gcgatcaagc gttcaacaag   3900
tccgtgacgg ttaacggcaa aacgtattac ttcggtaatg atggtaccgc gcaaaccgcg   3960
ggtaacccga aggccaaat cttcaaggac ggcagcgttc tgcgtttcta tagcatggaa   4020
ggccagctgg taattggcag cggctggtat tccaacgcgc aaggccaatg gctgtatgtg   4080
aagaatggta aagtgttgac cggtttgcag accgtcggtt cccagcgcgt gtactttgat   4140
gagaatggca ttcaagcaaa aggcaaagcg gttcgcacga gcgacggcaa aattcgctac   4200
ttcgacgaga acagcggtag catgatcacc aatcaatgga gtttgttta cggtcaatac   4260 tattactttg gtaatgacgg tgcggcaatc taccgtggtt ggaattaa              4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
```

```
            20                  25                  30
Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Asn Asn Arg Ala
    50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
            115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asp Lys
        435                 440                 445
```

```
Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
    530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
            675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
            755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
850                 855                 860
```

```
Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
                900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
        930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
                980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
    1010                1015                1020

Asp Lys Asp Gly Val Gln Ala Lys Asp Lys Ile Ile Val Thr Arg
    1025                1030                1035

Asp Gly Lys Val Arg Tyr Phe Asp Gln His Asn Gly Asn Ala Val
    1040                1045                1050

Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Glu Gln Val Lys Gly Asp
    1085                1090                1095

Phe Val Thr Ser His Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Ser Gly Ala
    1130                1135                1140

Gln Thr Ile Arg Gly Gln Lys Leu Tyr Phe Lys Ala Tyr Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asn Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
```

```
            1265                1270               1275
Val Thr Arg Thr Asp Gly Lys Val Arg Tyr Tyr Asp Ala Asn Ser
        1280               1285              1290

Gly Asp Gln Ala Phe Asn Lys Ser Val Thr Val Asn Gly Lys Thr
    1295              1300              1305

Tyr Tyr Phe Gly Asn Asp Gly Thr Ala Gln Thr Ala Gly Asn Pro
    1310              1315              1320

Lys Gly Gln Ile Phe Lys Asp Gly Ser Val Leu Arg Phe Tyr Ser
    1325              1330              1335

Met Glu Gly Gln Leu Val Ile Gly Ser Gly Trp Tyr Ser Asn Ala
    1340              1345              1350

Gln Gly Gln Trp Leu Tyr Val Lys Asn Gly Lys Val Leu Thr Gly
    1355              1360              1365

Leu Gln Thr Val Gly Ser Gln Arg Val Tyr Phe Asp Glu Asn Gly
    1370              1375              1380

Ile Gln Ala Lys Gly Lys Ala Val Arg Thr Ser Asp Gly Lys Ile
    1385              1390              1395

Arg Tyr Phe Asp Glu Asn Ser Gly Ser Met Ile Thr Asn Gln Trp
    1400              1405              1410

Lys Phe Val Tyr Gly Gln Tyr Tyr Phe Gly Asn Asp Gly Ala
    1415              1420              1425

Ala Ile Tyr Arg Gly Trp Asn
    1430              1435

<210> SEQ ID NO 27
<211> LENGTH: 4023
<212> TYPE: DNA
<213> ORGANISM: Streptococcus salivarius

<400> SEQUENCE: 27
atgattgacg gcaaatacta ctacgtaaac aaagatggct cgcacaaaga gaatttcgca      60
attaccgtga atggtcagtt gttgtatttc ggtaaggacg gtgcattgac gtctagcagc     120
acctacagct ttacgcaggg caccaccaac atcgttgatg gctttagcaa aaacaaccgt     180
gcgtacgatt ccagcgaggc gagctttgaa ctgatcgacg ttatctgac cgcggactcc      240
tggtatcgtc cggtgagcat tatcaaggac ggcgttacgt ggcaagccag caccaaagag     300
gactttcgcc gctgctgat ggcctggtgg ccgaatgttg acacccaggt caactacctg      360
aattacatgt cgaaggtgtt taacctggac gcgaagtata cgagcaccga caaacaggtt     420
gacctgaatc gcgcagccaa ggacattcag gttaagattg agcaaaagat tcaggccgag     480
aagagcactc aatggctgcg tgaagcgatt tcggccttcg tcaaaaccca gccgcagtgg     540
aataagaaa cggagaactt ctccaagggt ggtggtgagg atcatctgca aggtggtgca      600
ctgctgtacg ttaacgaccc gcgtaccccg tgggctaact ccaactaccg cctgctgaat     660
cgtactgcga ccaaccagac cggcacgatc gacaagagcc ttctggacga acagagcgat     720
cctaaccaca tgggcggctt cgattttctg ctggcgaatg acgtcgatac cagcaatccg     780
gtggtgcagg cggaacaact gaatcagatc cactacctga tgaattgggg ttccattgtt     840
atgggcgaca aagatgcaaa cttcgatggt atccgcgtgg acgcggtcga taacgttgac     900
gcagatatgc tgcaactgta caccaactac tttcgtgagt attatggcgt gaacaaaagc     960
gaggcaaacg ctttggcgca catctcggtc ctggaagcgt ggagcttgaa tgataatcac    1020
tataatgaca agactgacgg tgcggccctg gcgatggaga acaaacagcg tttggcccctg   1080
```

```
ctgtttagct tggcgaaacc gatcaaagaa cgtacccctg cggtgagccc gctgtacaac    1140
aacactttca acacgacgca gcgtgacgaa aagaccgatt ggattaacaa agacggtagc    1200
aaagcctata atgaggacgg caccgtcaag cagtccacca tcggcaagta caacgagaaa    1260
tacggcgacg cgtccggcaa ttatgtgttc attcgcgccc acgataacaa cgtccaagac    1320
attattgcag agatcattaa gaaagaaatc aatccgaaaa gcgacggttt caccattacc    1380
gacgccgaaa tgaaaaaggc attcgaaatc tacaacaaag atatgctgtc ctctgataag    1440
aaatacaccc tgaacaacat cccagcggcc tacgcggtga tgctgcaaaa catggaaacc    1500
attactcgtg tgtattacgg cgatctgtat accgacgatg ccattacat ggaaaccaag    1560 agcccgtact acgacaccat tgtgaacctg atgaagaacc gtatcaaata cgtgtccggt    1620
ggtcaagcgc aacgttccta ttggctgccg accgacggta agatggataa agcgatgtc    1680 gaactgtatc gcaccaacga ggtgtacacc agcgtccgtt acggtaagga catcatgact    1740
gccgatgaca cccaaggtag caagtacagc cgtaccagcg gtcaggtgac cctggtggtg    1800
aacaacccga agctgtcttt ggataagagc gcgaagctgg acgtcgaaat gggcaagatc    1860
catgcaaacc agaaataccg tgctctgatc gtgggtacgc cgaacggcat caaaaacttc    1920
acgagcgacg ccgaggcaat cgcggctggc tacgtgaaag aaaccgacgg caatggtgtg    1980
ctgaccttcg gtgcaaatga catcaaaggt tacgaaacgt ttgacatgag cggtttcgtt    2040
gcagtttggg ttccggtagg tgcaagcgat gatcaagaca tccgtgtcgc cgcaagcacc    2100
gcggcaaaga aagaaggtga gctgactttg aaggcaactg aggcgtatga ctctcagctg    2160
atttacgaag gttttcgaa ttttcagacc attccggatg gtagcgatcc gagcgtttac    2220
accaatcgta agatcgcgga aaatgttgat ttgttcaaga gctggggtgt gacctctttc    2280
gaaatggcgc cacagtttgt gagcgcagac gacggtacgt ttctggacag cgttatccag    2340
aacggctatg cgtttgcgga ccgttatgat ctggcgatgt ccaaaaacaa taagtacggt    2400
tcgaaagaag atctgcgtaa cgcgttgaag cttttgcaca aggccggcat ccaagccatt    2460
gcggactggg ttccggatca gatctaccaa ctgccgggca agaagtagt gaccgccact    2520 cgtaccgatg gtgccggtcg taagattagc gatgcaatta tcgatcacag cctgtacgtc    2580
gcaaacagca agtcgtctgg caaagactat caagctaaat acggtggtga gttcctggcc    2640
gagctgaaag caaagtaccc ggaaatgttt aaagtcaaca tgattagcac gggtaaaccg    2700
atcgacgact ctgtcaaact gaagcaatgg aaggcggagt actttaacgg tacgaatgtt    2760
ctggaccgtg tgttggtta cgtcctgagc gatgaggcga cgggcaagta ctttaccgtt    2820
acgaaagagg gtaactttat cccactgcaa ttgaaaggta cgagaaagt tatcacgggc    2880 ttcagctctg acggcaaggg cattacctat ttcggcaccc tcggtaatca agcgaaaagc    2940
gcttttgtca cgttcaatgg taatacctac tattttgacg cgcgtggcca catggttacc    3000
aacggcgaat atagccctaa tggtaaggat gtgtatcgtt tcctgccgaa tggtattatg    3060
ttgagcaatg cattctacgt tgacggtaac ggcaatacct acctgtacaa ctccaagggc    3120
caaatgtaca aggtggtta tagcaaattc gacgttacgg aaaccaaaga tggtaaagag    3180
agcaaagtgg tgaaatttcg ctactttacc aatgaaggtg tgatggcaaa aggtgttacc    3240
gtggtggacg gcttcactca atacttcaac gaagatggca ttcagagcaa ggacgaactg    3300
gtgacctaca atggtaaaac ctattacttc gaagcgcata ccggtaatgc gatcaaaaac    3360
acgtggcgca atatcaaggg taagtggtat cactttgatg cgaatggcgt ggcggcaacg    3420
ggtgcacagg ttatcaatgg tcagcacctg tactttaatg aggatggttc ccaggtgaag    3480
```

-continued

| | |
|---|---|
| ggtggcgtcg tgaagaatgc ggatggtacc ttcagcaagt ataaagatgg ttccggtgac | 3540 |
| ctggtggtca atgagttctt cactactggt gataacgtgt ggtactacgc tggtgccaac | 3600 |
| ggcaaaactg tgacgggtgc ccaggtcatc aatggccaac acctgttttt caaagaggac | 3660 |
| ggtagccagg ttaagggtga tttcgttaag aacagcgacg gcacctactc taagtatgat | 3720 |
| gcggccagcg gcgaacgcct gacgaatgag ttttcacga ccggtgacaa ccactggtac | 3780 |
| tatattggtg ccaatggcaa aaccgttacc ggcgaagtca agatcggtga tgatacgtac | 3840 |
| ttcttcgcaa agatggcaa gcagctgaag ggccagatcg tgacgacccg cagcggtcgt | 3900 |
| atcagctact acttcggcga ctctggtaag aaggcgatta gcacctgggt ggagattcag | 3960 |
| ccgggtgttt tcgtgttttt cgacaaaaat ggcctggcat atccgccgga aaacatgaat | 4020 |
| taa | 4023 |

<210> SEQ ID NO 28
<211> LENGTH: 1340
<212> TYPE: PRT
<213> ORGANISM: Streptococcus salivarius

<400> SEQUENCE: 28

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
            35                  40                  45

Thr Asn Ile Val Asp Gly Phe Ser Lys Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Val Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175

Gln Pro Gln Trp Asn Lys Glu Thr Glu Asn Phe Ser Lys Gly Gly
            180                 185                 190

Glu Asp His Leu Gln Gly Gly Ala Leu Leu Tyr Val Asn Asp Pro Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Thr Ser Asn Pro Val Val Gln Ala Glu Gln Leu Asn Gln Ile His Tyr
            260                 265                 270
```

```
Leu Met Asn Trp Gly Ser Ile Val Met Gly Asp Lys Asp Ala Asn Phe
            275                 280                 285

Asp Gly Ile Arg Val Asp Ala Val Asp Asn Val Ala Asp Met Leu
290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
            450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr Tyr Asp Thr Ile Val
            515                 520                 525

Asn Leu Met Lys Asn Arg Ile Lys Tyr Val Ser Gly Gly Gln Ala Gln
            530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
                580                 585                 590

Ser Gly Gln Val Thr Leu Val Asn Asn Pro Lys Leu Ser Leu Asp
            595                 600                 605

Lys Ser Ala Lys Leu Asp Val Glu Met Gly Lys Ile His Ala Asn Gln
            610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
            675                 680                 685
```

```
Ser Asp Asp Gln Asp Ile Arg Val Ala Ala Ser Thr Ala Ala Lys Lys
690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
                740                 745                 750
Lys Ser Trp Gly Val Thr Ser Phe Glu Met Ala Pro Gln Phe Val Ser
                755                 760                 765
Ala Asp Asp Gly Thr Phe Leu Asp Ser Val Ile Gln Asn Gly Tyr Ala
770                 775                 780
Phe Ala Asp Arg Tyr Asp Leu Ala Met Ser Lys Asn Asn Lys Tyr Gly
785                 790                 795                 800
Ser Lys Glu Asp Leu Arg Asn Ala Leu Lys Ala Leu His Lys Ala Gly
                805                 810                 815
Ile Gln Ala Ile Ala Asp Trp Val Pro Asp Gln Ile Tyr Gln Leu Pro
                820                 825                 830
Gly Lys Glu Val Val Thr Ala Thr Arg Thr Asp Gly Ala Gly Arg Lys
                835                 840                 845
Ile Ser Asp Ala Ile Ile Asp His Ser Leu Tyr Val Ala Asn Ser Lys
850                 855                 860
Ser Ser Gly Lys Asp Tyr Gln Ala Lys Tyr Gly Gly Glu Phe Leu Ala
865                 870                 875                 880
Glu Leu Lys Ala Lys Tyr Pro Glu Met Phe Lys Val Asn Met Ile Ser
                885                 890                 895
Thr Gly Lys Pro Ile Asp Asp Ser Val Lys Leu Lys Gln Trp Lys Ala
                900                 905                 910
Glu Tyr Phe Asn Gly Thr Asn Val Leu Asp Arg Gly Val Gly Tyr Val
                915                 920                 925
Leu Ser Asp Glu Ala Thr Gly Lys Tyr Phe Thr Val Thr Lys Glu Gly
930                 935                 940
Asn Phe Ile Pro Leu Gln Leu Lys Gly Asn Glu Lys Val Ile Thr Gly
945                 950                 955                 960
Phe Ser Ser Asp Gly Lys Gly Ile Thr Tyr Phe Gly Thr Ser Gly Asn
                965                 970                 975
Gln Ala Lys Ser Ala Phe Val Thr Phe Asn Gly Asn Thr Tyr Tyr Phe
                980                 985                 990
Asp Ala Arg Gly His Met Val Thr Asn Gly Glu Tyr Ser Pro Asn Gly
                995                 1000                1005
Lys Asp Val Tyr Arg Phe Leu Pro Asn Gly Ile Met Leu Ser Asn
    1010                1015                1020
Ala Phe Tyr Val Asp Gly Asn Gly Asn Thr Tyr Leu Tyr Asn Ser
    1025                1030                1035
Lys Gly Gln Met Tyr Lys Gly Gly Tyr Ser Lys Phe Asp Val Thr
    1040                1045                1050
Glu Thr Lys Asp Gly Lys Glu Ser Lys Val Val Lys Phe Arg Tyr
    1055                1060                1065
Phe Thr Asn Glu Gly Val Met Ala Lys Gly Val Thr Val Val Asp
    1070                1075                1080
Gly Phe Thr Gln Tyr Phe Glu Asp Gly Ile Gln Ser Lys Asp
    1085                1090                1095
Glu Leu Val Thr Tyr Asn Gly Lys Thr Tyr Tyr Phe Glu Ala His
```

| | | | | | | | | | |
|---|---|---|---|---|---|---|---|---|---|
| | | 1100 | | | 1105 | | | 1110 | |
| Thr | Gly | Asn | Ala | Ile | Lys | Asn | Thr | Trp | Arg | Asn | Ile | Lys | Gly | Lys |
| | 1115 | | | | 1120 | | | | 1125 | |

Thr Gly Asn Ala Ile Lys Asn Thr Trp Arg Asn Ile Lys Gly Lys
    1115                1120                1125

Trp Tyr His Phe Asp Ala Asn Gly Val Ala Thr Gly Ala Gln
    1130                1135                1140

Val Ile Asn Gly Gln His Leu Tyr Phe Asn Glu Asp Gly Ser Gln
    1145                1150                1155

Val Lys Gly Gly Val Val Lys Asn Ala Asp Gly Thr Phe Ser Lys
    1160                1165                1170

Tyr Lys Asp Gly Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
    1295                1300                1305

Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 29
<211> LENGTH: 4026
<212> TYPE: DNA
<213> ORGANISM: Streptococcus salivarius

<400> SEQUENCE: 29

```
atgacggacg gtaaatacta ttatgtaaat gaggacggca gccacaaaga gaatttcgca      60
attacggtaa acggtcaact gttgtacttt ggcaaggacg cgctctctga cgagcagcagc    120 acgcacagct tcacgccggg tactacgaat attgtggacg gtttctcgat caacaaccgt    180
gcgtacgata gcagcgaagc gagctttgag ctgatcaacg gttacctgac ggcggattcc    240
tggtatcgcc cggtttctat catcaaggat ggcgtcacgt ggcaggcaag cactgccgag    300
gattttcgtc cgctgttgat ggcctggtgg ccgaacgttg atacccaggt gaactatctg    360
aactatatgt ccaaggtctt taacctggaa gccaagtaca ccagcaccga taaacaggct    420
gatctgaacc gtgctgcaaa ggatatccag gtcaagatcg aacagaagat ccaggcggaa    480
aagagcacgc agtggctgcg tgagactatc tccgcgtttg ttaaaaccca gccgcaatgg    540
aacaaagaga ctgagaatta ctccaagggt ggtggcgaag atcatctgca aggcggtgcg    600
ctgttgtacg tgaacgacag ccgtaccccg tgggcgaata gcaattaccg cctgctgaat    660
```

| | |
|---|---|
| cgcacggcaa cgaaccagac cggtaccatt aacaagtcgg tgttggacga gcaatccgat | 720 |
| ccaaatcaca tgggtggctt cgacttcctg ctggcaaacg atgtggatct gagcaatcct | 780 |
| gttgtgcagg ccgagcagct gaatcaaatc cattatctga tgaactgggg cagcattgtt | 840 |
| atgggtgaca aagacgcgaa ttttgatggt atccgtgtgg acgccgttga caacgtgaac | 900 |
| gctgacatgt tgcagctgta cacgaactac tttcgtgagt attacggcgt caacaaaagc | 960 |
| gaagcgcaag cgctggcgca cattagcgtt ctggaagcgt ggagcttgaa cgataaccac | 1020 |
| tataacgaca aaaccgatgg tgcggcactg gcgatggaga ataagcaacg tctggccttg | 1080 |
| ctgttctctc tggccaagcc gatcaaagat cgtactccgg cagtgagccc actgtataac | 1140 |
| aatactttca ataccaccca acgtgacttc aagacggatt ggattaacaa ggacggtagc | 1200 |
| accgcctaca atgaggatgg caccgcgaaa caatctacca tcggtaagta caatgagaaa | 1260 |
| tatggtgatg caagcggtaa ctatgtgttt attcgtgccc atgacaataa cgtccaagac | 1320 |
| attattgcgg agatcattaa gaaagaaatc aataagaaga gcgatggttt taccatcagc | 1380 |
| gatagcgaaa tgaaacaggc gttcgaaatc tacaacaaag atatgctgag cagcaataag | 1440 |
| aaatacactc tgaataacat tccggcagcg tacgccgtga tgctgcaaaa catggagact | 1500 |
| atcacccgtg tgtattatgg tgacctgtac accgacgacg gtcactatat ggaaaccaag | 1560 |
| agcccgtatc atgacaccat tgtgaacctg atgaaaaacc gtatcaagta cgtttctggt | 1620 |
| ggccaggccc aacgctccta ttggctgccg accgacggta aaatggacaa tagcgatgtc | 1680 |
| gaactgtacc gtactagcga ggtctatacc agcgttcgct acggtaagga cattatgacg | 1740 |
| gcggatgaca ccgagggtag caagtactcc cgcacgagcg gtcaggttac cctggttgtt | 1800 |
| aacaacccga agctgactct gcatgaaagc gccaaactga acgtcgagat gggtaagatc | 1860 |
| cacgcaaacc agaaataccg tgcgctgatt gtgggtaccg ccgatggcat caaaaacttt | 1920 |
| acgtctgatg ccgaagcgat cgcggcaggc tacgtaaaag aaacggacag caatggtgtt | 1980 |
| ctgaccttcg gcgcaaatga tatcaaaggt tacgagactt tcgatatgag cggtttcgtc | 2040 |
| gcagtttggg tgccggtggg tgcgagcgat gatcaggaca tccgcgtggc gccgtcgacg | 2100 |
| gaagcgaaga aagaaggtga actgacgctg aaagccacgg aagcgtatga tagccagttg | 2160 |
| atttatgaag gcttctccaa tttccagacc attccggatg gcagcgaccc gagcgtttat | 2220 |
| accaaccgca aaattgctga gaatgttgat ctgtttaagt cctggggtgt cactagcttc | 2280 |
| gaaatggctc cgcagtttgt ttcggcggac gacggcacct tcctggatag cgttatccag | 2340 |
| aacggttacg cctttgcgga ccgttatgat ttggccatga gcaagaacaa caagtacggt | 2400 |
| tctaaagagg atctgcgcga cgcactgaaa gcgctgcaca agctggcat tcaggcaatc | 2460 |
| gcggactggg tcccagacca aatctaccaa ctgccaggca agaagtggt tacggcgacg | 2520 |
| cgcacggacg gtgcgggtcg caagatcgcg gacgccatca ttgatcatag cctgtatgtt | 2580 |
| gctaactcca agagctccgg tcgcgattac caagcgcagt atggtggcga gtttctggca | 2640 |
| gagctgaaag cgaagtaccc gaaaatgttc acggaaaaca tgattagcac gggtaagccg | 2700 |
| atcgatgaca gcgtcaaact gaagcaatgg aaagccaagt atttcaatgg tacgaatgtg | 2760 |
| ctggaccgtg gtgtcggtta cgtcctgtcc gacgaggcga ccgcaaata cttcaccgtt | 2820 |
| accaaagagg gtaacttcat tccgctgcaa ctgaccggca atgaaaaagc ggtgaccggt | 2880 |
| ttcagcaacg acggcaaggg tatcacctac tttggtacga gcgtaatca ggccaagagc | 2940 |
| gcgttcgtca cctttaacgg caatacgtac tatttcgacg cgcgtggcca catggtcacg | 3000 |

```
aacggcgagt atagcccgaa cggcaaagat gtctaccgtt ttctgccaaa tggtattatg    3060
ttgtcgaacg cgtttatgt cgacgcaaac ggtaatacgt acttgtcaa ctacaagggc     3120 cagatgtaca aggtggtta tacgaaattt gatgtcaccg aaactgataa agatggtaat    3180
gagagcaagg tggtcaagtt tcgttatttc accaatgagg gcgtcatggc taagggtctg   3240
accgtcattg acggtagcac ccagtacttt ggtgaggatg gttttcaaac gaaggacaag   3300
ctggcgacct ataaaggtaa gacttattac ttcgaggcac acacgggcaa tgcgatcaaa   3360
aacacctggc gtaacatcga cggtaagtgg tatcacttcg atgagaatgg cgttgccgcg   3420
accggtgcac aagtgattaa cggtcaaaaa ctgtatttca acgaggatgg ctcgcaagtg   3480
aagggcggtg ttgttaagaa cgccgacggt acctacagca aatacaaaga gggcagcggt   3540
gagctggtta ccaacgagtt tttcacgacc gacggtaatg tgtggtacta tgctggtgcg   3600
gatggcaaga ctgtgaccgg tgctcaggtc attaatggtc agcacctgta ctttaaagaa   3660
gatggcagcc aggtgaaagg tggtgtggtg aaaaacgcgg acggtacgta cagcaagtat   3720
gacgccgcca ccggtgaacg cttgaccaat gagttcttta ccacgggcga taacaattgg   3780
tactatattg gttctaatgg taagaccgta accggtgaag tcaaaatcgg tgcggacacc   3840
tattactttg ccaaagatgg caaacaggtc aagggccaaa ccgtcaccgc aggcaatggc   3900
cgcatctcct attactacgg cgattctggt aagaaagcaa tcagcacgtg gatcgaaatt   3960
caaccgggta tctatgtcta ttttgataag acgggcatcg cgtacccacc gcgtgtgctg   4020
aattaa                                                              4026
```

<210> SEQ ID NO 30
<211> LENGTH: 1341
<212> TYPE: PRT
<213> ORGANISM: Streptococcus salivarius

<400> SEQUENCE: 30

```
Met Thr Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr His Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asn Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Glu Ala Lys Tyr Thr Ser Thr Asp Lys Gln Ala Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190
```

```
Glu Asp His Leu Gln Gly Gly Ala Leu Leu Tyr Val Asn Asp Ser Arg
            195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Gln Ala Glu Gln Leu Asn Gln Ile His Tyr
            260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asn Ala Asp Met Leu
            290                 295                 300

Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Asp Arg Thr Pro Ala Val Ser Pro Leu Tyr Asn Asn Thr Phe Asn
            370                 375                 380

Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Lys Lys Ser Asp Gly Phe Thr Ile Ser Asp Ser Glu Met
            450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr His Asp Thr Ile Val
            515                 520                 525

Asn Leu Met Lys Asn Arg Ile Lys Tyr Val Ser Gly Gly Gln Ala Gln
            530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
            595                 600                 605
```

```
Glu Ser Ala Lys Leu Asn Val Glu Met Gly Lys Ile His Ala Asn Gln
610                 615                 620
Lys Tyr Arg Ala Leu Ile Val Gly Thr Ala Asp Gly Ile Lys Asn Phe
625                 630                 635                 640
Thr Ser Asp Ala Glu Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
                660                 665                 670
Thr Phe Asp Met Ser Gly Phe Val Ala Val Trp Val Pro Val Gly Ala
                675                 680                 685
Ser Asp Asp Gln Asp Ile Arg Val Ala Pro Ser Thr Glu Ala Lys Lys
690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
                740                 745                 750
Lys Ser Trp Gly Val Thr Ser Phe Glu Met Ala Pro Gln Phe Val Ser
                755                 760                 765
Ala Asp Asp Gly Thr Phe Leu Asp Ser Val Ile Gln Asn Gly Tyr Ala
770                 775                 780
Phe Ala Asp Arg Tyr Asp Leu Ala Met Ser Lys Asn Asn Lys Tyr Gly
785                 790                 795                 800
Ser Lys Glu Asp Leu Arg Asp Ala Leu Lys Ala Leu His Lys Ala Gly
                805                 810                 815
Ile Gln Ala Ile Ala Asp Trp Val Pro Asp Gln Ile Tyr Gln Leu Pro
                820                 825                 830
Gly Lys Glu Val Val Thr Ala Thr Arg Thr Asp Gly Ala Gly Arg Lys
                835                 840                 845
Ile Ala Asp Ala Ile Ile Asp His Ser Leu Tyr Val Ala Asn Ser Lys
850                 855                 860
Ser Ser Gly Arg Asp Tyr Gln Ala Gln Tyr Gly Gly Glu Phe Leu Ala
865                 870                 875                 880
Glu Leu Lys Ala Lys Tyr Pro Lys Met Phe Thr Glu Asn Met Ile Ser
                885                 890                 895
Thr Gly Lys Pro Ile Asp Asp Ser Val Lys Leu Lys Gln Trp Lys Ala
                900                 905                 910
Lys Tyr Phe Asn Gly Thr Asn Val Leu Asp Arg Gly Val Gly Tyr Val
                915                 920                 925
Leu Ser Asp Glu Ala Thr Gly Lys Tyr Phe Thr Val Thr Lys Glu Gly
930                 935                 940
Asn Phe Ile Pro Leu Gln Leu Thr Gly Asn Glu Lys Ala Val Thr Gly
945                 950                 955                 960
Phe Ser Asn Asp Gly Lys Gly Ile Thr Tyr Phe Gly Ser Gly Asn
                965                 970                 975
Gln Ala Lys Ser Ala Phe Val Thr Phe Asn Gly Asn Thr Tyr Tyr Phe
                980                 985                 990
Asp Ala Arg Gly His Met Val Thr Asn Gly Glu Tyr Ser Pro Asn Gly
                995                 1000                1005
Lys Asp Val Tyr Arg Phe Leu Pro Asn Gly Ile Met Leu Ser Asn
                1010                1015                1020
Ala Phe Tyr Val Asp Ala Asn Gly Asn Thr Tyr Leu Tyr Asn Tyr
```

Lys Gly Gln Met Tyr Lys Gly Gly Tyr Thr Lys Phe Asp Val Thr
1040             1045             1050

Glu Thr Asp Lys Asp Gly Asn Glu Ser Lys Val Val Lys Phe Arg
1055             1060             1065

Tyr Phe Thr Asn Glu Gly Val Met Ala Lys Gly Leu Thr Val Ile
1070             1075             1080

Asp Gly Ser Thr Gln Tyr Phe Gly Glu Asp Gly Phe Gln Thr Lys
1085             1090             1095

Asp Lys Leu Ala Thr Tyr Lys Gly Lys Thr Tyr Tyr Phe Glu Ala
1100             1105             1110

His Thr Gly Asn Ala Ile Lys Asn Thr Trp Arg Asn Ile Asp Gly
1115             1120             1125

Lys Trp Tyr His Phe Asp Glu Asn Gly Val Ala Ala Thr Gly Ala
1130             1135             1140

Gln Val Ile Asn Gly Gln Lys Leu Tyr Phe Asn Glu Asp Gly Ser
1145             1150             1155

Gln Val Lys Gly Gly Val Val Lys Asn Ala Asp Gly Thr Tyr Ser
1160             1165             1170

Lys Tyr Lys Glu Gly Ser Gly Glu Leu Val Thr Asn Glu Phe Phe
1175             1180             1185

Thr Thr Asp Gly Asn Val Trp Tyr Tyr Ala Gly Ala Asp Gly Lys
1190             1195             1200

Thr Val Thr Gly Ala Gln Val Ile Asn Gly Gln His Leu Tyr Phe
1205             1210             1215

Lys Glu Asp Gly Ser Gln Val Lys Gly Gly Val Val Lys Asn Ala
1220             1225             1230

Asp Gly Thr Tyr Ser Lys Tyr Asp Ala Ala Thr Gly Glu Arg Leu
1235             1240             1245

Thr Asn Glu Phe Phe Thr Thr Gly Asp Asn Asn Trp Tyr Tyr Ile
1250             1255             1260

Gly Ser Asn Gly Lys Thr Val Thr Gly Glu Val Lys Ile Gly Ala
1265             1270             1275

Asp Thr Tyr Tyr Phe Ala Lys Asp Gly Lys Gln Val Lys Gly Gln
1280             1285             1290

Thr Val Thr Ala Gly Asn Gly Arg Ile Ser Tyr Tyr Tyr Gly Asp
1295             1300             1305

Ser Gly Lys Lys Ala Ile Ser Thr Trp Ile Glu Ile Gln Pro Gly
1310             1315             1320

Ile Tyr Val Tyr Phe Asp Lys Thr Gly Ile Ala Tyr Pro Pro Arg
1325             1330             1335

Val Leu Asn
1340

<210> SEQ ID NO 31
<211> LENGTH: 3918
<212> TYPE: DNA
<213> ORGANISM: Streptococcus salivarius

<400> SEQUENCE: 31
atgatcgacg gcaaacagta ttatgtagag aacggtgtgg ttaagaaaaa tgcggcaatt        60
gaactggatg gccgcctgta ctactttgat gagactggcg caatggtcga tcagagcaaa       120
ccgttgtatc gtgcggacgc gattccgaac aactctatct acgccgtgta caaccaagcg       180

```
tatgatacca gcagcaaatc cttcgagcat ttggataact tcctgaccgc ggatagctgg    240
tatcgcccga acagattct gaaggacggt aaaaactgga ccgcaagcac tgagaaagac     300
tatcgtcctc tgctgatgac ctggtggccg acaaggtga cccaggtgaa ttacctgaac     360
tatatgtctc aacagggttt tggtaacaaa acgtacacca cggatatgat gagctacgac    420
ctggcggctg cggcagaaac ggtgcagcgt ggcatcgaag agcgtatcgg tcgcgagggt    480
aacaccacgt ggctgcgcca gctgatgagc gatttcatca aaacccagcc gggttggaat    540
agcgagagcg aggacaatct gctggttggt aaggaccatc tgcaaggtgg tgcgctgacc    600
tttctgaaca atagcgcaac gagccacgcg aatagcgact tcgtctgat gaaccgtacc     660
ccgaccaatc agaccggtac ccgtaaatac cacatcgatc gtagcaatgg cggctatgag    720
ctgctgctgg ctaacgacat tgataatagc aatccggcag ttcaagcaga gcaactgaat    780
tggctgcact acattatgaa tattggcagc atcttgggta atgacccgag cgcgaatttt    840
gacggtgttc gtatcgatgc ggtggataat gtggacgcgg atttgctgca aatcgcgtct    900
gattacttca agagaagta ccgtgtcgcg gacaacgagg caaacgcgat tgcccacctg     960
agcattctgg aagcgtggag ctataatgat catcagtaca acaaggacac gaagggcgca   1020
cagctgtcca tcgataaccc gctgcgcgaa accctgctga ctaccttcct gcgtaaaagc   1080
aattatcgtg gtagcttgga gcgcgttatt accaactccc tgaataaccg ctctagcgag   1140
caaaagcaca ctccgcgcga cgcgaactac atctttgtac gtgcgcatga cagcgaagtt   1200
caagacgtgc tggcgaatat cattagcaaa cagatcaacc caagacgga tggcttcacg    1260
ttcaccatgg atgaactgaa gcaggcgttc gagatctaca atgcggatat tgcgaaggcg   1320
gacaagaagt ataccccaata caacattccg gcagcttacg caaccatgct gacgaacaag   1380
gatagcatta cccgcgttta ctacggcgac ctgtttacgg atgacggtca gtatatggcc   1440
gagaaatccc cgtactataa cgcaattgac gctctgctgc gtgcgcgcat taagtacgtc   1500
gcgggtggtc aggacatgaa ggtgactaaa ctgaatggtt atgagattat gagcagcgtg   1560
cgttatggta aaggtgcaga agaggctaac cagctgggta cggcagaaac ccgcaatcaa   1620
ggtatgctgg ttctgacggc taaccgtccg gacatgaaac tgggtgcaaa cgatcgcctg   1680
gtcgtgaata tgggcgctgc ccacaaaaac caggcctacc gcccgttgct gttgtccaaa   1740
tctactggcc tggcgacgta tctgaaagat agcgacgttc cggcaggcct ggtgcgttat   1800
accgataacc agggtaatct gacctttacg gcggacgata ttgcaggcca tagcacggtt   1860
gaagtgagcg gttacttggc ggtctgggtt ccggtcggcg cgagcgagaa ccaggacgcg   1920
cgcacgaagg ccagctctac caagaagggc gagcaagttt tcgaatctag cgccgctctg   1980
gacagccagg ttatctacga aggtttctcc aatttccaag attttgtcaa gaccccgagc   2040
cagtacacca accgcgtgat cgcgcaaaat gcgaagctgt ttaaagaatg gggcatcact   2100
agctttgagt tcgcgcctca gtatgtttct agccaagacg gcacctttt ggatagcatc    2160
attgaaaacg gctacgcgtt cgaggatcgt tacgatatcg caatgagcaa gaacaataag   2220
tatggcagcc tgaaagattt gatggacgca ctgcgtgcgt tgcatgcgga aggcatcagc   2280
gcaatcgccg attgggtccc ggaccaaatc tataatctgc cgggtaaaga agttgtcacg   2340
gcgagccgta ccaacagcta tggtaccccg cgtccgaatg cggaaatcta caatagcctg   2400
tacgctgcta aaacgcgcac gttcggtaat gacttccagg gtaagtatgg tggcgcattt   2460
ctggacgaac tgaaagcaaa gtacccggcc atctttgagc gtgttcaaat cagcaacggt   2520
cgtaaaattga ccacgaatga gaagattacc cagtggagcg ccaaatactt taatggtagc   2580
```

```
aatattcagg gcacgggtgc gcgttacgtt ttgcaggaca acgctaccaa tcagtacttt    2640
agcgttaagg cgggtcagac tttcctgccg aagcagatga ccgaaattac cggcagcggt    2700
ttccgtcgtg tcggtgacga tgtccaatat ctgagcattg gtggttatct ggcgaagaat    2760
acctttatcc aggtcggtgc gaatcagtgg tattattttg acaaaaacgg caatatggtt    2820
acgggtgaac aggtgatcga tggtaaaaag tacttcttct tggataacgg tctgcaactg    2880
cgtcatgttc tgcgccaggg ctccgatggt cacgtctatt actatgaccc taaaggtgtg    2940
caagcgttca atggtttcta cgactttgca ggccctcgcc aagacgttcg ttacttcgat    3000
ggcaatggtc agatgtatcg cggcctgcac gatatgtacg gtacgacctt ttacttcgac    3060
gagaaaaccg gcatccaagc aaaagacaag ttcattcgct tcgcagacgg tcgtacccgt    3120
tacttcattc cggacaccgg taatctggca gtgaatcgtt tcgcccaaaa cccggagaac    3180
aaagcctggt attacctgga tagcaacggt tacgctgtca ccggcttgca gacgattaat    3240
ggcaagcagt attactttga caacgaaggc cgtcaggtta aggccacttt tgtgaccatt    3300
aacaaccagc gttactttct ggatggtgac tcgggcgaga tcgcgccatc gcgtttcgtt    3360
accgagaaca acaagtggta ctacgtcgac ggtaatggta agctggtcaa gggtgcacag    3420
gtgattaacg gtaaccacta ctacttcaat aacgactata gccaggtgaa gggtgcatgg    3480
gcgaacggtc gttactacga tggcgacagc ggtcaagcgg tcagcaacca gtttattcaa    3540
attgcggcga ccaatgggc atatctgaat caagatggcc acaaggtcac gggtctgcaa    3600
aacatcaaca ataaagtgta ctattttggc tctaatggcg cgcaagttaa gggtaaactg    3660
ctgaccgtgc aaggcaagaa atgctacttt gacgcccaca ccggtgagca agtcgttaat    3720
cgcttcgtgg aagctgcccg tggttgctgg tactatttca attccgctgg ccaggccgtt    3780
accggccaac aagtcatcaa cggtaagcag ttgtattttg atggttctgg tcgtcaagtc    3840
aaaggccgtt atgtgtacgt gggtggtaaa cgtttgttct gtgatgcgaa aacgggcgag    3900
ctgcgtcaac gccgttaa                                                   3918
```

<210> SEQ ID NO 32
<211> LENGTH: 1305
<212> TYPE: PRT
<213> ORGANISM: Streptococcus salivarius

<400> SEQUENCE: 32

```
Met Ile Asp Gly Lys Gln Tyr Tyr Val Glu Asn Gly Val Val Lys Lys
1               5                   10                  15

Asn Ala Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
        35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65                  70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
        115                 120                 125
```

```
Asn Lys Thr Tyr Thr Thr Asp Met Met Ser Tyr Asp Leu Ala Ala
    130                 135                 140
Ala Glu Thr Val Gln Arg Gly Ile Glu Arg Ile Gly Arg Glu Gly
145                 150                 155                 160
Asn Thr Thr Trp Leu Arg Gln Leu Met Ser Asp Phe Ile Lys Thr Gln
                165                 170                 175
Pro Gly Trp Asn Ser Glu Ser Glu Asp Asn Leu Leu Val Gly Lys Asp
                180                 185                 190
His Leu Gln Gly Gly Ala Leu Thr Phe Leu Asn Asn Ser Ala Thr Ser
                195                 200                 205
His Ala Asn Ser Asp Phe Arg Leu Met Asn Arg Thr Pro Thr Asn Gln
    210                 215                 220
Thr Gly Thr Arg Lys Tyr His Ile Asp Arg Ser Asn Gly Gly Tyr Glu
225                 230                 235                 240
Leu Leu Leu Ala Asn Asp Ile Asp Asn Ser Asn Pro Ala Val Gln Ala
                245                 250                 255
Glu Gln Leu Asn Trp Leu His Tyr Ile Met Asn Ile Gly Ser Ile Leu
                260                 265                 270
Gly Asn Asp Pro Ser Ala Asn Phe Asp Gly Val Arg Ile Asp Ala Val
    275                 280                 285
Asp Asn Val Asp Ala Asp Leu Leu Gln Ile Ala Ser Asp Tyr Phe Lys
290                 295                 300
Glu Lys Tyr Arg Val Ala Asp Asn Glu Ala Asn Ala Ile Ala His Leu
305                 310                 315                 320
Ser Ile Leu Glu Ala Trp Ser Tyr Asn Asp His Gln Tyr Asn Lys Asp
                325                 330                 335
Thr Lys Gly Ala Gln Leu Ser Ile Asp Asn Pro Leu Arg Glu Thr Leu
                340                 345                 350
Leu Thr Thr Phe Leu Arg Lys Ser Asn Tyr Arg Gly Ser Leu Glu Arg
                355                 360                 365
Val Ile Thr Asn Ser Leu Asn Asn Arg Ser Ser Glu Gln Lys His Thr
                370                 375                 380
Pro Arg Asp Ala Asn Tyr Ile Phe Val Arg Ala His Asp Ser Glu Val
385                 390                 395                 400
Gln Asp Val Leu Ala Asn Ile Ile Ser Lys Gln Ile Asn Pro Lys Thr
                405                 410                 415
Asp Gly Phe Thr Phe Thr Met Asp Glu Leu Lys Gln Ala Phe Glu Ile
                420                 425                 430
Tyr Asn Ala Asp Ile Ala Lys Ala Asp Lys Lys Tyr Thr Gln Tyr Asn
    435                 440                 445
Ile Pro Ala Ala Tyr Ala Thr Met Leu Thr Asn Lys Asp Ser Ile Thr
450                 455                 460
Arg Val Tyr Tyr Gly Asp Leu Phe Thr Asp Asp Gly Gln Tyr Met Ala
465                 470                 475                 480
Glu Lys Ser Pro Tyr Tyr Asn Ala Ile Asp Ala Leu Leu Arg Ala Arg
                485                 490                 495
Ile Lys Tyr Val Ala Gly Gly Gln Asp Met Lys Val Thr Lys Leu Asn
                500                 505                 510
Gly Tyr Glu Ile Met Ser Ser Val Arg Tyr Gly Lys Gly Ala Glu Glu
                515                 520                 525
Ala Asn Gln Leu Gly Thr Ala Glu Thr Arg Asn Gln Gly Met Leu Val
    530                 535                 540
Leu Thr Ala Asn Arg Pro Asp Met Lys Leu Gly Ala Asn Asp Arg Leu
```

```
           545                 550                 555                 560
       Val Val Asn Met Gly Ala Ala His Lys Asn Gln Ala Tyr Arg Pro Leu
                       565                 570                 575

Leu Leu Ser Lys Ser Thr Gly Leu Ala Thr Tyr Leu Lys Asp Ser Asp
                       580                 585                 590

Val Pro Ala Gly Leu Val Arg Tyr Thr Asp Asn Gln Gly Asn Leu Thr
                       595                 600                 605

Phe Thr Ala Asp Asp Ile Ala Gly His Ser Thr Val Glu Val Ser Gly
                       610                 615                 620

Tyr Leu Ala Val Trp Val Pro Val Gly Ala Ser Glu Asn Gln Asp Ala
       625                 630                 635                 640

Arg Thr Lys Ala Ser Ser Thr Lys Lys Gly Glu Gln Val Phe Glu Ser
                       645                 650                 655

Ser Ala Ala Leu Asp Ser Gln Val Ile Tyr Glu Gly Phe Ser Asn Phe
                       660                 665                 670

Gln Asp Phe Val Lys Thr Pro Ser Gln Tyr Thr Asn Arg Val Ile Ala
                       675                 680                 685

Gln Asn Ala Lys Leu Phe Lys Glu Trp Gly Ile Thr Ser Phe Glu Phe
                       690                 695                 700

Ala Pro Gln Tyr Val Ser Ser Gln Asp Gly Thr Phe Leu Asp Ser Ile
       705                 710                 715                 720

Ile Glu Asn Gly Tyr Ala Phe Glu Asp Arg Tyr Asp Ile Ala Met Ser
                       725                 730                 735

Lys Asn Asn Lys Tyr Gly Ser Leu Lys Asp Leu Met Asp Ala Leu Arg
                       740                 745                 750

Ala Leu His Ala Glu Gly Ile Ser Ala Ile Ala Asp Trp Val Pro Asp
                       755                 760                 765

Gln Ile Tyr Asn Leu Pro Gly Lys Glu Val Val Thr Ala Ser Arg Thr
                       770                 775                 780

Asn Ser Tyr Gly Thr Pro Arg Pro Asn Ala Glu Ile Tyr Asn Ser Leu
       785                 790                 795                 800

Tyr Ala Ala Lys Thr Arg Thr Phe Gly Asn Asp Phe Gln Gly Lys Tyr
                       805                 810                 815

Gly Gly Ala Phe Leu Asp Glu Leu Lys Ala Lys Tyr Pro Ala Ile Phe
                       820                 825                 830

Glu Arg Val Gln Ile Ser Asn Gly Arg Lys Leu Thr Thr Asn Glu Lys
                       835                 840                 845

Ile Thr Gln Trp Ser Ala Lys Tyr Phe Asn Gly Ser Asn Ile Gln Gly
       850                 855                 860

Thr Gly Ala Arg Tyr Val Leu Gln Asp Asn Ala Thr Asn Gln Tyr Phe
       865                 870                 875                 880

Ser Val Lys Ala Gly Gln Thr Phe Leu Pro Lys Gln Met Thr Glu Ile
                       885                 890                 895

Thr Gly Ser Gly Phe Arg Arg Val Gly Asp Asp Val Gln Tyr Leu Ser
                       900                 905                 910

Ile Gly Gly Tyr Leu Ala Lys Asn Thr Phe Ile Gln Val Gly Ala Asn
                       915                 920                 925

Gln Trp Tyr Tyr Phe Asp Lys Asn Gly Asn Met Val Thr Gly Glu Gln
                       930                 935                 940

Val Ile Asp Gly Lys Lys Tyr Phe Phe Leu Asp Asn Gly Leu Gln Leu
       945                 950                 955                 960

Arg His Val Leu Arg Gln Gly Ser Asp Gly His Val Tyr Tyr Tyr Asp
                       965                 970                 975
```

```
Pro Lys Gly Val Gln Ala Phe Asn Gly Phe Tyr Asp Phe Ala Gly Pro
            980                 985                 990

Arg Gln Asp Val Arg Tyr Phe Asp  Gly Asn Gly Gln Met  Tyr Arg Gly
        995                 1000                1005

Leu His Asp Met Tyr Gly Thr  Thr Phe Tyr Phe Asp  Glu Lys Thr
    1010                1015                1020

Gly Ile Gln Ala Lys Asp Lys  Phe Ile Arg Phe Ala  Asp Gly Arg
    1025                1030                1035

Thr Arg Tyr Phe Ile Pro Asp  Thr Gly Asn Leu Ala  Val Asn Arg
    1040                1045                1050

Phe Ala Gln Asn Pro Glu Asn  Lys Ala Trp Tyr Tyr  Leu Asp Ser
    1055                1060                1065

Asn Gly Tyr Ala Val Thr Gly  Leu Gln Thr Ile Asn  Gly Lys Gln
    1070                1075                1080

Tyr Tyr Phe Asp Asn Glu Gly  Arg Gln Val Lys Gly  His Phe Val
    1085                1090                1095

Thr Ile Asn Asn Gln Arg Tyr  Phe Leu Asp Gly Asp  Ser Gly Glu
    1100                1105                1110

Ile Ala Pro Ser Arg Phe Val  Thr Glu Asn Asn Lys  Trp Tyr Tyr
    1115                1120                1125

Val Asp Gly Asn Gly Lys Leu  Val Lys Gly Ala Gln  Val Ile Asn
    1130                1135                1140

Gly Asn His Tyr Tyr Phe Asn  Asn Asp Tyr Ser Gln  Val Lys Gly
    1145                1150                1155

Ala Trp Ala Asn Gly Arg Tyr  Tyr Asp Gly Asp Ser  Gly Gln Ala
    1160                1165                1170

Val Ser Asn Gln Phe Ile Gln  Ile Ala Ala Asn Gln  Trp Ala Tyr
    1175                1180                1185

Leu Asn Gln Asp Gly His Lys  Val Thr Gly Leu Gln  Asn Ile Asn
    1190                1195                1200

Asn Lys Val Tyr Tyr Phe Gly  Ser Asn Gly Ala Gln  Val Lys Gly
    1205                1210                1215

Lys Leu Leu Thr Val Gln Gly  Lys Lys Cys Tyr Phe  Asp Ala His
    1220                1225                1230

Thr Gly Glu Gln Val Val Asn  Arg Phe Val Glu Ala  Ala Arg Gly
    1235                1240                1245

Cys Trp Tyr Tyr Phe Asn Ser  Ala Gly Gln Ala Val  Thr Gly Gln
    1250                1255                1260

Gln Val Ile Asn Gly Lys Gln  Leu Tyr Phe Asp Gly  Ser Gly Arg
    1265                1270                1275

Gln Val Lys Gly Arg Tyr Val  Tyr Val Gly Gly Lys  Arg Leu Phe
    1280                1285                1290

Cys Asp Ala Lys Thr Gly Glu  Leu Arg Gln Arg Arg
    1295                1300                1305

<210> SEQ ID NO 33
<211> LENGTH: 4026
<212> TYPE: DNA
<213> ORGANISM: Streptococcus salivarius

<400> SEQUENCE: 33
atgatcgacg gcaaatacta ctatgtaaac gaggacggca gccacaaaga gaatttcgcg      60
attacggtaa acggtcagct gctgtacttt ggtaaggacg tgctctctga gagcagctcc     120
```

-continued

```
acgtacagct ttaccccggg tacgaccaat attgtcgatg gcttcagcat taacaaccgt      180
gcgtatgaca gcagcgaggc atcctttgag ctgatcgatg gttatttgac cgcggatagc      240
tggtatcgtc cggcgagcat cattaaggac ggcgttacgt ggcaggcctc gaccgcagaa      300
gattttcgtc cgctgctgat ggcttggtgg ccgaatgttg acacccaggt gaattatctg      360
aattacatgt ccaaggtttt caacctggat gcaaagtaca ccagcaccga caagcaggaa      420
accctgaacg tggctgcgaa agatatccaa gtcaagattg agcaaaagat tcaggcagag      480
aaatctaccc agtggctgcg tgaaacgatt agcgcgtttg ttaaaactca gccgcaatgg      540
aataaagaaa cggaaaacta ttccaagggt ggtggcgagg accatctgca aggcggtgcc      600
ctgttgtacg ttaacgattc gcgcaccccg tgggcgaact cgaactatcg cttgctgaac      660
cataccgcta ccaatcaaaa aggcactatt gacaaatctg tcctggacga gcagagcgac      720
ccgaaccaca tgggcggttt cgattttctg ctggcgaacg acgtcgacct gagcaacccg      780
gtggtgcagg ccgaacaact gaaccagatt cactacctga tgaattgggg tagcatcgtg      840
atgggtgata aagatgcgaa ctttgacggc attcgtgtcg atgcggtcga taacgtggac      900
gccgacatgt tgcagctgta cacgaactac tttcgtgagt actacggcgt taacaagagc      960
gaagcaaatg ccctggcgca tatcagcgtt ctggaagcgt ggagcctgaa tgacaatcac     1020
tataacgata agacggacgg tgcggccctg gcaatggaga ataaacaacg tctggcgctg     1080
ctgttcagcc tggcgaaacc gatcaaagag cgtacgccgg ctgtgagccc actgtataac     1140
aacaccttca atactacgca gcgtgacgag aaaacggact ggattaacaa agacggtagc     1200
aaagcgtata cgaggatgg taccgtcaag caatcgacca ttggtaagta caatgagaag     1260
tatggcgacg caagcggtaa ttacgtgttc attcgtgccc acgacaacaa tgttcaagac     1320
atcatcgccg aaatcatcaa gaaagagatc aaccctaaga gcgacggttt caccatcacc     1380
gacgcagaga tgaagaaggc ctttgaaatc tacaacaagg acatgttgag cagcgataag     1440
aagtatactc tgaacaacat tccggctgcg tacgcggtga tgttgcagaa tatggaaacc     1500
atcacgcgtg tttactatgg tgatctgtat accgataatg caactacat ggaaacgaaa      1560 agcccgtact atgacaccat tgttaatctg atgaagaatc gcatcaagta tgtgtctggc     1620
ggtcaagcgc agcgttctta ctggctgccg accgatggta agatggacaa tagcgatgtg     1680
gaactgtacc gcaccaacga ggtatacgct tctgtgcgct atggtaaaga cattatgacc     1740
gccgatgata ccgagggttc caagtactcc cgtacgagcg gccaagttac cttggtggca     1800
aacaacccga aattgaccct ggaccaaagc gcgaaactga agtggagat gggtaagatc     1860 cacgcaaatc aaaagtaccg tgcactgatt gtcggtaccg ccgacggtat caagaatttc     1920
accagcgatg cggatgcgat tgcagcaggc tatgttaaag agactgatag caatggtgtg     1980
ctgacgtttg gtgcgaacga cattaaaggc tatgaaacgt ttgacatgag cggtttcgtt     2040
gcggtgtggg tgcctgtggg tgctagcgat gatcaggata tccgtgtcgc gccgagcacc     2100
gaggcaaaga aagaaggtga gctgacgttg aaagcgaccg aggcctatga cagccagttg     2160
atttacgaag gtttcagcaa tttccaaacc attccagacg gttccgatcc gagcgtctac     2220
accaatcgca aaatcgcgga aaacgttgat ctgttcaaaa gctggggtgt gaccagcttc     2280
gaaatggcac cgcaattcgt tagcgcggac gatggtacgt tcttggacag cgttatccaa     2340
aatggctatg cgttcgccga tcgttatgac ttggcgatga gcaaaaacaa caaatacggc     2400
agcaaagagg atctgcgcga cgccctgaaa gcgctgcata agcgggtat tcaagccatc      2460 gctgactggg ttccggacca gatctaccag ctgccgggta agaagtcgt taccgcgacc      2520
```

```
cgcaccgatg gcgctggccg taagatcgcg gatgcaatta tcgatcatag cttgtatgtg    2580
gccaatacta aaagctccgg taaggattac caggcgaaat atggtggtga atttctggct    2640
gagctgaagg ccaaataccc ggagatgttc aaggtcaaca tgattagcac cggcaaacct    2700
attgatgact ctgtcaaatt gaaacaatgg aaggcagagt atttcaatgg cactaacgtc    2760
ctggaacgtg gtgttggtta cgtgctgagc gacgaggcga ccggtaaata cttcaccgtt    2820
acgaaggacg gcaatttcat cccgctgcaa ctgaccggta atgagaaggt tgtgacgggt    2880 tttctaatg acggtaaggg cattacctac ttcggtacct cgggtaccca ggcaaagagc    2940
gcattcgtga cgtttaacgg taacacctac tactttgatg cacgcggcca catggtgacg    3000
aacggcgagt acagcccgaa cggcaaggat gtttatcgct tcctgccgaa tggcatcatg    3060
ctgtccaatg cgttttacgt cgatgcaaat ggtaatactt acctgtacaa cagcaagggt    3120
cagatgtata agggcggtta taccaagttc gacgttactg aaacggacaa ggacggtaaa    3180
gagagcaaag tagtgaagtt tcgttatttc acgaacgaag cgtcatggc gaaaggtgtc    3240 accgttattg atggctttac ccagtatttc ggtgaagatg ctttcaagc gaaggacaag    3300 ctggtgacct ttaagggcaa aacctactat tttgacgcgc acacgggcaa cgccatcaag    3360
aacacctggc gtaatatcga cggtaagtgg tatcattttg atgcgaacgg tgtggcggcg    3420
accggcgcac aggtcattaa tggtcaaaaa ctgtacttta atgaggacgg tagccaagtc    3480
aaaggtggcg tcgtcaagaa tgcagatggc acctatagca aatacaaaga gggctccggt    3540
gagctggtta ccaacgagtt ctttaccacg gatggtaacg tctggtacta tgctggtgcg    3600
aatggcaaga ccgttaccgg tgcacaggtt atcaacggcc agcacctgta cttcaatgcg    3660
gatggctctc aagtgaaggg cggtgtcgtc aaaaacgcgg acggtacgta ctccaaatac    3720
gatgccgcga ccggtgaacg tctgaccaat gagttttta cgactggtga caacaattgg    3780
tactacatcg gcgccaacgg taagacggtt acgggcgaag tgaaaattgg cgacgatacg    3840
tactacttcg caaaagatgg taaacaggtg aaaggtcaga cggtttccgc tggtaatggc    3900
cgcatcagct actattacgg tgactctggt aaacgtgcgg ttagcacgtg ggttgaaatt    3960
caaccgggcg tgtatgtcta ttttgataag aatggcctgg catatccacc gcgcgttttg    4020
aattaa                                                               4026
```

<210> SEQ ID NO 34
<211> LENGTH: 1341
<212> TYPE: PRT
<213> ORGANISM: Streptococcus salivarius

<400> SEQUENCE: 34

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95
```

```
Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
            115                 120                 125

Leu Asp Ala Lys Tyr Thr Ser Thr Asp Lys Gln Glu Thr Leu Asn Val
            130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
            165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
            195                 200                 205

Thr Pro Trp Ala Asn Ser Asn Tyr Arg Leu Leu Asn His Thr Ala Thr
            210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
            245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
            290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
            325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
            450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asn Gly Asn Tyr Met Glu Thr Lys Ser Pro Tyr Tyr Asp Thr Ile Val
```

```
            515                 520                 525
Asn Leu Met Lys Asn Arg Ile Lys Tyr Val Ser Gly Gly Gln Ala Gln
530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Ala Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Lys Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Thr Val Thr Lys Asp Gly
    930                 935                 940
```

```
Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
                980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asn Thr Trp Arg Asn Ile Asp Gly
    1115                1120                1125

Lys Trp Tyr His Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Thr Val Thr Gly Glu Val Lys Ile Gly Asp
    1265                1270                1275

Asp Thr Tyr Tyr Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Val Glu Ile Gln Pro Gly
    1310                1315                1320

Val Tyr Val Tyr Phe Asp Lys Asn Gly Leu Ala Tyr Pro Pro Arg
    1325                1330                1335
```

Val Leu Asn
   1340

<210> SEQ ID NO 35
<211> LENGTH: 3996
<212> TYPE: DNA
<213> ORGANISM: Streptococcus salivarius

<400> SEQUENCE: 35

```
atggtcgacg gcaaatacta ctacgtgaaa gaggatggca gctacaaaac gaacttcgca      60
gtttccgtca acggccaact gctgtatttc ggcaaggatg gcgcgctgac gtccaccagc     120
acccatagct ttacgccagg cactaccaat ctggttgatg cgttcagctc ccataaccgc     180
gcctacgact ccaaaaagga gagcttcgaa ctggtggatg gttatctgac gccgaactct     240
tggtatcgtc cggtcactat cctggaaaat ggtgaaaaat ggcgtgttag caccgagaag     300
gactttcgcc cgttgttgat ggcctggtgg ccggatgtcg acacgcaagt tgcctatctg     360
aacacctttt ctaaacactt caacctgaac gcgacgtact ctacttctca gagccaaagc     420
gagctgaatg cggcagctaa aaccatccaa atcaaaatcg aacaggagat tagcgcgaaa     480
aagagcacgg agtggctgcg ccaggcaatt gagtcctttg tcaaggagca ggatcagtgg     540
aacaccacga ccgagaacta cacctggcg gatcatttgc agggcggtgc gctgctgtat     600
gtgaacaatg acaagacgcc gtgggcgaac agcgactatc gtctgctgaa ccgtactccg     660
agcaaccagg acggcagcct gaacggtact ggccgttatc tgggtggtta cgagtttctg     720
ctggcgaatg acgtggacaa tagcaatccg gtggtccagg ctgagcagct gaatcaaatt     780
cactatctgg tcaactgggg cagcattgtc atgggtgaca aggacgcgaa tttcgacggc     840
attcgtgttg acgccgttga caatgtggac gccgatctgt tgcaggttta cacgaactac     900
ttccgtgcgg cgtttggtgt ggataaaagc gaagcgaacg cactggccca catcagcatt     960
ctggaggcgt gggatctgaa cgacaatgcg tacaaccaga acatgacgg tgcggccttg    1020
gcaatggata caacctgcg ttacgcgatc atgggtgcac tgtatggtag cggtagctcg    1080
ctgaaagatc tgattaccag cagcctgacc gaccgtacga ataactccaa atatggtgat    1140
acccaagcaa actacatctt cgcccgtgct catgataatc tggtccagga cattattcgt    1200
gacatcgtgc agaaagagat caatccgaag agcgacggct acacgatgac cgatgcggag    1260
ctgaagcgtg cgtttgaaat ctacaacgag atatgaaaa aggccgaaaa acgctacact    1320
atcaacaaca tcccggcagc gtatgcactg attttgcaga acatggaaca ggttactcgt    1380
gtgtactacg tgatctgta taccgacaat ggtcagtaca tggcgaccaa aagcccgtac    1440
tacgacgcga ttacgaccct gctgaaaaat cgtatgaagt atgtgagcgg cggtcagagc    1500
atgaaagttg acactttcaa cggtaaagaa ttctgtcgt ctgttcgtta cggtaaggac    1560
atcatgaccg cggaccaaac gaccggtgtc gcagaaacca gcaagcacag cggcatgctg    1620
accctgatcg ccaataacca ggattttttct ctgggcgatg gcaccttgaa agtgaacatg    1680
ggcaagctgc acgcgaacca ggcgtatcgc ccgctgctgc tgggcacgga taagggcatc    1740
gttacctatg aaaatgacgc ggctgcggca ggcaaaatca gtacacgga cgcagagggt    1800
aatctgacct tcagcggtga cgagatcaag ggctatcgca ccgtggacat gcgcggctac    1860
ctgggtgtgt gggtcccggt cggcgcaccg gacaatcaag acattcgcgt taagggtagc    1920
gataagaaac tggacaagac tttcagcgca accgaagctc tggatagcca ggtgatttac    1980
gaaggtttta gcaactttca ggacttcgtg gaaaaagaca gccagtacac caacaagctg    2040
```

-continued

```
attgcggaaa acgcggaact gtttaagagc tggggtatta ctagctttga aatggcccct    2100
cagtttgtca gcgcagacga tcgtaccttc ctggatagcg ttatccaaaa cggttatgcg    2160
tttaccgatc gttacgatct ggccatgtct aagaataaca agtatggcag caaagaagat    2220
ctgcgtgatg cgctgaaggc gctgcacaag cagggcattc aagcaattgc cgactgggtt    2280
ccggatcaac tgtaccaact gccgggtcaa gaggttgtca ccgctacccg tgcaaatagc    2340
tacggcaccc cgaaggccaa tgcctacatt aacaatacgc tgtatgttgc caatagcaag    2400
agcagcggta aagacttcca ggctcaatac ggtggcgagt cctggatgaa attgcagaag    2460
aagtacccgc agttgttcga ggatgtgatg atcagcacgg gtaaaaagat tgacccgagc    2520
gtgaaaatca agcagtggag cgccaaatac atgaatggca ccaacattct gggtcgtggc    2580
aaccgttacg ttctgtcgaa tgacgccacc ggtcgctatt atcaagtgac cgacaacggc    2640
attttcttgc cgaagccgct gacggatcag ggtggtaaga ccggcttcta ttacgatggt    2700
aagggcatgg cctatttcga caattccggc tttcaagcga aaatgcgtt catcaagtac    2760 gcgggtaact actactactt cgataaagag ggctatatgc tgacgggccg tcaagatatt    2820
gacagcaaga cgtatttctt tctgccgaat ggtatccaac tgcgtgatag catttaccaa    2880
caagatggca agtactacta ttttggtagc ttcggcgaac aatacaaaga cggttatttc    2940
gtctttgacg tgccaaaaga gggcaccagc gaaaccgagg ctaagttccg ctactttct    3000 ccgacgggtg agatggcagt gggttttgacc tatgcgggtg tggtctgca atactttgat    3060 gagaacggtt ccaggcgaa gggtacgaag tatgttacgc cggatggtaa gttgtatttc    3120
ttcgacaaga atagcggcaa cgcgtacacc aatcgttggg cggagatcga tggtatttgg    3180
tacgagttta atgaccaagg ttacgcgcag gcgaagaaag gtgagtttta caccacggat    3240
ggtagcacgt ggttttaccg cgacgcagca ggtaaaaacg ttaccggtgc cctgaccctg    3300
gacggtcacg agtattactt tcgtgcgaac ggtgcgcagg tgaaaggcga gttcgtcacc    3360
gaaaacggta agattagcta ttacaccgtt gataacggtt acaaggtaaa agacaagttc    3420
ttcgaagtca atggtaagtg gtatcacgct gataaggacg gtaatttggc gacgggtcgt    3480
cagaccatcg accatctgaa ttactacttc aacgcggacg gctcccaggt taagtccgat    3540
ttcttcactc tggatggtgg taaaacctgg tattatgcca agacaacgg tgagattgtg    3600 accggtgcgt actcggtgcg tggcaagaac tattacttca agaggacgg tagccaagtt    3660 aagggcgatt tcgtcaaaaa tgcggacggt tccctgagct attatgacaa ggatagcggc    3720
gaacgtctga caaccgtttc cttgaccacg ggtaacaatg tctggtatta ctttaaggat    3780
ggtaaagcgg tcacgggtcg ccagaacatc gacggtaagg agtactactt tgatcacctg    3840
ggtcgtcaag tcaaaggctc cccgattagc actccgaagg gcgttgagta ttatgagtct    3900
gtgctgggtg agcgtgtcac caacacctgg atcaccttcc aagacggcaa aaccgtgttc    3960
tttgatgaaa atggctacgc ggactttgat aagtaa                              3996
```

```
<210> SEQ ID NO 36
<211> LENGTH: 1331
<212> TYPE: PRT
<213> ORGANISM: Streptococcus salivarius

<400> SEQUENCE: 36
```

```
Met Val Asp Gly Lys Tyr Tyr Val Lys Glu Asp Gly Ser Tyr Lys
1               5                   10                  15

Thr Asn Phe Ala Val Ser Val Asn Gly Gln Leu Leu Tyr Phe Gly Lys
            20                  25                  30
```

-continued

```
Asp Gly Ala Leu Thr Ser Thr Ser Thr His Ser Phe Thr Pro Gly Thr
        35                  40                  45
Thr Asn Leu Val Asp Ala Phe Ser Ser His Asn Arg Ala Tyr Asp Ser
 50                  55                  60
Lys Lys Glu Ser Phe Glu Leu Val Asp Gly Tyr Leu Thr Pro Asn Ser
 65                  70                  75                  80
Trp Tyr Arg Pro Val Thr Ile Leu Glu Asn Gly Glu Lys Trp Arg Val
                 85                  90                  95
Ser Thr Glu Lys Asp Phe Arg Pro Leu Leu Met Ala Trp Trp Pro Asp
                100                 105                 110
Val Asp Thr Gln Val Ala Tyr Leu Asn Thr Phe Ser Lys His Phe Asn
            115                 120                 125
Leu Asn Ala Thr Tyr Ser Thr Ser Gln Ser Gln Ser Glu Leu Asn Ala
            130                 135                 140
Ala Ala Lys Thr Ile Gln Ile Lys Ile Glu Gln Glu Ile Ser Ala Lys
145                 150                 155                 160
Lys Ser Thr Glu Trp Leu Arg Gln Ala Ile Glu Ser Phe Val Lys Glu
                165                 170                 175
Gln Asp Gln Trp Asn Thr Thr Thr Glu Asn Tyr Thr Leu Ala Asp His
            180                 185                 190
Leu Gln Gly Gly Ala Leu Leu Tyr Val Asn Asn Asp Lys Thr Pro Trp
            195                 200                 205
Ala Asn Ser Asp Tyr Arg Leu Leu Asn Arg Thr Pro Ser Asn Gln Asp
            210                 215                 220
Gly Ser Leu Asn Gly Thr Gly Arg Tyr Leu Gly Gly Tyr Glu Phe Leu
225                 230                 235                 240
Leu Ala Asn Asp Val Asp Asn Ser Asn Pro Val Val Gln Ala Glu Gln
                245                 250                 255
Leu Asn Gln Ile His Tyr Leu Val Asn Trp Gly Ser Ile Val Met Gly
            260                 265                 270
Asp Lys Asp Ala Asn Phe Asp Gly Ile Arg Val Asp Ala Val Asp Asn
            275                 280                 285
Val Asp Ala Asp Leu Leu Gln Val Tyr Thr Asn Tyr Phe Arg Ala Ala
            290                 295                 300
Phe Gly Val Asp Lys Ser Glu Ala Asn Ala Leu Ala His Ile Ser Ile
305                 310                 315                 320
Leu Glu Ala Trp Asp Leu Asn Asp Asn Ala Tyr Asn Gln Lys His Asp
                325                 330                 335
Gly Ala Ala Leu Ala Met Asp Asn Asn Leu Arg Tyr Ala Ile Met Gly
            340                 345                 350
Ala Leu Tyr Gly Ser Gly Ser Ser Leu Lys Asp Leu Ile Thr Ser Ser
            355                 360                 365
Leu Thr Asp Arg Thr Asn Asn Ser Lys Tyr Gly Asp Thr Gln Ala Asn
            370                 375                 380
Tyr Ile Phe Ala Arg Ala His Asp Asn Leu Val Gln Asp Ile Ile Arg
385                 390                 395                 400
Asp Ile Val Gln Lys Glu Ile Asn Pro Lys Ser Asp Gly Tyr Thr Met
                405                 410                 415
Thr Asp Ala Glu Leu Lys Arg Ala Phe Glu Ile Tyr Asn Glu Asp Met
            420                 425                 430
Lys Lys Ala Glu Lys Arg Tyr Thr Ile Asn Asn Ile Pro Ala Ala Tyr
            435                 440                 445
```

```
Ala Leu Ile Leu Gln Asn Met Glu Gln Val Thr Arg Val Tyr Tyr Gly
    450                 455                 460
Asp Leu Tyr Thr Asp Asn Gly Gln Tyr Met Ala Thr Lys Ser Pro Tyr
465                 470                 475                 480
Tyr Asp Ala Ile Thr Thr Leu Leu Lys Asn Arg Met Lys Tyr Val Ser
                485                 490                 495
Gly Gly Gln Ser Met Lys Val Asp Thr Phe Asn Gly Lys Glu Ile Leu
                500                 505                 510
Ser Ser Val Arg Tyr Gly Lys Asp Ile Met Thr Ala Asp Gln Thr Thr
            515                 520                 525
Gly Val Ala Glu Thr Ser Lys His Ser Gly Met Leu Thr Leu Ile Ala
530                 535                 540
Asn Asn Gln Asp Phe Ser Leu Gly Asp Gly Thr Leu Lys Val Asn Met
545                 550                 555                 560
Gly Lys Leu His Ala Asn Gln Ala Tyr Arg Pro Leu Leu Gly Thr
                565                 570                 575
Asp Lys Gly Ile Val Thr Tyr Glu Asn Asp Ala Ala Ala Gly Lys
                580                 585                 590
Ile Lys Tyr Thr Asp Ala Glu Gly Asn Leu Thr Phe Ser Gly Asp Glu
        595                 600                 605
Ile Lys Gly Tyr Arg Thr Val Asp Met Arg Gly Tyr Leu Gly Val Trp
        610                 615                 620
Val Pro Val Gly Ala Pro Asp Asn Gln Asp Ile Arg Val Lys Gly Ser
625                 630                 635                 640
Asp Lys Lys Leu Asp Lys Thr Phe Ser Ala Thr Glu Ala Leu Asp Ser
                645                 650                 655
Gln Val Ile Tyr Glu Gly Phe Ser Asn Phe Gln Asp Phe Val Glu Lys
                660                 665                 670
Asp Ser Gln Tyr Thr Asn Lys Leu Ile Ala Glu Asn Ala Glu Leu Phe
            675                 680                 685
Lys Ser Trp Gly Ile Thr Ser Phe Glu Met Ala Pro Gln Phe Val Ser
        690                 695                 700
Ala Asp Asp Arg Thr Phe Leu Asp Ser Val Ile Gln Asn Gly Tyr Ala
705                 710                 715                 720
Phe Thr Asp Arg Tyr Asp Leu Ala Met Ser Lys Asn Asn Lys Tyr Gly
                725                 730                 735
Ser Lys Glu Asp Leu Arg Asp Ala Leu Lys Ala Leu His Lys Gln Gly
                740                 745                 750
Ile Gln Ala Ile Ala Asp Trp Val Pro Asp Gln Leu Tyr Gln Leu Pro
            755                 760                 765
Gly Gln Glu Val Val Thr Ala Thr Arg Ala Asn Ser Tyr Gly Thr Pro
        770                 775                 780
Lys Ala Asn Ala Tyr Ile Asn Asn Thr Leu Tyr Val Ala Asn Ser Lys
785                 790                 795                 800
Ser Ser Gly Lys Asp Phe Gln Ala Gln Tyr Gly Gly Glu Phe Leu Asp
                805                 810                 815
Glu Leu Gln Lys Lys Tyr Pro Gln Leu Phe Glu Asp Val Met Ile Ser
            820                 825                 830
Thr Gly Lys Lys Ile Asp Pro Ser Val Lys Ile Lys Gln Trp Ser Ala
            835                 840                 845
Lys Tyr Met Asn Gly Thr Asn Ile Leu Gly Arg Gly Asn Arg Tyr Val
        850                 855                 860
Leu Ser Asn Asp Ala Thr Gly Arg Tyr Tyr Gln Val Thr Asp Asn Gly
```

-continued

```
              865                 870                 875                 880
        Ile Phe Leu Pro Lys Pro Leu Thr Asp Gln Gly Gly Lys Thr Gly Phe
                        885                 890                 895
        Tyr Tyr Asp Gly Lys Gly Met Ala Tyr Phe Asp Asn Ser Gly Phe Gln
                        900                 905                 910
        Ala Lys Asn Ala Phe Ile Lys Tyr Ala Gly Asn Tyr Tyr Tyr Phe Asp
                        915                 920                 925
        Lys Glu Gly Tyr Met Leu Thr Gly Arg Gln Asp Ile Asp Ser Lys Thr
                        930                 935                 940
        Tyr Phe Phe Leu Pro Asn Gly Ile Gln Leu Arg Asp Ser Ile Tyr Gln
        945                 950                 955                 960
        Gln Asp Gly Lys Tyr Tyr Phe Gly Ser Phe Gly Glu Gln Tyr Lys
                            965                 970                 975
        Asp Gly Tyr Phe Val Phe Asp Val Pro Lys Glu Gly Ser Glu Thr
                        980                 985                 990
        Glu Ala Lys Phe Arg Tyr Phe Ser Pro Thr Gly Glu Met Ala Val Gly
                        995                 1000                1005
        Leu Thr Tyr Ala Gly Gly Gly Leu Gln Tyr Phe Asp Glu Asn Gly
                1010                1015                1020
        Phe Gln Ala Lys Gly Thr Lys Tyr Val Thr Pro Asp Gly Lys Leu
                1025                1030                1035
        Tyr Phe Phe Asp Lys Asn Ser Gly Asn Ala Tyr Thr Asn Arg Trp
                1040                1045                1050
        Ala Glu Ile Asp Gly Ile Trp Tyr Glu Phe Asn Asp Gln Gly Tyr
                1055                1060                1065
        Ala Gln Ala Lys Lys Gly Glu Phe Tyr Thr Thr Asp Gly Ser Thr
                1070                1075                1080
        Trp Phe Tyr Arg Asp Ala Ala Gly Lys Asn Val Thr Gly Ala Leu
                1085                1090                1095
        Thr Leu Asp Gly His Glu Tyr Tyr Phe Arg Ala Asn Gly Ala Gln
                1100                1105                1110
        Val Lys Gly Glu Phe Val Thr Glu Asn Gly Lys Ile Ser Tyr Tyr
                1115                1120                1125
        Thr Val Asp Asn Gly Tyr Lys Val Lys Asp Lys Phe Phe Glu Val
                1130                1135                1140
        Asn Gly Lys Trp Tyr His Ala Asp Lys Asp Gly Asn Leu Ala Thr
                1145                1150                1155
        Gly Arg Gln Thr Ile Asp His Leu Asn Tyr Tyr Phe Asn Ala Asp
                1160                1165                1170
        Gly Ser Gln Val Lys Ser Asp Phe Phe Thr Leu Asp Gly Gly Lys
                1175                1180                1185
        Thr Trp Tyr Tyr Ala Lys Asp Asn Gly Glu Ile Val Thr Gly Ala
                1190                1195                1200
        Tyr Ser Val Arg Gly Lys Asn Tyr Tyr Phe Lys Glu Asp Gly Ser
                1205                1210                1215
        Gln Val Lys Gly Asp Phe Val Lys Asn Ala Asp Gly Ser Leu Ser
                1220                1225                1230
        Tyr Tyr Asp Lys Asp Ser Gly Glu Arg Leu Asn Asn Arg Phe Leu
                1235                1240                1245
        Thr Thr Gly Asn Asn Val Trp Tyr Tyr Phe Lys Asp Gly Lys Ala
                1250                1255                1260
        Val Thr Gly Arg Gln Asn Ile Asp Gly Lys Glu Tyr Tyr Phe Asp
                1265                1270                1275
```

```
His Leu Gly Arg Gln Val Lys Gly Ser Pro Ile Ser Thr Pro Lys
    1280                1285                1290

Gly Val Glu Tyr Tyr Glu Ser Val Leu Gly Glu Arg Val Thr Asn
    1295                1300                1305

Thr Trp Ile Thr Phe Gln Asp Gly Lys Thr Val Phe Phe Asp Glu
    1310                1315                1320

Asn Gly Tyr Ala Asp Phe Asp Lys
    1325                1330

<210> SEQ ID NO 37
<211> LENGTH: 3918
<212> TYPE: DNA
<213> ORGANISM: Streptococcus salivarius

<400> SEQUENCE: 37
atgattgacg gcaaacagta ttatgtagag aacggtgtgg ttaagaagaa tacggcgatt      60
gaactggatg gccgtctgta ttactttgac gaaaccggtg caatggttga tcaatctaag     120
ccgctgtatc gcgcggatgc aatcccgaac aactctatct acgcagttta caaccaggct     180
tacgacacca gcagcaagag ctttgaacac ctggacaact ttctgacggc cgatagctgg     240
taccgtccga agcagatttt gaaagacggc aagaattgga ccgcctcgac ggagaaggac     300
tatcgtcctt tgctgatgac gtggtggccg gataaagtca cgcaagtcaa ctacctgaac     360
tatatgtccc aacagggctt tggtaacaag acctacacca cggatatgat gagctacgac     420
ctggcggcag cggcggaaac ggttcagcgt ggcatcgaag agcgtattgg tcgtgagggt     480
aatacgacgt ggctgcgtca gttgatgagc gacttcatca aacccagcc gggctggaat      540 agcgagagcg aagataatct gctggtcggt aaggatcatc tgcaaggtgg tgcactgacg     600
tttctgaaca atagcaccac gagccatgcg aacagcgatt ccgcctgat gaatcgtacc      660 ccgacgaacc agaccggcac ccgcaaatac cacatcgatc gtagcaatgg tggctacgaa     720
ctgctgctgg cgaacgacat cgacaatagc aatccggccg tccaagcgga acagctgaac     780
tggctgcatt acatcatgaa catcggctct atcctgggca atgacccaag cgcgaatttt     840
gatggcgtcc gtatcgatgc agttgacaat gtggatgcgg acttgttgca aattgcgtct     900
gactacttta aggaaaagta ccgtgttgcc gataacgagg caaacgctat gcgcacctg      960 tcgattctgg aggcatggtc ctacaatgat catcaataca caaagacac gaaggggcgct    1020 caactgagca ttgataatcc gctgcgtgag actttgctga cgaccttcct gcgcaagtct    1080
aactaccgtg gttccctgga gcgtgtgatc accaactcgt tgaacaaccg tagcagcgaa    1140
cagaagcaca cgccgcgtga cgccaactac attttgtgc gtgctcacga cagcgaagtt    1200
caagcggtgc tggcaaacat catctctaaa cagatcaacc cgaaaaccga cggtttacc     1260 tttacgatgg atgagctgaa gcaggcgttt gagatttaca cgcagacat gcgtaaggcg    1320 gataagaagt acacgcagta caacattccg gcagcttacg ccaccatgct gaccaataag    1380
gatagcatca cccgtgtgta ctatggtgat tgtttaccg acgacggtca atacatggcg    1440
gagaaaagcc cgtactataa cgcaattgac gccctgctgc gtgctcgcat caaatacgtc    1500
gcgggtggtc aggacatgaa ggtgaccaaa ttgaacggct atgagatcat gtcctccgtt    1560
cgctacggta aggcgcaga ggaagctaat cagctgggca ccgcagaaac ccgcaatcaa     1620
ggcatgctgg tcctgaccgc gaatcgccca gacatgaagc tgggtacgaa tgatcgcctg    1680
gtcgtcaata tgggtgcagc ccacaagaat caggcgtatc gtccgctgct gctgtccaag    1740
```

```
tccaccggct tggcaaccta cctgaaagac agcgacgtcc ctgcgggcct ggtgcgttac    1800
acggacaatc aaggtaatct gaccttcacg gcggacgaca tcaccggcca tagcaccgta    1860
gaggtgagcg gttacctggc ggtttgggtg ccggtgggtg cgagcgagaa ccaagatgcg    1920
cgcacgaaag cgagcacgac gaaaaagggc gaacaagttt ttgaaagctc cgcagcgctg    1980
gatagccagg tcatctatga gggtttctcc aacttccagg attttgttaa gaccccttcc    2040
cagtacacga tcgcgttat cgcacagaac gcgaagcgct ttaaggagtg gggtatcacc      2100
agctttgagt tcgcgcctca atatgttagc agccaagacg gtacctttct ggatagcatt    2160
attgagaacg gctacgcgtt cgaggaccgt tacgatatcg cgatgagcaa aaacaacaag    2220
tacggcagcc tgaaggatct gatggacgcg ctgcgtgcac tgcacgcgga gggtatcagc    2280
gccattgctg actgggttcc ggaccaaatc tataacctgc cgggtaagga agttgtaacc    2340
gcaagccgca cgaatagcta cggtacgccg cgtccgaacg cggaaatcta taacagcctg    2400
tatgcggcga aaacgcgtac gtttggcaat gattttcagg gtaaatacgg tggcgcgttt    2460
ctggatgaac tgaaagcaaa gtacccggcg atcttcgagc gtgtgcaaat ttcgaatggt    2520
cgtaagctga ctaccaatga gaaaatcacg caatggagcg cgaagtactt taatggcagc    2580
aacattcaag gtaccggtgc gcgttacgtt ctgcaagata tgccacgaa ccagtatttc      2640
aacctgaagg ccggtcaaac ctttctgcca aagcagatga ccgagattac cgcaacgggc    2700
ttccgtcgtg tcggtgacaa agtgcaatac ctgtccacgt ccggctacct ggcgaagaat    2760
acctttatcc agattggtgc gaaccagtgg tattacttcg acaagaatgg caacatggtg    2820
accggtgagc aagtgattga tggtaaaaag tatttcttcc tggataacgg tctgcaactg    2880
cgtcatgtct tgcgtcaagg ttctgacggt cacgtgtatt actacgatcc gaaaggcgtc    2940
caggcgttta tggtttcta tgactttgcg ggtccgcgcc aagatgtccg ttatttcgac      3000
ggtaatggtc agatgtaccg tggtctgcat gatatgtatg gtaccacgtt ctactttgat    3060
gaaaagacgg gtatccaggc taaggataag tttatccgtt cgccgacgg ccgtacccgt      3120
tactttattc cggacaccgg caatttggct gtgaatcgct tcgctcagaa tccggaaaac    3180
aaggcgtggt actacctgga cagcaacggt tatgcagtga cgggtttgca gaccattaat    3240
ggcaaacaat actatttcga caacgagggc cgtcaggtca agggccactt cgttactatc    3300
aacaatcagc gctacttctt ggacggtgac tcgggtgaga tcgcacgtag ccgcttcgtg    3360
acggagaaca caaatggta ctatgtggat ggtaacggta aattggtcaa gggtgcacaa      3420
gtcatcaacg gtaaccacta ttacttcaat aatgattatt ctcaggtgaa aggtgcttgg    3480
gccaatggcc gctactacga cggcgatagc ggccaggcgg tcacgaatcg tttcgtgcag    3540
gtcggtgcaa accagtgggc ctatctgaat cagaacggtc agaaggttgt gggcttgcaa    3600
cacatcaatg gcaagctgta ctactttgaa ggcaacggtg tccaagcaaa aggcaagctg    3660
ctgacctata agggtaagaa atactacttc gatgctaaca gcggtgaggc agtcaccaac    3720
cgctttattc aaatctctcg cggtgtttgg tactatttca atgcgagcgg tcaagcagtg    3780
accggcgagc aagttatcaa tggtcaacac ctgtacttcg acgcaagcgg tcgccaggtt    3840
aaaggccgct atgtctggat taaaggccag cgccgttatt acgacgcgaa cactggtgcc    3900
tgggtacgta atcgttaa                                                  3918

<210> SEQ ID NO 38
<211> LENGTH: 1305
<212> TYPE: PRT
<213> ORGANISM: Streptococcus salivarius
```

<400> SEQUENCE: 38

```
Met Ile Asp Gly Lys Gln Tyr Tyr Val Glu Asn Gly Val Lys Lys
1               5                   10                  15

Asn Thr Ala Ile Glu Leu Asp Gly Arg Leu Tyr Tyr Phe Asp Glu Thr
            20                  25                  30

Gly Ala Met Val Asp Gln Ser Lys Pro Leu Tyr Arg Ala Asp Ala Ile
            35                  40                  45

Pro Asn Asn Ser Ile Tyr Ala Val Tyr Asn Gln Ala Tyr Asp Thr Ser
    50                  55                  60

Ser Lys Ser Phe Glu His Leu Asp Asn Phe Leu Thr Ala Asp Ser Trp
65              70                  75                  80

Tyr Arg Pro Lys Gln Ile Leu Lys Asp Gly Lys Asn Trp Thr Ala Ser
                85                  90                  95

Thr Glu Lys Asp Tyr Arg Pro Leu Leu Met Thr Trp Trp Pro Asp Lys
            100                 105                 110

Val Thr Gln Val Asn Tyr Leu Asn Tyr Met Ser Gln Gln Gly Phe Gly
            115                 120                 125

Asn Lys Thr Tyr Thr Thr Asp Met Met Ser Tyr Asp Leu Ala Ala Ala
    130                 135                 140

Ala Glu Thr Val Gln Arg Gly Ile Glu Glu Arg Ile Gly Arg Glu Gly
145                 150                 155                 160

Asn Thr Thr Trp Leu Arg Gln Leu Met Ser Asp Phe Ile Lys Thr Gln
                165                 170                 175

Pro Gly Trp Asn Ser Glu Ser Glu Asp Asn Leu Leu Val Gly Lys Asp
            180                 185                 190

His Leu Gln Gly Gly Ala Leu Thr Phe Leu Asn Asn Ser Thr Thr Ser
            195                 200                 205

His Ala Asn Ser Asp Phe Arg Leu Met Asn Arg Thr Pro Thr Asn Gln
    210                 215                 220

Thr Gly Thr Arg Lys Tyr His Ile Asp Arg Ser Asn Gly Gly Tyr Glu
225                 230                 235                 240

Leu Leu Leu Ala Asn Asp Ile Asp Asn Ser Asn Pro Ala Val Gln Ala
                245                 250                 255

Glu Gln Leu Asn Trp Leu His Tyr Ile Met Asn Ile Gly Ser Ile Leu
            260                 265                 270

Gly Asn Asp Pro Ser Ala Asn Phe Asp Gly Val Arg Ile Asp Ala Val
            275                 280                 285

Asp Asn Val Asp Ala Asp Leu Leu Gln Ile Ala Ser Asp Tyr Phe Lys
    290                 295                 300

Glu Lys Tyr Arg Val Ala Asp Asn Glu Ala Asn Ala Ile Ala His Leu
305                 310                 315                 320

Ser Ile Leu Glu Ala Trp Ser Tyr Asn Asp His Gln Tyr Asn Lys Asp
                325                 330                 335

Thr Lys Gly Ala Gln Leu Ser Ile Asp Asn Pro Leu Arg Glu Thr Leu
            340                 345                 350

Leu Thr Thr Phe Leu Arg Lys Ser Asn Tyr Arg Gly Ser Leu Glu Arg
            355                 360                 365

Val Ile Thr Asn Ser Leu Asn Asn Arg Ser Ser Glu Gln Lys His Thr
    370                 375                 380

Pro Arg Asp Ala Asn Tyr Ile Phe Val Arg Ala His Asp Ser Glu Val
385                 390                 395                 400

Gln Ala Val Leu Ala Asn Ile Ile Ser Lys Gln Ile Asn Pro Lys Thr
```

```
                405                 410                 415
Asp Gly Phe Thr Phe Thr Met Asp Glu Leu Lys Gln Ala Phe Glu Ile
            420                 425                 430

Tyr Asn Ala Asp Met Arg Lys Ala Asp Lys Lys Tyr Thr Gln Tyr Asn
            435                 440                 445

Ile Pro Ala Ala Tyr Ala Thr Met Leu Thr Asn Lys Asp Ser Ile Thr
            450                 455                 460

Arg Val Tyr Tyr Gly Asp Leu Phe Thr Asp Asp Gly Gln Tyr Met Ala
465                 470                 475                 480

Glu Lys Ser Pro Tyr Tyr Asn Ala Ile Asp Ala Leu Leu Arg Ala Arg
            485                 490                 495

Ile Lys Tyr Val Ala Gly Gly Gln Asp Met Lys Val Thr Lys Leu Asn
            500                 505                 510

Gly Tyr Glu Ile Met Ser Ser Val Arg Tyr Gly Lys Gly Ala Glu Glu
            515                 520                 525

Ala Asn Gln Leu Gly Thr Ala Glu Thr Arg Asn Gln Gly Met Leu Val
            530                 535                 540

Leu Thr Ala Asn Arg Pro Asp Met Lys Leu Gly Thr Asn Asp Arg Leu
545                 550                 555                 560

Val Val Asn Met Gly Ala Ala His Lys Asn Gln Ala Tyr Arg Pro Leu
            565                 570                 575

Leu Leu Ser Lys Ser Thr Gly Leu Ala Thr Tyr Leu Lys Asp Ser Asp
            580                 585                 590

Val Pro Ala Gly Leu Val Arg Tyr Thr Asp Asn Gln Gly Asn Leu Thr
            595                 600                 605

Phe Thr Ala Asp Asp Ile Thr Gly His Ser Thr Val Glu Val Ser Gly
            610                 615                 620

Tyr Leu Ala Val Trp Val Pro Val Gly Ala Ser Glu Asn Gln Asp Ala
625                 630                 635                 640

Arg Thr Lys Ala Ser Thr Thr Lys Lys Gly Glu Gln Val Phe Glu Ser
            645                 650                 655

Ser Ala Ala Leu Asp Ser Gln Val Ile Tyr Glu Gly Phe Ser Asn Phe
            660                 665                 670

Gln Asp Phe Val Lys Thr Pro Ser Gln Tyr Thr Asn Arg Val Ile Ala
            675                 680                 685

Gln Asn Ala Lys Arg Phe Lys Glu Trp Gly Ile Thr Ser Phe Glu Phe
            690                 695                 700

Ala Pro Gln Tyr Val Ser Ser Gln Asp Gly Thr Phe Leu Asp Ser Ile
705                 710                 715                 720

Ile Glu Asn Gly Tyr Ala Phe Glu Asp Arg Tyr Asp Ile Ala Met Ser
            725                 730                 735

Lys Asn Asn Lys Tyr Gly Ser Leu Lys Asp Leu Met Asp Ala Leu Arg
            740                 745                 750

Ala Leu His Ala Glu Gly Ile Ser Ala Ile Ala Asp Trp Val Pro Asp
            755                 760                 765

Gln Ile Tyr Asn Leu Pro Gly Lys Glu Val Val Thr Ala Ser Arg Thr
            770                 775                 780

Asn Ser Tyr Gly Thr Pro Arg Pro Asn Ala Glu Ile Tyr Asn Ser Leu
785                 790                 795                 800

Tyr Ala Ala Lys Thr Arg Thr Phe Gly Asn Asp Phe Gln Gly Lys Tyr
            805                 810                 815

Gly Gly Ala Phe Leu Asp Glu Leu Lys Ala Lys Tyr Pro Ala Ile Phe
            820                 825                 830
```

```
Glu Arg Val Gln Ile Ser Asn Gly Arg Lys Leu Thr Thr Asn Glu Lys
        835                 840                 845

Ile Thr Gln Trp Ser Ala Lys Tyr Phe Asn Gly Ser Asn Ile Gln Gly
        850                 855                 860

Thr Gly Ala Arg Tyr Val Leu Gln Asp Asn Ala Thr Asn Gln Tyr Phe
865                 870                 875                 880

Asn Leu Lys Ala Gly Gln Thr Phe Leu Pro Lys Gln Met Thr Glu Ile
                885                 890                 895

Thr Ala Thr Gly Phe Arg Arg Val Gly Asp Lys Val Gln Tyr Leu Ser
                900                 905                 910

Thr Ser Gly Tyr Leu Ala Lys Asn Thr Phe Ile Gln Ile Gly Ala Asn
        915                 920                 925

Gln Trp Tyr Tyr Phe Asp Lys Asn Gly Asn Met Val Thr Gly Glu Gln
        930                 935                 940

Val Ile Asp Gly Lys Lys Tyr Phe Phe Leu Asp Asn Gly Leu Gln Leu
945                 950                 955                 960

Arg His Val Leu Arg Gln Gly Ser Asp Gly His Val Tyr Tyr Tyr Asp
                965                 970                 975

Pro Lys Gly Val Gln Ala Phe Asn Gly Phe Tyr Asp Phe Ala Gly Pro
        980                 985                 990

Arg Gln Asp Val Arg Tyr Phe Asp Gly Asn Gly Gln Met Tyr Arg Gly
        995                 1000                1005

Leu His Asp Met Tyr Gly Thr Thr Phe Tyr Phe Asp Glu Lys Thr
        1010                1015                1020

Gly Ile Gln Ala Lys Asp Lys Phe Ile Arg Phe Ala Asp Gly Arg
        1025                1030                1035

Thr Arg Tyr Phe Ile Pro Asp Thr Gly Asn Leu Ala Val Asn Arg
        1040                1045                1050

Phe Ala Gln Asn Pro Glu Asn Lys Ala Trp Tyr Tyr Leu Asp Ser
        1055                1060                1065

Asn Gly Tyr Ala Val Thr Gly Leu Gln Thr Ile Asn Gly Lys Gln
        1070                1075                1080

Tyr Tyr Phe Asp Asn Glu Gly Arg Gln Val Lys Gly His Phe Val
        1085                1090                1095

Thr Ile Asn Asn Gln Arg Tyr Phe Leu Asp Gly Asp Ser Gly Glu
        1100                1105                1110

Ile Ala Arg Ser Arg Phe Val Thr Glu Asn Asn Lys Trp Tyr Tyr
        1115                1120                1125

Val Asp Gly Asn Gly Lys Leu Val Lys Gly Ala Gln Val Ile Asn
        1130                1135                1140

Gly Asn His Tyr Tyr Phe Asn Asn Asp Tyr Ser Gln Val Lys Gly
        1145                1150                1155

Ala Trp Ala Asn Gly Arg Tyr Tyr Asp Gly Asp Ser Gly Gln Ala
        1160                1165                1170

Val Thr Asn Arg Phe Val Gln Val Gly Ala Asn Gln Trp Ala Tyr
        1175                1180                1185

Leu Asn Gln Asn Gly Gln Lys Val Val Gly Leu Gln His Ile Asn
        1190                1195                1200

Gly Lys Leu Tyr Tyr Phe Glu Gly Asn Gly Val Gln Ala Lys Gly
        1205                1210                1215

Lys Leu Leu Thr Tyr Lys Gly Lys Lys Tyr Tyr Phe Asp Ala Asn
        1220                1225                1230
```

| Ser | Gly | Glu | Ala | Val | Thr | Asn | Arg | Phe | Ile | Gln | Ile | Ser | Arg | Gly |
| | 1235 | | | | 1240 | | | | | 1245 | | | | |

| Val | Trp | Tyr | Tyr | Phe | Asn | Ala | Ser | Gly | Gln | Ala | Val | Thr | Gly | Glu |
| 1250 | | | | | 1255 | | | | | 1260 | | | | |

| Gln | Val | Ile | Asn | Gly | Gln | His | Leu | Tyr | Phe | Asp | Ala | Ser | Gly | Arg |
| 1265 | | | | | 1270 | | | | | 1275 | | | | |

| Gln | Val | Lys | Gly | Arg | Tyr | Val | Trp | Ile | Lys | Gly | Gln | Arg | Arg | Tyr |
| 1280 | | | | | 1285 | | | | | 1290 | | | | |

| Tyr | Asp | Ala | Asn | Thr | Gly | Ala | Trp | Val | Arg | Asn | Arg |
| 1295 | | | | | 1300 | | | | | 1305 | |

<210> SEQ ID NO 39
<211> LENGTH: 3933
<212> TYPE: DNA
<213> ORGANISM: Streptococcus gallolyticus

<400> SEQUENCE: 39

| | | | | | |
|---|---|---|---|---|---|
| atgatcgacg | gcaaatacta | ctatgttcag | gcagatggca | gcgttaagaa | gaatttcgcg | 60 |
| attacggtca | acggtcagct | gctgtacttt | gatgctgaga | ctggcgctct | gacgagcacg | 120 |
| agcacttata | gctttaccga | aggcctgacc | aatctggtgg | ataactttag | caagaacaat | 180 |
| caagcgtatg | acagcacgga | gaaatccttt | gagctggttg | atggctacct | gacggcgaac | 240 |
| agctggtatc | gtccgactaa | agttttggag | aatggcgaaa | cctgggttga | cagcaccgaa | 300 |
| gagagcttcc | gtccactggt | gatggcttgg | tggcctgacg | tcgataccca | gattaactac | 360 |
| ctgaacagca | tgagcgaata | ctttggtttg | aataagaagt | attctgcatc | ggatagccaa | 420 |
| gcatctctga | atgtggcggc | tgaagcgatc | caggtgaaaa | ttgagcagga | gattgcgcgt | 480 |
| cgtggttcga | ccgagtggtt | gcgtgaggtc | attagctctt | tgttacgac | ccaagataag | 540 |
| tggaatatga | cagcgaaga | tcgcgacact | gaccacctgc | aaggtggcgc | actgctgtat | 600 |
| gtcaacagcg | atctgactga | gtgggccaat | agcgattacc | gcctgctgaa | ccgcgctccg | 660 |
| acctatcaaa | ctggtgaaac | taagtaccac | aaagccgacc | gcacgggtgg | ctacgacttc | 720 |
| ctgctggcga | tgatgttga | caatagcaat | ccggttgttc | aggccgaaca | actgaatcag | 780 |
| ctgtactacc | tgatgaactg | gggtaagatt | gtgttcggtg | acgcagatgc | aaacttcgat | 840 |
| ggcgtccgtg | ttgacgcggt | ggacaacgtg | gatgctgatc | tgttgcaaat | ctacacgaat | 900 |
| ctgtttgaag | cggcctacgg | cgtcgataag | accgaagcac | aagcgctggc | gcatattagc | 960 |
| atcttggaag | cgtggagctt | caacgacccg | gactataatc | acgacaccaa | cggtgcagca | 1020 |
| ctggccatcg | acaacggtct | gcgtatggcc | ttcctggatg | ctctgactcg | tcctctggac | 1080 |
| tcccgcacta | atttggagag | cctgattcac | aacgatctgg | gcatgactga | ccgtaccgtc | 1140 |
| gatagcgcgt | atggtgatgc | tatgccgagc | tatgccttcg | tccgtgccca | cgactctgaa | 1200 |
| gttcagggca | tcattgcatc | tatcatcgcc | ggtcagatca | atccgaaaac | ggacggtttt | 1260 |
| acctttacct | tggatgagct | gcaaaaggca | ttcgaaatct | acaacgccga | catgaactcc | 1320 |
| gtgcacaaga | agtatacccca | tttcaatatc | ccagcagcat | acgctttgct | gctgaccaac | 1380 |
| atggagagcg | ttccgcgtgt | atactatggc | gatttgttca | ccgataacgg | tcagtacatg | 1440 |
| gccgttaaaa | gcccgtacta | cgaccagatc | accgcgctgc | tgaagtctcg | tatcaagtac | 1500 |
| gcggcaggcg | tcaagccat | gaatgtgcaa | tacccggatg | gtgcgggtgc | gggtatcctg | 1560 |
| acttctgtgc | gcttcggcta | tgcattatg | acggcggatc | aaaaagcgac | cgacgacagc | 1620 |
| gttactacca | gcggcattgt | caccattgtt | tccaacaacc | cgaacctgaa | actgaatagc | 1680 |

```
agcgacaaaa ttgcggtgca agttggtctg gcacacgcag gccaatacta ccgtccgctg    1740
ctgtctccga cggagaatgg tctgcaagtg ttcctgaatg attccgacac cgacatcacc    1800
aagctggtcg atgataacgg ttacatctat ttcacgggtg atgagatcaa aggtttcgag    1860
actgtggaca tgaatggctt cctgaccgtt tgggttccgg tgggtgcggc agccgatcag    1920
gatattcgcg tcaaggcgag cacggaagcg aagaaggatg gtgagctgac ctatgaaacc    1980
tctgcggcgc tggattctca ggtcattttt gaaggcttta gcaactttca agactttgtt    2040
caggacccaa gccagtacac caataaggtg attgcggaga atgcggatct gttcgcgagc    2100
tggggcatca cgtctttcga gctggcaccg cagtatgtta gcagcacgga cggtacgttc    2160
ctggacagca ttattcagaa cggttatgct tttacggatc gttatgactt ggcgatgtct    2220
aagaacaata gtatggtag cgcagaagat ttgcgcaatg cgattaaagc gctgcacgca    2280
cgcggtattc aagtgattgc tgattgggtc cctgaccaga tttatgcgct gcctggtgaa    2340
gagattgtga cggcgacccg tgttaatgac tacggcgaag aacgtgaagg cgcgcaaatc    2400
aagaacaaac cgtatgcggc gaatacgaaa agctccggtg aggattacca gcccaatac    2460 ggtggcgagt tcttggaata tctgcaagag aattacccgg agttgtttga aaaggtcatg    2520
attagcacgg gtaagaccat tgacccatcg acgaagatca aggtctggaa agcggagtat    2580
ttcaacggca cgaatattct gggtaagggt gccgattacg tcctgaacga tgcggccacc    2640
ggcacctact tcaccgtaac ggagaacggc gccttcctgc cgaaacaaat gacgagcgat    2700
accgcccaaa cgggtttcta ttatgatggc accggcatga cgtactattc tacctcgggt    2760
taccaagcta agtctagctt cgtgctgtac aacggcaacc gttactattt cgatgaaaac    2820
ggtcacatgg ttacgggtat gcgcgatatt gatggtcaga cgtactactt tctgccgaat    2880
ggtatcgaac tgcgtgacgc gatctatgag gacgcgaacg gtaatcagta ttactttggc    2940
aaatcgggta accgctacgc gggtcattac tacgcctttg aaaccacgag caccgttgac    3000 ggtgtccacca agaccactac taactggcgc tattttgatg aaaacggcgt tatggcacgc    3060
ggcctggtga aaatcggtaa tgattatcaa tactacgacg ataacggcaa tcagatcaag    3120
ggtcaactgg tgacggacaa ggacggcaac acccgttact ttaaagctga cagcggtgca    3180
atggttacgg gtgagtttgc actggtgaat ggtggttggt actacttcga tgacaatggt    3240
gttgcagtca aggtgctcga gaccattaac ggtcaacagt tgtacttcga cgagaatggt    3300
gtccaagcaa aaggtgtgtt cgtgaccaat gaggatggca cccgtagcta ttacgacgcc    3360
aagtccggtg agaagtttgt tggcgacttc tttacgaccg cgacaaccca ttggtactat    3420
gccgacgaga acggcaattt ggcaacgggt agccaggtta tccgtggtca agttgtat    3480 tttgcagccg atggtttgca ggcgaaaggt atctttacca ccgacgccga aggtaaccgc    3540
cacttctacg acccggactc cggcgatctg gcggaaaaca gtttatcgc ggatggtgac    3600 gactggtact attttgacga aacgggtcat gttgttaccg cgcagcaagt gatcaacggc    3660
caacagctgt atttcgacga aaatggcgtt caggcgaagg gtgttttcgt gaccgatgat    3720
aatggtaata gcgttactta tgatgcacag acgggtgaga tggtggtgaa ccagacgctg    3780
acggtggatg tgtggaata taccttggt gcggatggcc tcgcggtggt taatgcacaa    3840
gatagcgacg aacaaagcga aagcacggat gaaacgcaag tgaccagcga tgacgcgacg    3900
gttgcaaaga cggaaaccag ctctgctgaa taa                                  3933
```

<210> SEQ ID NO 40
<211> LENGTH: 1310

```
<212> TYPE: PRT
<213> ORGANISM: Streptococcus gallolyticus

<400> SEQUENCE: 40

Met Ile Asp Gly Lys Tyr Tyr Val Gln Ala Asp Gly Ser Val Lys
1               5                   10                  15

Lys Asn Phe Ala Ile Thr Val Asn Gly Gln Leu Leu Tyr Phe Asp Ala
            20                  25                  30

Glu Thr Gly Ala Leu Thr Ser Thr Ser Thr Tyr Ser Phe Thr Glu Gly
                35                  40                  45

Leu Thr Asn Leu Val Asp Asn Phe Ser Lys Asn Asn Gln Ala Tyr Asp
    50                  55                  60

Ser Thr Glu Lys Ser Phe Glu Leu Val Asp Gly Tyr Leu Thr Ala Asn
65                  70                  75                  80

Ser Trp Tyr Arg Pro Thr Lys Val Leu Glu Asn Gly Thr Trp Val
                85                  90                  95

Asp Ser Thr Glu Glu Ser Phe Arg Pro Leu Val Met Ala Trp Trp Pro
                100                 105                 110

Asp Val Asp Thr Gln Ile Asn Tyr Leu Asn Ser Met Ser Glu Tyr Phe
            115                 120                 125

Gly Leu Asn Lys Lys Tyr Ser Ala Ser Asp Ser Gln Ala Ser Leu Asn
        130                 135                 140

Val Ala Ala Glu Ala Ile Gln Val Lys Ile Glu Gln Glu Ile Ala Arg
145                 150                 155                 160

Arg Gly Ser Thr Glu Trp Leu Arg Glu Val Ile Ser Ser Phe Val Thr
                165                 170                 175

Thr Gln Asp Lys Trp Asn Met Asn Ser Glu Asp Arg Asp Thr Asp His
            180                 185                 190

Leu Gln Gly Gly Ala Leu Leu Tyr Val Asn Ser Asp Leu Thr Glu Trp
        195                 200                 205

Ala Asn Ser Asp Tyr Arg Leu Leu Asn Arg Ala Pro Thr Tyr Gln Thr
    210                 215                 220

Gly Glu Thr Lys Tyr His Lys Ala Asp Arg Thr Gly Gly Tyr Asp Phe
225                 230                 235                 240

Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Lys Ile Val Phe
            260                 265                 270

Gly Asp Ala Asp Ala Asn Phe Asp Gly Val Arg Val Asp Ala Val Asp
        275                 280                 285

Asn Val Asp Ala Asp Leu Leu Gln Ile Tyr Thr Asn Leu Phe Glu Ala
    290                 295                 300

Ala Tyr Gly Val Asp Lys Thr Glu Ala Gln Leu Ala His Ile Ser
305                 310                 315                 320

Ile Leu Glu Ala Trp Ser Phe Asn Asp Pro Asp Tyr Asn His Asp Thr
                325                 330                 335

Asn Gly Ala Ala Leu Ala Ile Asp Asn Gly Leu Arg Met Ala Phe Leu
            340                 345                 350

Asp Ala Leu Thr Arg Pro Leu Asp Ser Arg Thr Asn Leu Glu Ser Leu
        355                 360                 365

Ile His Asn Asp Leu Gly Met Thr Arg Thr Val Asp Ser Ala Tyr
    370                 375                 380

Gly Asp Ala Met Pro Ser Tyr Ala Phe Val Arg Ala His Asp Ser Glu
385                 390                 395                 400
```

```
Val Gln Gly Ile Ile Ala Ser Ile Ile Ala Gly Gln Ile Asn Pro Lys
                405                 410                 415

Thr Asp Gly Phe Thr Phe Thr Leu Asp Glu Leu Gln Lys Ala Phe Glu
            420                 425                 430

Ile Tyr Asn Ala Asp Met Asn Ser Val His Lys Lys Tyr Thr His Phe
        435                 440                 445

Asn Ile Pro Ala Ala Tyr Ala Leu Leu Leu Thr Asn Met Glu Ser Val
    450                 455                 460

Pro Arg Val Tyr Tyr Gly Asp Leu Phe Thr Asp Asn Gly Gln Tyr Met
465                 470                 475                 480

Ala Val Lys Ser Pro Tyr Tyr Asp Gln Ile Thr Ala Leu Leu Lys Ser
                485                 490                 495

Arg Ile Lys Tyr Ala Ala Gly Gly Gln Ala Met Asn Val Gln Tyr Pro
            500                 505                 510

Asp Gly Ala Gly Ala Gly Ile Leu Thr Ser Val Arg Phe Gly Tyr Gly
        515                 520                 525

Ile Met Thr Ala Asp Gln Lys Ala Thr Asp Asp Ser Val Thr Thr Ser
    530                 535                 540

Gly Ile Val Thr Ile Val Ser Asn Asn Pro Asn Leu Lys Leu Asn Ser
545                 550                 555                 560

Ser Asp Lys Ile Ala Val Gln Val Gly Leu Ala His Ala Gly Gln Tyr
                565                 570                 575

Tyr Arg Pro Leu Leu Ser Pro Thr Glu Asn Gly Leu Gln Val Phe Leu
            580                 585                 590

Asn Asp Ser Asp Thr Asp Ile Thr Lys Leu Val Asp Asp Asn Gly Tyr
        595                 600                 605

Ile Tyr Phe Thr Gly Asp Glu Ile Lys Gly Phe Glu Thr Val Asp Met
    610                 615                 620

Asn Gly Phe Leu Thr Val Trp Val Pro Val Gly Ala Ala Ala Asp Gln
625                 630                 635                 640

Asp Ile Arg Val Lys Ala Ser Thr Glu Ala Lys Lys Asp Gly Glu Leu
                645                 650                 655

Thr Tyr Glu Thr Ser Ala Ala Leu Asp Ser Gln Val Ile Phe Glu Gly
            660                 665                 670

Phe Ser Asn Phe Gln Asp Phe Val Gln Asp Pro Ser Gln Tyr Thr Asn
        675                 680                 685

Lys Val Ile Ala Glu Asn Ala Asp Leu Phe Ala Ser Trp Gly Ile Thr
    690                 695                 700

Ser Phe Glu Leu Ala Pro Gln Tyr Val Ser Ser Thr Asp Gly Thr Phe
705                 710                 715                 720

Leu Asp Ser Ile Ile Gln Asn Gly Tyr Ala Phe Thr Asp Arg Tyr Asp
                725                 730                 735

Leu Ala Met Ser Lys Asn Asn Lys Tyr Gly Ser Ala Glu Asp Leu Arg
            740                 745                 750

Asn Ala Ile Lys Ala Leu His Ala Arg Gly Ile Gln Val Ile Ala Asp
        755                 760                 765

Trp Val Pro Asp Gln Ile Tyr Ala Leu Pro Gly Glu Glu Ile Val Thr
    770                 775                 780

Ala Thr Arg Val Asn Asp Tyr Gly Glu Glu Arg Glu Gly Ala Gln Ile
785                 790                 795                 800

Lys Asn Lys Pro Tyr Ala Ala Asn Thr Lys Ser Ser Gly Glu Asp Tyr
                805                 810                 815
```

```
Gln Ala Gln Tyr Gly Gly Glu Phe Leu Glu Tyr Leu Gln Glu Asn Tyr
                820                 825                 830

Pro Glu Leu Phe Glu Lys Val Met Ile Ser Thr Gly Lys Thr Ile Asp
            835                 840                 845

Pro Ser Thr Lys Ile Lys Val Trp Lys Ala Glu Tyr Phe Asn Gly Thr
        850                 855                 860

Asn Ile Leu Gly Lys Gly Ala Asp Tyr Val Leu Asn Asp Ala Ala Thr
865                 870                 875                 880

Gly Thr Tyr Phe Thr Val Thr Glu Asn Gly Ala Phe Leu Pro Lys Gln
                885                 890                 895

Met Thr Ser Asp Thr Ala Gln Thr Gly Phe Tyr Tyr Asp Gly Thr Gly
            900                 905                 910

Met Thr Tyr Tyr Ser Thr Ser Gly Tyr Gln Ala Lys Ser Ser Phe Val
        915                 920                 925

Leu Tyr Asn Gly Asn Arg Tyr Tyr Phe Asp Glu Asn Gly His Met Val
930                 935                 940

Thr Gly Met Arg Asp Ile Asp Gly Gln Thr Tyr Tyr Phe Leu Pro Asn
945                 950                 955                 960

Gly Ile Glu Leu Arg Asp Ala Ile Tyr Glu Asp Ala Asn Gly Asn Gln
                965                 970                 975

Tyr Tyr Phe Gly Lys Ser Gly Asn Arg Tyr Ala Gly His Tyr Tyr Ala
            980                 985                 990

Phe Glu Thr Thr Ser Thr Val Asp Gly Val Thr Lys Thr Thr Thr Asn
        995                 1000                1005

Trp Arg Tyr Phe Asp Glu Asn Gly Val Met Ala Arg Gly Leu Val
        1010                1015                1020

Lys Ile Gly Asn Asp Tyr Gln Tyr Tyr Asp Asp Asn Gly Asn Gln
        1025                1030                1035

Ile Lys Gly Gln Leu Val Thr Asp Lys Asp Gly Asn Thr Arg Tyr
        1040                1045                1050

Phe Lys Ala Asp Ser Gly Ala Met Val Thr Gly Glu Phe Ala Leu
        1055                1060                1065

Val Asn Gly Gly Trp Tyr Tyr Phe Asp Asp Asn Gly Val Ala Val
        1070                1075                1080

Lys Gly Ala Gln Thr Ile Asn Gly Gln Gln Leu Tyr Phe Asp Glu
        1085                1090                1095

Asn Gly Val Gln Ala Lys Gly Val Phe Val Thr Asn Glu Asp Gly
        1100                1105                1110

Thr Arg Ser Tyr Tyr Asp Ala Lys Ser Gly Glu Lys Phe Val Gly
        1115                1120                1125

Asp Phe Phe Thr Thr Gly Asp Asn His Trp Tyr Tyr Ala Asp Glu
        1130                1135                1140

Asn Gly Asn Leu Ala Thr Gly Ser Gln Val Ile Arg Gly Gln Lys
        1145                1150                1155

Leu Tyr Phe Ala Ala Asp Gly Leu Gln Ala Lys Gly Ile Phe Thr
        1160                1165                1170

Thr Asp Ala Glu Gly Asn Arg His Phe Tyr Asp Pro Asp Ser Gly
        1175                1180                1185

Asp Leu Ala Glu Asn Lys Phe Ile Ala Asp Gly Asp Asp Trp Tyr
        1190                1195                1200

Tyr Phe Asp Glu Thr Gly His Val Val Thr Gly Glu Gln Val Ile
        1205                1210                1215

Asn Gly Gln Gln Leu Tyr Phe Asp Glu Asn Gly Val Gln Ala Lys
```

| | | | | | | | | | |
|---|---|---|---|---|---|---|---|---|---|
| | | 1220 | | | 1225 | | | 1230 | |
| Gly | Val | Phe | Val | Thr | Asp | Asp | Asn | Gly | Asn | Lys | Arg | Tyr | Tyr | Asp |
| | | 1235 | | | | 1240 | | | | | 1245 | | | |
| Ala | Gln | Thr | Gly | Glu | Met | Val | Val | Asn | Gln | Thr | Leu | Thr | Val | Asp |
| | | 1250 | | | | 1255 | | | | | 1260 | | | |
| Gly | Val | Glu | Tyr | Thr | Phe | Gly | Ala | Asp | Gly | Val | Ala | Val | Val | Asn |
| | | 1265 | | | | 1270 | | | | | 1275 | | | |
| Ala | Gln | Asp | Ser | Asp | Glu | Gln | Ser | Glu | Ser | Thr | Asp | Glu | Thr | Gln |
| | | 1280 | | | | 1285 | | | | | 1290 | | | |
| Val | Thr | Ser | Asp | Asp | Ala | Thr | Val | Ala | Lys | Thr | Glu | Thr | Ser | Ser |
| | | 1295 | | | | 1300 | | | | | 1305 | | | |
| Ala | Glu | | | | | | | | | | | | | |
| | | 1310 | | | | | | | | | | | | |

<210> SEQ ID NO 41
<211> LENGTH: 3804
<212> TYPE: DNA
<213> ORGANISM: Streptococcus mutans

<400> SEQUENCE: 41

| | |
|---|---|
| atggtcaatg gcaaatacta ctactacaaa gaggacggta cgttgcagaa gaactacgca | 60 |
| ctgaacatta acggcaagac cttttctttt gacgagactg gcgccctgag caataacacc | 120 |
| ctgccgagca agaaaggtaa catcaccaat aacgacaata ccaatagctt cgcgcaatac | 180 |
| aatcaggtgt attcgacgga tgcagcgaac ttcgaacatg tcgatcacta cctgacggcg | 240 |
| gagtcctggt atcgcccgaa gtatattctg aaagatggca agacgtggac tcagtccacg | 300 |
| gagaaagatt ttcgcccgtt gttgatgacc tggtggccgg atcaggaaac ccagcgtcag | 360 |
| tatgtaaact atatgaatgc ccagctgggt attcaccaga cctacaacac ggcgaccagc | 420 |
| ccgttgcaac tgaatctggc ggcacagacg atccagacca agattgaaga agatcacg | 480 |
| gcggagaaga cactaattg gctgcgtcaa acgatttcgg cctttgtcaa aacccagagc | 540 |
| gcgtggaact cggacagcga aaaaccgttt gacgatcatc tgcaaaaggg tgcactgctg | 600 |
| tactctaaca atagcaagtt gacctctcaa gctaatagca actaccgtat tctgaaccgt | 660 |
| accccaacca accaaaccgg caagaaagat ccgcgttata ccgctgaccg taccatcggt | 720 |
| ggttatgagt tcttgctggc gaacgatgtg gataatagca atcctgttgt tcaagcggaa | 780 |
| cagctgaact ggctgcactt cctgatgaac tttggcaata tctatgcaaa cgaccctgac | 840 |
| gccaactttg acagcatccg tgtagacgcc gtggacaacg tggatgcaga tttgttgcaa | 900 |
| atcgctggtg actatctgaa ggctgcaaag gcatccata gaacgacaa agcagcgaac | 960 |
| gaccacctgt cgatcctgga agcatggagc tataatgaca ccccgtatct gcacgacgac | 1020 |
| ggtgacaaca tgatcaatat ggacaaccgt ctgcgtctga gcctgctgta tagcctggcg | 1080 |
| aagccgttga ccagcgttc gggcatgaac ccgctgatca cgaacagcct ggttaaccgt | 1140 |
| accgatgaca acgcagaaac cgcagcggtc ccgagctaca gctttatccg tgcacacgat | 1200 |
| agcgaggttc aagacctgat tcgtaacatt attcgtgctg agattaatcc gaacgtcgtc | 1260 |
| ggttatagct tcacgatgga agagatcaag aaggcctttg agatttacaa caaggatctg | 1320 |
| ctggcgacgg aaaagaaata cacccactat aacaccgcgc tgagctacgc gctgctgctg | 1380 |
| accaataaga gcagcgttcc gcgtgtgtat acggtgata tgtttactga cgacggtcag | 1440 |
| tacatggcac ataaaacgat caactacgag gctatcgaaa cgctgttgaa ggcgcgcatt | 1500 |
| aagtacgtgt ctggtggcca agcgatgcgt aatcaacagg tgggtaatag cgaaatcatt | 1560 |

```
acgagcgtcc gctatggcaa gggcgcactg aaagcgacgg ataccggcga tcgtaccacg   1620
cgcaccagcg gcgttgcggt tattgaaggc aataacccga gcctgcgctt gaaggcgagc   1680
gaccgcgtcg ttgttaacat gggtgcagca cacaagaacc aggcatatcg tccgctgttg   1740
ctgaccactg ataatggcat caaagcgtat cacagcgatc aggaagctgc gggcctggtg   1800
cgctatacca atgatcgtgg tgaattgatc ttcacggcag ctgacattaa aggttatgca   1860
aatccgcaag tcagcggtta tctgggcgtc tgggtgccgg tcggcgcagc ggctgatcaa   1920
gacgtgcgtg tggccgcgag caccgcgcca tcgaccgacg gtaaaagcgt gcaccagaat   1980
gcggcgctgg acagccgtgt catgtttgag ggttttagca actttcaagc ctttgcaacg   2040
aagaaagaag agtacaccaa cgtcgtcatc gcgaagaacg tcgataagtt cgcggaatgg   2100
ggcgttaccg atttcgaaat ggcaccgcag tatgtgtcta gcaccgatgg ctcgtttctg   2160
gattccgtga tccaaaatgg ttatgcattt accgaccgct atgacctggg cattagcaag   2220
ccgaataagt atggtacggc ggatgatctg gttaaagcga tcaaggcgct gcattctaaa   2280
ggtattaagg ttatggccga ctgggttcca gatcagatgt atgctttccc ggaaaaagaa   2340
gtggtgacgg ccacccgcgt ggacaaatat ggtacgccgg tcgcgggcag ccagatcaaa   2400
aacactctgt atgtcgtgga tggcaaaagc tccggtaaag atcagcaagc gaaatatggc   2460
ggtgccttcc tggaagagtt gcaggcgaaa tacccggaac tgttcgcgcg taagcagatc   2520
agcactggtg ttccgatgga cccgagcgtg aagattaaac aatggtccgc gaaatacttt   2580
aacggcacga acatcctggg tcgtggtgcc ggctacgtgc tgaaagacca ggcaacgaat   2640
acgtacttta gcttggtgtc cgacaatacg tttctgccga agtctctggt caacccgaac   2700
cacggtacga gcagctctgt gaccggcctg gtgttcgatg gtaagggcta cgtgtactac   2760
tctaccagcg gttaccaggc caagaatacg ttcatcagcc tgggtaacaa ctggtattac   2820
ttcgacaata acggttacat ggtcacgggt gcgcagagca tcaacggtgc caactactat   2880
tttctgagca acggcattca gctgcgtaat gcgatttacg acaatggcaa taaggttctg   2940
agctactacg gtaatgacgg tcgtcgttat gagaatggct attacctgtt tggccaacag   3000
tggcgctact ttcaaaatgg tattatggcc gtcggtctga cccgtgtcca cggtgcggtg   3060
cagtattttg acgccagcgg cttccaagcc aagggccagt tcatcaccac tgcggacggt   3120
aaactgcgtt actttgaccg tgacagcggc aaccaaatca gcaatcgttt tgttcgtaac   3180
agcaagggtg aatggttttt gttcgatcat aacggcgtgg cggttaccgg caccgttact   3240
ttcaatggtc aacgtctgta ctttaagccg aacggtgttc aggcaaaggg tgagttcatt   3300
cgcgacgcgg atggtcactt gcgttactac gaccctaatt ccggtaatga ggttcgtaac   3360
cgtttcgtcc gcaactctaa gggcgaatgg ttcctgtttg accacaatgg catcgcagtc   3420
accggcgctc gtgtggtcaa cggccaacgc ttgtacttca aaagcaatgg cgtccaagct   3480
aagggtgagc tgattaccga acgtaagggc cgtattaagt attatgatcc taacagcggt   3540
aacgaagtgc gtaaccgcta cgtccgcacc agcagcggta attggtacta ttttggtaac   3600
gatggttacg cgctgatcgg ctggcatgtt gttgagggtc gtcgtgtgta ctttgatgag   3660
aacggtgtct atcgttacgc gagccacgac cagcgtaatc attggaacta cgactatcgt   3720
cgcgatttcg gtcgtggtag cagctccgct atccgttttc gccatagccg taacggcttt   3780
ttcgacaact tcttccgctt ctaa                                          3804

<210> SEQ ID NO 42
```

```
<211> LENGTH: 1267
<212> TYPE: PRT
<213> ORGANISM: Streptococcus mutans

<400> SEQUENCE: 42
```

| | | | | | | | | | | | | | | |
|---|---|---|---|---|---|---|---|---|---|---|---|---|---|---|
| Met | Val | Asn | Gly | Lys | Tyr | Tyr | Tyr | Lys | Glu | Asp | Gly | Thr | Leu | Gln |
| 1 | | | | 5 | | | | | 10 | | | | | 15 |
| Lys | Asn | Tyr | Ala | Leu | Asn | Ile | Asn | Gly | Lys | Thr | Phe | Phe | Asp | Glu |
| | | | 20 | | | | | 25 | | | | | 30 | |
| Thr | Gly | Ala | Leu | Ser | Asn | Asn | Thr | Leu | Pro | Ser | Lys | Lys | Gly | Asn | Ile |
| | | 35 | | | | | 40 | | | | | 45 | | |
| Thr | Asn | Asn | Asp | Asn | Thr | Asn | Ser | Phe | Ala | Gln | Tyr | Asn | Gln | Val | Tyr |
| 50 | | | | | 55 | | | | | 60 | | | | |
| Ser | Thr | Asp | Ala | Ala | Asn | Phe | Glu | His | Val | Asp | His | Tyr | Leu | Thr | Ala |
| 65 | | | | | 70 | | | | | 75 | | | | | 80 |
| Glu | Ser | Trp | Tyr | Arg | Pro | Lys | Tyr | Ile | Leu | Lys | Asp | Gly | Lys | Thr | Trp |
| | | | | 85 | | | | | 90 | | | | | 95 | |
| Thr | Gln | Ser | Thr | Glu | Lys | Asp | Phe | Arg | Pro | Leu | Leu | Met | Thr | Trp | Trp |
| | | | 100 | | | | | 105 | | | | | 110 | | |
| Pro | Asp | Gln | Glu | Thr | Gln | Arg | Gln | Tyr | Val | Asn | Tyr | Met | Asn | Ala | Gln |
| | | 115 | | | | | 120 | | | | | 125 | | | |
| Leu | Gly | Ile | His | Gln | Thr | Tyr | Asn | Thr | Ala | Thr | Ser | Pro | Leu | Gln | Leu |
| 130 | | | | | 135 | | | | | 140 | | | | | |
| Asn | Leu | Ala | Ala | Gln | Thr | Ile | Gln | Thr | Lys | Ile | Glu | Glu | Lys | Ile | Thr |
| 145 | | | | | 150 | | | | | 155 | | | | | 160 |
| Ala | Glu | Lys | Asn | Thr | Asn | Trp | Leu | Arg | Gln | Thr | Ile | Ser | Ala | Phe | Val |
| | | | | 165 | | | | | 170 | | | | | 175 | |
| Lys | Thr | Gln | Ser | Ala | Trp | Asn | Ser | Asp | Ser | Glu | Lys | Pro | Phe | Asp | Asp |
| | | | 180 | | | | | 185 | | | | | 190 | | |
| His | Leu | Gln | Lys | Gly | Ala | Leu | Leu | Tyr | Ser | Asn | Asn | Ser | Lys | Leu | Thr |
| | | 195 | | | | | 200 | | | | | 205 | | | |
| Ser | Gln | Ala | Asn | Ser | Asn | Tyr | Arg | Ile | Leu | Asn | Arg | Thr | Pro | Thr | Asn |
| 210 | | | | | 215 | | | | | 220 | | | | | |
| Gln | Thr | Gly | Lys | Lys | Asp | Pro | Arg | Tyr | Thr | Ala | Asp | Arg | Thr | Ile | Gly |
| 225 | | | | | 230 | | | | | 235 | | | | | 240 |
| Gly | Tyr | Glu | Phe | Leu | Leu | Ala | Asn | Asp | Val | Asp | Asn | Ser | Asn | Pro | Val |
| | | | | 245 | | | | | 250 | | | | | 255 | |
| Val | Gln | Ala | Glu | Gln | Leu | Asn | Trp | Leu | His | Phe | Leu | Met | Asn | Phe | Gly |
| | | | 260 | | | | | 265 | | | | | 270 | | |
| Asn | Ile | Tyr | Ala | Asn | Asp | Pro | Asp | Ala | Asn | Phe | Asp | Ser | Ile | Arg | Val |
| | | 275 | | | | | 280 | | | | | 285 | | | |
| Asp | Ala | Val | Asp | Asn | Val | Asp | Ala | Asp | Leu | Leu | Gln | Ile | Ala | Gly | Asp |
| | 290 | | | | | 295 | | | | | 300 | | | | |
| Tyr | Leu | Lys | Ala | Ala | Lys | Gly | Ile | His | Lys | Asn | Asp | Lys | Ala | Ala | Asn |
| 305 | | | | | 310 | | | | | 315 | | | | | 320 |
| Asp | His | Leu | Ser | Ile | Leu | Glu | Ala | Trp | Ser | Tyr | Asn | Asp | Thr | Pro | Tyr |
| | | | | 325 | | | | | 330 | | | | | 335 | |
| Leu | His | Asp | Asp | Gly | Asp | Asn | Met | Ile | Asn | Met | Asp | Asn | Arg | Leu | Arg |
| | | | 340 | | | | | 345 | | | | | 350 | | |
| Leu | Ser | Leu | Leu | Tyr | Ser | Leu | Ala | Lys | Pro | Leu | Asn | Gln | Arg | Ser | Gly |
| | | | 355 | | | | | 360 | | | | | 365 | | |
| Met | Asn | Pro | Leu | Ile | Thr | Asn | Ser | Leu | Val | Asn | Arg | Thr | Asp | Asp | Asn |
| | 370 | | | | | 375 | | | | | 380 | | | | |
| Ala | Glu | Thr | Ala | Ala | Val | Pro | Ser | Tyr | Ser | Phe | Ile | Arg | Ala | His | Asp |

```
            385                 390                 395                 400
        Ser Glu Val Gln Asp Leu Ile Arg Asn Ile Ile Arg Ala Glu Ile Asn
                        405                 410                 415

Pro Asn Val Val Gly Tyr Ser Phe Thr Met Glu Glu Ile Lys Lys Ala
                        420                 425                 430

Phe Glu Ile Tyr Asn Lys Asp Leu Leu Ala Thr Glu Lys Lys Tyr Thr
                        435                 440                 445

His Tyr Asn Thr Ala Leu Ser Tyr Ala Leu Leu Leu Thr Asn Lys Ser
                    450                 455                 460

Ser Val Pro Arg Val Tyr Tyr Gly Asp Met Phe Thr Asp Asp Gly Gln
        465                 470                 475                 480

Tyr Met Ala His Lys Thr Ile Asn Tyr Glu Ala Ile Glu Thr Leu Leu
                        485                 490                 495

Lys Ala Arg Ile Lys Tyr Val Ser Gly Gln Ala Met Arg Asn Gln
                        500                 505                 510

Gln Val Gly Asn Ser Glu Ile Ile Thr Ser Val Arg Tyr Gly Lys Gly
                    515                 520                 525

Ala Leu Lys Ala Thr Asp Thr Gly Asp Arg Thr Thr Arg Thr Ser Gly
                    530                 535                 540

Val Ala Val Ile Glu Gly Asn Asn Pro Ser Leu Arg Leu Lys Ala Ser
        545                 550                 555                 560

Asp Arg Val Val Asn Met Gly Ala Ala His Lys Asn Gln Ala Tyr
                        565                 570                 575

Arg Pro Leu Leu Leu Thr Thr Asp Asn Gly Ile Lys Ala Tyr His Ser
                    580                 585                 590

Asp Gln Glu Ala Ala Gly Leu Val Arg Tyr Thr Asn Asp Arg Gly Glu
                    595                 600                 605

Leu Ile Phe Thr Ala Ala Asp Ile Lys Gly Tyr Ala Asn Pro Gln Val
                    610                 615                 620

Ser Gly Tyr Leu Gly Val Trp Val Pro Val Gly Ala Ala Ala Asp Gln
        625                 630                 635                 640

Asp Val Arg Val Ala Ala Ser Thr Ala Pro Ser Thr Asp Gly Lys Ser
                        645                 650                 655

Val His Gln Asn Ala Ala Leu Asp Ser Arg Val Met Phe Glu Gly Phe
                        660                 665                 670

Ser Asn Phe Gln Ala Phe Ala Thr Lys Lys Glu Glu Tyr Thr Asn Val
                    675                 680                 685

Val Ile Ala Lys Asn Val Asp Lys Phe Ala Glu Trp Gly Val Thr Asp
                    690                 695                 700

Phe Glu Met Ala Pro Gln Tyr Val Ser Ser Thr Asp Gly Ser Phe Leu
        705                 710                 715                 720

Asp Ser Val Ile Gln Asn Gly Tyr Ala Phe Thr Asp Arg Tyr Asp Leu
                        725                 730                 735

Gly Ile Ser Lys Pro Asn Lys Tyr Gly Thr Ala Asp Asp Leu Val Lys
                        740                 745                 750

Ala Ile Lys Ala Leu His Ser Lys Gly Ile Lys Val Met Ala Asp Trp
                    755                 760                 765

Val Pro Asp Gln Met Tyr Ala Phe Pro Glu Lys Glu Val Val Thr Ala
                    770                 775                 780

Thr Arg Val Asp Lys Tyr Gly Thr Pro Val Ala Gly Ser Gln Ile Lys
        785                 790                 795                 800

Asn Thr Leu Tyr Val Val Asp Gly Lys Ser Ser Gly Lys Asp Gln Gln
                        805                 810                 815
```

```
Ala Lys Tyr Gly Gly Ala Phe Leu Glu Glu Leu Gln Ala Lys Tyr Pro
        820             825                 830

Glu Leu Phe Ala Arg Lys Gln Ile Ser Thr Gly Val Pro Met Asp Pro
        835                 840                 845

Ser Val Lys Ile Lys Gln Trp Ser Ala Lys Tyr Phe Asn Gly Thr Asn
    850                 855                 860

Ile Leu Gly Arg Gly Ala Gly Tyr Val Leu Lys Asp Gln Ala Thr Asn
865             870                 875                     880

Thr Tyr Phe Ser Leu Val Ser Asp Asn Thr Phe Leu Pro Lys Ser Leu
                885                 890                 895

Val Asn Pro Asn His Gly Thr Ser Ser Val Thr Gly Leu Val Phe
                900                 905                 910

Asp Gly Lys Gly Tyr Val Tyr Tyr Ser Thr Ser Gly Tyr Gln Ala Lys
            915                 920                 925

Asn Thr Phe Ile Ser Leu Gly Asn Asn Trp Tyr Tyr Phe Asp Asn Asn
            930                 935                 940

Gly Tyr Met Val Thr Gly Ala Gln Ser Ile Asn Gly Ala Asn Tyr Tyr
945                 950                 955                 960

Phe Leu Ser Asn Gly Ile Gln Leu Arg Asn Ala Ile Tyr Asp Asn Gly
                965                 970                 975

Asn Lys Val Leu Ser Tyr Tyr Gly Asn Asp Gly Arg Arg Tyr Glu Asn
            980                 985                 990

Gly Tyr Tyr Leu Phe Gly Gln Gln Trp Arg Tyr Phe Gln Asn Gly Ile
            995                 1000                1005

Met Ala Val Gly Leu Thr Arg Val His Gly Ala Val Gln Tyr Phe
    1010                1015                1020

Asp Ala Ser Gly Phe Gln Ala Lys Gly Gln Phe Ile Thr Thr Ala
    1025                1030                1035

Asp Gly Lys Leu Arg Tyr Phe Asp Arg Asp Ser Gly Asn Gln Ile
    1040                1045                1050

Ser Asn Arg Phe Val Arg Asn Ser Lys Gly Glu Trp Phe Leu Phe
    1055                1060                1065

Asp His Asn Gly Val Ala Val Thr Gly Thr Val Thr Phe Asn Gly
    1070                1075                1080

Gln Arg Leu Tyr Phe Lys Pro Asn Gly Val Gln Ala Lys Gly Glu
    1085                1090                1095

Phe Ile Arg Asp Ala Asp Gly His Leu Arg Tyr Tyr Asp Pro Asn
    1100                1105                1110

Ser Gly Asn Glu Val Arg Asn Arg Phe Val Arg Asn Ser Lys Gly
    1115                1120                1125

Glu Trp Phe Leu Phe Asp His Asn Gly Ile Ala Val Thr Gly Ala
    1130                1135                1140

Arg Val Val Asn Gly Gln Arg Leu Tyr Phe Lys Ser Asn Gly Val
    1145                1150                1155

Gln Ala Lys Gly Glu Leu Ile Thr Glu Arg Lys Gly Arg Ile Lys
    1160                1165                1170

Tyr Tyr Asp Pro Asn Ser Gly Asn Glu Val Arg Asn Arg Tyr Val
    1175                1180                1185

Arg Thr Ser Ser Gly Asn Trp Tyr Tyr Phe Gly Asn Asp Gly Tyr
    1190                1195                1200

Ala Leu Ile Gly Trp His Val Val Glu Gly Arg Arg Val Tyr Phe
    1205                1210                1215
```

| | | | | | | | | | | |
|---|---|---|---|---|---|---|---|---|---|---|
| Asp | Glu | Asn | Gly | Val | Tyr | Arg | Tyr | Ala | Ser | His | Asp | Gln | Arg | Asn |
| | 1220 | | | | 1225 | | | | 1230 | |

His Trp Asn Tyr Asp Tyr Arg Arg Asp Phe Gly Arg Gly Ser Ser
   1235                       1240                   1245

Ser Ala Ile Arg Phe Arg His Ser Arg Asn Gly Phe Phe Asp Asn
   1250                       1255                   1260

Phe Phe Arg Phe
   1265

```
<210> SEQ ID NO 43
<211> LENGTH: 3864
<212> TYPE: DNA
<213> ORGANISM: Streptococcus mutans

<400> SEQUENCE: 43
atgattgacg gcaaatacta ctacatcggc agcgacggtc agccaaagaa gaattttgcg      60
ttgacggtta acaataaagt cctgtatttt gacaagaaca cgggtgcgct gaccgacacc     120
agccaatatc agttcaaaca aggtctgacg aagctgaaca acgactacac ccctcacaat     180
cagattgtca actttgaaaa tactagcctg gaaactattg ataactatgt tactgccgac     240
tcttggtatc gtccgaaaga cattctgaag aacggtaaga cgtggaccgc gtcctctgag     300
agcgatctgc gtccgctgct gatgtcctgg tggcctgata gcagaccca gatcgcatac      360 ctgaactaca tgaaccaaca aggcttgggc actggcgaga actataccgc tgatagctct     420
caagagagcc tgaacctggc ggcacaaacc gttcaagtca aaatcgaaac caagatcagc     480
caaacgcaac agactcagtg gctgcgtgac atcattaact ctttcgttaa gacgcaaccg     540
aactggaata gccaaaccga gtctgacacg agcgctggtg aaaaagatca tttgcagggc     600
ggtgccctgc tgtatagcaa ttcggacaaa accgcatacg caaatagcga ctatcgtctg     660
ctgaaccgta ccccgaccag ccagactggt aagccgaaat acttcgagga caatagcagc     720
ggtggttacg acttcctgtt ggcaaacgat attgataatt ccaatccggt ggtgcaggct     780
gagcagctga attggctgca ttacctgatg aattacggta gcattgtcgc aaatgacccg     840
gaagcgaatt cgatggtgt ccgtgttgac gcggtggata cgtgaacgc agacctgttg      900 cagatcgcaa gcgattatct gaaagcccat tatggtgttg ataagagcga agaatgcg      960 atcaaccacc tgagcatcct ggaagcgtgg tctgacaacg acccacagta taacaaagac    1020
accaaaggtg cccagctgcc gatcgacaac aaactgcgtc tgtcgttgct gtacgcactg    1080
acccgtccgc tggagaagga tgcaagcaac aaaaatgaga ttcgtagcgg tctggagccg    1140
gttattacca attccctgaa taatcgttcc gctgagggca agaactctga acgcatggcg    1200
aattacatct tcatccgtgc tcacgattct gaagttcaaa cggtgatcgc aaagatcatc    1260
aaagcgcaga ttaacccgaa aacggatggc ctgaccttca ccctggatga gctgaaacag    1320
gcgttcaaaa tctataacga ggatatgcgc aggcgaaga agaagtatac ccagagcaat    1380
atcccgacgg catacgccct gatgctgagc aataaggact ccatcacgcg cctgtattac    1440
ggtgatatgt acagcgatga tggccaatac atggcgacca aatccccgta ctacgatgcg    1500
attgacaccc tgctgaaggc gcgcattaag tatgccgctg gcggtcagga tatgaagatc    1560
acctacgttg agggtgacaa aagccacatg gactgggact atacgggtgt cctgacgagc    1620
gttcgctacg gcacgggcgc aaacgaagcg accgaccagg gcagcgaagc taccaagacg    1680
caaggtatgg ccgtcatcac ttctaacaac cgtcccctga gctgaatca gaacgacaag    1740 gtcattgtca atatgggcac cgctcacaaa aatcaggaat accgtccgtt gctgctgacc    1800
```

```
accaaagacg gtctgaccag ctacaccagc gacgccgctg ccaagagcct gtaccgtaaa    1860
acgaacgata agggcgagtt ggtgttcgat gcaagcgaca ttcagggcta tctgaatccg    1920
caagtgagcg gttacctggc tgtttgggtg cctgtgggtg cgagcgacaa ccaggatgtg    1980
cgtgtcgcgg ccagcaataa agccaatgcg accggccaag tctatgaaag cagcagcgca    2040
ctggatagcc aactgattta tgagggtttt tccaactttc aggacttcgt caccaaggat    2100
tctgattaca ccaataaaaa gatcgcgcaa aatgtccagc tgtttaagag ctggggcgtc    2160
accagctttg agatggctcc gcaatacgtc agcagcgagg acggcagctt tttggacagc    2220
attatccaga acggctatgc gttcgaggat cgttacgacc tggcgatgag caaaaacaac    2280
aaatacggct cccagcagga catgatcaac gcggttaagg cgctgcataa gagcggtatc    2340
caagtgatcg cggactgggt cccggatcaa atctacaatt tgccgggtaa agaggtcgtc    2400
accgcgaccc gtgtgaacga ctacggcgag tatcgcaagg actccgaaat caaaaacacc    2460
ctgtacgccg ccaacaccaa aagcaacggt aaagattatc aagcaaagta cggtggcgcc    2520
tttttgagcg agctggccgc caaatatccg agcatcttta accgcactca gattagcaat    2580
ggcaagaaga tcgacccgtc tgaaaagatc accgcctgga aggccaaata cttcaatggt    2640
acgaacattt gggtcgcgg cgttggttac gtcttgaaag acaatgccag cgacaagtat    2700
tttgagctga agggcaatca gacttatctg ccgaagcaaa tgacgaataa agaagcctcg    2760
actggtttcg ttaatgacgg caatggtatg accttttaca gcacgagcgg ttatcaagcg    2820
aagaacagct tcgttcagga cgcaaaaggc aactggtact actttgacaa caatggccac    2880
atggtttacg gtctgcaaca tctgaacggc gaggtgcaat acttcctgag caatggcgtg    2940
caactgcgtg aatccttctt ggaaaatgcc gacggcagca aaaactattt cggtcacctg    3000
ggcaaccgtt atagcaatgg ttactacagc ttcgataatg atagcaaatg cgctatttc    3060 gatgcgagcg tgttatggc agtgggtctg aaaactatta cggtaacac ccagtatttc    3120 gatcaagacg gctaccaagt gaagggtgca tggattaccg gcagcgatgg taagaagcgt    3180
tacttcgacg acggtagcgg caatatggca gttaatcgct ttgctaacga caagaatggc    3240
gattggtatt acctgaatag cgacggtatt gcactggtgg gtgttcagac catcaacggc    3300
aaaacgtatt actttggcca agatggtaaa caaatcaaag gcaaaatcat taccgataat    3360
ggtaaactga aatactttct ggcgaacagc ggtgagctgg cgcgtaacat ttttgcgacc    3420
gacagccaga caactggta ttacttcggc tcggatggtg ttgcggttac gggttcgcag    3480
acgattgcgg gtaaaagtt gtactttgcg tccgacggta acaggtgaa gggtagcttt    3540 gttacttaca atggtaaagt gcactattac catgcggaca cggcgaact gcaagtcaac    3600 cgtttcgagg cggataaaga cggtaattgg tactatctgg acagcaacgg tgaggcactg    3660
acgggtagcc agcgtatcaa tggtcaacgt gtgttttca cccgcgaggg caaacaggtt    3720
aagggtgatg tcgcgtatga tgaacgcggc ttgctgcgct attacgacaa aaacagcggt    3780
aatatggtgt acaacaaggt ggtcacgctg gcgaacggtc gtcgtattgg tattgaccgc    3840
tggggtattg ctcgctatta ctaa                                          3864
```

<210> SEQ ID NO 44
<211> LENGTH: 1287
<212> TYPE: PRT
<213> ORGANISM: Streptococcus mutans

<400> SEQUENCE: 44

Met Ile Asp Gly Lys Tyr Tyr Tyr Ile Gly Ser Asp Gly Gln Pro Lys
1               5                   10                  15

Lys Asn Phe Ala Leu Thr Val Asn Asn Lys Val Leu Tyr Phe Asp Lys
            20                  25                  30

Asn Thr Gly Ala Leu Thr Asp Thr Ser Gln Tyr Gln Phe Lys Gln Gly
        35                  40                  45

Leu Thr Lys Leu Asn Asn Asp Tyr Thr Pro His Asn Gln Ile Val Asn
50                  55                  60

Phe Glu Asn Thr Ser Leu Glu Thr Ile Asp Asn Tyr Val Thr Ala Asp
65                  70                  75                  80

Ser Trp Tyr Arg Pro Lys Asp Ile Leu Lys Asn Gly Lys Thr Trp Thr
                85                  90                  95

Ala Ser Ser Glu Ser Asp Leu Arg Pro Leu Leu Met Ser Trp Trp Pro
            100                 105                 110

Asp Lys Gln Thr Gln Ile Ala Tyr Leu Asn Tyr Met Asn Gln Gln Gly
            115                 120                 125

Leu Gly Thr Gly Glu Asn Tyr Thr Ala Asp Ser Ser Gln Glu Ser Leu
        130                 135                 140

Asn Leu Ala Ala Gln Thr Val Gln Val Lys Ile Glu Thr Lys Ile Ser
145                 150                 155                 160

Gln Thr Gln Gln Thr Gln Trp Leu Arg Asp Ile Ile Asn Ser Phe Val
                165                 170                 175

Lys Thr Gln Pro Asn Trp Asn Ser Gln Thr Glu Ser Asp Thr Ser Ala
            180                 185                 190

Gly Glu Lys Asp His Leu Gln Gly Gly Ala Leu Leu Tyr Ser Asn Ser
            195                 200                 205

Asp Lys Thr Ala Tyr Ala Asn Ser Asp Tyr Arg Leu Leu Asn Arg Thr
        210                 215                 220

Pro Thr Ser Gln Thr Gly Lys Pro Lys Tyr Phe Glu Asp Asn Ser Ser
225                 230                 235                 240

Gly Gly Tyr Asp Phe Leu Leu Ala Asn Asp Ile Asp Asn Ser Asn Pro
                245                 250                 255

Val Val Gln Ala Glu Gln Leu Asn Trp Leu His Tyr Leu Met Asn Tyr
            260                 265                 270

Gly Ser Ile Val Ala Asn Asp Pro Glu Ala Asn Phe Asp Gly Val Arg
        275                 280                 285

Val Asp Ala Val Asp Asn Val Asn Ala Asp Leu Leu Gln Ile Ala Ser
        290                 295                 300

Asp Tyr Leu Lys Ala His Tyr Gly Val Asp Lys Ser Glu Lys Asn Ala
305                 310                 315                 320

Ile Asn His Leu Ser Ile Leu Glu Ala Trp Ser Asp Asn Asp Pro Gln
                325                 330                 335

Tyr Asn Lys Asp Thr Lys Gly Ala Gln Leu Pro Ile Asp Asn Lys Leu
            340                 345                 350

Arg Leu Ser Leu Leu Tyr Ala Leu Thr Arg Pro Leu Lys Asp Ala
            355                 360                 365

Ser Asn Lys Asn Glu Ile Arg Ser Gly Leu Glu Pro Val Ile Thr Asn
        370                 375                 380

Ser Leu Asn Asn Arg Ser Ala Glu Gly Lys Asn Ser Glu Arg Met Ala
385                 390                 395                 400

Asn Tyr Ile Phe Ile Arg Ala His Asp Ser Glu Val Gln Thr Val Ile
                405                 410                 415

Ala Lys Ile Ile Lys Ala Gln Ile Asn Pro Lys Thr Asp Gly Leu Thr

```
            420             425             430
Phe Thr Leu Asp Glu Leu Lys Gln Ala Phe Lys Ile Tyr Asn Glu Asp
            435             440             445
Met Arg Gln Ala Lys Lys Tyr Thr Gln Ser Asn Ile Pro Thr Ala
450             455             460
Tyr Ala Leu Met Leu Ser Asn Lys Asp Ser Ile Thr Arg Leu Tyr Tyr
465             470             475             480
Gly Asp Met Tyr Ser Asp Gly Gln Tyr Met Ala Thr Lys Ser Pro
            485             490             495
Tyr Tyr Asp Ala Ile Asp Thr Leu Leu Lys Ala Arg Ile Lys Tyr Ala
            500             505             510
Ala Gly Gly Gln Asp Met Lys Ile Thr Tyr Val Glu Gly Asp Lys Ser
            515             520             525
His Met Asp Trp Asp Tyr Thr Gly Val Leu Thr Ser Val Arg Tyr Gly
            530             535             540
Thr Gly Ala Asn Glu Ala Thr Asp Gln Gly Ser Glu Ala Thr Lys Thr
545             550             555             560
Gln Gly Met Ala Val Ile Thr Ser Asn Asn Pro Ser Leu Lys Leu Asn
            565             570             575
Gln Asn Asp Lys Val Ile Val Asn Met Gly Thr Ala His Lys Asn Gln
            580             585             590
Glu Tyr Arg Pro Leu Leu Leu Thr Thr Lys Asp Gly Leu Thr Ser Tyr
            595             600             605
Thr Ser Asp Ala Ala Lys Ser Leu Tyr Arg Lys Thr Asn Asp Lys
            610             615             620
Gly Glu Leu Val Phe Asp Ala Ser Asp Ile Gln Gly Tyr Leu Asn Pro
625             630             635             640
Gln Val Ser Gly Tyr Leu Ala Val Trp Val Pro Val Gly Ala Ser Asp
            645             650             655
Asn Gln Asp Val Arg Val Ala Ala Ser Asn Lys Ala Asn Ala Thr Gly
            660             665             670
Gln Val Tyr Glu Ser Ser Ala Leu Asp Ser Gln Leu Ile Tyr Glu
            675             680             685
Gly Phe Ser Asn Phe Gln Asp Phe Val Thr Lys Asp Ser Asp Tyr Thr
690             695             700
Asn Lys Lys Ile Ala Gln Asn Val Gln Leu Phe Lys Ser Trp Gly Val
705             710             715             720
Thr Ser Phe Glu Met Ala Pro Gln Tyr Val Ser Ser Glu Asp Gly Ser
            725             730             735
Phe Leu Asp Ser Ile Ile Gln Asn Gly Tyr Ala Phe Glu Asp Arg Tyr
            740             745             750
Asp Leu Ala Met Ser Lys Asn Lys Tyr Gly Ser Gln Gln Asp Met
            755             760             765
Ile Asn Ala Val Lys Ala Leu His Lys Ser Gly Ile Gln Val Ile Ala
            770             775             780
Asp Trp Val Pro Asp Gln Ile Tyr Asn Leu Pro Gly Lys Glu Val Val
785             790             795             800
Thr Ala Thr Arg Val Asn Asp Tyr Gly Glu Tyr Arg Lys Asp Ser Glu
            805             810             815
Ile Lys Asn Thr Leu Tyr Ala Ala Asn Thr Lys Ser Asn Gly Lys Asp
            820             825             830
Tyr Gln Ala Lys Tyr Gly Gly Ala Phe Leu Ser Glu Leu Ala Ala Lys
            835             840             845
```

Tyr Pro Ser Ile Phe Asn Arg Thr Gln Ile Ser Asn Gly Lys Lys Ile
850                 855                 860

Asp Pro Ser Glu Lys Ile Thr Ala Trp Lys Ala Lys Tyr Phe Asn Gly
865                 870                 875                 880

Thr Asn Ile Leu Gly Arg Gly Val Gly Tyr Val Leu Lys Asp Asn Ala
            885                 890                 895

Ser Asp Lys Tyr Phe Glu Leu Lys Gly Asn Gln Thr Tyr Leu Pro Lys
        900                 905                 910

Gln Met Thr Asn Lys Glu Ala Ser Thr Gly Phe Val Asn Asp Gly Asn
            915                 920                 925

Gly Met Thr Phe Tyr Ser Thr Ser Gly Tyr Gln Ala Lys Asn Ser Phe
        930                 935                 940

Val Gln Asp Ala Lys Gly Asn Trp Tyr Phe Asp Asn Asn Gly His
945                 950                 955                 960

Met Val Tyr Gly Leu Gln His Leu Asn Gly Glu Val Gln Tyr Phe Leu
            965                 970                 975

Ser Asn Gly Val Gln Leu Arg Glu Ser Phe Leu Glu Asn Ala Asp Gly
        980                 985                 990

Ser Lys Asn Tyr Phe Gly His Leu Gly Asn Arg Tyr Ser Asn Gly Tyr
        995                 1000                1005

Tyr Ser Phe Asp Asn Asp Ser Lys Trp Arg Tyr Phe Asp Ala Ser
    1010                1015                1020

Gly Val Met Ala Val Gly Leu Lys Thr Ile Asn Gly Asn Thr Gln
    1025                1030                1035

Tyr Phe Asp Gln Asp Gly Tyr Gln Val Lys Gly Ala Trp Ile Thr
    1040                1045                1050

Gly Ser Asp Gly Lys Lys Arg Tyr Phe Asp Asp Gly Ser Gly Asn
    1055                1060                1065

Met Ala Val Asn Arg Phe Ala Asn Asp Lys Asn Gly Asp Trp Tyr
    1070                1075                1080

Tyr Leu Asn Ser Asp Gly Ile Ala Leu Val Gly Val Gln Thr Ile
    1085                1090                1095

Asn Gly Lys Thr Tyr Tyr Phe Gly Gln Asp Gly Lys Gln Ile Lys
    1100                1105                1110

Gly Lys Ile Ile Thr Asp Asn Gly Lys Leu Lys Tyr Phe Leu Ala
    1115                1120                1125

Asn Ser Gly Glu Leu Ala Arg Asn Ile Phe Ala Thr Asp Ser Gln
    1130                1135                1140

Asn Asn Trp Tyr Tyr Phe Gly Ser Asp Gly Val Ala Val Thr Gly
    1145                1150                1155

Ser Gln Thr Ile Ala Gly Lys Lys Leu Tyr Phe Ala Ser Asp Gly
    1160                1165                1170

Lys Gln Val Lys Gly Ser Phe Val Thr Tyr Asn Gly Lys Val His
    1175                1180                1185

Tyr Tyr His Ala Asp Ser Gly Glu Leu Gln Val Asn Arg Phe Glu
    1190                1195                1200

Ala Asp Lys Asp Gly Asn Trp Tyr Tyr Leu Asp Ser Asn Gly Glu
    1205                1210                1215

Ala Leu Thr Gly Ser Gln Arg Ile Asn Gly Gln Arg Val Phe Phe
    1220                1225                1230

Thr Arg Glu Gly Lys Gln Val Lys Gly Asp Val Ala Tyr Asp Glu
    1235                1240                1245

```
  Arg Gly Leu Leu Arg Tyr Tyr Asp Lys Asn Ser Gly Asn Met Val
      1250                1255                1260

Tyr Asn Lys Val Val Thr Leu Ala Asn Gly Arg Arg Ile Gly Ile
          1265                1270                1275

Asp Arg Trp Gly Ile Ala Arg Tyr Tyr
      1280                1285

<210> SEQ ID NO 45
<211> LENGTH: 4068
<212> TYPE: DNA
<213> ORGANISM: Streptococcus gallolyticus

<400> SEQUENCE: 45
atgatcgacg gcaaatacta ctatattgac gaggacggta acgtaaagaa gaatttcgcg      60
attacggtgg atggtcagtt gctgtacttc gacgctgaaa cgggtgctct gaccagcacg     120
tccacctata gcttctccga gggcctgact aatctggtcg ataacttcag cattaacaac     180
cagtcctacg acagcaccga agagtcgttt gagctgatcg acggttacct gaccgtcaat     240
acttggtacc gtccgaccaa aattctggaa acggtgaaa cctgggtcga tagcaccgaa     300
acggatttcc gtccgctgct gatggcctgg tggccggatg ttgacaccca aattgactac     360
ttgaactaca tgagcgatta cttcgatctg ggtacgacct atagcgctga cgattcccaa     420
gcgagcctga atctggcagc tgaggcggtt caggtgaaaa ttgaacaaga aattacccgt     480
caagagaaca ccgcctggct gcgcgagatc atctctagct ttgttaccac ccaggataaa     540
tggaatatca ataccgagaa tgagggcacc gaccatctgc aaggtggtgc cctgctgtac     600
gttaacagcg acttgactcc gtgggcaaac agcgattatc gcctgctgaa ccgcaccccg     660
acgtaccaga cgggtgagac taattacttt aaagcagatc gtactggtgg ctacgaattt     720
ctgctggcaa tgacgtgga taattctaac ccggtcgttc aagccgaaca gttgaaccag     780
ctgtactact tgatgaattg gggctctatt gtattcggtg atgacgacgc caattttgat     840
ggcgtgcgtg ttgacgcggt ggacaatgtg aacgctgacc tgttgcagat ttacacgaac     900
ctgttcgaag cggcgtatgg tgttaacgag tctgaggcgc aggccctggc tcacattagc     960
atcctggaag cgtggtctta taacgacccg gactacaacc acgacacgaa tggcgctgcc    1020
ctggcaatcg acaatggtct gcgtctgagc tttctgtact ctttgacgcg ccctacggac    1080
gagcgcagcg gtttggagcc actgatcacc tctgagattg gcctgaccga tcgttccgag    1140
gactctgcat acggtgacac catgccgagc tatgttttcg tccgtgcaca tgacagcgag    1200
gttcagacca ttattgcgag cattatcgca gaacagatca cccggaaac cgatggctat    1260 accttcaccc tggacgagct gaaccaggcg tttgagattt acaacgcgga tatgaacagc    1320
gtggataaag agtatacgca ttacaatatc ccggctgcgt atagcctgct gctgaccaac    1380
atggaaagcg tcccgcgtgt ttactacggt gacctgtata cggataacgg tcagtacatg    1440
gcgactaaga gcccgtatta tgaccagatc accaccctgc tgcaagcgcg cattcgttac    1500
gcggcgggtg gccaatctat ggctgttacg tactacaccc ctgcgtcgag catgtctacc    1560
gacaatgcgg atagcgtcct gaatgagact ggtgtgctga cttctgtgcg ttacggctat    1620
ggcatcatga ccgccgacca agaggccacg gacgactccg ttctgacctc tggtattgtt    1680
actattatca gcaacaaccc taatttgcag ctggatgatt ccgaagtgat tgcagtccag    1740
gttggtgtgg cgcacgctgg tcagtattat cgtccgctgt tgtacccgac ggcggatggt    1800
ctgcaaagct acctgaacga tagcgatacc gacattacta agctggtcga tgataatggt    1860
```

| | |
|---|---|
| tatatctact ttacggcaga tgagattaaa ggctacgaaa cggttgacat gaatggctac | 1920 |
| ctgagcgttt gggtcccggt tggtgcagac gagaatcagg acatccgtgt cagcgcagac | 1980 |
| accagcgcgt acaccgaggg tgaattgatc tatcaagcaa ccgcagcgct ggatagccaa | 2040 |
| gtgatctacg agggtttcag caacttccaa gatttcgtta cctctaacag cgagtacact | 2100 |
| aacaagctga tcgcggagaa cgtcgatctg tttaccagct ggggcattac gagctttgag | 2160 |
| atggcgccac agtatgtgag caccgatgac ggtacttttc tggatagcat cattcaaaac | 2220 |
| ggttatgcat ttgacgatcg ctacgacctg gcaatgagcc agaataacaa gtatggtagc | 2280 |
| gctgaagatt tgcgtaatgc catcaaggcc ctgcacgctg ctggcattca ggtcattgct | 2340 |
| gactgggtgc cggatcaaat ctattcgctg ccaggcgaag aagtcgttac ggcgactcgc | 2400 |
| gtgaatgact atggcgaaga aaccgaaggc gcgtacatta caatacgtt gtatgtggcg | 2460 |
| aacagcaaaa gcagcggcga ggactaccag gcacagtatg tggtgagtt cctggattac | 2520 |
| ttgcaagaaa cctacccgga aatgttcgaa gttgcgatga ttagcacggg tgagccgatt | 2580 |
| gatccgagca ccaagatcaa gatttggaaa gcagaatact ttaatggtac gaacattctg | 2640 |
| ggtaagggcg ctggttacgt gctgagcgat gccgcgactg gcacgtactt taccgtgact | 2700 |
| gagaatggca cgtttctgcc gaagcagctg accaccgact ccgccattac gggtttctat | 2760 |
| tacgacggta cgggtatgtc ttactttagc acctcgggtt atcgcgctaa agcgagcttc | 2820 |
| attgtttaca acggctacta ctactatttt gatgataacg gctacatggt cactggcacg | 2880 |
| gtggaaatca acggtaagac ctactatttc ctgccgaatg gtattcagct gcgtgatgcg | 2940 |
| atttacgaag acgagaacgg taatcagtac tatttcggtc cgttgggcaa ccagtatttc | 3000 |
| aacaactatt acagctttga cgttgaagag gtggtggacg gtgtaacgac tacggtaacg | 3060 |
| aagtggcgtc attttgacga gaacggcgtg atggcgcgtg gtttggtcga gattgatggt | 3120 |
| gtctaccagt attacgatga aaacggctac caggtcaaag gtgagctgat caccgatgct | 3180 |
| gatggtaatt gcgttatttt caaagaagat agccggtgaaa tggttgttag cgattttgtg | 3240 |
| aagatcggcg ataacaactg gtactacttt gacgaaaacg gtattgcagt cacgggtgcc | 3300 |
| caaaccattg ccggccagaa cttgtatttc gatgacaacg gtgtgcaggc gaaaggtgcc | 3360 |
| tttgtcacga acgccgatgg cacgcgcagc tattatgacg cggacagcgg tgagaagatc | 3420 |
| gtggcagatt tcttcactac gggcgataat gactggtatt atgcagatga aaatggcaat | 3480 |
| ctggtgactg gtagccaaac tatcaatggt caaaacctgt actttgctga ggacggtttg | 3540 |
| caggccaagg gtgtgttgt taccgatacg gctggtaaca ttcactatta tgatgcgaac | 3600 |
| tctggcgagt tggcggttaa taccttcgtt ggtgatggcg acgactggta ttactttgat | 3660 |
| gagaatggca tcgcagttac cggcgcacaa gtcattaacg tcaacacct gtatttcgca | 3720 |
| gacaacggca tccaagtgaa aggtgaaatc gtcaccgacg caaacggcaa ccgctattac | 3780 |
| tacgatgcag attccggcga aatggcagtt aacacctttg tggagattga cggtgtttgg | 3840 |
| tactatttg gtgccgatgg tatcgcggtg acgggtgcac aagtaattga tggtcagaat | 3900 |
| ttgtactta acgcagacgg tagccaagtc aagggtgacg ttgtccgtat caacggtttg | 3960 |
| cgttactact acgacgctaa tagcggcgaa caggtgcgca atcagtgggt cacgctgccg | 4020 |
| gatggtactg ttgttttctt taatgcgcgt ggctatactt ggggctaa | 4068 |

<210> SEQ ID NO 46
<211> LENGTH: 1355
<212> TYPE: PRT
<213> ORGANISM: Streptococcus gallolyticus

<400> SEQUENCE: 46

```
Met Ile Asp Gly Lys Tyr Tyr Tyr Ile Asp Glu Asp Gly Asn Val Lys
1               5                   10                  15

Lys Asn Phe Ala Ile Thr Val Asp Gly Gln Leu Leu Tyr Phe Asp Ala
            20                  25                  30

Glu Thr Gly Ala Leu Thr Ser Thr Ser Thr Tyr Ser Phe Ser Glu Gly
        35                  40                  45

Leu Thr Asn Leu Val Asp Asn Phe Ser Ile Asn Asn Gln Ser Tyr Asp
50                  55                  60

Ser Thr Glu Glu Ser Phe Glu Leu Ile Asp Gly Tyr Leu Thr Val Asn
65                  70                  75                  80

Thr Trp Tyr Arg Pro Thr Lys Ile Leu Glu Asn Gly Glu Thr Trp Val
                85                  90                  95

Asp Ser Thr Glu Thr Asp Phe Arg Pro Leu Leu Met Ala Trp Trp Pro
            100                 105                 110

Asp Val Asp Thr Gln Ile Asp Tyr Leu Asn Tyr Met Ser Asp Tyr Phe
        115                 120                 125

Asp Leu Gly Thr Thr Tyr Ser Ala Asp Asp Ser Gln Ala Ser Leu Asn
130                 135                 140

Leu Ala Ala Glu Ala Val Gln Val Lys Ile Glu Gln Glu Ile Thr Arg
145                 150                 155                 160

Gln Glu Asn Thr Ala Trp Leu Arg Glu Ile Ile Ser Ser Phe Val Thr
                165                 170                 175

Thr Gln Asp Lys Trp Asn Ile Asn Thr Glu Asn Glu Gly Thr Asp His
            180                 185                 190

Leu Gln Gly Gly Ala Leu Leu Tyr Val Asn Ser Asp Leu Thr Pro Trp
        195                 200                 205

Ala Asn Ser Asp Tyr Arg Leu Leu Asn Arg Thr Pro Thr Tyr Gln Thr
210                 215                 220

Gly Glu Thr Asn Tyr Phe Lys Ala Asp Arg Thr Gly Tyr Glu Phe
225                 230                 235                 240

Leu Leu Ala Asn Asp Val Asp Asn Ser Asn Pro Val Val Gln Ala Glu
                245                 250                 255

Gln Leu Asn Gln Leu Tyr Tyr Leu Met Asn Trp Gly Ser Ile Val Phe
            260                 265                 270

Gly Asp Asp Asp Ala Asn Phe Asp Gly Val Arg Val Asp Ala Val Asp
        275                 280                 285

Asn Val Asn Ala Asp Leu Leu Gln Ile Tyr Thr Asn Leu Phe Glu Ala
290                 295                 300

Ala Tyr Gly Val Asn Glu Ser Glu Ala Gln Ala Leu Ala His Ile Ser
305                 310                 315                 320

Ile Leu Glu Ala Trp Ser Tyr Asn Asp Pro Asp Tyr Asn His His Asp Thr
                325                 330                 335

Asn Gly Ala Ala Leu Ala Ile Asp Asn Gly Leu Arg Leu Ser Phe Leu
            340                 345                 350

Tyr Ser Leu Thr Arg Pro Thr Asp Glu Arg Ser Gly Leu Glu Pro Leu
        355                 360                 365

Ile Thr Ser Glu Ile Gly Leu Thr Asp Arg Ser Glu Asp Ser Ala Tyr
370                 375                 380

Gly Asp Thr Met Pro Ser Tyr Val Phe Val Arg Ala His Asp Ser Glu
385                 390                 395                 400

Val Gln Thr Ile Ile Ala Ser Ile Ile Ala Glu Gln Ile Asn Pro Glu
```

```
            405                 410                 415
Thr Asp Gly Tyr Thr Phe Thr Leu Asp Glu Leu Asn Gln Ala Phe Glu
            420                 425                 430
Ile Tyr Asn Ala Asp Met Asn Ser Val Asp Lys Glu Tyr Thr His Tyr
            435                 440                 445
Asn Ile Pro Ala Ala Tyr Ser Leu Leu Leu Thr Asn Met Glu Ser Val
            450                 455                 460
Pro Arg Val Tyr Tyr Gly Asp Leu Tyr Thr Asp Asn Gly Gln Tyr Met
465                 470                 475                 480
Ala Thr Lys Ser Pro Tyr Tyr Asp Gln Ile Thr Thr Leu Leu Gln Ala
            485                 490                 495
Arg Ile Arg Tyr Ala Ala Gly Gly Gln Ser Met Ala Val Thr Tyr Tyr
            500                 505                 510
Thr Pro Ala Ser Ser Met Ser Thr Asp Asn Ala Asp Ser Val Leu Asn
            515                 520                 525
Glu Thr Gly Val Leu Thr Ser Val Arg Tyr Gly Tyr Gly Ile Met Thr
            530                 535                 540
Ala Asp Gln Glu Ala Thr Asp Asp Ser Val Leu Thr Ser Gly Ile Val
545                 550                 555                 560
Thr Ile Ile Ser Asn Asn Pro Asn Leu Gln Leu Asp Asp Ser Glu Val
            565                 570                 575
Ile Ala Val Gln Val Gly Val Ala His Ala Gly Gln Tyr Tyr Arg Pro
            580                 585                 590
Leu Leu Tyr Pro Thr Ala Asp Gly Leu Gln Ser Tyr Leu Asn Asp Ser
            595                 600                 605
Asp Thr Asp Ile Thr Lys Leu Val Asp Asp Asn Gly Tyr Ile Tyr Phe
            610                 615                 620
Thr Ala Asp Glu Ile Lys Gly Tyr Glu Thr Val Asp Met Asn Gly Tyr
625                 630                 635                 640
Leu Ser Val Trp Val Pro Val Gly Ala Asp Glu Asn Gln Asp Ile Arg
            645                 650                 655
Val Ser Ala Asp Thr Ser Ala Tyr Thr Glu Gly Glu Leu Ile Tyr Gln
            660                 665                 670
Ala Thr Ala Ala Leu Asp Ser Gln Val Ile Tyr Glu Gly Phe Ser Asn
            675                 680                 685
Phe Gln Asp Phe Val Thr Ser Asn Ser Glu Tyr Thr Asn Lys Leu Ile
            690                 695                 700
Ala Glu Asn Val Asp Leu Phe Thr Ser Trp Gly Ile Thr Ser Phe Glu
705                 710                 715                 720
Met Ala Pro Gln Tyr Val Ser Thr Asp Gly Thr Phe Leu Asp Ser
            725                 730                 735
Ile Ile Gln Asn Gly Tyr Ala Phe Asp Asp Arg Tyr Asp Leu Ala Met
            740                 745                 750
Ser Gln Asn Asn Lys Tyr Gly Ser Ala Glu Asp Leu Arg Asn Ala Ile
            755                 760                 765
Lys Ala Leu His Ala Ala Gly Ile Gln Val Ile Ala Asp Trp Val Pro
            770                 775                 780
Asp Gln Ile Tyr Ser Leu Pro Gly Glu Glu Val Val Thr Ala Thr Arg
785                 790                 795                 800
Val Asn Asp Tyr Gly Glu Glu Thr Gly Ala Tyr Ile Asn Asn Thr
            805                 810                 815
Leu Tyr Val Ala Asn Ser Lys Ser Ser Gly Glu Asp Tyr Gln Ala Gln
            820                 825                 830
```

-continued

Tyr Gly Gly Glu Phe Leu Asp Tyr Leu Gln Glu Thr Tyr Pro Glu Met
            835                 840                 845

Phe Glu Val Ala Met Ile Ser Thr Gly Glu Pro Ile Asp Pro Ser Thr
850                 855                 860

Lys Ile Lys Ile Trp Lys Ala Glu Tyr Phe Asn Gly Thr Asn Ile Leu
865                 870                 875                 880

Gly Lys Gly Ala Gly Tyr Val Leu Ser Asp Ala Ala Thr Gly Thr Tyr
            885                 890                 895

Phe Thr Val Thr Glu Asn Gly Thr Phe Leu Pro Lys Gln Leu Thr Thr
            900                 905                 910

Asp Ser Ala Ile Thr Gly Phe Tyr Tyr Asp Gly Thr Gly Met Ser Tyr
            915                 920                 925

Phe Ser Thr Ser Gly Tyr Arg Ala Lys Ala Ser Phe Ile Val Tyr Asn
930                 935                 940

Gly Tyr Tyr Tyr Phe Asp Asp Asn Gly Tyr Met Val Thr Gly Thr
945                 950                 955                 960

Val Glu Ile Asn Gly Lys Thr Tyr Tyr Phe Leu Pro Asn Gly Ile Gln
            965                 970                 975

Leu Arg Asp Ala Ile Tyr Glu Asp Glu Asn Gly Asn Tyr Tyr Phe
            980                 985                 990

Gly Pro Leu Gly Asn Gln Tyr Phe Asn Asn Tyr Tyr Ser Phe Asp Val
            995                 1000                1005

Glu Glu Val Val Asp Gly Val Thr Thr Thr Val Thr Lys Trp Arg
    1010                1015                1020

His Phe Asp Glu Asn Gly Val Met Ala Arg Gly Leu Val Glu Ile
    1025                1030                1035

Asp Gly Val Tyr Gln Tyr Tyr Asp Glu Asn Gly Tyr Gln Val Lys
    1040                1045                1050

Gly Glu Leu Ile Thr Asp Ala Asp Gly Asn Leu Arg Tyr Phe Lys
    1055                1060                1065

Glu Asp Ser Gly Glu Met Val Val Ser Asp Phe Val Lys Ile Gly
    1070                1075                1080

Asp Asn Asn Trp Tyr Tyr Phe Asp Glu Asn Gly Ile Ala Val Thr
    1085                1090                1095

Gly Ala Gln Thr Ile Ala Gly Gln Asn Leu Tyr Phe Asp Asp Asn
    1100                1105                1110

Gly Val Gln Ala Lys Gly Ala Phe Val Thr Asn Ala Asp Gly Thr
    1115                1120                1125

Arg Ser Tyr Tyr Asp Ala Asp Ser Gly Glu Lys Ile Val Ala Asp
    1130                1135                1140

Phe Phe Thr Thr Gly Asp Asn Asp Trp Tyr Tyr Ala Asp Glu Asn
    1145                1150                1155

Gly Asn Leu Val Thr Gly Ser Gln Thr Ile Asn Gly Gln Asn Leu
    1160                1165                1170

Tyr Phe Ala Glu Asp Gly Leu Gln Ala Lys Gly Val Phe Val Thr
    1175                1180                1185

Asp Thr Ala Gly Asn Ile His Tyr Tyr Asp Ala Asn Ser Gly Glu
    1190                1195                1200

Leu Ala Val Asn Thr Phe Val Gly Asp Gly Asp Trp Tyr Tyr
    1205                1210                1215

Phe Asp Glu Asn Gly Ile Ala Val Thr Gly Ala Gln Val Ile Asn
    1220                1225                1230

```
Gly Gln His Leu Tyr Phe Ala Asp Asn Gly Ile Gln Val Lys Gly
    1235                1240                1245

Glu Ile Val Thr Asp Ala Asn Gly Asn Arg Tyr Tyr Tyr Asp Ala
    1250                1255                1260

Asp Ser Gly Glu Met Ala Val Asn Thr Phe Val Glu Ile Asp Gly
    1265                1270                1275

Val Trp Tyr Tyr Phe Gly Ala Asp Gly Ile Ala Val Thr Gly Ala
    1280                1285                1290

Gln Val Ile Asp Gly Gln Asn Leu Tyr Phe Asn Ala Asp Gly Ser
    1295                1300                1305

Gln Val Lys Gly Asp Val Val Arg Ile Asn Gly Leu Arg Tyr Tyr
    1310                1315                1320

Tyr Asp Ala Asn Ser Gly Glu Gln Val Arg Asn Gln Trp Val Thr
    1325                1330                1335

Leu Pro Asp Gly Thr Val Val Phe Phe Asn Ala Arg Gly Tyr Thr
    1340                1345                1350

Trp Gly
    1355

<210> SEQ ID NO 47
<211> LENGTH: 4047
<212> TYPE: DNA
<213> ORGANISM: Streptococcus sanguinis

<400> SEQUENCE: 47
atgatcgatg gcaagaaata ctatgttcag gacgacggta cggtaaagaa gaatttcgcg      60
gttgaactga acggcaaggt cctgtatttc gatgcagaaa ccggtgccct ggtcgacagc     120
gcggagtacc agtttcaaca gggtacgagc tccctgaata acgagttcag ccgcatgaat     180
gcgttccatg gcacgacgga gaaagatatt gaaaccgtcg atggctatct gaccgcagat     240
acgtggtacc gcccgaaggc catcctgaaa gatggcaaaa cctggactca gagcaccgaa     300
accgatctgc gtccgctgct gatggcatgg tggccggaca acaaacgca ggtaagctac      360 ttgaactata tgaaccagca gggtctgggt gcgggtgcgt ttgagaacaa agttgagcag     420
gcaatcttga cgggcgcaag ccagcaggtg cagcgcaaga tcgaagaacg tattggcaaa     480
gacggcgata ccaaatggct gcgtaccctg atgggtgcat tgtgaaaac ccagccgaat      540 tggaatatca agacggagag cgaaaccacg ggtactaata aggatcatct gcaaggtggt     600
gcgctgctgt acaccaactc tgaaaagacg agccacgcga acagcaaata ccgtattctg     660
aatcgtaccc cgaccaatca gaccggtacg ccgaagtatt tcatcgacaa atcgaatggt     720
ggttacgagt tcttgctggc aaatgatttt gataatagca acccagcagt ccaagcggaa     780
cagctgaatt ggctgcactt tatgatgaat ttcggcagca ttgttgcaaa tgacccgacc     840
gcaaacttcg atggcgtgcg tgtggatgcg gtggacaatg ttaatgccga tttgctgcaa     900
attgccagcg actatttcaa atctcgttac aaagtgggcg agagcgaaga caagcgatt      960 aaacatctga gcatcctgga agcctggagc gacaacgatc cggactataa caaagacacc    1020
aaaggcgccc aactgccgat cgacaataag ctgcgtctga gcctgttgta cagctttatg    1080
cgtaagctga gcattcgcag cggtgtcgaa ccgacgatta ccaacagcct gaacgaccgt    1140
tctgcggaga agaagaacgg tgagcgcatg gcaaactata tctttgttcg tgcgcatgat    1200
tccgaagtgc agacggtcat tgccgacatt attcgcgaga atatcaatcc gaacacggat    1260
ggtctgacct ttaccatgga cgagctgaaa caggcgttca gatctacaa tgaagatatg     1320
```

-continued

```
cgcaaggcgg ataagaagta tacccaattc aatattccga ccgctcacgc gttgatgttg    1380
agcaacaagg attccattac gcgtgtgtac tacggtgacc tgtatacgga tgatggtcag    1440
tatatggaaa agaaaagccc ttattacgac gcgatcgacg cgctgctgcg cgcacgcatt    1500
aagtacgttg cgggtggcca ggacatgaaa gttacctaca tgggtgtgcc gcgtgaaacc    1560
gacaaatgga gctacaacgg catcctgacc agcgtccgct acggcaccgg cgcaaatgag    1620
gctacggacg agggtactgc cgagactcgc acccagggta tggccgtcat cgcaagcaac    1680
aatccgaatt tgaaactgaa cgagtgggat aagttgcagg tcaacatggg tgcggcacac    1740
aagaaccaat actatcgtcc ggtgctgctg accaccaagg acggtattag ccgttacctg    1800
accgacgaag aagttccgca aagcctgtgg aagaaaaccg atgcaaacgg catcttgacg    1860
ttcgacatga acgatatcgc aggttacagc aatgtccaag tatctggcta cttggctgtg    1920
tgggtgccgg ttggtgccaa agcggatcaa gacgcgcgtg ttactgcgtc gaagaagaaa    1980
aacgccagcg gtcaggtgta tgagtccagc gctgcactgg acagccaact gatttatgaa    2040
ggcttctcta acttccaaga cttcgcgacc cgcgacgatc aatacaccaa caaagttatt    2100
gccaaaaatg ttaatctgtt taaagagtgg ggtgtgacca gctttgagct gccacctcag    2160
tatgtttcca gccaggatgg cacgtttttg gatagcatca tccagaatgg ctacgcattt    2220
gaagatcgtt atgacatggc gatgagcaaa aacaataagt acggtagcct ggacgacctg    2280
ctgaacgcgc tgcgtgcctt gcacagcgtc aacatccaag cgatcgcgga ctgggtcccg    2340
gatcagattt acaacctgcc gggcaaagaa gtggttacgg ctacgcgtgt caacaattat    2400
ggtacctatc gtgagggtgc ggaaatcaaa gaaaatctgt acgtggcaaa cacgaaaacc    2460
aacggcaccg actatcaagg caaatacggt ggtgcgttcc tggacgaact gaaagcgaaa    2520
tatcctgaga tcttcgaacg tgttcaaatt tccaatggtc aaaagatgac caccgatgag    2580
aagattacga atggagcgc gaaacacttc aatggtacca acattctggg ccgtggtgca    2640
tactacgtgc tgaaagattg ggccagcaat gagtatctga acaataagaa tggtgagatg    2700
gtgttgccga agcaactggt taacaaaaac gcgtacaccg gctttgttaa ggacaccacc    2760
ggttttaagt actatagcac ctcgggctat caagcgcgta atagcttcat ccaagatgag    2820
aacggtaatt ggtactactt tgacaaacgt ggttacctgg cgactggtgc acacgaaatc    2880
gacggcaagc aggtctattt cctgaaaaac ggcattcaac tgcgcgactc tctgcgtgag    2940
gacgagaacg gcaatcagta ctattacgac aagaccggtg cgcaggtgct gaaccgctac    3000
tacaccaccg acggccagaa ctggcgttac ttcgacgcca aggtgttat ggcgcgtggc    3060 ctggttacca tgggtggtaa ccaacaattc ttcgaccaga acggttatca ggtgaaaggc    3120
aagatcgcgc gtgccaagga tggtaaactg cgctacttcg acaaagacag cggtaacgca    3180
gcggcgaatc gctttgcaca gggcgataat ccgagcgatt ggtattactt tggtgccgat    3240
ggcgtcgctg ttaccggttt gcaaaaactg ggtcaacaaa ctctgtactt tgatcaagaa    3300
ggtaaacaag tgaagggcaa gattgtcacg ctggctgata agtccatccg ttacttcgat    3360
gcgaacagcg gcgagatggc tgtcggtaag tttgctgagg gtagcaagaa cgaatggtac    3420
tatttcgatc agacgggcaa agcggttacg ggtctgcaaa agattggcca gcagaccctg    3480
tattttgacc aagatggtaa gcaggtaaag ggtaaagtgg taaccctggc agataagtcg    3540
attcgctact tgatgcaaa ctccggcgaa atggcggtgg gtaagttcgc cgagggtgct    3600
aagaatgagt ggtactactt tgaccaggcg ggcaaggcgg tgaccggctt gcagaaaatt    3660
ggtcagcaaa cgctgtattt tgatcaggac ggcaaacaag tcaaaggcca actggtgacg    3720
```

-continued

```
ctggcggaca agagcattcg ttatttcgac gcaaacagcg gtgagatggc ctctaacaag    3780
ttcgttgagg gtgccaaaaa cgaatggtac tatttcgacc aagccggtaa agcagtgacc    3840
ggtctgcaac aaatcggtca gcagaccttg tacttcgacc aaaacggtaa acaggtcaaa    3900
ggtaaaatcg tgtatgttaa cggtgccaat cgttactttg acgccaattc gggtgaaatg    3960
gcgcgcaata agtggatcca actggaagat ggtagctgga tgtacttcga tcgtaacggt    4020
cgtggtcgtc gtttcggctg gaattaa                                       4047
```

<210> SEQ ID NO 48
<211> LENGTH: 1348
<212> TYPE: PRT
<213> ORGANISM: Streptococcus sanguinis

<400> SEQUENCE: 48

Met Ile Asp Gly Lys Lys Tyr Tyr Val Gln Asp Asp Gly Thr Val Lys
1               5                   10                  15

Lys Asn Phe Ala Val Glu Leu Asn Gly Lys Val Leu Tyr Phe Asp Ala
            20                  25                  30

Glu Thr Gly Ala Leu Val Asp Ser Ala Glu Tyr Gln Phe Gln Gln Gly
        35                  40                  45

Thr Ser Ser Leu Asn Asn Glu Phe Ser Arg Met Asn Ala Phe His Gly
    50                  55                  60

Thr Thr Glu Lys Asp Ile Glu Thr Val Asp Gly Tyr Leu Thr Ala Asp
65                  70                  75                  80

Thr Trp Tyr Arg Pro Lys Ala Ile Leu Lys Asp Gly Lys Thr Trp Thr
                85                  90                  95

Gln Ser Thr Glu Thr Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Asp Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Thr Asn Ser Glu
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Gln Ala Ile

```
            305                 310                 315                 320

Lys His Leu Ser Ile Leu Glu Ala Trp Ser Asp Asn Asp Pro Asp Tyr
                    325                 330                 335

Asn Lys Asp Thr Lys Gly Ala Gln Leu Pro Ile Asp Asn Lys Leu Arg
                    340                 345                 350

Leu Ser Leu Leu Tyr Ser Phe Met Arg Lys Leu Ser Ile Arg Ser Gly
                    355                 360                 365

Val Glu Pro Thr Ile Thr Asn Ser Leu Asn Asp Arg Ser Ala Glu Lys
        370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                    405                 410                 415

Pro Asn Thr Asp Gly Leu Thr Phe Thr Met Asp Glu Leu Lys Gln Ala
                420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
        450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr Tyr Asp Ala Ile Asp Ala Leu Leu
                485                 490                 495

Arg Ala Arg Ile Lys Tyr Val Ala Gly Gly Gln Asp Met Lys Val Thr
                    500                 505                 510

Tyr Met Gly Val Pro Arg Glu Thr Asp Lys Trp Ser Tyr Asn Gly Ile
                515                 520                 525

Leu Thr Ser Val Arg Tyr Gly Thr Gly Ala Asn Glu Ala Thr Asp Glu
            530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                    565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Val Pro Gln Ser
                595                 600                 605

Leu Trp Lys Lys Thr Asp Ala Asn Gly Ile Leu Thr Phe Asp Met Asn
        610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                    645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
            675                 680                 685

Ala Thr Arg Asp Asp Gln Tyr Thr Asn Lys Val Ile Ala Lys Asn Val
        690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735
```

```
Gly Tyr Ala Phe Glu Asp Arg Tyr Asp Met Ala Met Ser Lys Asn Asn
                740                 745                 750

Lys Tyr Gly Ser Leu Asp Asp Leu Asn Ala Leu Arg Ala Leu His
755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Asn Leu Tyr Val Ala
                805                 810                 815

Asn Thr Lys Thr Asn Gly Thr Asp Tyr Gln Gly Lys Tyr Gly Gly Ala
                820                 825                 830

Phe Leu Asp Glu Leu Lys Ala Lys Tyr Pro Glu Ile Phe Glu Arg Val
                835                 840                 845

Gln Ile Ser Asn Gly Gln Lys Met Thr Thr Asp Glu Lys Ile Thr Lys
                850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
                900                 905                 910

Thr Gly Phe Val Lys Asp Thr Thr Gly Phe Lys Tyr Tyr Ser Thr Ser
                915                 920                 925

Gly Tyr Gln Ala Arg Asn Ser Phe Ile Gln Asp Glu Asn Gly Asn Trp
                930                 935                 940

Tyr Tyr Phe Asp Lys Arg Gly Tyr Leu Ala Thr Gly Ala His Glu Ile
945                 950                 955                 960

Asp Gly Lys Gln Val Tyr Phe Leu Lys Asn Gly Ile Gln Leu Arg Asp
                965                 970                 975

Ser Leu Arg Glu Asp Glu Asn Gly Asn Gln Tyr Tyr Asp Lys Thr
                980                 985                 990

Gly Ala Gln Val Leu Asn Arg Tyr  Tyr Thr Thr Asp Gly  Gln Asn Trp
                995                 1000                1005

Arg Tyr  Phe Asp Ala Lys Gly  Val Met Ala Arg Gly  Leu Val Thr
    1010                1015                1020

Met Gly  Gly Asn Gln Gln Phe  Phe Asp Gln Asn Gly  Tyr Gln Val
    1025                1030                1035

Lys Gly  Lys Ile Ala Arg Ala  Lys Asp Gly Lys Leu  Arg Tyr Phe
    1040                1045                1050

Asp Lys  Asp Ser Gly Asn Ala  Ala Ala Asn Arg Phe  Ala Gln Gly
    1055                1060                1065

Asp Asn  Pro Ser Asp Trp Tyr  Tyr Phe Gly Ala Asp  Gly Val Ala
    1070                1075                1080

Val Thr  Gly Leu Gln Lys Leu  Gly Gln Gln Thr Leu  Tyr Phe Asp
    1085                1090                1095

Gln Glu  Gly Lys Gln Val Lys  Gly Lys Ile Val Thr  Leu Ala Asp
    1100                1105                1110

Lys Ser  Ile Arg Tyr Phe Asp  Ala Asn Ser Gly Glu  Met Ala Val
    1115                1120                1125

Gly Lys  Phe Ala Glu Gly Ser  Lys Asn Glu Trp Tyr  Tyr Phe Asp
    1130                1135                1140
```

| | | | | | | | | | | |
|---|---|---|---|---|---|---|---|---|---|---|
| Gln | Thr | Gly | Lys | Ala | Val | Thr | Gly | Leu | Gln | Lys | Ile | Gly | Gln | Gln |
| | 1145 | | | | 1150 | | | | 1155 | |

Gln Thr Gly Lys Ala Val Thr Gly Leu Gln Lys Ile Gly Gln Gln
        1145                    1150                   1155

Thr Leu Tyr Phe Asp Gln Asp Gly Lys Val Lys Gly Lys Val
        1160                    1165                   1170

Val Thr Leu Ala Asp Lys Ser Ile Arg Tyr Phe Asp Ala Asn Ser
        1175                    1180                   1185

Gly Glu Met Ala Val Gly Lys Phe Ala Glu Gly Ala Lys Asn Glu
        1190                    1195                   1200

Trp Tyr Tyr Phe Asp Gln Ala Gly Lys Ala Val Thr Gly Leu Gln
        1205                    1210                   1215

Lys Ile Gly Gln Gln Thr Leu Tyr Phe Asp Gln Asp Gly Lys Gln
        1220                    1225                   1230

Val Lys Gly Gln Leu Val Thr Leu Ala Asp Lys Ser Ile Arg Tyr
        1235                    1240                   1245

Phe Asp Ala Asn Ser Gly Glu Met Ala Ser Asn Lys Phe Val Glu
        1250                    1255                   1260

Gly Ala Lys Asn Glu Trp Tyr Tyr Phe Asp Gln Ala Gly Lys Ala
        1265                    1270                   1275

Val Thr Gly Leu Gln Gln Ile Gly Gln Gln Thr Leu Tyr Phe Asp
        1280                    1285                   1290

Gln Asn Gly Lys Gln Val Lys Gly Lys Ile Val Tyr Val Asn Gly
        1295                    1300                   1305

Ala Asn Arg Tyr Phe Asp Ala Asn Ser Gly Glu Met Ala Arg Asn
        1310                    1315                   1320

Lys Trp Ile Gln Leu Glu Asp Gly Ser Trp Met Tyr Phe Asp Arg
        1325                    1330                   1335

Asn Gly Arg Gly Arg Arg Phe Gly Trp Asn
        1340                    1345

<210> SEQ ID NO 49
<211> LENGTH: 4284
<212> TYPE: DNA
<213> ORGANISM: Streptococcus salivarius

<400> SEQUENCE: 49

```
atgaaggatg gcaaatacta ctacttgttg aagatggct cgcacaaaaa gaatttcgca      60
atcaccgtca atggtcaagt gctgtatttt gacgagaacg gtgcgctgag cagcaccagc     120
acgtacagct tcacgcagga aaccaccaat ctggttacgg actttacgaa gaataatgcg     180
gcgtatgact ccacgaaagc gtctttcgaa ttggtggacg gctatctgac cgcagacagc     240
tggtatcgcc cgaaagagat tctggaagcc ggcaccacct ggaaggcgag caccgaaaag     300
gacttccgtc cgctgctgat gtcctggtgg ccggataagg acacgcaagt tgcttatctg     360
aattacatga cgaaagcact gtcgaacggc gaagaaacca aggatgtctt tacgatcgaa     420
aacagccaag cgagcctgaa tgcggcagcg caaatcctgc aacgtaagat tgaggtcaag     480
attgcggcca acaagagcac cgactggctg cgccaaagca tcgaggcgtt tgtcaaagac     540
caagataagt ggaatatcaa tagcgaaagc cctggcaaag agcatttcca gaagggtgcg     600
ctgctgtttg ttaatagcga cagcaccaag tgggcgaact ccgattatcg taaactgaat     660
cagaccgcga cgtcttacat caagaatcat aagatcgtga acggtagcga tggtggttac     720
gagttcttgc tgagcaacga catcgacaac agcaacccgg tggtccaggc agagatgctg     780
aatcaactgt actactttat gaactggggt cagattgtgt cggcgataaa agataaagac     840
gcacatttcg atggcatccg tgtggacgcg gtggacaatg ttagcgttga catgctgcaa     900
```

```
ctggtcagca gctacatgaa ggcggcatac aaggtcaatg aatctgaagc ccgtgcgctg    960
gcgaatatca gcattttgga agcgtggagc cataatgacc cgtattatgt gaacgagcac   1020
aatacggcag cactgagcat ggataacggt ctgcgtctgt ctattgtgca tggtctgacg   1080
cgtccggtga ctaacaaagg cacgggtgct cgtaacgcca gcatgaagga cctgatcaac   1140
ggcggttact ttggcttgag caaccgtgcg gaagttacta gctacgacca gctgggcttt   1200
gccacttacc tgtttgtgcg tgcgcatgac agcgaggttc agacggttat cgctgatatt   1260
atttctaaaa agattgaccc gaccaccgac ggttttacct ttaccctgga ccagctgaag   1320
caggcttttg atatttataa cgcggacatg ttgaaggttg ataaagagta tacgcatagc   1380
aacatcccgg ctgcgtatgc gctgatgctg caaacgatgg gtgcagcgac ccgcgtgtat   1440
tacggcgatc tgtacactga taacggccaa tacatggcga aaaagagccc gtattttgat   1500
cagattacca cgctgttgaa ggcccgtccg aagtacgtgg cgggtggcca gacgagctac   1560
atccacaacc tggcaggcga tggtgtcagc tcggccaaag ataacaaaga ggttctggtt   1620
agcgtgcgct acggtcagga tctgatgagc aaaacggata ctgagggcgg taaatacggt   1680
cgtaacagcg gtatgctgac tctgatcgcg aacaacccgg acctgaagct ggccgatggt   1740
gagactatca cggttaacat gggtgctgcc cacaaaaatc aggcgtatcg tccgttgctg   1800
ctgggcacgg aaaagggtat tgtcagcagc ctgaacgata gcgacaccaa aatcgtgaag   1860
tatacggacg cccaaggtaa cctggttttc accgccgacg agatcaaggg cttcaaaacc   1920
gtggacatgt ctggctacct gtctgtttgg gttccggttg gtgccacgga tgaccagaac   1980
gtcctggcga aaccgagcac caaagcatac aaagaaggtg ataaggttta cagcagcagc   2040
gcggctctgg aagctcaggt tatctatgaa ggttttagca atttccagga tttcgtgaaa   2100
gaagatagcc agtataccaa taagctgatt gcggctaatg cggacctgtt taagagctgg   2160
ggtatcacga gcttgagat cgcaccgcaa tatgtgagca gcaaagatgg tactttcctg   2220
gacagcatca ttgaaaatgg ttacgcgttc accgatcgtt atgacttcgc gatgagcaag   2280
aacaataagt atggtagcaa agaggatctg cgcgacgcgc tgaaggcact gcacaaacaa   2340
ggcatccaag tcatcgcgga ttgggtgccg gatcagctgt ataccctgcc gggcaaagag   2400
gtggttacgg caacccgtac cgatacgcac ggtaaagtgc tggatgacac gagcctggtg   2460
aataaactgt atgtgaccaa tacgaagtct agcggtaacg atttccaggc acagtatggt   2520
ggtgcgttcc tggataaact gcaaaagctg tacccagaga ttttcaaaga agttatggaa   2580
gcgtccggca agaccatcga cccaagcgtc aagattaaac aatgggaagc taaatacttt   2640
aatggcacga atattcaaaa gcgtggttcc gattatgttc tgagcgatgg caaactgtac   2700
tttacggtta acgataaggg caccttcctg cctgctgccc tgacgggtga caccaaggct   2760
aaaacgggtt tgcctacga tggtacgggt gtcacgtatt acactaccag cggtactcaa   2820
gctaagagcc agtttgtgac gtataatggt aagcaatact acttcaacga caagggttac   2880
ttggttaccg gcgagcagac gattgatggc tccaactatt tcttcctgcc gaatggtgtt   2940
atgtttaccg atggtgtgcg taaaaacgcg aagggtcaga gcctggttta tggcaagtct   3000
ggtaagctga ccacgcaaac gggctggaaa gaagtgaccg ttaaagatga tagcggcaaa   3060
gaagaaaagt tttaccagta tttcttcaag ggtggcatca tggcgaccgg cctgacggaa   3120
gttgaaggta aagagaagta tttctatgac aatggctacc aggctaaagg cgtcttttgtc   3180
ccgaccaaag acggccacct gatgttcttt tgcggcgaca gcggtgagcg taaatacagc   3240
```

```
ggtttctttg aacaagacgg taactggtac tatgcgaatg acaagggcta cgtcgcgacc    3300
ggctttacca aggtgggtaa acaaaatctg tatttcaatg agaaaggcgt ccaggtcaaa    3360
aaccgctttt tccaagtggg tgacgccacc tattacgcga ataacgaggg cgacgtgctg    3420
cgtggtgcgc aaaccatcaa tggtgatgag ctgtacttcg acgaaagcgg caaacaagtt    3480
aagggtgagt cgtgaataa cccagacggc acgacctctt actatgatgc gatcacgggc    3540
gttaagctgg tcgataccte gctggttgtt gatggtcaga cgttcaacgt ggatgcgaag    3600
ggtgtcgtaa ccaaggcgca cacgccgggt ttctacacca cgggcgacaa caactggttc    3660
tacgcagata gctatggtcg taatgttacc ggtgcgcaag taatcaacgg ccaacacctg    3720
tatttcgatg caaatggtcg tcaagtgaaa ggcggctttg tcacgaacac ggacggtagc    3780
cgtagctttt accactggaa taccggcgac aaactggtgt ccacgttctt tgcgacgggt    3840
cacgatcgct ggtactacgc tgatgatcgt ggcaacgtcg tcacgggtgc acaggtcatc    3900
aacggtcaga agctgttctt tgacaccgat ggtaaacaag tcaaaggtgc tttcgcgacc    3960
aacgcgaatg gttcccgtag ctattatcat tggaatacgg caacaagct ggtgagcacc    4020
ttcttcacct cgggtgacaa taactggtat tacgcggacg ccaaaggtga ggttgtggtc    4080
ggtgaacaga cgattaatgg ccagcacctg tactttgacc agactggcaa gcaagtgaag    4140
ggcgcgactg caacgaaccc ggacggctcg atcagctatt atgatgtgca cacgggtgaa    4200
aaggctatca atcgttgggt gaagattccg agcggtcaat gggtgtactt caatgcgcag    4260
ggcaaaggtt acgtcagcaa ctaa                                          4284

<210> SEQ ID NO 50
<211> LENGTH: 1427
<212> TYPE: PRT
<213> ORGANISM: Streptococcus salivarius

<400> SEQUENCE: 50

Met Lys Asp Gly Lys Tyr Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Thr Tyr Ser Phe Thr Gln Glu Thr
        35                  40                  45

Thr Asn Leu Val Thr Asp Phe Thr Lys Asn Asn Ala Ala Tyr Asp Ser
    50                  55                  60

Thr Lys Ala Ser Phe Glu Leu Val Asp Gly Tyr Leu Thr Ala Asp Ser
65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
        115                 120                 125

Asn Gly Glu Glu Thr Lys Asp Val Phe Thr Ile Glu Asn Ser Gln Ala
    130                 135                 140

Ser Leu Asn Ala Ala Gln Ile Leu Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190
```

```
Lys Glu His Phe Gln Lys Gly Ala Leu Leu Phe Val Asn Ser Asp Ser
            195                 200                 205

Thr Lys Trp Ala Asn Ser Asp Tyr Arg Lys Leu Asn Gln Thr Ala Thr
    210                 215                 220

Ser Tyr Ile Lys Asn His Lys Ile Val Asn Gly Ser Asp Gly Gly Tyr
225                 230                 235                 240

Glu Phe Leu Leu Ser Asn Asp Ile Asp Asn Ser Asn Pro Val Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
            275                 280                 285

Asp Ala Val Asp Asn Val Ser Val Asp Met Leu Gln Leu Val Ser Ser
            290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser His Asn Asp Pro Tyr Tyr
                325                 330                 335

Val Asn Glu His Asn Thr Ala Ala Leu Ser Met Asp Asn Gly Leu Arg
            340                 345                 350

Leu Ser Ile Val His Gly Leu Thr Arg Pro Val Thr Asn Lys Gly Thr
            355                 360                 365

Gly Ala Arg Asn Ala Ser Met Lys Asp Leu Ile Asn Gly Gly Tyr Phe
            370                 375                 380

Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
            420                 425                 430

Thr Phe Thr Leu Asp Gln Leu Lys Gln Ala Phe Asp Ile Tyr Asn Ala
            435                 440                 445

Asp Met Leu Lys Val Asp Lys Glu Tyr Thr His Ser Asn Ile Pro Ala
            450                 455                 460

Ala Tyr Ala Leu Met Leu Gln Thr Met Gly Ala Ala Thr Arg Val Tyr
465                 470                 475                 480

Tyr Gly Asp Leu Tyr Thr Asp Asn Gly Gln Tyr Met Ala Lys Lys Ser
                485                 490                 495

Pro Tyr Phe Asp Gln Ile Thr Thr Leu Leu Lys Ala Arg Pro Lys Tyr
                500                 505                 510

Val Ala Gly Gly Gln Thr Ser Tyr Ile His Asn Leu Ala Gly Asp Gly
            515                 520                 525

Val Ser Ser Ala Lys Asp Asn Lys Glu Val Leu Val Ser Val Arg Tyr
530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
            580                 585                 590

Asn Gln Ala Tyr Arg Pro Leu Leu Leu Gly Thr Glu Lys Gly Ile Val
            595                 600                 605
```

```
Ser Ser Leu Asn Asp Ser Asp Thr Lys Ile Val Lys Tyr Thr Asp Ala
    610             615                 620

Gln Gly Asn Leu Val Phe Thr Ala Asp Glu Ile Lys Gly Phe Lys Thr
625             630                 635                 640

Val Asp Met Ser Gly Tyr Leu Ser Val Trp Val Pro Val Gly Ala Thr
                645                 650                 655

Asp Asp Gln Asn Val Leu Ala Lys Pro Ser Thr Lys Ala Tyr Lys Glu
            660                 665                 670

Gly Asp Lys Val Tyr Ser Ser Ala Ala Leu Glu Ala Gln Val Ile
        675                 680                 685

Tyr Glu Gly Phe Ser Asn Phe Gln Asp Phe Val Lys Glu Asp Ser Gln
    690                 695                 700

Tyr Thr Asn Lys Leu Ile Ala Ala Asn Ala Asp Leu Phe Lys Ser Trp
705             710                 715                 720

Gly Ile Thr Ser Phe Glu Ile Ala Pro Gln Tyr Val Ser Ser Lys Asp
                725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Asn Lys Tyr Gly Ser Lys Glu
        755                 760                 765

Asp Leu Arg Asp Ala Leu Lys Ala Leu His Lys Gln Gly Ile Gln Val
    770                 775                 780

Ile Ala Asp Trp Val Pro Asp Gln Leu Tyr Thr Leu Pro Gly Lys Glu
785             790                 795                 800

Val Val Thr Ala Thr Arg Thr Asp Thr His Gly Lys Val Leu Asp Asp
                805                 810                 815

Thr Ser Leu Val Asn Lys Leu Tyr Val Thr Asn Thr Lys Ser Ser Gly
            820                 825                 830

Asn Asp Phe Gln Ala Gln Tyr Gly Gly Ala Phe Leu Asp Lys Leu Gln
        835                 840                 845

Lys Leu Tyr Pro Glu Ile Phe Lys Glu Val Met Glu Ala Ser Gly Lys
    850                 855                 860

Thr Ile Asp Pro Ser Val Lys Ile Lys Gln Trp Glu Ala Lys Tyr Phe
865             870                 875                 880

Asn Gly Thr Asn Ile Gln Lys Arg Gly Ser Asp Tyr Val Leu Ser Asp
                885                 890                 895

Gly Lys Leu Tyr Phe Thr Val Asn Asp Lys Gly Thr Phe Leu Pro Ala
            900                 905                 910

Ala Leu Thr Gly Asp Thr Lys Ala Lys Thr Gly Phe Ala Tyr Asp Gly
        915                 920                 925

Thr Gly Val Thr Tyr Tyr Thr Thr Ser Gly Thr Gln Ala Lys Ser Gln
    930                 935                 940

Phe Val Thr Tyr Asn Gly Lys Gln Tyr Tyr Phe Asn Asp Lys Gly Tyr
945             950                 955                 960

Leu Val Thr Gly Glu Gln Thr Ile Asp Gly Ser Asn Tyr Phe Phe Leu
                965                 970                 975

Pro Asn Gly Val Met Phe Thr Asp Gly Val Arg Lys Asn Ala Lys Gly
            980                 985                 990

Gln Ser Leu Val Tyr Gly Lys Ser  Gly Lys Leu Thr Thr  Gln Thr Gly
        995                 1000                 1005

Trp Lys  Glu Val Thr Val Lys  Asp Asp Ser Gly Lys  Glu Glu Lys
    1010                 1015                 1020

Phe Tyr  Gln Tyr Phe Phe Lys  Gly Gly Ile Met Ala  Thr Gly Leu
```

```
                     1025               1030                1035
Thr Glu Val Glu Gly Lys Glu Lys Tyr Phe Tyr Asp Asn Gly Tyr
         1040                1045                1050

Gln Ala Lys Gly Val Phe Val Pro Thr Lys Asp Gly His Leu Met
         1055                1060                1065

Phe Phe Cys Gly Asp Ser Gly Glu Arg Lys Tyr Ser Gly Phe Phe
         1070                1075                1080

Glu Gln Asp Gly Asn Trp Tyr Tyr Ala Asn Asp Lys Gly Tyr Val
         1085                1090                1095

Ala Thr Gly Phe Thr Lys Val Gly Lys Gln Asn Leu Tyr Phe Asn
         1100                1105                1110

Glu Lys Gly Val Gln Val Lys Asn Arg Phe Phe Gln Val Gly Asp
         1115                1120                1125

Ala Thr Tyr Tyr Ala Asn Asn Glu Gly Asp Val Leu Arg Gly Ala
         1130                1135                1140

Gln Thr Ile Asn Gly Asp Glu Leu Tyr Phe Asp Glu Ser Gly Lys
         1145                1150                1155

Gln Val Lys Gly Glu Phe Val Asn Asn Pro Asp Gly Thr Thr Ser
         1160                1165                1170

Tyr Tyr Asp Ala Ile Thr Gly Val Lys Leu Val Asp Thr Ser Leu
         1175                1180                1185

Val Val Asp Gly Gln Thr Phe Asn Val Asp Ala Lys Gly Val Val
         1190                1195                1200

Thr Lys Ala His Thr Pro Gly Phe Tyr Thr Thr Gly Asp Asn Asn
         1205                1210                1215

Trp Phe Tyr Ala Asp Ser Tyr Gly Arg Asn Val Thr Gly Ala Gln
         1220                1225                1230

Val Ile Asn Gly Gln His Leu Tyr Phe Asp Ala Asn Gly Arg Gln
         1235                1240                1245

Val Lys Gly Gly Phe Val Thr Asn Thr Asp Gly Ser Arg Ser Phe
         1250                1255                1260

Tyr His Trp Asn Thr Gly Asp Lys Leu Val Ser Thr Phe Phe Ala
         1265                1270                1275

Thr Gly His Asp Arg Trp Tyr Tyr Ala Asp Asp Arg Gly Asn Val
         1280                1285                1290

Val Thr Gly Ala Gln Val Ile Asn Gly Gln Lys Leu Phe Phe Asp
         1295                1300                1305

Thr Asp Gly Lys Gln Val Lys Gly Ala Phe Ala Thr Asn Ala Asn
         1310                1315                1320

Gly Ser Arg Ser Tyr Tyr His Trp Asn Thr Gly Asn Lys Leu Val
         1325                1330                1335

Ser Thr Phe Phe Thr Ser Gly Asp Asn Asn Trp Tyr Tyr Ala Asp
         1340                1345                1350

Ala Lys Gly Glu Val Val Gly Glu Gln Thr Ile Asn Gly Gln
         1355                1360                1365

His Leu Tyr Phe Asp Gln Thr Gly Lys Gln Val Lys Gly Ala Thr
         1370                1375                1380

Ala Thr Asn Pro Asp Gly Ser Ile Ser Tyr Tyr Asp Val His Thr
         1385                1390                1395

Gly Glu Lys Ala Ile Asn Arg Trp Val Lys Ile Pro Ser Gly Gln
         1400                1405                1410

Trp Val Tyr Phe Asn Ala Gln Gly Lys Gly Tyr Val Ser Asn
         1415                1420                1425
```

<210> SEQ ID NO 51
<211> LENGTH: 4182
<212> TYPE: DNA
<213> ORGANISM: Unknown
<220> FEATURE:
<223> OTHER INFORMATION: unknown Streptococcus species

<400> SEQUENCE: 51

| | | | | | |
|---|---|---|---|---|---|
| atgatcaatg | gcaaacagta | ctatgtaaat | tcggacggta | gcgtgcgtaa | gaatttcgtt | 60 |
| tttgaacagg | atggtaagag | ctactacttt | gacgcggaaa | ctggcgcgct | ggccactaaa | 120 |
| agccaagatg | aatttagcac | ggagccgatt | aaagcagcag | tggacttctc | tagcggcaac | 180 |
| cagctgtaca | aaaatgacaa | caaatcgctg | gatcagctgg | atacgtttat | caccgctgac | 240 |
| gcatggtacc | gccctaagtc | tattctgaag | gatggcaaaa | cctggaccgc | gtctaccgaa | 300 |
| gctgataagc | gtccgttgct | gatggtgtgg | tggccggaca | agtccaccca | agttaactac | 360 |
| ctgaactaca | tgcagaacca | gggtttgggt | gcgggtagct | tcagcaccaa | tagcagccaa | 420 |
| gaatccctga | atctggctgc | gaaagcagtt | cagaccaaga | tcgaagaacg | catcgcacgt | 480 |
| gagggtaaca | ccaattggct | gcgtaccagc | attgaccaat | tcattaagac | gcagccaggc | 540 |
| tggaacagca | gcactgagaa | tagcagctat | gatcacttgc | agggtggtca | actgctgttc | 600 |
| aataacagca | aggtgatac | gggtaaccgc | accagctatg | cgaatagcga | ctatcgtctg | 660 |
| ctgaaccgta | ccccaactaa | tcaaagcggc | acccgtaagt | actttaagga | taattccatc | 720 |
| ggtggtctgg | aatttctgct | ggcaaacgac | atcgacaaca | gcaaccctgc | cgttcaggcg | 780 |
| gagcagctga | actggctgca | cttcatgatg | aacattggtt | ctatcatggc | gaatgacccg | 840 |
| acggcgaact | ttgatggttt | gcgtgtggac | gcgttggata | cgtggatgc | ggacctgttg | 900 |
| cagatcgcga | gcgattactt | caaggcagtc | tacggtgttg | ataaatccga | ggcgaatgcg | 960 |
| atcaagcacc | tgagctatct | ggaggcgtgg | agcgccaatg | acccgtatta | caacaaggat | 1020 |
| accaaaggcg | cgcaactgcc | gattgacaac | gcgctgcgca | acgcactgac | caacctgttg | 1080 |
| atgcgtgaca | agaatacgcg | catgcagctg | ggtgacatga | cggcgtttat | gaatagctct | 1140 |
| ctgaacccac | gtggtgcgaa | tgacaaaaac | ggcgagcgta | tggcgaatta | cattttcacc | 1200 |
| cgcgcacacg | ataccgaggc | gcagaccatc | attcagcgta | ttatccgcga | tcgtatcaat | 1260 |
| ccgaacctgt | ttggctacaa | tttcacccgc | gatgaaatca | aaaaggcgtt | tgagatctac | 1320 |
| aacgcggaca | ttaacacggc | gcataagacg | tacgcgagct | acaatctgcc | gtccgtctac | 1380 |
| gcactgatgc | tgacgaataa | ggacagcgtg | acccgtgtgt | attacggtga | cctgtatcgt | 1440 |
| gaggacggtc | actacatggc | caagaaaacg | ccttatttcg | atgcaatcga | taccctgctg | 1500 |
| cgtgcgcgca | tcaaatacgt | ggcgggtggt | caagacatgg | aggtgaagaa | agttggtaat | 1560 |
| gacggcttgc | tgacgagcgt | ccgctatggc | aagggtgcga | caatagcac | cgactggggc | 1620 |
| acgactgaaa | cccgtaccca | aggtatgggc | gttatcctga | cgaacaacta | tgatttccgc | 1680 |
| ctgggcagca | acgaaaccgt | cacgatgaac | atgggccgtg | cgcatcgcaa | tcagctgtat | 1740 |
| cgtccgctgc | tgctgacgac | caaggatggt | ctggccacgt | acctgaatga | tagcgacgtg | 1800 |
| ccttcgaatt | tgctgaaacg | cacggactgg | aatggtaact | tgaccttta | tgccaacgat | 1860 |
| gtgtttggtg | tagagaacgt | ccaggtcagc | ggttacctgg | tgttgggt | accggttggt | 1920 |
| gctaaagcta | accaggatgc | gcgtacccaa | ccgagcaacc | gtgcgaacag | cgatggtcag | 1980 |
| gtctataagt | cgtctgcggc | attggacagc | caggtcatgt | atgaggcgtt | tagcaatttt | 2040 |

-continued

```
caggcatttg cggacgatca accggaactg tacatgaacc gcgttctggc gaagaacacc    2100
gatctgctga aagcgtgggg cgttactagc gttggcttgc cgccacaata cgttagcagc    2160
aaagacggca ccttcctgga tagcactatt gataacggct atgcgttcga tgatcgttac    2220
gacatggcgc tgagccagaa caacaaatac ggttctctgg aggacttgct gaacgttctg    2280
cgcgctctgc acaaagacgg tattcaggcg attgcggact gggtcccgga tcaaatctac    2340
aatttgccgg gtaaagaggt tgttaatgcg acgcgtgtta acggttacgg ttaccatcag    2400
cagggctacc agattgttga ccaggcgtac gttgcaaaca cccgtacgga tggtaccgat    2460
tatcagggtc gttacggtgg tgcttttctg gacgaactga aggcgaagta cccgagcatt    2520
ttcaatcgtg tccagattag caacggtaaa cagctgccaa ccaatgagaa aatcacgaaa    2580
tggtccgcga atacttcaa tggcacgaac atcctgggcc gtggtattaa ctatgtgctg    2640
cgcgacgaca agaccaatca gtatttcaac accagcgcaa acggccaact gctgccgacg    2700
ccactgcgcg acaccggtgc catcaccagc acgcaagttt tccagcgtcg tggccaagac    2760
gtctattttc tgcgtgataa ccaggttatc aaaaacgagt tgtgcaaga tggtaacggt    2820 aattggtact acttcggtgc cgacggtaaa atgacgaagg gtgcacaaaa catcaatagc    2880
aaggattact atttcttcga taatggcgtc cagctgcgta atgcgctgcg tcgcgcgtcc    2940
aatggttaca cctactatta tggcctggac ggtgccatga tcaagaacgc tttcgtcgat    3000
tttgatgata agcaccaaca ggtgcgtgcg tttactacgc agggcacgat ggtggtcggt    3060
aatttgcact ggagcggtca cccacttctat tttgaccgcg aaacgggtat ccaagccaaa    3120
gaccgcattg tgcgtaccga tgatggcaag ctgcactatt atgtcgcaca aaccggcgat    3180
atgggccgca atgtgtttgc gaccgacagc cgcacgggca agcgctatta ctttgatgcg    3240
gacggcaaca ccgttacggg ctcccgtgtc atcgacggca agacctacta cttcaaccag    3300
gacggttcgg tcgtaccgc gtacagcaat cgtgcggata gcattatctt tgagaatggc    3360
aaggctcgct atatcactcc ggctggcgag attggccgtt ccatttttgt ctacaacccg    3420
gcgaccaaag cgtggaatta cttcgacaag gaaggtaacc gtgtcaccgg tcgtcagtat    3480
attgacggca atctgtacta ctttaaagag acggctccc aagtgaaagg tgcgattgtt    3540
gaagagaacg gtatcaagta ctactacgaa ccgggcagcg gtatcctggc gagcggtcgt    3600
tatctgcaag tcggtgacga ccaatggatc tacttcaaac acgacggtag cctggcgatc    3660
ggtcaggttc gtgcagacgg tggttacttg aaatactttg ataagaatgg catccaggtc    3720
aagggccaaa ccattgtgga ggatggtcat acctattact acgatgccga ctccggtgct    3780 ctggtgaccct ctagcttcgc ggagattgct ccgaaccagt gggcctactt caataccgag    3840
ggccaagccc tgaagggcaa atggaccatc aatggtaaag agtactattt tgatcagaac    3900
ggcattcagt ataaaggcaa ggcagttaag gtcggcagcc gttacaaata ctatgacgag    3960
aatgacggtc aaccggtcac taaccgtttt gcccagattg agccgaacgt ctgggcgtac    4020
tttggtgccg atggctacgc agttactggc gaacaggtga ttaatggcca gcacctgtac    4080
ttcgatcagt cgggtcgtca ggttaaaggt gcgtacgtca ccgtgaatgg tcaacgtcgt    4140
tactacgacg caaacacggg tgaatacatt ccgggtcgtt aa                        4182
```

<210> SEQ ID NO 52
<211> LENGTH: 1393
<212> TYPE: PRT
<213> ORGANISM: Unknown
<220> FEATURE:
<223> OTHER INFORMATION: unknown Streptococcus species

<400> SEQUENCE: 52

| | | | | | | | | | | | | | | |
|---|---|---|---|---|---|---|---|---|---|---|---|---|---|---|
|Met|Ile|Asn|Gly|Lys|Gln|Tyr|Tyr|Val|Asn|Ser|Asp|Gly|Ser|Val|Arg|
|1| | | |5| | | | |10| | | | |15| |

Lys Asn Phe Val Phe Glu Gln Asp Gly Lys Ser Tyr Tyr Phe Asp Ala
            20                  25                  30

Glu Thr Gly Ala Leu Ala Thr Lys Ser Gln Asp Glu Phe Ser Thr Glu
        35                  40                  45

Pro Ile Lys Ala Ala Val Asp Phe Ser Ser Gly Asn Gln Leu Tyr Lys
50                  55                  60

Asn Asp Asn Lys Ser Leu Asp Gln Leu Asp Thr Phe Ile Thr Ala Asp
65                  70                  75                  80

Ala Trp Tyr Arg Pro Lys Ser Ile Leu Lys Asp Gly Lys Thr Trp Thr
                85                  90                  95

Ala Ser Thr Glu Ala Asp Lys Arg Pro Leu Leu Met Val Trp Trp Pro
            100                 105                 110

Asp Lys Ser Thr Gln Val Asn Tyr Leu Asn Tyr Met Gln Asn Gln Gly
        115                 120                 125

Leu Gly Ala Gly Ser Phe Ser Thr Asn Ser Ser Gln Glu Ser Leu Asn
130                 135                 140

Leu Ala Ala Lys Ala Val Gln Thr Lys Ile Glu Glu Arg Ile Ala Arg
145                 150                 155                 160

Glu Gly Asn Thr Asn Trp Leu Arg Thr Ser Ile Asp Gln Phe Ile Lys
                165                 170                 175

Thr Gln Pro Gly Trp Asn Ser Thr Glu Asn Ser Ser Tyr Asp His
            180                 185                 190

Leu Gln Gly Gly Gln Leu Leu Phe Asn Asn Ser Lys Gly Asp Thr Gly
        195                 200                 205

Asn Arg Thr Ser Tyr Ala Asn Ser Asp Tyr Arg Leu Leu Asn Arg Thr
210                 215                 220

Pro Thr Asn Gln Ser Gly Thr Arg Lys Tyr Phe Lys Asp Asn Ser Ile
225                 230                 235                 240

Gly Gly Leu Glu Phe Leu Leu Ala Asn Asp Ile Asp Asn Ser Asn Pro
                245                 250                 255

Ala Val Gln Ala Glu Gln Leu Asn Trp Leu His Phe Met Met Asn Ile
            260                 265                 270

Gly Ser Ile Met Ala Asn Asp Pro Thr Ala Asn Phe Asp Gly Leu Arg
        275                 280                 285

Val Asp Ala Leu Asp Asn Val Asp Ala Asp Leu Leu Gln Ile Ala Ser
290                 295                 300

Asp Tyr Phe Lys Ala Val Tyr Gly Val Asp Lys Ser Glu Ala Asn Ala
305                 310                 315                 320

Ile Lys His Leu Ser Tyr Leu Glu Ala Trp Ser Ala Asn Asp Pro Tyr
                325                 330                 335

Tyr Asn Lys Asp Thr Lys Gly Ala Gln Leu Pro Ile Asn Ala Leu
            340                 345                 350

Arg Asn Ala Leu Thr Asn Leu Leu Met Arg Asp Lys Asn Thr Arg Met
        355                 360                 365

Gln Leu Gly Asp Met Thr Ala Phe Met Asn Ser Ser Leu Asn Pro Arg
370                 375                 380

Gly Ala Asn Asp Lys Asn Gly Glu Arg Met Ala Asn Tyr Ile Phe Thr
385                 390                 395                 400

Arg Ala His Asp Thr Glu Ala Gln Thr Ile Ile Gln Arg Ile Ile Arg

```
            405                 410                 415
Asp Arg Ile Asn Pro Asn Leu Phe Gly Tyr Asn Phe Thr Arg Asp Glu
            420                 425                 430

Ile Lys Lys Ala Phe Glu Ile Tyr Asn Ala Asp Ile Asn Thr Ala His
            435                 440                 445

Lys Thr Tyr Ala Ser Tyr Asn Leu Pro Ser Val Tyr Ala Leu Met Leu
    450                 455                 460

Thr Asn Lys Asp Ser Val Thr Arg Val Tyr Tyr Gly Asp Leu Tyr Arg
465                 470                 475                 480

Glu Asp Gly His Tyr Met Ala Lys Lys Thr Pro Tyr Phe Asp Ala Ile
                485                 490                 495

Asp Thr Leu Leu Arg Ala Arg Ile Lys Tyr Val Ala Gly Gly Gln Asp
            500                 505                 510

Met Glu Val Lys Lys Val Gly Asn Asp Gly Leu Leu Thr Ser Val Arg
            515                 520                 525

Tyr Gly Lys Gly Ala Asn Asn Ser Thr Asp Trp Gly Thr Thr Glu Thr
    530                 535                 540

Arg Thr Gln Gly Met Gly Val Ile Leu Thr Asn Asn Tyr Asp Phe Arg
545                 550                 555                 560

Leu Gly Ser Asn Glu Thr Val Thr Met Asn Met Gly Arg Ala His Arg
                565                 570                 575

Asn Gln Leu Tyr Arg Pro Leu Leu Thr Thr Lys Asp Gly Leu Ala
            580                 585                 590

Thr Tyr Leu Asn Asp Ser Asp Val Pro Ser Asn Leu Leu Lys Arg Thr
            595                 600                 605

Asp Trp Asn Gly Asn Leu Thr Phe Asn Ala Asn Asp Val Phe Gly Val
    610                 615                 620

Glu Asn Val Gln Val Ser Gly Tyr Leu Gly Val Trp Val Pro Val Gly
625                 630                 635                 640

Ala Lys Ala Asn Gln Asp Ala Arg Thr Gln Pro Ser Asn Arg Ala Asn
                645                 650                 655

Ser Asp Gly Gln Val Tyr Lys Ser Ser Ala Ala Leu Asp Ser Gln Val
            660                 665                 670

Met Tyr Glu Ala Phe Ser Asn Phe Gln Ala Phe Ala Asp Asp Gln Pro
    675                 680                 685

Glu Leu Tyr Met Asn Arg Val Leu Ala Lys Asn Thr Asp Leu Leu Lys
            690                 695                 700

Ala Trp Gly Val Thr Ser Val Gly Leu Pro Pro Gln Tyr Val Ser Ser
705                 710                 715                 720

Lys Asp Gly Thr Phe Leu Asp Ser Thr Ile Asp Asn Gly Tyr Ala Phe
                725                 730                 735

Asp Asp Arg Tyr Asp Met Ala Leu Ser Gln Asn Asn Lys Tyr Gly Ser
            740                 745                 750

Leu Glu Asp Leu Leu Asn Val Leu Arg Ala Leu His Lys Asp Gly Ile
            755                 760                 765

Gln Ala Ile Ala Asp Trp Val Pro Asp Gln Ile Tyr Asn Leu Pro Gly
    770                 775                 780

Lys Glu Val Val Asn Ala Thr Arg Val Asn Gly Tyr Gly Tyr His Gln
785                 790                 795                 800

Gln Gly Tyr Gln Ile Val Asp Gln Ala Tyr Val Ala Asn Thr Arg Thr
                805                 810                 815

Asp Gly Thr Asp Tyr Gln Gly Arg Tyr Gly Gly Ala Phe Leu Asp Glu
            820                 825                 830
```

```
Leu Lys Ala Lys Tyr Pro Ser Ile Phe Asn Arg Val Gln Ile Ser Asn
        835                 840                 845

Gly Lys Gln Leu Pro Thr Asn Glu Lys Ile Thr Lys Trp Ser Ala Lys
850                 855                 860

Tyr Phe Asn Gly Thr Asn Ile Leu Gly Arg Gly Ile Asn Tyr Val Leu
865                 870                 875                 880

Arg Asp Asp Lys Thr Asn Gln Tyr Phe Asn Thr Ser Ala Asn Gly Gln
                885                 890                 895

Leu Leu Pro Thr Pro Leu Arg Asp Thr Gly Ala Ile Thr Ser Thr Gln
                900                 905                 910

Val Phe Gln Arg Arg Gly Gln Asp Val Tyr Phe Leu Arg Asp Asn Gln
                915                 920                 925

Val Ile Lys Asn Glu Phe Val Gln Asp Gly Asn Gly Asn Trp Tyr Tyr
        930                 935                 940

Phe Gly Ala Asp Gly Lys Met Thr Lys Gly Ala Gln Asn Ile Asn Ser
945                 950                 955                 960

Lys Asp Tyr Tyr Phe Phe Asp Asn Gly Val Gln Leu Arg Asn Ala Leu
                965                 970                 975

Arg Arg Ala Ser Asn Gly Tyr Thr Tyr Tyr Tyr Gly Leu Asp Gly Ala
                980                 985                 990

Met Ile Lys Asn Ala Phe Val Asp Phe Asp Asp Lys His Gln Gln Val
        995                 1000                1005

Arg Ala Phe Thr Thr Gln Gly Thr Met Val Val Gly Asn Leu His
    1010                1015                1020

Trp Ser Gly His His Phe Tyr Phe Asp Arg Glu Thr Gly Ile Gln
    1025                1030                1035

Ala Lys Asp Arg Ile Val Arg Thr Asp Asp Gly Lys Leu His Tyr
    1040                1045                1050

Tyr Val Ala Gln Thr Gly Asp Met Gly Arg Asn Val Phe Ala Thr
    1055                1060                1065

Asp Ser Arg Thr Gly Lys Arg Tyr Tyr Phe Asp Ala Asp Gly Asn
    1070                1075                1080

Thr Val Thr Gly Ser Arg Val Ile Asp Gly Lys Thr Tyr Tyr Phe
    1085                1090                1095

Asn Gln Asp Gly Ser Val Gly Thr Ala Tyr Ser Asn Arg Ala Asp
    1100                1105                1110

Ser Ile Ile Phe Glu Asn Gly Lys Ala Arg Tyr Ile Thr Pro Ala
    1115                1120                1125

Gly Glu Ile Gly Arg Ser Ile Phe Val Tyr Asn Pro Ala Thr Lys
    1130                1135                1140

Ala Trp Asn Tyr Phe Asp Lys Glu Gly Asn Arg Val Thr Gly Arg
    1145                1150                1155

Gln Tyr Ile Asp Gly Asn Leu Tyr Tyr Phe Lys Glu Asp Gly Ser
    1160                1165                1170

Gln Val Lys Gly Ala Ile Val Glu Glu Asn Gly Ile Lys Tyr Tyr
    1175                1180                1185

Tyr Glu Pro Gly Ser Gly Ile Leu Ala Ser Gly Arg Tyr Leu Gln
    1190                1195                1200

Val Gly Asp Asp Gln Trp Ile Tyr Phe Lys His Asp Gly Ser Leu
    1205                1210                1215

Ala Ile Gly Gln Val Arg Ala Asp Gly Gly Tyr Leu Lys Tyr Phe
    1220                1225                1230
```

| | | | | | | | | | | |
|---|---|---|---|---|---|---|---|---|---|---|
|Asp|Lys|Asn|Gly|Ile|Gln|Val|Lys|Gly|Gln|Thr|Ile|Val|Glu|Asp|
| |1235| | | |1240| | | |1245| |

Gly His Thr Tyr Tyr Tyr Asp Ala Asp Ser Gly Ala Leu Val Thr
    1250              1255              1260

Ser Ser Phe Ala Glu Ile Ala Pro Asn Gln Trp Ala Tyr Phe Asn
    1265              1270              1275

Thr Glu Gly Gln Ala Leu Lys Gly Lys Trp Thr Ile Asn Gly Lys
    1280              1285              1290

Glu Tyr Tyr Phe Asp Gln Asn Gly Ile Gln Tyr Lys Gly Lys Ala
    1295              1300              1305

Val Lys Val Gly Ser Arg Tyr Lys Tyr Tyr Asp Glu Asn Asp Gly
    1310              1315              1320

Gln Pro Val Thr Asn Arg Phe Ala Gln Ile Glu Pro Asn Val Trp
    1325              1330              1335

Ala Tyr Phe Gly Ala Asp Gly Tyr Ala Val Thr Gly Glu Gln Val
    1340              1345              1350

Ile Asn Gly Gln His Leu Tyr Phe Asp Gln Ser Gly Arg Gln Val
    1355              1360              1365

Lys Gly Ala Tyr Val Thr Val Asn Gly Gln Arg Arg Tyr Tyr Asp
    1370              1375              1380

Ala Asn Thr Gly Glu Tyr Ile Pro Gly Arg
    1385              1390

<210> SEQ ID NO 53
<211> LENGTH: 3789
<212> TYPE: DNA
<213> ORGANISM: Leuconostoc citreum

<400> SEQUENCE: 53

```
atgattaacg gccacaatta ctatttcgac agcttgggtc aactgaagaa aggtttcacg      60
ggcgtgatcg acggtcaggt ccgttacttc gaccaggagt ccggtcagga agttagcacc     120
accgacagcc aaatcaaaga gggcttgacg agccaaacga ccgactacac cgcccataac     180
gcggtccaca gcacggactc cgcagatttt gacaacttca tggttacct gaccgcgagc     240
agctggtatc gtcctaagga cgttctgcgt aacggccaac attgggaagc caccaccgcg     300
aatgacttcc gtcctatcgt cagcgtgtgg tggccgagca agcaaacgca ggtcaactac     360
ctgaactata tgagccagat gggtttgatc gataaccgtc aaatgttctc gttgaaagat     420
aaccaagcga tgctgaacat cgcgtgcacg accgtgcaac aagcaatcga actaaaatc     480
ggtgtggcga atagcaccgc gtggctgaaa accgcgatcg atgactttat ccgtacccag     540
ccgcagtgga acatgagcag cgaagatccg aagaatgacc atctgcaaaa tggcgccctg     600
acgtttgtta acagcccgct gaccccggat acgaatagca atttccgcct gctgaatcgt     660
accccgacca atcaaaccgg tgttccgaaa tacaccatcg accaaagcaa aggtggtttt     720
gaactgctgc tggcgaatga cgtggataat tcgaacccgg ttgtgcaggc cgagcagttg     780
aactggctgc actacctgat gaactttggt agcattactg cgaatgacag cgcagcaaac     840
ttcgacggta ttcgcgttga cgcagtggat aacgtggatg cggacctgct gcaaattgcg     900
gcagattact tcaaagcagc atacggtgtg acaagaacga cgcaacggc aaatcagcat     960
ctgtcgatcc tggaagattg gagccacaac gacccggagt acgttaaaga cttcggcaat    1020
aaccaactga ccatggacga ttacatggac acgcagctga tctggagcct gacgaaagac    1080
atgcgtatgc gtggtacgat gcagcgcttt atggactact atctggttaa ccgcaatcac    1140
```

```
gacagcaccg agaatactgc cattccgaat tacagctttg tccgtgccca tgacagcgaa    1200
gttcaaacgg ttattgcgca gatcatttct gagctgcatc cagacgtgaa gaatagcctg    1260
gcgccgaccg cggatcaact ggctgaggcg ttcaaaatct acaacaacga cgagaagcaa    1320
gctgataaga agtatacccc aatacaatatg ccaagcgcgt acgcaatgct gttgaccaat    1380
aaagataccg ttccgcgtgt ttactacggt gacctgtata ccgatgacgg tcagtatatg    1440
gctaacaaat ccccgtattt tgacgctatc aacggtctgc tgaagagccg tatcaaatat    1500
gtggcaggcg gtcaaagcat ggcggtggat cagaatgata tcctgacgaa tgtgcgctat    1560
ggcaaaggtg ccatgagcgt gacggatagc ggcaacgcgg atacgcgtac ccagggcatc    1620
ggcgttattg ttagcaacaa agaaaacctg gctctgaaat ccggcgacac cgttaccctg    1680
cacatgggcg cagcgcacaa gaaccaggcg tttcgcctgc tgttgggtac gacggcggac    1740
aacctgagct actacgacaa tgacaatgcg ccggtgaagt acaccaatga tcaaggtgat    1800
ctgattttcg ataataccga gatttatggt gttcgcaatc cgcaagtctc tggttttctg    1860
gcggtgtggg tcccggttgg tgccgatagc catcaagatg ctcgcacttt gagcgacgat    1920
acggcacacc acgacggcaa gaccttccac tcgaacgcag cactggatag ccaggtgatt    1980
tacgaaggtt ttagcaactt ccaagcattt gcaacgaata cggaagatta cactaacgct    2040
gtgatcgcca aaaacggcca gctgttcaag gattggggca tcacctcgtt ccagctggct    2100
ccgcagtatc gcagctccac cgatacgagc ttcctggata gcattattca gaacggctat    2160
gccttcacgg accgttatga cctgggctat ggcaccccga cgaagtatgg caccgtggac    2220
cagctgcgcg atgcaatcaa ggctctgcac gccaatggca tccaagcaat tgccgactgg    2280
gttccggacc agatctacaa cctgccgggt caggagctgg ccacggtgac ccgtacgaac    2340
tcctatggta taaagacac caatagcgat attgatcaga gcttgtacgt gatccaatcg    2400
cgcggtggcg gtaagtatca agcccaatac ggtggtgcat tcctgagcga cattcaaaag    2460
aagtatccgc tctgttcga gactaaacag atcagcacgg gtctgccgat ggacccgagc    2520
caaaagatta ccgagtggag cggcaagtac ttcaacggta gcaatattca aggtaagggc    2580
gctggttacg tcctgaagga cagcggcacc gaccagtact ataaagtgac gagcaacaat    2640
aacaaccgtg atttcctgcc gaaacagctg acggatgatc tgtctgaaac cggttttgtg    2700
cgtgacaata ttggcatggt ctattacacc ctgtctggct acctggcacg caataccttc    2760
atccaggacg acaacggtaa ctattactac tttgatagca ccggtcacct ggttacgggt    2820
ttccagaaca ttaacaacca ccactacttt tccttgccga acggcattga actggttcag    2880
agctttctgc aaaacgctga tggtagcacg atctacttcg atcaaaaggg tcgtcaagtt    2940
ttcaaccagt atatcactga tcagactggt accgcgtact acttccagaa cgacggcacc    3000
atggtcactt ctggctttac tgagatcgat ggccacaagc agtatttcta taagaatggc    3060
actcaggtta agggtcagtt tgtgagcgac accgatggtc acgtcttttta cctggaagcg    3120 ggtaatggta atgtcgccac gcaacgtttc gcacagaaca gccagggtca atggttctac    3180
ttgggtaatg atggcattgc gttgacgggt ttgcagacga tcaacggtgt tcagaactac    3240
ttttatgcgg acggtcatca aagcaagggt gacttcatca ccatccagaa tcatgtcctg    3300
tacaccaacc cgctgacggg tgccatcacg accggcatgc aacagatcgg cgacaaaatc    3360
ttcgtgtttg ataatacggg taatatgctg acgaaccagt attatcagac gctggatggt    3420
cagtggctgc acctgagcac ccagggtcca gcagatacgg gtctggtcaa tatcaatggt    3480
aatctgaagt attttcaggc aaatggtcgt caggtgaaag gccaattcgt caccgacccg    3540
```

```
attaccaacg tcagctacta catgaacgcg acggacggta gcgcagtgtt caatgactat    3600
ttcacctatc agggccaatg gtatttgacg gactccaact atcagttggt caaaggcttc    3660
aaagtggtga acaacaaact gcaacatttc gatgaaatca ccggtgtgca aaccaagagc    3720
gctcacatta ttgttaacaa tcgtacctac atttttgacg accagggcta ttttgtcagc    3780
gtggcataa                                                            3789
```

<210> SEQ ID NO 54
<211> LENGTH: 1262
<212> TYPE: PRT
<213> ORGANISM: Leuconostoc citreum

<400> SEQUENCE: 54

```
Met Ile Asn Gly His Asn Tyr Tyr Phe Asp Ser Leu Gly Gln Leu Lys
1               5                   10                  15

Lys Gly Phe Thr Gly Val Ile Asp Gly Gln Val Arg Tyr Phe Asp Gln
            20                  25                  30

Glu Ser Gly Gln Glu Val Ser Thr Asp Ser Gln Ile Lys Glu Gly
        35                  40                  45

Leu Thr Ser Gln Thr Thr Asp Tyr Thr Ala His Asn Ala Val His Ser
    50                  55                  60

Thr Asp Ser Ala Asp Phe Asp Asn Phe Asn Gly Tyr Leu Thr Ala Ser
65                  70                  75                  80

Ser Trp Tyr Arg Pro Lys Asp Val Leu Arg Asn Gly Gln His Trp Glu
                85                  90                  95

Ala Thr Thr Ala Asn Asp Phe Arg Pro Ile Val Ser Val Trp Trp Pro
            100                 105                 110

Ser Lys Gln Thr Gln Val Asn Tyr Leu Asn Tyr Met Ser Gln Met Gly
        115                 120                 125

Leu Ile Asp Asn Arg Gln Met Phe Ser Leu Lys Asp Asn Gln Ala Met
    130                 135                 140

Leu Asn Ile Ala Cys Thr Thr Val Gln Gln Ala Ile Glu Thr Lys Ile
145                 150                 155                 160

Gly Val Ala Asn Ser Thr Ala Trp Leu Lys Thr Ala Ile Asp Asp Phe
                165                 170                 175

Ile Arg Thr Gln Pro Gln Trp Asn Met Ser Ser Glu Asp Pro Lys Asn
            180                 185                 190

Asp His Leu Gln Asn Gly Ala Leu Thr Phe Val Asn Ser Pro Leu Thr
        195                 200                 205

Pro Asp Thr Asn Ser Asn Phe Arg Leu Leu Asn Arg Thr Pro Thr Asn
    210                 215                 220

Gln Thr Gly Val Pro Lys Tyr Thr Ile Asp Gln Ser Lys Gly Gly Phe
225                 230                 235                 240

Glu Leu Leu Leu Ala Asn Asp Val Asp Asn Ser Asn Pro Val Val Gln
                245                 250                 255

Ala Glu Gln Leu Asn Trp Leu His Tyr Leu Met Asn Phe Gly Ser Ile
            260                 265                 270

Thr Ala Asn Asp Ser Ala Ala Asn Phe Asp Gly Ile Arg Val Asp Ala
        275                 280                 285

Val Asp Asn Val Asp Ala Asp Leu Leu Gln Ile Ala Ala Asp Tyr Phe
    290                 295                 300

Lys Ala Ala Tyr Gly Val Asp Lys Asn Asp Ala Thr Ala Asn Gln His
305                 310                 315                 320
```

-continued

```
Leu Ser Ile Leu Glu Asp Trp Ser His Asn Asp Pro Glu Tyr Val Lys
            325                 330                 335

Asp Phe Gly Asn Asn Gln Leu Thr Met Asp Asp Tyr Met His Thr Gln
            340                 345                 350

Leu Ile Trp Ser Leu Thr Lys Asp Met Arg Met Arg Gly Thr Met Gln
            355                 360                 365

Arg Phe Met Asp Tyr Tyr Leu Val Asn Arg Asn His Asp Ser Thr Glu
            370                 375                 380

Asn Thr Ala Ile Pro Asn Tyr Ser Phe Val Arg Ala His Asp Ser Glu
385                 390                 395                 400

Val Gln Thr Val Ile Ala Gln Ile Ile Ser Glu Leu His Pro Asp Val
                405                 410                 415

Lys Asn Ser Leu Ala Pro Thr Ala Asp Gln Leu Ala Glu Ala Phe Lys
            420                 425                 430

Ile Tyr Asn Asn Asp Glu Lys Gln Ala Asp Lys Lys Tyr Thr Gln Tyr
            435                 440                 445

Asn Met Pro Ser Ala Tyr Ala Met Leu Leu Thr Asn Lys Asp Thr Val
            450                 455                 460

Pro Arg Val Tyr Tyr Gly Asp Leu Tyr Thr Asp Asp Gly Gln Tyr Met
465                 470                 475                 480

Ala Asn Lys Ser Pro Tyr Phe Asp Ala Ile Asn Gly Leu Leu Lys Ser
                485                 490                 495

Arg Ile Lys Tyr Val Ala Gly Gly Gln Ser Met Ala Val Asp Gln Asn
            500                 505                 510

Asp Ile Leu Thr Asn Val Arg Tyr Gly Lys Gly Ala Met Ser Val Thr
            515                 520                 525

Asp Ser Gly Asn Ala Asp Thr Arg Thr Gln Gly Ile Gly Val Ile Val
530                 535                 540

Ser Asn Lys Glu Asn Leu Ala Leu Lys Ser Gly Asp Thr Val Thr Leu
545                 550                 555                 560

His Met Gly Ala Ala His Lys Asn Gln Ala Phe Arg Leu Leu Leu Gly
                565                 570                 575

Thr Thr Ala Asp Asn Leu Ser Tyr Tyr Asp Asn Asp Asn Ala Pro Val
            580                 585                 590

Lys Tyr Thr Asn Asp Gln Gly Asp Leu Ile Phe Asp Asn Thr Glu Ile
            595                 600                 605

Tyr Gly Val Arg Asn Pro Gln Val Ser Gly Phe Leu Ala Val Trp Val
            610                 615                 620

Pro Val Gly Ala Asp Ser His Gln Asp Ala Arg Thr Leu Ser Asp Asp
625                 630                 635                 640

Thr Ala His His Asp Gly Lys Thr Phe His Ser Asn Ala Ala Leu Asp
                645                 650                 655

Ser Gln Val Ile Tyr Glu Gly Phe Ser Asn Phe Gln Ala Phe Ala Thr
            660                 665                 670

Asn Thr Glu Asp Tyr Thr Asn Ala Val Ile Ala Lys Asn Gly Gln Leu
            675                 680                 685

Phe Lys Asp Trp Gly Ile Thr Ser Phe Gln Leu Ala Pro Gln Tyr Arg
            690                 695                 700

Ser Ser Thr Asp Thr Ser Phe Leu Asp Ser Ile Ile Gln Asn Gly Tyr
705                 710                 715                 720

Ala Phe Thr Asp Arg Tyr Asp Leu Gly Tyr Gly Thr Pro Thr Lys Tyr
                725                 730                 735

Gly Thr Val Asp Gln Leu Arg Asp Ala Ile Lys Ala Leu His Ala Asn
```

-continued

Gly Ile Gln Ala Ile Ala Asp Trp Val Pro Asp Gln Ile Tyr Asn Leu
    740                 745                 750
    755                 760                 765

Pro Gly Gln Glu Leu Ala Thr Val Thr Arg Thr Asn Ser Tyr Gly Asp
    770                 775                 780

Lys Asp Thr Asn Ser Asp Ile Asp Gln Ser Leu Tyr Val Ile Gln Ser
785                 790                 795                 800

Arg Gly Gly Gly Lys Tyr Gln Ala Gln Tyr Gly Gly Ala Phe Leu Ser
                    805                 810                 815

Asp Ile Gln Lys Lys Tyr Pro Ala Leu Phe Glu Thr Lys Gln Ile Ser
                    820                 825                 830

Thr Gly Leu Pro Met Asp Pro Ser Gln Lys Ile Thr Glu Trp Ser Gly
                    835                 840                 845

Lys Tyr Phe Asn Gly Ser Asn Ile Gln Gly Lys Gly Ala Gly Tyr Val
                    850                 855                 860

Leu Lys Asp Ser Gly Thr Asp Gln Tyr Tyr Lys Val Thr Ser Asn Asn
865                 870                 875                 880

Asn Asn Arg Asp Phe Leu Pro Lys Gln Leu Thr Asp Asp Leu Ser Glu
                    885                 890                 895

Thr Gly Phe Val Arg Asp Asn Ile Gly Met Val Tyr Tyr Thr Leu Ser
                    900                 905                 910

Gly Tyr Leu Ala Arg Asn Thr Phe Ile Gln Asp Asp Gly Asn Tyr
                    915                 920                 925

Tyr Tyr Phe Asp Ser Thr Gly His Leu Val Thr Gly Phe Gln Asn Ile
                    930                 935                 940

Asn Asn His His Tyr Phe Phe Leu Pro Asn Gly Ile Glu Leu Val Gln
945                 950                 955                 960

Ser Phe Leu Gln Asn Ala Asp Gly Ser Thr Ile Tyr Phe Asp Gln Lys
                    965                 970                 975

Gly Arg Gln Val Phe Asn Gln Tyr Ile Thr Asp Gln Thr Gly Thr Ala
                    980                 985                 990

Tyr Tyr Phe Gln Asn Asp Gly Thr Met Val Thr Ser Gly Phe Thr Glu
                    995                 1000                1005

Ile Asp Gly His Lys Gln Tyr Phe Tyr Lys Asn Gly Thr Gln Val
    1010                1015                1020

Lys Gly Gln Phe Val Ser Asp Thr Asp Gly His Val Phe Tyr Leu
    1025                1030                1035

Glu Ala Gly Asn Gly Asn Val Ala Thr Gln Arg Phe Ala Gln Asn
    1040                1045                1050

Ser Gln Gly Gln Trp Phe Tyr Leu Gly Asn Asp Gly Ile Ala Leu
    1055                1060                1065

Thr Gly Leu Gln Thr Ile Asn Gly Val Gln Asn Tyr Phe Tyr Ala
    1070                1075                1080

Asp Gly His Gln Ser Lys Gly Asp Phe Ile Thr Ile Gln Asn His
    1085                1090                1095

Val Leu Tyr Thr Asn Pro Leu Thr Gly Ala Ile Thr Thr Gly Met
    1100                1105                1110

Gln Gln Ile Gly Asp Lys Ile Phe Val Phe Asp Asn Thr Gly Asn
    1115                1120                1125

Met Leu Thr Asn Gln Tyr Tyr Gln Thr Leu Asp Gly Gln Trp Leu
    1130                1135                1140

His Leu Ser Thr Gln Gly Pro Ala Asp Thr Gly Leu Val Asn Ile
    1145                1150                1155

-continued

```
Asn Gly Asn Leu Lys Tyr Phe Gln Ala Asn Gly Arg Gln Val Lys
    1160                1165                1170

Gly Gln Phe Val Thr Asp Pro Ile Thr Asn Val Ser Tyr Tyr Met
    1175                1180                1185

Asn Ala Thr Asp Gly Ser Ala Val Phe Asn Asp Tyr Phe Thr Tyr
    1190                1195                1200

Gln Gly Gln Trp Tyr Leu Thr Asp Ser Asn Tyr Gln Leu Val Lys
    1205                1210                1215

Gly Phe Lys Val Val Asn Asn Lys Leu Gln His Phe Asp Glu Ile
    1220                1225                1230

Thr Gly Val Gln Thr Lys Ser Ala His Ile Ile Val Asn Asn Arg
    1235                1240                1245

Thr Tyr Ile Phe Asp Asp Gln Gly Tyr Phe Val Ser Val Ala
    1250                1255                1260

<210> SEQ ID NO 55
<211> LENGTH: 4284
<212> TYPE: DNA
<213> ORGANISM: Streptococcus salivarius

<400> SEQUENCE: 55
atgaaagacg gcaagtacta ttacctgttg gaggacggta gccacaagaa aaactttgcg      60
atcacggtca acggccaagt gctgtatttc gatgagaacg gtgcactgag cagcacgtct     120
acctattcgt ttacccagga gactaccaac ctggttaccg atttcactaa gaataatgct     180
gcgtacgaca gcaccaaggc ttccttcgag ctggttgatg ctacctgac tgcggacagc      240 tggtatcgtc cgaaggaaat cctggaggct ggcaccacct ggaaagcgag caccgagaaa     300
gactttcgtc cgctgctgat gagctggtgg ccggataaag acacccaggt tgcgtacctg     360
aattacatga cgaaggcgct gagcaatggc gaggaaacga agacgtgtt tacgatcgag      420 aactcccaag catctctgaa cgcagccgct cagatcatcc aacgcaagat cgaggtcaag     480
attgcagcga acaaaagcac ggactggctg cgccagagca tcgaggcgtt cgtgaaagat     540
caagacaagt ggaatatcaa ttcggagagc ccgggtaaag agcatttcca aaaaggtgct     600
ctgctgttcg ttaacagcga cctgaccaaa tgggcgaata gcgactatcg taaactggac     660
caaacggcga ccagccgtct gccgaaagac aagattaaga gcggcagcga tgcgggctac     720 gagttttgc tgtcctctga cattgataac agcaacccga ttgttcaggc ggagatgctg     780
aaccaactgt actatttcat gaactggggt cagattgtgt ttggcgacaa agataaggat     840
gcccatttcg acggtatccg cgtcgacgcc gtagacaacg ttagcattga tatgctgcaa     900
ctggttagct cttatatgaa ggcggcatac aaagttaatg aaagcgaagc gcgtgcactg     960
gcaaacattt ccattctgga ggcttggagc cagaacgatc cgtactacgt tgatgaacac    1020
aacacggctg cgctgtctat ggacaacggt ctgcgcctga gcatcgttca cggtttgacc    1080
cgtccggtta ctaacaaggg taccggtgcc cgtaatgcaa gcatgaaaga cctgatcaac    1140
ggtggctact tcggcttgtc caatcgtgca gaagttacga gctacgatca gctgggcttc    1200
gccacctacc tgtttgtgcg tgcccatgac tctgaagttc agaccgttat cgcggacatt    1260
atctcgaaga aaatcgatcc aaccacggac ggtttcacgt tcaccctgga ccagttgaaa    1320
caagccttcg acatctacaa cgccgatatg ctgaaggttg ataaggagta cacgcacagc    1380
aacatcccgg ctgcgtatgc cctgatgctg caaactatgg gtgcggctac gcgcgtgtat    1440
tatggtgatt tgtatacgga caatggccag tacatggcga aaaagagccc gtactttgat    1500
```

```
cagatcacga ccctgctgaa ggcgcgtagc aagtacgttg cgggtggcca gaccagctac   1560
atccataacc tggcgggtga tggtgtcagc agcgcgaagg ataacaaaga ggtgttggtc   1620
agcgtccgct acggtcagga tttgatgagc aaaaccgaca ccgagggtgg taagtatggt   1680
cgtaacagcg gtatgctgac cctgatcgcc aacaaccctg atctgaagct ggcagacggt   1740
gaaaccatca ccgtcaacat gggcgcagcg cacaagaatc aagcatatcg tccgttgttg   1800
ctgggcaccg aaaagggcat tgtgagcagc ctgaatgatt ccgacacgaa aattgttaag   1860
tataccgacg cgcaaggcaa tctggttttt accgctgatg agatcaaagg tttcaaaacc   1920
gtggatatga gcggttacct gtccgtgtgg gtgccggttg gcgcgaccga ggaccaaaac   1980
gtgctggcca agccgagcac gaaggtctac aaagagggtg ataaagttta ttcgagcagc   2040
gcggcactgg aagcacaggt gatctacgag ggttttagca attttcaaga cttcgtgaag   2100
gaagatagcc agtataccaa caagctgatt gcggccaatg cggacctgtt caaaagctgg   2160
ggtattacga gctttgaaat cgctccgcag tatgttagct ccaaggatgg caccttcctg   2220
gatagcatca ttgagaatgg ctacgcgttt accgatcgtt acgacttcgc gatgtcgaaa   2280
aacaataagt acggctccaa agaggatctg cgtgacgcgt tgaaagccct gcacaaacaa   2340
ggcattcaag ttattgcaga ttgggtcccg gaccagctgt acaccctgcc gggtaaggaa   2400
gtggtcacgg cgaccgcac ggacacccac ggtaaagtcc tggatgacac ctccctggtc   2460
aataaactgt acgttaccaa taccaaatct agcggtaacg acttccaggc gcaatacggc   2520
ggtgcattcc tggacaaact gcaaaagttg tacccggaga ttttcaagga agtgatggag   2580
gctagcggca aaaccattga tccgtccgtc aaaatcaagc agtgggaggc aaagtatttc   2640
aacggtacga acattcagaa acgcggtagc gactacgttc tgagcgacgg caaactgtat   2700
ttcacggtaa acgacaaagg taccttcttg ccggcagctc tgaccggtga cacgaaggca   2760
aagaccggtt tcgcctatga cggtactggc gtcacttact atacgacctc cggcacgcag   2820
gcaaagagcc aatttgtcac ctacaatggc aagcagtact atttcaatga caaaggttat   2880
ctggtcacgg gtgaacaggc gattgacggt agcaactact tcttcctgcc gaacggcgtt   2940
atgtttacgg acggtgtgat caaaaatgct aaaggtcagt ctctggtcta cggcaaatct   3000
ggtaagctga ccacgcaaac cggttggaag gaagttacgg tgaaggatga tagcggcaag   3060 gaaagagaaat tctaccaata cttctttaag ggtggcatta tggcgacggg tctgaccgag   3120
gttgaaggta agagaaata cttttatgat aatggttatc aggctaaagg tatttcatc    3180 cctaccaaag acggccatct gatgttttc tgcggtgata cggtgagcg taaatacagc   3240 ggtttcttcg aacaagacgg taactggtat tacgcaaacg ataaaggtta cgtcgcgacc   3300
ggttttacca aagtgggtaa gcagaacttg tactttaacg agaaaggtgt gcaggtcaag   3360
aaccgtttct ttcaggttgg tgatgctact tattacgcga ataacgaggg tgatgtactg   3420
cgtggtgcac agacgatcaa cggcgacgaa ctgtacttcg acgaaagcgg caagcaagtc   3480
aaaggtgaat ttgtgaataa cccggacggt accacgagct attatgacgc aattaccggt   3540
gtgaaactgg tggacaccag cttggtcgtt aatggtcaaa cgttcaacat tgacgctaaa   3600
ggcgttgtca ccaaggcgca cacgccgggt ttctatacca ctggcgacaa caattggttt   3660
tatgcagata gccacggtcg caatgtcact ggcgcacaga tcattaacgg ccaacacctg   3720
tatttcgatg cgaatggccg tcaggtgaag ggcggctttg ttatgaacac tgatggttct   3780
cgttcgttct atcattggaa taccggtgat aaactggtga gcacgttctt tacgaccggc   3840
```

```
cacgatcgtt ggtactacgc cgacgacaaa ggtaacgtgg tgaccggcgc acaagtcatc      3900
aacggtcaga aattgttctt cgcgaccgac ggtaaacaag ttaagggcga tttcgcgacc      3960
aacgcaaatg gttcccgttc ttactatcac ggtgccacgg gtaataagct ggtcagcacc      4020
ttctttacca cgggcgataa caactggtac tatgcagacg cgaagggcga ggttgtcgtt      4080
ggtgaacaaa cgattaacgg tcaaaatctg tattttgatc agaccggtaa gcaagtgaaa      4140
ggtgcgaccg cgaccaatcc agatggcagc atttcttatt acgatgttca cacgggcgag      4200
aaggtcatca accgctgggt caaaattccg agcggtcaat gggtgtactt caacgcgcag      4260
ggtaagggtt acgtcagcaa ttaa                                             4284
```

```
<210> SEQ ID NO 56
<211> LENGTH: 1427
<212> TYPE: PRT
<213> ORGANISM: Streptococcus salivarius

<400> SEQUENCE: 56

Met Lys Asp Gly Lys Tyr Tyr Tyr Leu Leu Glu Asp Gly Ser His Lys
1               5                   10                  15

Lys Asn Phe Ala Ile Thr Val Asn Gly Gln Val Leu Tyr Phe Asp Glu
            20                  25                  30

Asn Gly Ala Leu Ser Ser Thr Ser Thr Tyr Ser Phe Thr Gln Glu Thr
        35                  40                  45

Thr Asn Leu Val Thr Asp Phe Thr Lys Asn Asn Ala Ala Tyr Asp Ser
    50                  55                  60

Thr Lys Ala Ser Phe Glu Leu Val Asp Gly Tyr Leu Thr Ala Asp Ser
65                  70                  75                  80

Trp Tyr Arg Pro Lys Glu Ile Leu Glu Ala Gly Thr Thr Trp Lys Ala
                85                  90                  95

Ser Thr Glu Lys Asp Phe Arg Pro Leu Leu Met Ser Trp Trp Pro Asp
            100                 105                 110

Lys Asp Thr Gln Val Ala Tyr Leu Asn Tyr Met Thr Lys Ala Leu Ser
        115                 120                 125

Asn Gly Glu Glu Thr Lys Asp Val Phe Thr Ile Glu Asn Ser Gln Ala
    130                 135                 140

Ser Leu Asn Ala Ala Ala Gln Ile Ile Gln Arg Lys Ile Glu Val Lys
145                 150                 155                 160

Ile Ala Ala Asn Lys Ser Thr Asp Trp Leu Arg Gln Ser Ile Glu Ala
                165                 170                 175

Phe Val Lys Asp Gln Asp Lys Trp Asn Ile Asn Ser Glu Ser Pro Gly
            180                 185                 190

Lys Glu His Phe Gln Lys Gly Ala Leu Leu Phe Val Asn Ser Asp Leu
        195                 200                 205

Thr Lys Trp Ala Asn Ser Asp Tyr Arg Lys Leu Asp Gln Thr Ala Thr
    210                 215                 220

Ser Arg Leu Pro Lys Asp Lys Ile Lys Ser Gly Ser Asp Ala Gly Tyr
225                 230                 235                 240

Glu Phe Leu Leu Ser Ser Asp Ile Asp Asn Ser Asn Pro Ile Val Gln
                245                 250                 255

Ala Glu Met Leu Asn Gln Leu Tyr Tyr Phe Met Asn Trp Gly Gln Ile
            260                 265                 270

Val Phe Gly Asp Lys Asp Lys Asp Ala His Phe Asp Gly Ile Arg Val
        275                 280                 285

Asp Ala Val Asp Asn Val Ser Ile Asp Met Leu Gln Leu Val Ser Ser
```

```
              290                 295                 300

Tyr Met Lys Ala Ala Tyr Lys Val Asn Glu Ser Glu Ala Arg Ala Leu
305                 310                 315                 320

Ala Asn Ile Ser Ile Leu Glu Ala Trp Ser Gln Asn Asp Pro Tyr Tyr
                325                 330                 335

Val Asp Glu His Asn Thr Ala Ala Leu Ser Met Asp Asn Gly Leu Arg
                340                 345                 350

Leu Ser Ile Val His Gly Leu Thr Arg Pro Val Thr Asn Lys Gly Thr
            355                 360                 365

Gly Ala Arg Asn Ala Ser Met Lys Asp Leu Ile Asn Gly Gly Tyr Phe
        370                 375                 380

Gly Leu Ser Asn Arg Ala Glu Val Thr Ser Tyr Asp Gln Leu Gly Phe
385                 390                 395                 400

Ala Thr Tyr Leu Phe Val Arg Ala His Asp Ser Glu Val Gln Thr Val
                405                 410                 415

Ile Ala Asp Ile Ile Ser Lys Lys Ile Asp Pro Thr Thr Asp Gly Phe
                420                 425                 430

Thr Phe Thr Leu Asp Gln Leu Lys Gln Ala Phe Asp Ile Tyr Asn Ala
            435                 440                 445

Asp Met Leu Lys Val Asp Lys Glu Tyr Thr His Ser Asn Ile Pro Ala
        450                 455                 460

Ala Tyr Ala Leu Met Leu Gln Thr Met Gly Ala Ala Thr Arg Val Tyr
465                 470                 475                 480

Tyr Gly Asp Leu Tyr Thr Asp Asn Gly Gln Tyr Met Ala Lys Lys Ser
                485                 490                 495

Pro Tyr Phe Asp Gln Ile Thr Thr Leu Leu Lys Ala Arg Ser Lys Tyr
                500                 505                 510

Val Ala Gly Gly Gln Thr Ser Tyr Ile His Asn Leu Ala Gly Asp Gly
            515                 520                 525

Val Ser Ser Ala Lys Asp Asn Lys Glu Val Leu Val Ser Val Arg Tyr
        530                 535                 540

Gly Gln Asp Leu Met Ser Lys Thr Asp Thr Glu Gly Gly Lys Tyr Gly
545                 550                 555                 560

Arg Asn Ser Gly Met Leu Thr Leu Ile Ala Asn Asn Pro Asp Leu Lys
                565                 570                 575

Leu Ala Asp Gly Glu Thr Ile Thr Val Asn Met Gly Ala Ala His Lys
                580                 585                 590

Asn Gln Ala Tyr Arg Pro Leu Leu Leu Gly Thr Glu Lys Gly Ile Val
            595                 600                 605

Ser Ser Leu Asn Asp Ser Asp Thr Lys Ile Val Lys Tyr Thr Asp Ala
        610                 615                 620

Gln Gly Asn Leu Val Phe Thr Ala Asp Glu Ile Lys Gly Phe Lys Thr
625                 630                 635                 640

Val Asp Met Ser Gly Tyr Leu Ser Val Trp Val Pro Val Gly Ala Thr
                645                 650                 655

Glu Asp Gln Asn Val Leu Ala Lys Pro Ser Thr Lys Val Tyr Lys Glu
                660                 665                 670

Gly Asp Lys Val Tyr Ser Ser Ala Ala Leu Glu Ala Gln Val Ile
            675                 680                 685

Tyr Glu Gly Phe Ser Asn Phe Gln Asp Phe Val Lys Glu Asp Ser Gln
        690                 695                 700

Tyr Thr Asn Lys Leu Ile Ala Ala Asn Ala Asp Leu Phe Lys Ser Trp
705                 710                 715                 720
```

-continued

Gly Ile Thr Ser Phe Glu Ile Ala Pro Gln Tyr Val Ser Lys Asp
            725                 730                 735

Gly Thr Phe Leu Asp Ser Ile Ile Glu Asn Gly Tyr Ala Phe Thr Asp
            740                 745                 750

Arg Tyr Asp Phe Ala Met Ser Lys Asn Lys Tyr Gly Ser Lys Glu
            755                 760                 765

Asp Leu Arg Asp Ala Leu Lys Ala Leu His Lys Gln Gly Ile Gln Val
770                 775                 780

Ile Ala Asp Trp Val Pro Asp Gln Leu Tyr Thr Leu Pro Gly Lys Glu
785                 790                 795                 800

Val Val Thr Ala Thr Arg Thr Asp Thr His Gly Lys Val Leu Asp Asp
                    805                 810                 815

Thr Ser Leu Val Asn Lys Leu Tyr Val Thr Asn Thr Lys Ser Ser Gly
                    820                 825                 830

Asn Asp Phe Gln Ala Gln Tyr Gly Gly Ala Phe Leu Asp Lys Leu Gln
            835                 840                 845

Lys Leu Tyr Pro Glu Ile Phe Lys Glu Val Met Glu Ala Ser Gly Lys
850                 855                 860

Thr Ile Asp Pro Ser Val Lys Ile Lys Gln Trp Glu Ala Lys Tyr Phe
865                 870                 875                 880

Asn Gly Thr Asn Ile Gln Lys Arg Gly Ser Asp Tyr Val Leu Ser Asp
                    885                 890                 895

Gly Lys Leu Tyr Phe Thr Val Asn Asp Lys Gly Thr Phe Leu Pro Ala
            900                 905                 910

Ala Leu Thr Gly Asp Thr Lys Ala Lys Thr Gly Phe Ala Tyr Asp Gly
            915                 920                 925

Thr Gly Val Thr Tyr Tyr Thr Thr Ser Gly Thr Gln Ala Lys Ser Gln
            930                 935                 940

Phe Val Thr Tyr Asn Gly Lys Gln Tyr Phe Asn Asp Lys Gly Tyr
945                 950                 955                 960

Leu Val Thr Gly Glu Gln Ala Ile Asp Gly Ser Asn Tyr Phe Phe Leu
                    965                 970                 975

Pro Asn Gly Val Met Phe Thr Asp Gly Val Ile Lys Asn Ala Lys Gly
            980                 985                 990

Gln Ser Leu Val Tyr Gly Lys Ser Gly Lys Leu Thr Thr Gln Thr Gly
            995                 1000                1005

Trp Lys Glu Val Thr Val Lys Asp Asp Ser Gly Lys Glu Glu Lys
    1010                1015                1020

Phe Tyr Gln Tyr Phe Phe Lys Gly Gly Ile Met Ala Thr Gly Leu
    1025                1030                1035

Thr Glu Val Glu Gly Lys Glu Lys Tyr Phe Tyr Asp Asn Gly Tyr
    1040                1045                1050

Gln Ala Lys Gly Ile Phe Ile Pro Thr Lys Asp Gly His Leu Met
    1055                1060                1065

Phe Phe Cys Gly Asp Ser Gly Glu Arg Lys Tyr Ser Gly Phe Phe
    1070                1075                1080

Glu Gln Asp Gly Asn Trp Tyr Tyr Ala Asn Asp Lys Gly Tyr Val
    1085                1090                1095

Ala Thr Gly Phe Thr Lys Val Gly Lys Gln Asn Leu Tyr Phe Asn
    1100                1105                1110

Glu Lys Gly Val Gln Val Lys Asn Arg Phe Phe Gln Val Gly Asp
    1115                1120                1125

| | | | | | | | | | | |
|---|---|---|---|---|---|---|---|---|---|---|
| Ala | Thr | Tyr | Tyr | Ala | Asn | Asn | Glu | Gly | Asp | Val | Leu | Arg | Gly | Ala |
| | 1130 | | | | | 1135 | | | | 1140 | | | | |
| Gln | Thr | Ile | Asn | Gly | Asp | Glu | Leu | Tyr | Phe | Asp | Glu | Ser | Gly | Lys |
| 1145 | | | | | 1150 | | | | | 1155 | | | | |
| Gln | Val | Lys | Gly | Glu | Phe | Val | Asn | Asn | Pro | Asp | Gly | Thr | Thr | Ser |
| 1160 | | | | | 1165 | | | | | 1170 | | | | |
| Tyr | Tyr | Asp | Ala | Ile | Thr | Gly | Val | Lys | Leu | Val | Asp | Thr | Ser | Leu |
| 1175 | | | | | 1180 | | | | | 1185 | | | | |
| Val | Val | Asn | Gly | Gln | Thr | Phe | Asn | Ile | Asp | Ala | Lys | Gly | Val | Val |
| 1190 | | | | | 1195 | | | | | 1200 | | | | |
| Thr | Lys | Ala | His | Thr | Pro | Gly | Phe | Tyr | Thr | Thr | Gly | Asp | Asn | Asn |
| 1205 | | | | | 1210 | | | | | 1215 | | | | |
| Trp | Phe | Tyr | Ala | Asp | Ser | His | Gly | Arg | Asn | Val | Thr | Gly | Ala | Gln |
| 1220 | | | | | 1225 | | | | | 1230 | | | | |
| Ile | Ile | Asn | Gly | Gln | His | Leu | Tyr | Phe | Asp | Ala | Asn | Gly | Arg | Gln |
| 1235 | | | | | 1240 | | | | | 1245 | | | | |
| Val | Lys | Gly | Gly | Phe | Val | Met | Asn | Thr | Asp | Gly | Ser | Arg | Ser | Phe |
| 1250 | | | | | 1255 | | | | | 1260 | | | | |
| Tyr | His | Trp | Asn | Thr | Gly | Asp | Lys | Leu | Val | Ser | Thr | Phe | Phe | Thr |
| 1265 | | | | | 1270 | | | | | 1275 | | | | |
| Thr | Gly | His | Asp | Arg | Trp | Tyr | Tyr | Ala | Asp | Asp | Lys | Gly | Asn | Val |
| 1280 | | | | | 1285 | | | | | 1290 | | | | |
| Val | Thr | Gly | Ala | Gln | Val | Ile | Asn | Gly | Gln | Lys | Leu | Phe | Phe | Ala |
| 1295 | | | | | 1300 | | | | | 1305 | | | | |
| Thr | Asp | Gly | Lys | Gln | Val | Lys | Gly | Asp | Phe | Ala | Thr | Asn | Ala | Asn |
| 1310 | | | | | 1315 | | | | | 1320 | | | | |
| Gly | Ser | Arg | Ser | Tyr | Tyr | His | Gly | Ala | Thr | Gly | Asn | Lys | Leu | Val |
| 1325 | | | | | 1330 | | | | | 1335 | | | | |
| Ser | Thr | Phe | Phe | Thr | Thr | Gly | Asp | Asn | Asn | Trp | Tyr | Tyr | Ala | Asp |
| 1340 | | | | | 1345 | | | | | 1350 | | | | |
| Ala | Lys | Gly | Glu | Val | Val | Val | Gly | Glu | Gln | Thr | Ile | Asn | Gly | Gln |
| 1355 | | | | | 1360 | | | | | 1365 | | | | |
| Asn | Leu | Tyr | Phe | Asp | Gln | Thr | Gly | Lys | Gln | Val | Lys | Gly | Ala | Thr |
| 1370 | | | | | 1375 | | | | | 1380 | | | | |
| Ala | Thr | Asn | Pro | Asp | Gly | Ser | Ile | Ser | Tyr | Tyr | Asp | Val | His | Thr |
| 1385 | | | | | 1390 | | | | | 1395 | | | | |
| Gly | Glu | Lys | Val | Ile | Asn | Arg | Trp | Val | Lys | Ile | Pro | Ser | Gly | Gln |
| 1400 | | | | | 1405 | | | | | 1410 | | | | |
| Trp | Val | Tyr | Phe | Asn | Ala | Gln | Gly | Lys | Gly | Tyr | Val | Ser | Asn | |
| 1415 | | | | | 1420 | | | | | 1425 | | | | |

<210> SEQ ID NO 57
<211> LENGTH: 5208
<212> TYPE: DNA
<213> ORGANISM: Lactobacillus reuteri

<400> SEQUENCE: 57

```
atggatcagc aagtacaaag cagcaccacc caggagcaga cgagcacggt taacgcggac    60
acgactaaaa ccgtcaatct ggataccaac actgaccagc cggctcagac gaccgataag   120
aatcaggtcg cgaatgatac caccaccaac caaagcaaga cggacagcac cagcacgacg   180
gttaagaatc cgacgtttat tcctgttagc actttgtcca gctccgataa cgaaaagcag   240
agccagaatt acaataaacc agataacggt aattacggta atgttgatgc ggcctacttc   300
aataacaatc agctgcacat tagcggttgg cacgcaacca acgcgagcca gggtacggat   360
```

```
agccgccaag taatcgtacg cgacattacc accaagaccg agctgggtcg tactaatgtg    420
accaacaatg ttctgcgtcc ggacgtgaaa aatgttcaca acgtctacaa cgctgacaac    480
agcggctttg atgtgaatat caatattgat ttcagcaaga tgaaagacta tcgtgacagc    540
atcgagatcg tttctcgtta tagcggcaac ggcaagagcc ttgactggtg gtcgcagccg    600
atcacgtttg acaaaaacaa ttatgcttat ctggacactt tcgaggtgaa gaacggtgaa    660
ctgcatgcaa cgggctggaa tgccaccaac aaggctatca attacaatca ccacttcgtt    720
attctgtttg atcgtacgaa tggcaaagaa gtcacccgcc aagaggtgcg tgatggtcaa    780
agccgtccgg atgtggcgaa ggtatacccg caagtcgttg gcgcgaacaa tagcggtttt    840
gacgttacgt ttaacattgg tgatttggac tacacccatc agtaccagat cctgtctcgt    900
tacagcaacg cagacaacgg tgaaggcgat tatgtgacct attggtttgc gccgcagagc    960
atcgctccgg cgaatcaaag caaccaaggt tacctggaca gcttcgatat ttcgaaaaac    1020
ggtgaggtga ccgtgacggg ttggaatgcg acggatctga gcgagttgca aacgaatcac    1080
tacgtgatcc tgtttgatca gacggcgggt caacaggttg catccgctaa ggtcgacctg    1140
atcagccgtc cagacgtcgc gaaggcgtac cctaccgtta aaacggcaga aacctccggt    1200
ttcaaggtca cgtttaaggt tagcaatctg caaccgggcc accaatacag cgtcgttagc    1260
cgctttagcg ccgatgaaaa cggtaatggc aacgacaaac gccacacgga ctactggtac    1320
tctccggtta ccctgaacca aacggctagc aacattgaca ctatcaccat gacttccaac    1380
ggtctgcaca tcaccggctg gatggcgagc gataatagca ttaacgaagc gaccccgtac    1440
gcgattatcc tgaacaacgg tcgcgaggtg acgcgccaga aactgaccct gatcgcgcgt    1500
ccggatgttg cggcagtgta tccgagcctg tacaatagcg cggttagcgg cttcgacacc    1560
accatcaagc tgactaacgc gcaatatcaa gcattgaacg gccagctgca agtgctgctg    1620
cgctttagca aggcggtgga cggtaacccg aatggtacca ataccgtcac ggatcaattt    1680
agcaaaaact acgcaacgac cggtggtaat ttcgattacg tcaaggttaa tggtaaccaa    1740
attgagtttt ctggctggca cgcgacgaat cagagcaatg ataagaacag ccaatggatt    1800
atcgtcttgg ttaacggtaa agaggtcaaa cgccagctgg tcaatgacac gaaagacggc    1860
gcagccggct tcaatcgtaa tgatgtgtat aaagtgaacc cagcgatcga aaatagcatt    1920
atgtctggct tccagggcat tatcacgttg ccggttacgg tgaaagacga aaacgtgcag    1980
ctggtgcacc gcttctccaa tgacgcaaaa acgggtgagg gcaattatgt cgatttctgg    2040
agcgaggtga tgtctgtgaa ggactctttc caaaagggta atggtccgct gaaccagttt    2100
ggcctgcaaa ccatcaacgg ccaacaatac tatattgacc cgacgaccgg ccagccgcgt    2160
aagaatttcc tgctgcaaaa cggcaacgat tggatttact tcgacaaaga cactggcgca    2220
ggcaccaacg cgctgaaatt gcagtttgat aagggcacga ttagcgctga cgaacaatac    2280
cgtcgcggca acgaggcgta ctcctacgat gataagagca ttgaaaatgt caacggttac    2340
ttgacggcgg acacgtggta ccgcccgaag cagatcctga aggatggcac cacttggacc    2400
gattccaaag aaaccgatat gcgtccgatc ttgatggtct ggtggccaaa cacggtgact    2460
caggcgtact atctgaacta catgaaacaa tatggcaatc tgctgccggc gagcctgccg    2520
agctttagca ccgacgccga tagcgcggag ttgaatcatt attccgagct ggtccaacag    2580
aatatcgaga aacgtattag cgagactggt agcactgatt ggctgcgtac cctgatgcac    2640
gagttcgtga cgaagaatag catgtggaac aaagatagcg agaacgttga ctacggtggc    2700
```

```
ctgcaactgc aaggtggttt cctgaagtac gttaacagcg acctgacgaa gtacgcaaac    2760
tctgattggc gtctgatgaa ccgtaccgcg acgaacattg acggtaagaa ttacggtggt    2820
gccgagtttc tgctggcgaa tgacatcgac aactctaacc cggtggtgca ggccgaagaa    2880
ttgaattggc tgtattatct gatgaacttc ggtaccatca ccggtaacaa cccagaagct    2940
aacttcgacg gcatccgtgt cgacgcggtc gataatgtgg atgttgatct gctgagcatt    3000
gcccgtgact actttaatgc agcgtataac atggaacaaa gcgatgctag cgcgaataag    3060
cacatcaata ttctggaaga ttggggctgg gacgatccgg cgtacgtgaa caaaatcggc    3120
aatccacagt tgaccatgga tgaccgcctg cgtaatgcaa ttatggacac cctgagcggt    3180
gcgccggata agaaccaagc gctgaacaag ctgattactc agtctctggt gaatcgcgca    3240
aatgataata ctgaaaacgc ggtgatccct tcctacaact ttgtccgcgc tcatgacagc    3300
aatgcccagg accagatccg tcaagcgatc caggcggcaa ccggcaaacc ttatggcgag    3360
ttcaacttgg atgatgagaa aagggtatg gaggcttaca tcaatgacca aaatagcacc    3420
aataagaaat ggaacctgta caacatgccg agcgcatata ccatcctgct gacgaataag    3480
gactcggtcc cgcgtgtcta ctatggcgac ttgtaccagg atggtggcca gtacatggaa    3540
cacaaaactc gttactttga caccatcacg aatctgctga aaacccgcgt caagtatgtc    3600
gcaggcggcc agaccatgtc tgtggataag aatggcattt tgactaatgt ccgtttcggt    3660
aagggtgcga tgaacgcaac tgacacgggt accgatgaaa cccgcaccga aggtatcggc    3720
gttgttatca gcaacaatac gaatttgaaa ctgaatgacg gcgaaagcgt tgtgctgcac    3780
atgggcgctg cccataagaa tcagaagtat cgtgcagtga tcctgaccac ggaggacggt    3840
gtgaagaatt acaccaacga caccgatgcg ccggtcgcat acaccgacgc gaacggcgat    3900
ttgcatttca ccaatactaa cctggacggt cagcaatata ccgccgttcg tggctacgca    3960
aacccggacg ttacgggtta tctggccgtc tgggttcctg ctggtgccgc cgatgaccaa    4020
gacgcacgta ccgctccgag cgacgaggcc cacaccacga aaacggcgta tcgttccaat    4080
gcggcattgg actccaacgt catctacgaa ggcttttcga actttatcta ttggccgacg    4140
accgagagcg agcgcacgaa tgtccgcatc gcgcagaacg cggatctgtt caaatcgtgg    4200
ggtatcacca ccttcgagct ggcgccacag tacaatagca gcaaggacgg tacgtttctg    4260
gattcgatca ttgacaatgg ttacgcgttt accgatcgtt atgacctggg tatgtctacc    4320
ccgaacaagt acggtagcga tgaggatctg cgtaacgccc tgcaagcact gcacaaggcc    4380
ggtctgcaag ccatcgcaga ttgggttccg gaccaaatct acaatctgcc gggcaaagag    4440
gctgtcacgg ttactcgtag cgatgaccac ggcactacct gggaggttag cccgatcaag    4500
aatgtggtgt atatcactaa taccatcggt ggtggcgaat accagaaaaa gtatggtggt    4560
gaatttctgg acaccttgca aaaagaatat ccgcagctgt ttagccaagt ttacccggtg    4620
acccaaacga cgattgaccc tagcgttaag attaaagagt ggtccgcgaa gtacttcaat    4680
ggtactaata tcctgcatcg cggtgcgggt tacgtcctgc gtagcaatga tggtaagtat    4740
tacaacctgg gtactagcac ccagcagttc ctgccgagcc agctgagcgt tcaagataat    4800
gagggttacg gtttcgttaa agagggtaac aactatcact attatgacga gaacaaacaa    4860
atggttaagg acgcgtttat ccaggatagc gtcggcaatt ggtactattt tgataagaac    4920
ggcaatatgg ttgcaaacca aagcccggtt gaaatcagca gcaacggtgc gagcggcacc    4980
tacttgtttt tgaataatgg taccagcttc cgcagcggcc tggtcaaaac ggatgcaggc    5040
acctattact acgatggtga cggtcgcatg gttcgtaatc aaacggtttc tgacggtgcc    5100
```

```
atgacgtacg ttctggacga aaatggtaaa ctggtcagcg aatcttttga tagcagcgcg    5160
accgaggccc atccgctgaa accgggcgat ctgaacggtc aaaagtaa                 5208
```

<210> SEQ ID NO 58
<211> LENGTH: 1735
<212> TYPE: PRT
<213> ORGANISM: Lactobacillus reuteri

<400> SEQUENCE: 58

| | | | | | | | | | | | | | | |
|---|---|---|---|---|---|---|---|---|---|---|---|---|---|---|
| Met | Asp | Gln | Gln | Val | Gln | Ser | Ser | Thr | Thr | Gln | Glu | Gln | Thr | Ser | Thr |
| 1 | | | | 5 | | | | | 10 | | | | | 15 | |
| Val | Asn | Ala | Asp | Thr | Thr | Lys | Thr | Val | Asn | Leu | Asp | Thr | Asn | Thr | Asp |
| | | | 20 | | | | | 25 | | | | | 30 | | |
| Gln | Pro | Ala | Gln | Thr | Thr | Asp | Lys | Asn | Gln | Val | Ala | Asn | Asp | Thr | Thr |
| | | 35 | | | | | 40 | | | | | 45 | | | |
| Thr | Asn | Gln | Ser | Lys | Thr | Asp | Ser | Thr | Ser | Thr | Val | Lys | Asn | Pro | |
| 50 | | | | | 55 | | | | | 60 | | | | | |
| Thr | Phe | Ile | Pro | Val | Ser | Thr | Leu | Ser | Ser | Ser | Asp | Asn | Glu | Lys | Gln |
| 65 | | | | 70 | | | | | 75 | | | | | 80 | |
| Ser | Gln | Asn | Tyr | Asn | Lys | Pro | Asp | Asn | Gly | Asn | Tyr | Gly | Asn | Val | Asp |
| | | | | 85 | | | | | 90 | | | | | 95 | |
| Ala | Ala | Tyr | Phe | Asn | Asn | Asn | Gln | Leu | His | Ile | Ser | Gly | Trp | His | Ala |
| | | | 100 | | | | | 105 | | | | | 110 | | |
| Thr | Asn | Ala | Ser | Gln | Gly | Thr | Asp | Ser | Arg | Gln | Val | Ile | Val | Arg | Asp |
| | | | 115 | | | | | 120 | | | | | 125 | | |
| Ile | Thr | Thr | Lys | Thr | Glu | Leu | Gly | Arg | Thr | Asn | Val | Thr | Asn | Asn | Val |
| | 130 | | | | | 135 | | | | | 140 | | | | |
| Leu | Arg | Pro | Asp | Val | Lys | Asn | Val | His | Asn | Val | Tyr | Asn | Ala | Asp | Asn |
| 145 | | | | | 150 | | | | | 155 | | | | | 160 |
| Ser | Gly | Phe | Asp | Val | Asn | Ile | Asn | Ile | Asp | Phe | Ser | Lys | Met | Lys | Asp |
| | | | | 165 | | | | | 170 | | | | | 175 | |
| Tyr | Arg | Asp | Ser | Ile | Glu | Ile | Val | Ser | Arg | Tyr | Ser | Gly | Asn | Gly | Lys |
| | | | 180 | | | | | 185 | | | | | 190 | | |
| Ser | Val | Asp | Trp | Trp | Ser | Gln | Pro | Ile | Thr | Phe | Asp | Lys | Asn | Asn | Tyr |
| | | | 195 | | | | | 200 | | | | | 205 | | |
| Ala | Tyr | Leu | Asp | Thr | Phe | Glu | Val | Lys | Asn | Gly | Glu | Leu | His | Ala | Thr |
| | 210 | | | | | 215 | | | | | 220 | | | | |
| Gly | Trp | Asn | Ala | Thr | Asn | Lys | Ala | Ile | Asn | Tyr | Asn | His | His | Phe | Val |
| 225 | | | | | 230 | | | | | 235 | | | | | 240 |
| Ile | Leu | Phe | Asp | Arg | Thr | Asn | Gly | Lys | Glu | Val | Thr | Arg | Gln | Glu | Val |
| | | | | 245 | | | | | 250 | | | | | 255 | |
| Arg | Asp | Gly | Gln | Ser | Arg | Pro | Asp | Val | Ala | Lys | Val | Tyr | Pro | Gln | Val |
| | | | 260 | | | | | 265 | | | | | 270 | | |
| Val | Gly | Ala | Asn | Asn | Ser | Gly | Phe | Asp | Val | Thr | Phe | Asn | Ile | Gly | Asp |
| | | | 275 | | | | | 280 | | | | | 285 | | |
| Leu | Asp | Tyr | Thr | His | Gln | Tyr | Gln | Ile | Leu | Ser | Arg | Tyr | Ser | Asn | Ala |
| | 290 | | | | | 295 | | | | | 300 | | | | |
| Asp | Asn | Gly | Glu | Gly | Asp | Tyr | Val | Thr | Tyr | Trp | Phe | Ala | Pro | Gln | Ser |
| 305 | | | | | 310 | | | | | 315 | | | | | 320 |
| Ile | Ala | Pro | Ala | Asn | Gln | Ser | Asn | Gln | Gly | Tyr | Leu | Asp | Ser | Phe | Asp |
| | | | | 325 | | | | | 330 | | | | | 335 | |
| Ile | Ser | Lys | Asn | Gly | Glu | Val | Thr | Val | Thr | Gly | Trp | Asn | Ala | Thr | Asp |
| | | | 340 | | | | | 345 | | | | | 350 | | |

```
Leu Ser Glu Leu Gln Thr Asn His Tyr Val Ile Leu Phe Asp Gln Thr
            355                 360                 365

Ala Gly Gln Gln Val Ala Ser Ala Lys Val Asp Leu Ile Ser Arg Pro
        370                 375                 380

Asp Val Ala Lys Ala Tyr Pro Thr Val Lys Thr Ala Glu Thr Ser Gly
385                 390                 395                 400

Phe Lys Val Thr Phe Lys Val Ser Asn Leu Gln Pro Gly His Gln Tyr
                405                 410                 415

Ser Val Val Ser Arg Phe Ser Ala Asp Glu Asn Gly Asn Gly Asn Asp
            420                 425                 430

Lys Arg His Thr Asp Tyr Trp Tyr Ser Pro Val Thr Leu Asn Gln Thr
        435                 440                 445

Ala Ser Asn Ile Asp Thr Ile Thr Met Thr Ser Asn Gly Leu His Ile
    450                 455                 460

Thr Gly Trp Met Ala Ser Asp Asn Ser Ile Asn Glu Ala Thr Pro Tyr
465                 470                 475                 480

Ala Ile Ile Leu Asn Asn Gly Arg Glu Val Thr Arg Gln Lys Leu Thr
                485                 490                 495

Leu Ile Ala Arg Pro Asp Val Ala Ala Val Tyr Pro Ser Leu Tyr Asn
            500                 505                 510

Ser Ala Val Ser Gly Phe Asp Thr Thr Ile Lys Leu Thr Asn Ala Gln
        515                 520                 525

Tyr Gln Ala Leu Asn Gly Gln Leu Gln Val Leu Leu Arg Phe Ser Lys
    530                 535                 540

Ala Val Asp Gly Asn Pro Asn Gly Thr Asn Thr Val Thr Asp Gln Phe
545                 550                 555                 560

Ser Lys Asn Tyr Ala Thr Thr Gly Gly Asn Phe Asp Tyr Val Lys Val
                565                 570                 575

Asn Gly Asn Gln Ile Glu Phe Ser Gly Trp His Ala Thr Asn Gln Ser
            580                 585                 590

Asn Asp Lys Asn Ser Gln Trp Ile Ile Val Leu Val Asn Gly Lys Glu
        595                 600                 605

Val Lys Arg Gln Leu Val Asn Asp Thr Lys Asp Gly Ala Ala Gly Phe
610                 615                 620

Asn Arg Asn Asp Val Tyr Lys Val Asn Pro Ala Ile Glu Asn Ser Ile
625                 630                 635                 640

Met Ser Gly Phe Gln Gly Ile Ile Thr Leu Pro Val Thr Val Lys Asp
                645                 650                 655

Glu Asn Val Gln Leu Val His Arg Phe Ser Asn Asp Ala Lys Thr Gly
            660                 665                 670

Glu Gly Asn Tyr Val Asp Phe Trp Ser Glu Val Met Ser Val Lys Asp
        675                 680                 685

Ser Phe Gln Lys Gly Asn Gly Pro Leu Asn Gln Phe Gly Leu Gln Thr
    690                 695                 700

Ile Asn Gly Gln Gln Tyr Tyr Ile Asp Pro Thr Thr Gly Gln Pro Arg
705                 710                 715                 720

Lys Asn Phe Leu Leu Gln Asn Gly Asn Asp Trp Ile Tyr Phe Asp Lys
                725                 730                 735

Asp Thr Gly Ala Gly Thr Asn Ala Leu Lys Leu Gln Phe Asp Lys Gly
            740                 745                 750

Thr Ile Ser Ala Asp Glu Gln Tyr Arg Arg Gly Asn Glu Ala Tyr Ser
        755                 760                 765

Tyr Asp Asp Lys Ser Ile Glu Asn Val Asn Gly Tyr Leu Thr Ala Asp
```

```
                770             775             780
Thr Trp Tyr Arg Pro Lys Gln Ile Leu Lys Asp Gly Thr Thr Trp Thr
785                 790             795                 800

Asp Ser Lys Glu Thr Asp Met Arg Pro Ile Leu Met Val Trp Trp Pro
                805             810              815

Asn Thr Val Thr Gln Ala Tyr Tyr Leu Asn Tyr Met Lys Gln Tyr Gly
                820             825              830

Asn Leu Leu Pro Ala Ser Leu Pro Ser Phe Ser Thr Asp Ala Asp Ser
            835             840              845

Ala Glu Leu Asn His Tyr Ser Glu Leu Val Gln Gln Asn Ile Glu Lys
        850             855             860

Arg Ile Ser Glu Thr Gly Ser Thr Asp Trp Leu Arg Thr Leu Met His
865             870             875              880

Glu Phe Val Thr Lys Asn Ser Met Trp Asn Lys Asp Ser Glu Asn Val
            885             890             895

Asp Tyr Gly Gly Leu Gln Leu Gln Gly Gly Phe Leu Lys Tyr Val Asn
            900             905             910

Ser Asp Leu Thr Lys Tyr Ala Asn Ser Asp Trp Arg Leu Met Asn Arg
        915             920             925

Thr Ala Thr Asn Ile Asp Gly Lys Asn Tyr Gly Gly Ala Glu Phe Leu
        930             935             940

Leu Ala Asn Asp Ile Asp Asn Ser Asn Pro Val Val Gln Ala Glu Glu
945             950             955             960

Leu Asn Trp Leu Tyr Tyr Leu Met Asn Phe Gly Thr Ile Thr Gly Asn
                965             970             975

Asn Pro Glu Ala Asn Phe Asp Gly Ile Arg Val Asp Ala Val Asp Asn
            980             985             990

Val Asp Val Asp Leu Leu Ser Ile Ala Arg Asp Tyr Phe Asn Ala Ala
        995             1000            1005

Tyr Asn Met Glu Gln Ser Asp Ala Ser Ala Asn Lys His Ile Asn
    1010            1015            1020

Ile Leu Glu Asp Trp Gly Trp Asp Asp Pro Ala Tyr Val Asn Lys
    1025            1030            1035

Ile Gly Asn Pro Gln Leu Thr Met Asp Asp Arg Leu Arg Asn Ala
    1040            1045            1050

Ile Met Asp Thr Leu Ser Gly Ala Pro Asp Lys Asn Gln Ala Leu
    1055            1060            1065

Asn Lys Leu Ile Thr Gln Ser Leu Val Asn Arg Ala Asn Asp Asn
    1070            1075            1080

Thr Glu Asn Ala Val Ile Pro Ser Tyr Asn Phe Val Arg Ala His
    1085            1090            1095

Asp Ser Asn Ala Gln Asp Gln Ile Arg Gln Ala Ile Gln Ala Ala
    1100            1105            1110

Thr Gly Lys Pro Tyr Gly Glu Phe Asn Leu Asp Asp Glu Lys Lys
    1115            1120            1125

Gly Met Glu Ala Tyr Ile Asn Asp Gln Asn Ser Thr Asn Lys Lys
    1130            1135            1140

Trp Asn Leu Tyr Asn Met Pro Ser Ala Tyr Thr Ile Leu Leu Thr
    1145            1150            1155

Asn Lys Asp Ser Val Pro Arg Val Tyr Tyr Gly Asp Leu Tyr Gln
    1160            1165            1170

Asp Gly Gly Gln Tyr Met Glu His Lys Thr Arg Tyr Phe Asp Thr
    1175            1180            1185
```

```
Ile Thr Asn Leu Leu Lys Thr Arg Val Lys Tyr Val Ala Gly Gly
    1190                1195                1200

Gln Thr Met Ser Val Asp Lys Asn Gly Ile Leu Thr Asn Val Arg
    1205                1210                1215

Phe Gly Lys Gly Ala Met Asn Ala Thr Asp Thr Gly Thr Asp Glu
    1220                1225                1230

Thr Arg Thr Glu Gly Ile Gly Val Val Ile Ser Asn Asn Thr Asn
    1235                1240                1245

Leu Lys Leu Asn Asp Gly Glu Ser Val Val Leu His Met Gly Ala
    1250                1255                1260

Ala His Lys Asn Gln Lys Tyr Arg Ala Val Ile Leu Thr Thr Glu
    1265                1270                1275

Asp Gly Val Lys Asn Tyr Thr Asn Asp Thr Asp Ala Pro Val Ala
    1280                1285                1290

Tyr Thr Asp Ala Asn Gly Asp Leu His Phe Thr Asn Thr Asn Leu
    1295                1300                1305

Asp Gly Gln Gln Tyr Thr Ala Val Arg Gly Tyr Ala Asn Pro Asp
    1310                1315                1320

Val Thr Gly Tyr Leu Ala Val Trp Val Pro Ala Gly Ala Ala Asp
    1325                1330                1335

Asp Gln Asp Ala Arg Thr Ala Pro Ser Asp Glu Ala His Thr Thr
    1340                1345                1350

Lys Thr Ala Tyr Arg Ser Asn Ala Ala Leu Asp Ser Asn Val Ile
    1355                1360                1365

Tyr Glu Gly Phe Ser Asn Phe Ile Tyr Trp Pro Thr Thr Glu Ser
    1370                1375                1380

Glu Arg Thr Asn Val Arg Ile Ala Gln Asn Ala Asp Leu Phe Lys
    1385                1390                1395

Ser Trp Gly Ile Thr Thr Phe Glu Leu Ala Pro Gln Tyr Asn Ser
    1400                1405                1410

Ser Lys Asp Gly Thr Phe Leu Asp Ser Ile Ile Asp Asn Gly Tyr
    1415                1420                1425

Ala Phe Thr Asp Arg Tyr Asp Leu Gly Met Ser Thr Pro Asn Lys
    1430                1435                1440

Tyr Gly Ser Asp Glu Asp Leu Arg Asn Ala Leu Gln Ala Leu His
    1445                1450                1455

Lys Ala Gly Leu Gln Ala Ile Ala Asp Trp Val Pro Asp Gln Ile
    1460                1465                1470

Tyr Asn Leu Pro Gly Lys Glu Ala Val Thr Val Thr Arg Ser Asp
    1475                1480                1485

Asp His Gly Thr Thr Trp Glu Val Ser Pro Ile Lys Asn Val Val
    1490                1495                1500

Tyr Ile Thr Asn Thr Ile Gly Gly Gly Glu Tyr Gln Lys Lys Tyr
    1505                1510                1515

Gly Gly Glu Phe Leu Asp Thr Leu Gln Lys Glu Tyr Pro Gln Leu
    1520                1525                1530

Phe Ser Gln Val Tyr Pro Val Thr Gln Thr Thr Ile Asp Pro Ser
    1535                1540                1545

Val Lys Ile Lys Glu Trp Ser Ala Lys Tyr Phe Asn Gly Thr Asn
    1550                1555                1560

Ile Leu His Arg Gly Ala Gly Tyr Val Leu Arg Ser Asn Asp Gly
    1565                1570                1575
```

-continued

```
Lys Tyr Tyr Asn Leu Gly Thr Ser Thr Gln Gln Phe Leu Pro Ser
    1580                1585                1590

Gln Leu Ser Val Gln Asp Asn Glu Gly Tyr Gly Phe Val Lys Glu
    1595                1600                1605

Gly Asn Asn Tyr His Tyr Tyr Asp Glu Asn Lys Gln Met Val Lys
    1610                1615                1620

Asp Ala Phe Ile Gln Asp Ser Val Gly Asn Trp Tyr Tyr Phe Asp
    1625                1630                1635

Lys Asn Gly Asn Met Val Ala Asn Gln Ser Pro Val Glu Ile Ser
    1640                1645                1650

Ser Asn Gly Ala Ser Gly Thr Tyr Leu Phe Leu Asn Asn Gly Thr
    1655                1660                1665

Ser Phe Arg Ser Gly Leu Val Lys Thr Asp Ala Gly Thr Tyr Tyr
    1670                1675                1680

Tyr Asp Gly Asp Gly Arg Met Val Arg Asn Gln Thr Val Ser Asp
    1685                1690                1695

Gly Ala Met Thr Tyr Val Leu Asp Glu Asn Gly Lys Leu Val Ser
    1700                1705                1710

Glu Ser Phe Asp Ser Ser Ala Thr Glu Ala His Pro Leu Lys Pro
    1715                1720                1725

Gly Asp Leu Asn Gly Gln Lys
    1730                1735

<210> SEQ ID NO 59
<211> LENGTH: 1242
<212> TYPE: PRT
<213> ORGANISM: Unknown
<220> FEATURE:
<223> OTHER INFORMATION: unknown Streptococcus species

<400> SEQUENCE: 59

Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
            20                  25                  30

Glu Thr Gly Glu Leu Ser Asn Gln Lys Asp Tyr Arg Phe Asp Lys Asn
        35                  40                  45

Gly Gly Thr Gly Ser Ala Ala Asp Ser Thr Thr Asn Thr Asn Val Thr
    50                  55                  60

Val Asn Gly Asp Lys Asn Ala Phe Tyr Gly Thr Thr Glu Lys Asp Ile
65                  70                  75                  80

Glu Leu Val Asp Gly Tyr Phe Thr Ala Asn Thr Trp Tyr Arg Pro Lys
                85                  90                  95

Glu Ile Leu Lys Asp Gly Lys Glu Trp Thr Ala Ser Thr Glu Asn Asp
            100                 105                 110

Lys Arg Pro Leu Leu Thr Val Trp Trp Pro Ser Lys Ala Ile Gln Ala
        115                 120                 125

Ser Tyr Leu Asn Tyr Met Arg Glu Glu Gly Leu Gly Thr Asn Gln Thr
    130                 135                 140

Phe Thr Ser Tyr Ser Ser Gln Thr Gln Met Asp Gln Ala Ala Leu Glu
145                 150                 155                 160

Val Gln Lys Arg Ile Glu Glu Arg Ile Ala Arg Glu Gly Asn Thr Asp
                165                 170                 175

Trp Leu Arg Thr Thr Ile Lys Asn Phe Val Lys Thr Gln Pro Gly Trp
            180                 185                 190
```

-continued

Asn Ser Thr Ser Glu Asn Leu Asp Asn Ser Asp His Leu Gln Gly Gly
            195                 200                 205

Ala Leu Leu Tyr Asn Asn Ser Asn Arg Thr Ser Tyr Ala Asn Ser Asp
210                 215                 220

Tyr Arg Leu Leu Asn Arg Thr Pro Thr Gln Gln Asp Gly Thr Arg Arg
225                 230                 235                 240

Tyr Phe Lys Asp Asn Ser Ser Gly Gly Phe Glu Phe Leu Leu Ala Asn
            245                 250                 255

Asp Ile Asp Asn Ser Asn Pro Ala Val Gln Ala Glu Gln Leu Asn Trp
            260                 265                 270

Leu His Tyr Ile Met Asn Ile Gly Ser Leu Thr Gly Gly Ser Glu Asp
            275                 280                 285

Glu Asn Phe Asp Gly Val Arg Val Asp Ala Val Asp Asn Val Asn Ala
            290                 295                 300

Asp Leu Leu Gln Ile Ala Ser Asp Tyr Phe Lys Ala Lys Tyr Gly Val
305                 310                 315                 320

Glu Lys Ser Glu Glu Glu Ala Ile Lys His Leu Ser Ile Leu Glu Ala
            325                 330                 335

Trp Ser His Asn Asp Ala Tyr Tyr Asn Glu Asp Thr Lys Gly Ala Gln
            340                 345                 350

Leu Pro Met Asp Asp Pro Leu Arg Leu Ala Met Val Phe Ser Phe Leu
            355                 360                 365

Arg Pro Ile Gly Asn Arg Ser Gly Leu Glu Pro Leu Ile Thr Asn Ser
            370                 375                 380

Leu Asn Asp Arg Ser Glu Ser Lys Lys Asn Thr Lys Arg Met Ala Asn
385                 390                 395                 400

Tyr Thr Phe Val Arg Ala His Asp Ser Glu Val Gln Ser Val Ile Gly
            405                 410                 415

Gln Ile Ile Lys Asn Glu Ile Asn Pro Gln Ser Thr Gly Asn Thr Phe
            420                 425                 430

Thr Leu Asp Glu Met Lys Lys Ala Phe Lys Ile Tyr Asn Ala Asp Met
            435                 440                 445

Arg Ser Ala Asn Lys Arg Tyr Thr Gln Tyr Asn Ile Pro Ser Ala Tyr
450                 455                 460

Ala Phe Met Leu Thr Asn Lys Asp Thr Val Pro Arg Val Tyr Tyr Gly
465                 470                 475                 480

Asp Leu Tyr Thr Asp Asp Gly Gln Tyr Met Ala Gln Lys Ser Pro Tyr
            485                 490                 495

His Asp Ala Ile Ser Thr Leu Leu Gln Ala Arg Ile Arg Tyr Ala Ala
            500                 505                 510

Gly Gly Gln Asp Met Lys Met Ser Tyr Val Gly Ser Gly Asn Thr Asn
            515                 520                 525

Gly Trp Asp Ala Ser Gly Val Leu Thr Ser Val Arg Tyr Gly Lys Gly
            530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
            565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
            595                 600                 605

Asp Ala Asn Gly Ile Val Lys Tyr Thr Asp Ala Asn Gly Tyr Leu Thr

```
                  610                 615                 620
Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                    645                 650                 655

Arg Val Ala Ala Ser Lys Ser Lys Asn Ser Ser Gly Leu Val Tyr Asp
                660                 665                 670

Ser Ser Ala Ala Leu Asp Ser Gln Val Ile Tyr Glu Gly Phe Ser Asn
            675                 680                 685

Phe Gln Asp Phe Val Gln Asp Pro Ser Gln Tyr Thr Asn Lys Lys Ile
690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Ser Asp Gly Thr Phe Leu Asp Ser
                725                 730                 735

Val Ile Gln Asn Gly Tyr Ala Phe Ser Asp Arg Tyr Asp Ile Gly Met
                740                 745                 750

Ser Lys Asp Asn Lys Tyr Gly Ser Leu Ala Asp Leu Lys Ala Ala Leu
            755                 760                 765

Lys Ser Leu His Ala Val Gly Ile Ser Ala Ile Ala Asp Trp Val Pro
770                 775                 780

Asp Gln Ile Tyr Asn Leu Pro Gly Asp Glu Val Val Thr Ala Thr Arg
785                 790                 795                 800

Val Asn Asn Tyr Gly Glu Thr Lys Asp Gly Ala Ile Ile Asp His Ser
                805                 810                 815

Leu Tyr Val Ala Lys Thr Arg Thr Phe Gly Asn Asp Tyr Gln Gly Lys
            820                 825                 830

Tyr Gly Gly Ala Tyr Leu Asp Glu Leu Lys Arg Leu Tyr Pro Gln Phe
            835                 840                 845

Phe Asp Arg Val Gln Ile Ser Thr Gly Lys Arg Leu Thr Thr Asp Glu
850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
                900                 905                 910

Gln Ser Thr Asn Asn Asn Gln Asn Gly Asp Gly Ser Gly Arg Phe
            915                 920                 925

Glu Lys Ser Trp Gly Ser Val Tyr Tyr Arg Tyr Asn Asp Gly Gln Arg
930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe  Tyr Tyr Asp Glu Asn  Gly Ile Met
            995                 1000                1005

Ser Gln  Thr Gly Lys Pro Ser  Pro Lys Pro Glu Pro  Lys Pro Asp
    1010                1015                1020

Asn Asn  Thr Phe Ser Arg Asn  Gln Phe Ile Gln Ile  Gly Asn Asn
    1025                1030                1035
```

```
Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185

Leu Phe Asp Asn Asp Gly Lys Gln Val Lys Gly His Leu Val Arg
    1190                1195                1200

Val Asn Gly Val Ile Arg Tyr Tyr Asp Pro Asn Ser Gly Glu Met
    1205                1210                1215

Ala Val Asn Arg Trp Val Glu Ile Ser Ser Gly Trp Trp Val Tyr
    1220                1225                1230

Phe Asp Gly Glu Gly Arg Gly Gln Ile
    1235                1240

<210> SEQ ID NO 60
<211> LENGTH: 1518
<212> TYPE: PRT
<213> ORGANISM: Streptococcus salivarius

<400> SEQUENCE: 60

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Thr Thr Ala Thr
            100                 105                 110

Ala Asp Val Ala Val Ala Val Pro Asn Lys Glu Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
```

```
            145                 150                 155                 160
Ala Leu Lys Asp Ser Glu Val Glu Ala Leu Ser Leu Lys Asn Ile
                165                 170                 175
Lys Asn Ile Asp Gly Lys Tyr Tyr Val Asn Glu Asp Gly Ser His
                180                 185                 190
Lys Glu Asn Phe Ala Ile Thr Val Asn Gly Gln Leu Leu Tyr Phe Gly
                195                 200                 205
Lys Asp Gly Ala Leu Thr Ser Ser Ser Thr Tyr Ser Phe Thr Pro Gly
                210                 215                 220
Thr Thr Asn Ile Val Asp Gly Phe Ser Ile Asn Asn Arg Ala Tyr Asp
225                 230                 235                 240
Ser Ser Glu Ala Ser Phe Glu Leu Ile Asp Gly Tyr Leu Thr Ala Asp
                245                 250                 255
Ser Trp Tyr Arg Pro Ala Ser Ile Ile Lys Asp Gly Val Thr Trp Gln
                260                 265                 270
Ala Ser Thr Ala Glu Asp Phe Arg Pro Leu Leu Met Ala Trp Trp Pro
                275                 280                 285
Asn Val Asp Thr Gln Val Asn Tyr Leu Asn Tyr Met Ser Lys Val Phe
                290                 295                 300
Asn Leu Asp Ala Lys Tyr Ser Ser Thr Asp Lys Gln Glu Thr Leu Lys
305                 310                 315                 320
Val Ala Ala Lys Asp Ile Gln Ile Lys Ile Glu Gln Lys Ile Gln Ala
                325                 330                 335
Glu Lys Ser Thr Gln Trp Leu Arg Glu Thr Ile Ser Ala Phe Val Lys
                340                 345                 350
Thr Gln Pro Gln Trp Asn Lys Glu Thr Glu Asn Tyr Ser Lys Gly Gly
                355                 360                 365
Gly Glu Asp His Leu Gln Gly Gly Ala Leu Leu Tyr Val Asn Asp Ser
                370                 375                 380
Arg Thr Pro Trp Ala Asn Ser Asp Tyr Arg Arg Leu Asn Arg Thr Ala
385                 390                 395                 400
Thr Asn Gln Thr Gly Thr Ile Asp Lys Ser Ile Leu Asp Glu Gln Ser
                405                 410                 415
Asp Pro Asn His Met Gly Gly Phe Asp Phe Leu Leu Ala Asn Asp Val
                420                 425                 430
Asp Leu Ser Asn Pro Val Val Gln Ala Glu Gln Leu Asn Gln Ile His
                435                 440                 445
Tyr Leu Met Asn Trp Gly Ser Ile Val Met Gly Asp Lys Asp Ala Asn
                450                 455                 460
Phe Asp Gly Ile Arg Val Asp Ala Val Asp Asn Val Asp Ala Asp Met
465                 470                 475                 480
Leu Gln Leu Tyr Thr Asn Tyr Phe Arg Glu Tyr Tyr Gly Val Asn Lys
                485                 490                 495
Ser Glu Ala Asn Ala Leu Ala His Ile Ser Val Leu Glu Ala Trp Ser
                500                 505                 510
Leu Asn Asp Asn His Tyr Asn Asp Lys Thr Asp Gly Ala Ala Leu Ala
                515                 520                 525
Met Glu Asn Lys Gln Arg Leu Ala Leu Leu Phe Ser Leu Ala Lys Pro
                530                 535                 540
Ile Lys Glu Arg Thr Pro Ala Val Ser Pro Leu Tyr Asn Asn Thr Phe
545                 550                 555                 560
Asn Thr Thr Gln Arg Asp Glu Lys Thr Asp Trp Ile Asn Lys Asp Gly
                565                 570                 575
```

```
Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
        595                 600                 605

Arg Ala His Asp Asn Asn Val Gln Asp Ile Ile Ala Glu Ile Ile Lys
        610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
        690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Asn Leu
        770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
        850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
        930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
            980                 985                 990
```

-continued

Gly Ile Gln Ala Ile Ala Asp Trp Val Pro Asp Gln Ile Tyr Gln Leu
           995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035

Asn Ser Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Glu Gly Asn Phe Ile Pro Leu Gln Leu
    1115                1120                1125

Thr Gly Lys Glu Lys Val Ile Thr Gly Phe Ser Ser Asp Gly Lys
    1130                1135                1140

Gly Ile Thr Tyr Phe Gly Thr Ser Gly Thr Gln Ala Lys Ser Ala
    1145                1150                1155

Phe Val Thr Phe Asn Gly Asn Thr Tyr Tyr Phe Asp Ala Arg Gly
    1160                1165                1170

His Met Val Thr Asn Ser Glu Tyr Ser Pro Asn Gly Lys Asp Val
    1175                1180                1185

Tyr Arg Phe Leu Pro Asn Gly Ile Met Leu Ser Asn Ala Phe Tyr
    1190                1195                1200

Ile Asp Ala Asn Gly Asn Thr Tyr Leu Tyr Asn Ser Lys Gly Gln
    1205                1210                1215

Met Tyr Lys Gly Gly Tyr Thr Lys Phe Asp Val Ser Glu Thr Asp
    1220                1225                1230

Lys Asp Gly Lys Glu Ser Lys Val Val Lys Phe Arg Tyr Phe Thr
    1235                1240                1245

Asn Glu Gly Val Met Ala Lys Gly Val Thr Val Ile Asp Gly Phe
    1250                1255                1260

Thr Gln Tyr Phe Gly Glu Asp Gly Phe Gln Ala Lys Asp Lys Leu
    1265                1270                1275

Val Thr Phe Lys Gly Lys Thr Tyr Tyr Phe Asp Ala His Thr Gly
    1280                1285                1290

Asn Gly Ile Lys Asp Thr Trp Arg Asn Ile Asn Gly Lys Trp Tyr
    1295                1300                1305

Tyr Phe Asp Ala Asn Gly Val Ala Ala Thr Gly Ala Gln Val Ile
    1310                1315                1320

Asn Gly Gln Lys Leu Tyr Phe Asn Glu Asp Gly Ser Gln Val Lys
    1325                1330                1335

Gly Gly Val Val Lys Asn Ala Asp Gly Thr Tyr Ser Lys Tyr Lys
    1340                1345                1350

Glu Gly Phe Gly Glu Leu Val Thr Asn Glu Phe Phe Thr Thr Asp
    1355                1360                1365

Gly Asn Val Trp Tyr Tyr Ala Gly Ala Asn Gly Lys Thr Val Thr
    1370                1375                1380

Gly Ala Gln Val Ile Asn Gly Gln His Leu Tyr Phe Asn Ala Asp

-continued

```
            1385                1390                1395
Gly Ser Gln Val Lys Gly Val Val Lys Asn Ala Asp Gly Thr
    1400                1405                1410

Tyr Ser Lys Tyr Asn Ala Ser Thr Gly Glu Arg Leu Thr Asn Glu
    1415                1420                1425

Phe Phe Thr Thr Gly Asp Asn Asn Trp Tyr Tyr Ile Gly Ala Asn
    1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Leu Ala Tyr Pro Pro Arg Val Leu Asn
    1505                1510                1515
```

<210> SEQ ID NO 61
<211> LENGTH: 1528
<212> TYPE: PRT
<213> ORGANISM: Streptococcus salivarius

<400> SEQUENCE: 61

```
Met Thr Asn Lys Ile Thr Gly Lys Ile Ile Met Glu Asn Lys Val His
1               5                   10                  15

Tyr Lys Leu His Lys Val Lys Lys Gln Trp Val Thr Ile Ala Val Ala
            20                  25                  30

Ser Ala Ala Leu Ala Thr Val Val Gly Gly Leu Ser Ala Thr Thr Ser
        35                  40                  45

Ser Val Ser Ala Asp Glu Thr Gln Asp Lys Ile Val Thr Gln Pro Asn
    50                  55                  60

Leu Asp Thr Thr Ala Asp Leu Val Thr Ser Thr Glu Ala Thr Lys Glu
65                  70                  75                  80

Val Asp Lys Arg Thr Asn Thr Lys Glu Ala Asp Val Leu Thr Pro Ala
                85                  90                  95

Lys Glu Thr Asn Ala Val Glu Thr Ala Thr Thr Thr Asn Thr Gln Ala
            100                 105                 110

Thr Ala Glu Ala Ala Thr Thr Ala Thr Thr Ser Asp Val Ala Val Ala
        115                 120                 125

Ala Val Pro Asn Lys Glu Ala Val Val Thr Thr Asp Ala Pro Ala Val
    130                 135                 140

Thr Thr Glu Lys Ala Glu Glu Gln Pro Ala Thr Val Lys Ala Glu Val
145                 150                 155                 160

Val Asn Thr Glu Val Lys Ala Pro Gln Ala Ala Leu Lys Asp Ser Glu
                165                 170                 175

Val Glu Ala Ala Leu Ser Leu Lys Asn Ile Lys Tyr Thr Asp Gly Lys
            180                 185                 190

Tyr Tyr Tyr Val Asn Glu Asp Gly Ser His Lys Glu Asn Phe Ala Ile
        195                 200                 205

Thr Val Asn Gly Gln Leu Leu Tyr Phe Gly Lys Asp Gly Ala Leu Thr
    210                 215                 220

Ser Ser Ser Thr His Ser Phe Thr Pro Gly Thr Thr Asn Ile Val Asp
225                 230                 235                 240
```

-continued

```
Gly Phe Ser Ile Asn Asn Arg Ala Tyr Asp Ser Ser Glu Ala Ser Phe
                245                 250                 255

Glu Leu Ile Asn Gly Tyr Leu Thr Ala Asp Ser Trp Tyr Arg Pro Val
            260                 265                 270

Ser Ile Ile Lys Asp Gly Val Thr Trp Gln Ala Ser Thr Ala Glu Asp
        275                 280                 285

Phe Arg Pro Leu Leu Met Ala Trp Trp Pro Asn Val Asp Thr Gln Val
    290                 295                 300

Asn Tyr Leu Asn Tyr Met Ser Lys Val Phe Asn Leu Glu Ala Lys Tyr
305                 310                 315                 320

Thr Ser Thr Asp Lys Gln Ala Asp Leu Asn Arg Ala Ala Lys Asp Ile
                325                 330                 335

Gln Val Lys Ile Glu Gln Lys Ile Gln Ala Glu Lys Ser Thr Gln Trp
            340                 345                 350

Leu Arg Glu Thr Ile Ser Ala Phe Val Lys Thr Gln Pro Gln Trp Asn
        355                 360                 365

Lys Glu Thr Glu Asn Tyr Ser Lys Gly Gly Glu Asp His Leu Gln
    370                 375                 380

Gly Gly Ala Leu Leu Tyr Val Asn Asp Ser Arg Thr Pro Trp Ala Asn
385                 390                 395                 400

Ser Asn Tyr Arg Leu Leu Asn Arg Thr Ala Thr Asn Gln Thr Gly Thr
                405                 410                 415

Ile Asn Lys Ser Val Leu Asp Glu Gln Ser Asp Pro Asn His Met Gly
            420                 425                 430

Gly Phe Asp Phe Leu Leu Ala Asn Asp Val Asp Leu Ser Asn Pro Val
        435                 440                 445

Val Gln Ala Glu Gln Leu Asn Gln Ile His Tyr Leu Met Asn Trp Gly
    450                 455                 460

Ser Ile Val Met Gly Asp Lys Asp Ala Asn Phe Asp Gly Ile Arg Val
465                 470                 475                 480

Asp Ala Val Asp Asn Val Asn Ala Asp Met Leu Gln Leu Tyr Thr Asn
                485                 490                 495

Tyr Phe Arg Glu Tyr Tyr Gly Val Asn Lys Ser Glu Ala Gln Ala Leu
            500                 505                 510

Ala His Ile Ser Val Leu Glu Ala Trp Ser Leu Asn Asp Asn His Tyr
        515                 520                 525

Asn Asp Lys Thr Asp Gly Ala Ala Leu Ala Met Glu Asn Lys Gln Arg
    530                 535                 540

Leu Ala Leu Leu Phe Ser Leu Ala Lys Pro Ile Lys Asp Arg Thr Pro
545                 550                 555                 560

Ala Val Ser Pro Leu Tyr Asn Asn Thr Phe Asn Thr Thr Gln Arg Asp
                565                 570                 575

Phe Lys Thr Asp Trp Ile Asn Lys Asp Gly Ser Thr Ala Tyr Asn Glu
            580                 585                 590

Asp Gly Thr Ala Lys Gln Ser Thr Ile Gly Lys Tyr Asn Glu Lys Tyr
        595                 600                 605

Gly Asp Ala Ser Gly Asn Tyr Val Phe Ile Arg Ala His Asp Asn Asn
    610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
                645                 650                 655

Ile Tyr Asn Lys Asp Met Leu Ser Ser Asn Lys Lys Tyr Thr Leu Asn
```

-continued

```
                660                 665                 670
Asn Ile Pro Ala Ala Tyr Ala Val Met Leu Gln Asn Met Glu Thr Ile
            675                 680                 685
Thr Arg Val Tyr Tyr Gly Asp Leu Tyr Thr Asp Asp Gly His Tyr Met
        690                 695                 700
Glu Thr Lys Ser Pro Tyr His Asp Thr Ile Val Asn Leu Met Lys Asn
705                 710                 715                 720
Arg Ile Lys Tyr Val Ser Gly Gln Ala Gln Arg Ser Tyr Trp Leu
                725                 730                 735
Pro Thr Asp Gly Lys Met Asp Asn Ser Asp Val Glu Leu Tyr Arg Thr
            740                 745                 750
Ser Glu Val Tyr Thr Ser Val Arg Tyr Gly Lys Asp Ile Met Thr Ala
        755                 760                 765
Asp Asp Thr Glu Gly Ser Lys Tyr Ser Arg Thr Ser Gly Gln Val Thr
    770                 775                 780
Leu Val Val Asn Asn Pro Lys Leu Thr Leu His Glu Ser Ala Lys Leu
785                 790                 795                 800
Asn Val Glu Met Gly Lys Ile His Ala Asn Gln Lys Tyr Arg Ala Leu
                805                 810                 815
Ile Val Gly Thr Ala Asp Gly Ile Lys Asn Phe Thr Ser Asp Ala Glu
            820                 825                 830
Ala Ile Ala Ala Gly Tyr Val Lys Glu Thr Asp Ser Asn Gly Val Leu
        835                 840                 845
Thr Phe Gly Ala Asn Asp Ile Lys Gly Tyr Glu Thr Phe Asp Met Ser
    850                 855                 860
Gly Phe Val Ala Val Trp Val Pro Val Gly Ala Ser Asp Gln Asp
865                 870                 875                 880
Ile Arg Val Ala Pro Ser Thr Glu Ala Lys Lys Glu Gly Glu Leu Thr
                885                 890                 895
Leu Lys Ala Thr Glu Ala Tyr Asp Ser Gln Leu Ile Tyr Glu Gly Phe
            900                 905                 910
Ser Asn Phe Gln Thr Ile Pro Asp Gly Ser Asp Pro Ser Val Tyr Thr
        915                 920                 925
Asn Arg Lys Ile Ala Glu Asn Val Asp Leu Phe Lys Ser Trp Gly Val
    930                 935                 940
Thr Ser Phe Glu Met Ala Pro Gln Phe Val Ser Ala Asp Asp Gly Thr
945                 950                 955                 960
Phe Leu Asp Ser Val Ile Gln Asn Gly Tyr Ala Phe Ala Asp Arg Tyr
                965                 970                 975
Asp Leu Ala Met Ser Lys Asn Asn Lys Tyr Gly Ser Lys Glu Asp Leu
            980                 985                 990
Arg Asp Ala Leu Lys Ala Leu His  Lys Ala Gly Ile Gln  Ala Ile Ala
        995                 1000                1005
Asp Trp Val Pro Asp Gln Ile  Tyr Gln Leu Pro Gly  Lys Glu Val
    1010                1015                1020
Val Thr Ala Thr Arg Thr Asp  Gly Ala Gly Arg Lys  Ile Ala Asp
    1025                1030                1035
Ala Ile  Ile Asp His Ser Leu  Tyr Val Ala Asn Ser  Lys Ser Ser
    1040                1045                1050
Gly Arg  Asp Tyr Gln Ala Gln  Tyr Gly Gly Glu Phe  Leu Ala Glu
    1055                1060                1065
Leu Lys  Ala Lys Tyr Pro Lys  Met Phe Thr Glu Asn  Met Ile Ser
    1070                1075                1080
```

-continued

```
Thr Gly Lys Pro Ile Asp Asp Ser Val Lys Leu Lys Gln Trp Lys
    1085             1090                 1095

Ala Lys Tyr Phe Asn Gly Thr Asn Val Leu Asp Arg Gly Val Gly
    1100             1105                 1110

Tyr Val Leu Ser Asp Glu Ala Thr Gly Lys Tyr Phe Thr Val Thr
    1115             1120                 1125

Lys Glu Gly Asn Phe Ile Pro Leu Gln Leu Thr Gly Asn Glu Lys
    1130             1135                 1140

Ala Val Thr Gly Phe Ser Asn Asp Gly Lys Gly Ile Thr Tyr Phe
    1145             1150                 1155

Gly Thr Ser Gly Asn Gln Ala Lys Ser Ala Phe Val Thr Phe Asn
    1160             1165                 1170

Gly Asn Thr Tyr Tyr Phe Asp Ala Arg Gly His Met Val Thr Asn
    1175             1180                 1185

Gly Glu Tyr Ser Pro Asn Gly Lys Asp Val Tyr Arg Phe Leu Pro
    1190             1195                 1200

Asn Gly Ile Met Leu Ser Asn Ala Phe Tyr Val Asp Ala Asn Gly
    1205             1210                 1215

Asn Thr Tyr Leu Tyr Asn Tyr Lys Gly Gln Met Tyr Lys Gly Gly
    1220             1225                 1230

Tyr Thr Lys Phe Asp Val Thr Glu Thr Asp Lys Asp Gly Asn Glu
    1235             1240                 1245

Ser Lys Val Val Lys Phe Arg Tyr Phe Thr Asn Glu Gly Val Met
    1250             1255                 1260

Ala Lys Gly Leu Thr Val Ile Asp Gly Ser Thr Gln Tyr Phe Gly
    1265             1270                 1275

Glu Asp Gly Phe Gln Thr Lys Asp Lys Leu Ala Thr Tyr Lys Gly
    1280             1285                 1290

Lys Thr Tyr Tyr Phe Glu Ala His Thr Gly Asn Ala Ile Lys Asn
    1295             1300                 1305

Thr Trp Arg Asn Ile Asp Gly Lys Trp Tyr His Phe Asp Glu Asn
    1310             1315                 1320

Gly Val Ala Ala Thr Gly Ala Gln Val Ile Asn Gly Gln Lys Leu
    1325             1330                 1335

Tyr Phe Asn Glu Asp Gly Ser Gln Val Lys Gly Gly Val Val Lys
    1340             1345                 1350

Asn Ala Asp Gly Thr Tyr Ser Lys Tyr Lys Glu Gly Ser Gly Glu
    1355             1360                 1365

Leu Val Thr Asn Glu Phe Phe Thr Thr Asp Gly Asn Val Trp Tyr
    1370             1375                 1380

Tyr Ala Gly Ala Asp Gly Lys Thr Val Thr Gly Ala Gln Val Ile
    1385             1390                 1395

Asn Gly Gln His Leu Tyr Phe Lys Glu Asp Gly Ser Gln Val Lys
    1400             1405                 1410

Gly Gly Val Val Lys Asn Ala Asp Gly Thr Tyr Ser Lys Tyr Asp
    1415             1420                 1425

Ala Ala Thr Gly Glu Arg Leu Thr Asn Glu Phe Phe Thr Thr Gly
    1430             1435                 1440

Asp Asn Asn Trp Tyr Tyr Ile Gly Ser Asn Gly Lys Thr Val Thr
    1445             1450                 1455

Gly Glu Val Lys Ile Gly Ala Asp Thr Tyr Tyr Phe Ala Lys Asp
    1460             1465                 1470
```

```
<210> SEQ ID NO 62
<211> LENGTH: 1518
<212> TYPE: PRT
<213> ORGANISM: Streptococcus salivarius

<400> SEQUENCE: 62
```

| | | | | | | | | | | | | | | |
|---|---|---|---|---|---|---|---|---|---|---|---|---|---|---|
| Gly | Lys | Gln | Val | Lys | Gly | Gln | Thr | Val | Thr | Ala | Gly | Asn | Gly | Arg |
| | | 1475 | | | | 1480 | | | | 1485 | | | | |
| Ile | Ser | Tyr | Tyr | Tyr | Gly | Asp | Ser | Gly | Lys | Lys | Ala | Ile | Ser | Thr |
| | 1490 | | | | | 1495 | | | | | 1500 | | | |
| Trp | Ile | Glu | Ile | Gln | Pro | Gly | Ile | Tyr | Val | Tyr | Phe | Asp | Lys | Thr |
| 1505 | | | | | | 1510 | | | | | 1515 | | | |
| Gly | Ile | Ala | Tyr | Pro | Pro | Arg | Val | Leu | Asn | | | | | |
| | 1520 | | | | | 1525 | | | | | | | | |
| Met | Glu | Asn | Lys | Ile | His | Tyr | Lys | Leu | His | Lys | Val | Lys | Lys | Gln | Trp |
| 1 | | | | 5 | | | | | 10 | | | | | 15 | |
| Val | Thr | Ile | Ala | Val | Ala | Ser | Val | Ala | Leu | Ala | Thr | Val | Leu | Gly | Gly |
| | | | 20 | | | | | 25 | | | | | 30 | | |
| Leu | Ser | Val | Thr | Thr | Ser | Ser | Val | Ser | Ala | Asp | Glu | Thr | Gln | Asp | Lys |
| | | | 35 | | | | 40 | | | | | 45 | | | |
| Thr | Val | Thr | Gln | Ser | Asn | Ser | Gly | Thr | Thr | Ala | Ser | Leu | Val | Thr | Ser |
| | 50 | | | | | 55 | | | | | 60 | | | | |
| Pro | Glu | Ala | Thr | Lys | Glu | Ala | Asp | Lys | Arg | Thr | Asn | Thr | Lys | Glu | Ala |
| 65 | | | | | 70 | | | | | 75 | | | | | 80 |
| Asp | Val | Leu | Thr | Pro | Ala | Lys | Glu | Thr | Asn | Ala | Val | Glu | Thr | Ala | Thr |
| | | | | 85 | | | | | 90 | | | | | 95 | |
| Thr | Thr | Asn | Thr | Gln | Ala | Thr | Ala | Glu | Ala | Ala | Thr | Thr | Ala | Thr | Thr |
| | | | 100 | | | | | 105 | | | | | 110 | | |
| Ala | Asp | Val | Ala | Val | Ala | Ala | Val | Pro | Asn | Lys | Glu | Ala | Val | Val | Thr |
| | | | 115 | | | | | 120 | | | | | 125 | | |
| Thr | Asp | Ala | Pro | Ala | Val | Thr | Thr | Glu | Lys | Ala | Glu | Glu | Gln | Pro | Ala |
| | 130 | | | | | 135 | | | | | 140 | | | | |
| Thr | Val | Lys | Ala | Glu | Val | Val | Asn | Thr | Glu | Val | Lys | Ala | Pro | Glu | Ala |
| 145 | | | | | 150 | | | | | 155 | | | | | 160 |
| Ala | Leu | Lys | Asp | Ser | Glu | Val | Glu | Ala | Ala | Leu | Ser | Leu | Lys | Asn | Ile |
| | | | | 165 | | | | | 170 | | | | | 175 | |
| Lys | Asn | Ile | Asp | Gly | Lys | Tyr | Tyr | Tyr | Val | Asn | Glu | Asp | Gly | Ser | His |
| | | | 180 | | | | | 185 | | | | | 190 | | |
| Lys | Glu | Asn | Phe | Ala | Ile | Thr | Val | Asn | Gly | Gln | Leu | Leu | Tyr | Phe | Gly |
| | | | 195 | | | | | 200 | | | | | 205 | | |
| Lys | Asp | Gly | Ala | Leu | Thr | Ser | Ser | Thr | Tyr | Ser | Phe | Thr | Pro | Gly |
| | 210 | | | | | 215 | | | | | 220 | | | | |
| Thr | Thr | Asn | Ile | Val | Asp | Gly | Phe | Ser | Ile | Asn | Asn | Arg | Ala | Tyr | Asp |
| 225 | | | | | 230 | | | | | 235 | | | | | 240 |
| Ser | Ser | Glu | Ala | Ser | Phe | Glu | Leu | Ile | Asp | Gly | Tyr | Leu | Thr | Ala | Asp |
| | | | | 245 | | | | | 250 | | | | | 255 | |
| Ser | Trp | Tyr | Arg | Pro | Ala | Ser | Ile | Ile | Lys | Asp | Gly | Val | Thr | Trp | Gln |
| | | | 260 | | | | | 265 | | | | | 270 | | |
| Ala | Ser | Thr | Ala | Glu | Asp | Phe | Arg | Pro | Leu | Leu | Met | Ala | Trp | Trp | Pro |
| | | | 275 | | | | | 280 | | | | | 285 | | |
| Asn | Val | Asp | Thr | Gln | Val | Asn | Tyr | Leu | Asn | Tyr | Met | Ser | Lys | Val | Phe |
| | 290 | | | | | 295 | | | | | 300 | | | | |
| Asn | Leu | Asp | Ala | Lys | Tyr | Ser | Ser | Thr | Asp | Lys | Gln | Glu | Thr | Leu | Lys |
| 305 | | | | | 310 | | | | | 315 | | | | | 320 |

-continued

```
Val Ala Ala Lys Asp Ile Gln Ile Lys Ile Glu Gln Lys Ile Gln Ala
            325                 330                 335
Glu Lys Ser Thr Gln Trp Leu Arg Glu Thr Ile Ser Ala Phe Val Lys
            340                 345                 350
Thr Gln Pro Gln Trp Asn Lys Glu Thr Glu Asn Tyr Ser Lys Gly Gly
            355                 360                 365
Gly Glu Asp His Leu Gln Gly Gly Ala Leu Leu Tyr Val Asn Asp Ser
            370                 375                 380
Arg Thr Pro Trp Ala Asn Ser Asp Tyr Arg Arg Leu Asn Arg Thr Ala
385                 390                 395                 400
Thr Asn Gln Thr Gly Thr Ile Asp Lys Ser Ile Leu Asp Glu Gln Ser
            405                 410                 415
Asp Pro Asn His Met Gly Gly Phe Asp Phe Leu Leu Ala Asn Asp Val
            420                 425                 430
Asp Leu Ser Asn Pro Val Val Gln Ala Glu Gln Leu Asn Gln Ile His
            435                 440                 445
Tyr Leu Met Asn Trp Gly Ser Ile Val Met Gly Asp Lys Asp Ala Asn
            450                 455                 460
Phe Asp Gly Ile Arg Val Asp Ala Val Asp Asn Val Asp Ala Asp Met
465                 470                 475                 480
Leu Gln Leu Tyr Thr Asn Tyr Phe Arg Glu Tyr Tyr Gly Val Asn Lys
            485                 490                 495
Ser Glu Ala Asn Ala Leu Ala His Ile Ser Val Leu Glu Ala Trp Ser
            500                 505                 510
Leu Asn Asp Asn His Tyr Asn Asp Lys Thr Asp Gly Ala Ala Leu Ala
            515                 520                 525
Met Glu Asn Lys Gln Arg Leu Ala Leu Leu Phe Ser Leu Ala Lys Pro
            530                 535                 540
Ile Lys Glu Arg Thr Pro Ala Val Ser Pro Leu Tyr Asn Asn Thr Phe
545                 550                 555                 560
Asn Thr Thr Gln Arg Asp Glu Lys Thr Asp Trp Ile Asn Lys Asp Gly
            565                 570                 575
Ser Lys Ala Tyr Asn Glu Asp Gly Thr Val Lys Gln Ser Thr Ile Gly
            580                 585                 590
Lys Tyr Asn Glu Lys Tyr Gly Asp Ala Ser Gly Asn Tyr Val Phe Ile
            595                 600                 605
Arg Ala His Asp Asn Asn Val Gln Asp Ile Ile Ala Glu Ile Ile Lys
            610                 615                 620
Lys Glu Ile Asn Pro Lys Ser Asp Gly Phe Thr Ile Thr Asp Ala Glu
625                 630                 635                 640
Met Lys Gln Ala Phe Glu Ile Tyr Asn Lys Asp Met Leu Ser Ser Asp
            645                 650                 655
Lys Lys Tyr Thr Leu Asn Asn Ile Pro Ala Ala Tyr Ala Val Met Leu
            660                 665                 670
Gln Asn Met Glu Thr Ile Thr Arg Val Tyr Tyr Gly Asp Leu Tyr Thr
            675                 680                 685
Asp Asp Gly His Tyr Met Glu Thr Lys Ser Pro Tyr Tyr Asp Thr Ile
            690                 695                 700
Val Asn Leu Met Lys Ser Arg Ile Lys Tyr Val Ser Gly Gly Gln Ala
705                 710                 715                 720
Gln Arg Ser Tyr Trp Leu Pro Thr Asp Gly Lys Met Asp Asn Ser Asp
            725                 730                 735
```

Val Glu Leu Tyr Arg Thr Asn Glu Val Tyr Thr Ser Val Arg Tyr Gly
                740                 745                 750

Lys Asp Ile Met Thr Ala Asn Asp Thr Glu Gly Ser Lys Tyr Ser Arg
            755                 760                 765

Thr Ser Gly Gln Val Thr Leu Val Ala Asn Asn Pro Lys Leu Thr Leu
        770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
        835                 840                 845

Glu Thr Phe Asp Met Ser Gly Phe Val Ala Val Trp Val Pro Val Gly
    850                 855                 860

Ala Ser Asp Asp Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
    930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
            980                 985                 990

Gly Ile Gln Ala Ile Ala Asp Trp Val Pro Asp Gln Ile Tyr Gln Leu
        995                 1000                1005

Pro Gly Lys Glu Val Val Thr Ala Thr Arg Thr Asp Gly Ala Gly
    1010                1015                1020

Arg Lys Ile Ala Asp Ala Ile Asp His Ser Leu Tyr Val Ala
    1025                1030                1035

Asn Thr Lys Ser Ser Gly Lys Asp Tyr Gln Ala Lys Tyr Gly Gly
    1040                1045                1050

Glu Phe Leu Ala Glu Leu Lys Ala Lys Tyr Pro Glu Met Phe Lys
    1055                1060                1065

Val Asn Met Ile Ser Thr Gly Lys Pro Ile Asp Asp Ser Val Lys
    1070                1075                1080

Leu Lys Gln Trp Lys Ala Glu Tyr Phe Asn Gly Thr Asn Val Leu
    1085                1090                1095

Glu Arg Gly Val Gly Tyr Val Leu Ser Asp Glu Ala Thr Gly Lys
    1100                1105                1110

Tyr Phe Thr Val Thr Lys Asp Gly Asn Phe Ile Pro Leu Gln Leu
    1115                1120                1125

Thr Gly Asn Glu Lys Val Val Thr Gly Phe Ser Asn Asp Gly Lys
    1130                1135                1140

Gly Ile Thr Tyr Phe Gly Thr Ser Gly Thr Gln Ala Lys Ser Ala

```
                1145                1150                1155

Phe Val Thr Phe Asn Gly Asn Thr Tyr Tyr Phe Asp Ala Arg Gly
        1160                1165                1170

His Met Val Thr Asn Gly Glu Tyr Ser Pro Asn Gly Lys Asp Val
        1175                1180                1185

Tyr Arg Phe Leu Pro Asn Gly Ile Met Leu Ser Asn Ala Phe Tyr
        1190                1195                1200

Val Asp Ala Asn Gly Asn Thr Tyr Leu Tyr Asn Ser Lys Gly Gln
        1205                1210                1215

Met Tyr Lys Gly Gly Tyr Thr Lys Phe Asp Val Thr Glu Thr Asp
        1220                1225                1230

Lys Asp Gly Lys Glu Ser Lys Val Val Lys Phe Arg Tyr Phe Thr
        1235                1240                1245

Asn Glu Gly Val Met Ala Lys Gly Val Thr Val Ile Asp Gly Phe
        1250                1255                1260

Thr Gln Tyr Phe Gly Glu Asp Gly Phe Gln Ala Lys Asp Lys Leu
        1265                1270                1275

Val Thr Phe Lys Gly Lys Thr Tyr Tyr Phe Asp Ala His Thr Gly
        1280                1285                1290

Asn Ala Ile Lys Asp Thr Trp Arg Asn Ile Asn Gly Lys Trp Tyr
        1295                1300                1305

His Phe Asp Ala Asn Gly Val Ala Ala Thr Gly Ala Gln Val Ile
        1310                1315                1320

Asn Gly Gln Lys Leu Tyr Phe Asn Glu Asp Gly Ser Gln Val Lys
        1325                1330                1335

Gly Gly Val Val Lys Asn Ala Asp Gly Thr Tyr Ser Lys Tyr Lys
        1340                1345                1350

Glu Gly Ser Gly Glu Leu Val Thr Asn Glu Phe Phe Thr Thr Asp
        1355                1360                1365

Gly Asn Val Trp Tyr Tyr Ala Gly Ala Asn Gly Lys Thr Val Thr
        1370                1375                1380

Gly Ala Gln Val Ile Asn Gly Gln His Leu Tyr Phe Asn Ala Asp
        1385                1390                1395

Gly Ser Gln Val Lys Gly Gly Val Val Lys Asn Ala Asp Gly Thr
        1400                1405                1410

Tyr Ser Lys Tyr Asp Ala Ser Thr Gly Glu Arg Leu Thr Asn Glu
        1415                1420                1425

Phe Phe Thr Thr Gly Asp Asn Asn Trp Tyr Tyr Ile Gly Ala Asn
        1430                1435                1440

Gly Lys Ser Val Thr Gly Glu Val Lys Ile Gly Asp Asp Thr Tyr
        1445                1450                1455

Phe Phe Ala Lys Asp Gly Lys Gln Val Lys Gly Gln Thr Val Ser
        1460                1465                1470

Ala Gly Asn Gly Arg Ile Ser Tyr Tyr Tyr Gly Asp Ser Gly Lys
        1475                1480                1485

Arg Ala Val Ser Thr Trp Ile Glu Ile Gln Pro Gly Val Tyr Val
        1490                1495                1500

Tyr Phe Asp Lys Asn Gly Ile Ala Tyr Pro Pro Arg Val Leu Asn
        1505                1510                1515

<210> SEQ ID NO 63
<211> LENGTH: 1431
<212> TYPE: PRT
<213> ORGANISM: Streptococcus salivarius
```

<400> SEQUENCE: 63

```
Met Thr Lys Glu Thr Asn Thr Val Asp Ala Thr Thr Asn Thr
1               5                   10                  15

Gln Ala Ala Asp Ala Ala Thr Lys Thr Ala Asp Ala Ala Val Thr
            20                  25                  30

Ala Leu Pro Asn Lys Glu Ala Val Val Thr Thr Asp Ala Pro Ala Val
            35                  40                  45

Thr Thr Glu Lys Ala Ala Glu Gln Pro Ala Thr Val Lys Ser Glu Val
        50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
                100                 105                 110

Thr Val Asn Gly Gln Leu Leu Tyr Phe Gly Lys Asp Gly Ala Leu Thr
            115                 120                 125

Ser Ser Ser Thr Tyr Ser Phe Thr Gln Gly Thr Thr Asn Ile Val Asp
130                 135                 140

Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
                165                 170                 175

Ser Ile Ile Lys Asp Gly Val Thr Trp Gln Ala Ser Thr Lys Glu Asp
                180                 185                 190

Phe Arg Pro Leu Leu Met Ala Trp Trp Pro Asn Val Asp Thr Gln Val
                195                 200                 205

Asn Tyr Leu Asn Tyr Met Ser Lys Val Phe Asn Leu Asp Ala Lys Tyr
            210                 215                 220

Thr Ser Thr Asp Lys Gln Val Asp Leu Asn Arg Ala Ala Lys Asp Ile
225                 230                 235                 240

Gln Val Lys Ile Glu Gln Lys Ile Gln Ala Glu Lys Ser Thr Gln Trp
                245                 250                 255

Leu Arg Glu Ala Ile Ser Ala Phe Val Lys Thr Gln Pro Gln Trp Asn
            260                 265                 270

Lys Glu Thr Glu Asn Phe Ser Lys Gly Gly Glu Asp His Leu Gln
            275                 280                 285

Gly Gly Ala Leu Leu Tyr Val Asn Asp Pro Arg Thr Pro Trp Ala Asn
        290                 295                 300

Ser Asn Tyr Arg Leu Leu Asn Arg Thr Ala Thr Asn Gln Thr Gly Thr
305                 310                 315                 320

Ile Asp Lys Ser Val Leu Asp Glu Gln Ser Asp Pro Asn His Met Gly
                325                 330                 335

Gly Phe Asp Phe Leu Leu Ala Asn Asp Val Thr Ser Asn Pro Val
            340                 345                 350

Val Gln Ala Glu Gln Leu Asn Gln Ile His Tyr Leu Met Asn Trp Gly
            355                 360                 365

Ser Ile Val Met Gly Asp Lys Asp Ala Asn Phe Asp Gly Ile Arg Val
            370                 375                 380

Asp Ala Val Asp Asn Val Asp Ala Asp Met Leu Gln Leu Tyr Thr Asn
385                 390                 395                 400

Tyr Phe Arg Glu Tyr Tyr Gly Val Asn Lys Ser Glu Ala Asn Ala Leu
```

```
                405                 410                 415
Ala His Ile Ser Val Leu Glu Ala Trp Ser Leu Asn Asp Asn His Tyr
            420                 425                 430

Asn Asp Lys Thr Asp Gly Ala Ala Leu Ala Met Glu Asn Lys Gln Arg
            435                 440                 445

Leu Ala Leu Leu Phe Ser Leu Ala Lys Pro Ile Lys Glu Arg Thr Pro
450                 455                 460

Ala Val Ser Pro Leu Tyr Asn Asn Thr Phe Asn Thr Thr Gln Arg Asp
465                 470                 475                 480

Glu Lys Thr Asp Trp Ile Asn Lys Asp Gly Ser Lys Ala Tyr Asn Glu
            485                 490                 495

Asp Gly Thr Val Lys Gln Ser Thr Ile Gly Lys Tyr Asn Glu Lys Tyr
            500                 505                 510

Gly Asp Ala Ser Gly Asn Tyr Val Phe Ile Arg Ala His Asp Asn Asn
            515                 520                 525

Val Gln Asp Ile Ile Ala Glu Ile Ile Lys Lys Glu Ile Asn Pro Lys
            530                 535                 540

Ser Asp Gly Phe Thr Ile Thr Asp Ala Glu Met Lys Lys Ala Phe Glu
545                 550                 555                 560

Ile Tyr Asn Lys Asp Met Leu Ser Ser Asp Lys Lys Tyr Thr Leu Asn
                565                 570                 575

Asn Ile Pro Ala Ala Tyr Ala Val Met Leu Gln Asn Met Glu Thr Ile
            580                 585                 590

Thr Arg Val Tyr Tyr Gly Asp Leu Tyr Thr Asp Asp Gly His Tyr Met
            595                 600                 605

Glu Thr Lys Ser Pro Tyr Tyr Asp Thr Ile Val Asn Leu Met Lys Asn
        610                 615                 620

Arg Ile Lys Tyr Val Ser Gly Gln Ala Gln Arg Ser Tyr Trp Leu
625                 630                 635                 640

Pro Thr Asp Gly Lys Met Asp Lys Ser Asp Val Glu Leu Tyr Arg Thr
            645                 650                 655

Asn Glu Val Tyr Thr Ser Val Arg Tyr Gly Lys Asp Ile Met Thr Ala
            660                 665                 670

Asp Asp Thr Gln Gly Ser Lys Tyr Ser Arg Thr Ser Gly Gln Val Thr
            675                 680                 685

Leu Val Val Asn Asn Pro Lys Leu Ser Leu Asp Lys Ser Ala Lys Leu
            690                 695                 700

Asp Val Glu Met Gly Lys Ile His Ala Asn Gln Lys Tyr Arg Ala Leu
705                 710                 715                 720

Ile Val Gly Thr Pro Asn Gly Ile Lys Asn Phe Thr Ser Asp Ala Glu
            725                 730                 735

Ala Ile Ala Ala Gly Tyr Val Lys Glu Thr Asp Gly Asn Gly Val Leu
            740                 745                 750

Thr Phe Gly Ala Asn Asp Ile Lys Gly Tyr Glu Thr Phe Asp Met Ser
            755                 760                 765

Gly Phe Val Ala Val Trp Val Pro Val Gly Ala Ser Asp Asp Gln Asp
            770                 775                 780

Ile Arg Val Ala Ala Ser Thr Ala Ala Lys Lys Glu Gly Glu Leu Thr
785                 790                 795                 800

Leu Lys Ala Thr Glu Ala Tyr Asp Ser Gln Leu Ile Tyr Glu Gly Phe
            805                 810                 815

Ser Asn Phe Gln Thr Ile Pro Asp Gly Ser Asp Pro Ser Val Tyr Thr
            820                 825                 830
```

```
Asn Arg Lys Ile Ala Glu Asn Val Asp Leu Phe Lys Ser Trp Gly Val
        835                 840                 845

Thr Ser Phe Glu Met Ala Pro Gln Phe Val Ser Ala Asp Asp Gly Thr
850                 855                 860

Phe Leu Asp Ser Val Ile Gln Asn Gly Tyr Ala Phe Ala Asp Arg Tyr
865                 870                 875                 880

Asp Leu Ala Met Ser Lys Asn Asn Lys Tyr Gly Ser Lys Glu Asp Leu
            885                 890                 895

Arg Asn Ala Leu Lys Ala Leu His Lys Ala Gly Ile Gln Ala Ile Ala
        900                 905                 910

Asp Trp Val Pro Asp Gln Ile Tyr Gln Leu Pro Gly Lys Glu Val Val
            915                 920                 925

Thr Ala Thr Arg Thr Asp Gly Ala Gly Arg Lys Ile Ser Asp Ala Ile
        930                 935                 940

Ile Asp His Ser Leu Tyr Val Ala Asn Ser Lys Ser Ser Gly Lys Asp
945                 950                 955                 960

Tyr Gln Ala Lys Tyr Gly Gly Glu Phe Leu Ala Glu Leu Lys Ala Lys
            965                 970                 975

Tyr Pro Glu Met Phe Lys Val Asn Met Ile Ser Thr Gly Lys Pro Ile
        980                 985                 990

Asp Asp Ser Val Lys Leu Lys Gln Trp Lys Ala Glu Tyr Phe Asn Gly
        995                 1000                1005

Thr Asn Val Leu Asp Arg Gly Val Gly Tyr Val Leu Ser Asp Glu
    1010                1015                1020

Ala Thr Gly Lys Tyr Phe Thr Val Thr Lys Glu Gly Asn Phe Ile
    1025                1030                1035

Pro Leu Gln Leu Lys Gly Asn Glu Lys Val Ile Thr Gly Phe Ser
    1040                1045                1050

Ser Asp Gly Lys Gly Ile Thr Tyr Phe Gly Thr Ser Gly Asn Gln
    1055                1060                1065

Ala Lys Ser Ala Phe Val Thr Phe Asn Gly Asn Thr Tyr Tyr Phe
    1070                1075                1080

Asp Ala Arg Gly His Met Val Thr Asn Gly Glu Tyr Ser Pro Asn
    1085                1090                1095

Gly Lys Asp Val Tyr Arg Phe Leu Pro Asn Gly Ile Met Leu Ser
    1100                1105                1110

Asn Ala Phe Tyr Val Asp Gly Asn Gly Asn Thr Tyr Leu Tyr Asn
    1115                1120                1125

Ser Lys Gly Gln Met Tyr Lys Gly Gly Tyr Ser Lys Phe Asp Val
    1130                1135                1140

Thr Glu Thr Lys Asp Gly Lys Glu Ser Lys Val Val Lys Phe Arg
    1145                1150                1155

Tyr Phe Thr Asn Glu Gly Val Met Ala Lys Gly Val Thr Val Val
    1160                1165                1170

Asp Gly Phe Thr Gln Tyr Phe Asn Glu Asp Gly Ile Gln Ser Lys
    1175                1180                1185

Asp Glu Leu Val Thr Tyr Asn Gly Lys Thr Tyr Tyr Phe Glu Ala
    1190                1195                1200

His Thr Gly Asn Ala Ile Lys Asn Thr Trp Arg Asn Ile Lys Gly
    1205                1210                1215

Lys Trp Tyr His Phe Asp Ala Asn Gly Val Ala Ala Thr Gly Ala
    1220                1225                1230
```

```
Gln Val Ile Asn Gly Gln His Leu Tyr Phe Asn Glu Asp Gly Ser
    1235                1240                1245

Gln Val Lys Gly Gly Val Val Lys Asn Ala Asp Gly Thr Phe Ser
    1250                1255                1260

Lys Tyr Lys Asp Gly Ser Gly Asp Leu Val Val Asn Glu Phe Phe
    1265                1270                1275

Thr Thr Gly Asp Asn Val Trp Tyr Tyr Ala Gly Ala Asn Gly Lys
    1280                1285                1290

Thr Val Thr Gly Ala Gln Val Ile Asn Gly Gln His Leu Phe Phe
    1295                1300                1305

Lys Glu Asp Gly Ser Gln Val Lys Gly Asp Phe Val Lys Asn Ser
    1310                1315                1320

Asp Gly Thr Tyr Ser Lys Tyr Asp Ala Ala Ser Gly Glu Arg Leu
    1325                1330                1335

Thr Asn Glu Phe Phe Thr Thr Gly Asp Asn His Trp Tyr Tyr Ile
    1340                1345                1350

Gly Ala Asn Gly Lys Thr Val Thr Gly Glu Val Lys Ile Gly Asp
    1355                1360                1365

Asp Thr Tyr Phe Phe Ala Lys Asp Gly Lys Gln Leu Lys Gly Gln
    1370                1375                1380

Ile Val Thr Thr Arg Ser Gly Arg Ile Ser Tyr Tyr Phe Gly Asp
    1385                1390                1395

Ser Gly Lys Lys Ala Ile Ser Thr Trp Val Glu Ile Gln Pro Gly
    1400                1405                1410

Val Phe Val Phe Phe Asp Lys Asn Gly Leu Ala Tyr Pro Pro Glu
    1415                1420                1425

Asn Met Asn
    1430

<210> SEQ ID NO 64
<211> LENGTH: 1532
<212> TYPE: PRT
<213> ORGANISM: Unknown
<220> FEATURE:
<223> OTHER INFORMATION: unknown Streptococcus species

<400> SEQUENCE: 64

Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
                20                  25                  30

Leu Ser Ala Thr Thr Ser Ser Val Ser Ala Asp Glu Thr Gln Asp Lys
            35                  40                  45

Thr Val Thr Gln Pro Asn Ser Asp Thr Thr Ala Asp Leu Val Thr Ser
        50                  55                  60

Thr Glu Ala Thr Lys Glu Val Asp Lys Arg Thr Asn Thr Lys Glu Ala
65                  70                  75                  80

Asp Val Leu Thr Pro Ala Lys Glu Thr Asn Thr Val Glu Thr Ala Ala
                85                  90                  95

Thr Thr Asn Thr Gln Ala Thr Ala Glu Ala Ala Lys Thr Ala Thr Thr
            100                 105                 110

Thr Asn Thr Gln Ala Thr Ala Glu Val Ala Lys Thr Ala Thr Thr Ala
        115                 120                 125

Asp Val Ala Val Ala Ala Val Pro Asn Lys Glu Ala Val Val Thr Thr
    130                 135                 140
```

```
Asp Ala Pro Ala Val Thr Thr Glu Lys Ala Glu Gln Pro Ala Thr
145                 150                 155                 160

Val Lys Ala Glu Val Val Asn Thr Glu Val Lys Ala Pro Glu Ala Ala
                165                 170                 175

Leu Lys Asp Ser Glu Val Glu Ala Ala Leu Ser Leu Lys Asn Ile Lys
            180                 185                 190

Asn Ile Asp Gly Lys Tyr Tyr Val Asn Glu Asp Gly Ser His Lys
        195                 200                 205

Glu Asn Phe Ala Ile Thr Val Asn Gly Gln Leu Leu Tyr Phe Gly Lys
    210                 215                 220

Asp Gly Ala Leu Thr Ser Ser Thr Tyr Ser Phe Thr Gln Gly Thr
225                 230                 235                 240

Thr Asn Ile Val Asp Gly Phe Ser Ile Asn Asn Arg Ala Tyr Asp Ser
                245                 250                 255

Ser Glu Ala Ser Phe Glu Leu Ile Asp Gly Tyr Leu Thr Ala Asp Ser
            260                 265                 270

Trp Tyr Arg Pro Ala Ser Ile Ile Lys Asp Gly Val Thr Trp Gln Ala
        275                 280                 285

Ser Thr Ala Glu Asp Phe Arg Pro Leu Leu Met Ala Trp Trp Pro Asn
290                 295                 300

Val Asp Thr Gln Val Asn Tyr Leu Asn Tyr Met Ser Lys Val Phe Asn
305                 310                 315                 320

Leu Asp Ala Lys Tyr Ser Ser Thr Asp Lys Gln Glu Thr Leu Lys Val
                325                 330                 335

Ala Ala Lys Asp Ile Gln Ile Lys Ile Glu Gln Lys Ile Gln Ala Glu
            340                 345                 350

Lys Ser Thr Gln Trp Leu Arg Glu Thr Ile Ser Ala Phe Val Lys Thr
        355                 360                 365

Gln Pro Gln Trp Asn Lys Glu Thr Glu Asn Tyr Ser Lys Gly Gly Gly
370                 375                 380

Glu Asp His Leu Gln Gly Gly Ala Leu Leu Tyr Val Asn Asp Ser Arg
385                 390                 395                 400

Thr Pro Trp Ala Asn Ser Asn Tyr Arg Leu Leu Asn Arg Thr Ala Thr
                405                 410                 415

Asn Gln Thr Gly Thr Ile Asp Lys Ser Ile Leu Asp Glu Gln Ser Asp
            420                 425                 430

Pro Asn His Met Gly Gly Phe Asp Phe Leu Leu Ala Asn Asp Val Asp
        435                 440                 445

Leu Ser Asn Pro Val Val Gln Ala Glu Gln Leu Asn Gln Ile His Tyr
450                 455                 460

Leu Met Asn Trp Gly Ser Ile Val Met Gly Asp Lys Asp Ala Asn Phe
465                 470                 475                 480

Asp Gly Ile Arg Val Asp Ala Val Asp Asn Val Asp Ala Asp Met Leu
                485                 490                 495

Gln Leu Tyr Thr Asn Tyr Phe Arg Glu Tyr Tyr Gly Val Asn Lys Ser
            500                 505                 510

Glu Ala Asn Ala Leu Ala His Ile Ser Val Leu Glu Ala Trp Ser Leu
        515                 520                 525

Asn Asp Asn His Tyr Asn Asp Lys Thr Asp Val Ala Ala Leu Ala Met
530                 535                 540

Glu Asn Lys Gln Arg Leu Ala Leu Leu Phe Ser Leu Ala Lys Pro Ile
545                 550                 555                 560

Lys Glu Arg Thr Pro Ala Val Ser Pro Leu Tyr Asn Asn Thr Phe Asn
```

```
              565                 570                 575
Thr Thr Gln Arg Asp Glu Lys Thr Asp Trp Ile Asn Lys Asp Gly Ser
            580                 585                 590
Lys Ala Tyr Asn Glu Asp Gly Thr Val Lys Ser Thr Ile Gly Lys
            595                 600                 605
Tyr Asn Glu Lys Tyr Gly Asp Ala Ser Gly Asn Tyr Val Phe Ile Arg
            610                 615                 620
Ala His Asp Asn Val Gln Asp Ile Ile Ala Glu Ile Ile Lys Lys
625                 630                 635                 640
Glu Ile Asn Glu Lys Ser Asp Gly Phe Thr Ile Thr Asp Ser Glu Met
            645                 650                 655
Lys Arg Ala Phe Glu Ile Tyr Asn Lys Asp Met Leu Ser Asn Asp Lys
            660                 665                 670
Lys Tyr Thr Leu Asn Asn Ile Pro Ala Ala Tyr Ala Val Met Leu Gln
            675                 680                 685
Asn Met Glu Thr Ile Thr Arg Val Tyr Tyr Gly Asp Leu Tyr Thr Asp
            690                 695                 700
Asp Gly Asn Tyr Met Glu Ala Lys Ser Pro Tyr Tyr Asp Thr Ile Val
705                 710                 715                 720
Asn Leu Met Lys Ser Arg Ile Lys Tyr Val Ser Gly Gln Ala Gln
            725                 730                 735
Arg Ser Tyr Trp Leu Pro Thr Asp Gly Lys Met Asp Lys Ser Asp Val
            740                 745                 750
Glu Leu Tyr Arg Thr Asn Glu Val Tyr Thr Ser Val Arg Tyr Gly Lys
            755                 760                 765
Asp Ile Met Thr Ala Asp Asp Thr Gln Gly Ser Lys Tyr Ser Arg Thr
            770                 775                 780
Ser Gly Gln Val Thr Leu Val Val Asn Asn Pro Lys Leu Thr Leu Asp
785                 790                 795                 800
Gln Ser Ala Lys Leu Asn Val Val Met Gly Lys Ile His Ala Asn Gln
            805                 810                 815
Lys Tyr Arg Ala Leu Ile Val Gly Thr Pro Asn Gly Ile Lys Asn Phe
            820                 825                 830
Thr Ser Asp Ala Glu Ala Ile Ala Ala Gly Tyr Val Lys Glu Thr Asp
            835                 840                 845
Gly Asn Gly Val Leu Thr Phe Gly Ala Asn Asp Ile Lys Gly Tyr Glu
            850                 855                 860
Thr Phe Asp Met Ser Gly Phe Val Ala Val Trp Val Pro Val Gly Ala
865                 870                 875                 880
Ser Asp Asp Gln Asp Ile Arg Val Ala Ala Ser Thr Ala Ala Lys Lys
            885                 890                 895
Glu Gly Glu Leu Thr Leu Lys Ala Thr Glu Ala Tyr Asp Ser Gln Leu
            900                 905                 910
Ile Tyr Glu Gly Phe Ser Asn Phe Gln Thr Ile Pro Asp Gly Ser Asp
            915                 920                 925
Pro Ser Val Tyr Thr Asn Arg Lys Ile Ala Glu Asn Val Asp Leu Phe
            930                 935                 940
Lys Ser Trp Gly Val Thr Ser Phe Glu Met Ala Pro Gln Phe Val Ser
945                 950                 955                 960
Ala Asp Asp Gly Thr Phe Leu Asp Ser Val Ile Gln Asn Gly Tyr Ala
            965                 970                 975
Phe Ala Asp Arg Tyr Asp Leu Ala Met Ser Lys Asn Asn Lys Tyr Gly
            980                 985                 990
```

-continued

```
Ser Lys Glu Asp Leu Arg Asn Ala  Leu Lys Ala Leu His  Lys Ala Gly
    995                1000                 1005

Ile Gln Ala Ile Ala Asp Trp Val  Asp Gln Ile  Tyr Gln Leu
    1010            1015                 1020

Pro Gly Lys Glu Val Val Thr Ala  Thr Arg Thr  Asp Gly Ala Gly
    1025            1030                 1035

Arg Lys Ile Ser Asp Ala Ile  Ile Asp His Ser  Leu Tyr Val Ala
    1040            1045                 1050

Asn Ser Lys Ser Ser Gly Lys  Asp Tyr Gln Ala Lys  Tyr Gly Gly
    1055            1060                 1065

Glu Phe Leu Ala Glu Leu Lys  Ala Lys Tyr Pro Glu  Met Phe Lys
    1070            1075                 1080

Val Asn Met Ile Ser Thr Gly  Lys Pro Ile Asp  Asp Ser Val Lys
    1085            1090                 1095

Leu Lys Gln Trp Lys Ala Glu  Tyr Phe Asn Gly Thr  Asn Val Leu
    1100            1105                 1110

Asp Arg Gly Val Gly Tyr Val  Leu Ser Asp Glu Ala  Thr Gly Lys
    1115            1120                 1125

Tyr Phe Thr Val Thr Lys Glu  Gly Asn Phe Ile Pro  Leu Gln Leu
    1130            1135                 1140

Lys Gly Asn Lys Lys Val Ile  Thr Gly Phe Ser Ser  Asp Gly Lys
    1145            1150                 1155

Gly Ile Thr Tyr Phe Gly Thr  Ser Gly Asn Gln Ala  Lys Ser Ala
    1160            1165                 1170

Phe Val Thr Phe Asn Gly Asn  Thr Tyr Tyr Phe Asp  Ala Arg Gly
    1175            1180                 1185

His Met Val Thr Asn Gly Glu  Tyr Ser Pro Asn Gly  Lys Asp Val
    1190            1195                 1200

Tyr Arg Phe Leu Pro Asn Gly  Ile Met Leu Ser Asn  Ala Phe Tyr
    1205            1210                 1215

Val Asp Gly Asn Gly Asn Thr  Tyr Leu Tyr Asn Ser  Lys Gly Gln
    1220            1225                 1230

Met Tyr Lys Gly Gly Tyr Ser  Lys Phe Asp Val Thr  Glu Thr Lys
    1235            1240                 1245

Asp Gly Lys Glu Ser Lys Val  Val Lys Phe Arg Tyr  Phe Thr Asn
    1250            1255                 1260

Glu Gly Val Met Ala Lys Gly  Val Thr Val Val Asp  Gly Phe Thr
    1265            1270                 1275

Gln Tyr Phe Asn Glu Asp Gly  Ile Gln Ser Lys Asp  Glu Leu Val
    1280            1285                 1290

Thr Tyr Asn Gly Lys Thr Tyr  Tyr Phe Glu Ala His  Thr Gly Asn
    1295            1300                 1305

Ala Ile Lys Asn Thr Trp Arg  Asn Ile Lys Gly Lys  Trp Tyr His
    1310            1315                 1320

Phe Asp Ala Asn Gly Val Ala  Ala Thr Gly Ala Gln  Val Ile Asn
    1325            1330                 1335

Gly Gln His Leu Tyr Phe Asn  Glu Asp Gly Ser Gln  Val Lys Gly
    1340            1345                 1350

Ser Ile Val Lys Asn Ala Asp  Gly Thr Phe Ser Lys  Tyr Lys Asp
    1355            1360                 1365

Ser Ser Gly Asp Leu Val Val  Asn Glu Phe Phe Thr  Thr Gly Asp
    1370            1375                 1380
```

```
Asn Val Trp Tyr Tyr Ala Gly Ala Asn Gly Lys Thr Val Thr Gly
    1385                1390                1395

Ala Gln Val Ile Asn Gly Gln His Leu Phe Phe Lys Glu Asp Gly
    1400                1405                1410

Ser Gln Val Lys Gly Asp Phe Val Lys Asn Ser Asp Gly Thr Tyr
    1415                1420                1425

Ser Lys Tyr Asp Ala Ala Ser Gly Glu Arg Leu Thr Asn Glu Phe
    1430                1435                1440

Phe Thr Thr Gly Asp Asn His Trp Tyr Tyr Ile Gly Ala Asn Gly
    1445                1450                1455

Lys Thr Val Thr Gly Glu Val Lys Ile Gly Asp Asp Thr Tyr Phe
    1460                1465                1470

Phe Ala Lys Asp Gly Lys Gln Leu Lys Gly Gln Ile Val Thr Thr
    1475                1480                1485

Arg Ser Gly Arg Ile Ser Tyr Tyr Phe Gly Asp Ser Gly Lys Lys
    1490                1495                1500

Ala Ile Ser Thr Trp Val Glu Ile Gln Pro Gly Val Phe Val Phe
    1505                1510                1515

Phe Asp Lys Asn Gly Leu Ala Tyr Pro Pro Glu Asn Met Asn
    1520                1525                1530
```